(12) United States Patent
Praveen et al.

(10) Patent No.: US 11,674,177 B2
(45) Date of Patent: Jun. 13, 2023

(54) KELCH DOMAIN CONTAINING 7B (KLHDC7B) VARIANTS AND USES THEREOF

(71) Applicant: Regeneron Pharmaceuticals, Inc., Tarrytown, NY (US)

(72) Inventors: Kavita Praveen, Tarrytown, NY (US); Giovanni Coppola, Tarrytown, NY (US); Manuel Allen Revez Ferreira, Tarrytown, NY (US); Lauren Gurski, Tarrytown, NY (US); Aris Baras, Tarrytown, NY (US); Meghan Drummond Samuelson, Tarrytown, NY (US); Goncalo Abecasis, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 77 days.

(21) Appl. No.: 17/307,653

(22) Filed: May 4, 2021

(65) Prior Publication Data
US 2021/0348228 A1    Nov. 11, 2021

Related U.S. Application Data

(60) Provisional application No. 63/087,245, filed on Oct. 4, 2020, provisional application No. 63/020,746, filed on May 6, 2020.

(51) Int. Cl.
| | |
|---|---|
| *C12Q 1/68* | (2018.01) |
| *C12Q 1/6874* | (2018.01) |
| *C12Q 1/6851* | (2018.01) |
| *C12Q 1/6876* | (2018.01) |
| *G01N 33/68* | (2006.01) |
| *A61K 38/00* | (2006.01) |

(52) U.S. Cl.
CPC ........ *C12Q 1/6874* (2013.01); *C12Q 1/6851* (2013.01); *C12Q 1/6876* (2013.01); *G01N 33/6818* (2013.01); *A61K 38/00* (2013.01); *C12Q 2600/118* (2013.01); *C12Q 2600/158* (2013.01)

(58) Field of Classification Search
CPC ...................................................... C12Q 1/68
USPC ....................................................... 435/6.1
See application file for complete search history.

(56) References Cited

U.S. PATENT DOCUMENTS

| | | | |
|---|---|---|---|
| 2016/0090597 A1 | 3/2016 | Smith et al. | |
| 2017/0226570 A1* | 8/2017 | Weksberg | C12Q 1/6827 |
| 2017/0306406 A1* | 10/2017 | Weksberg | C12Q 1/6883 |

FOREIGN PATENT DOCUMENTS

WO    WO-2017161387 A1 *    9/2017    ............. A61K 31/12

OTHER PUBLICATIONS

Kalra et al, Biological insights from multi-omic analysis of 31 genomic risk loci for adult hearing difficulty, https://doi.org/10.1101/562405, Now published in PLOS Genetics doi: 10.1371/journal.pgen.1009025, Feb. 27, 2019.*

(Continued)

*Primary Examiner* — Aaron A Priest
(74) *Attorney, Agent, or Firm* — Armstrong Teasdale LLP

(57) ABSTRACT

The present disclosure provides methods of treating subjects having hearing loss, methods of identifying subjects having an increased risk of developing hearing loss, and methods of detecting Kelch Domain Containing 7B (KLHDC7B) variant nucleic acid molecules and variant polypeptides.

10 Claims, 4 Drawing Sheets

Specification includes a Sequence Listing.

(56) References Cited

OTHER PUBLICATIONS

Cherny et al., "Self-reported hearing loss questions provide a good measure for genetic studies: a polygenic risk score analysis from UK Biobank", European Journal of Human Genetics, 2020, 28(8), pp. 1056-1065.
Helena et al., "GWAS Identifies 44 Independent Associated Genomic Loci for Self-Reported Adult Hearing Difficulty in UK Biobank", The American Journal of Human Genetics, 2019, 105(4), pp. 788-802.
Kalra et al., "Biological insights from multi-omic analysis of 31 genomic risk loci for adult hearing difficulty", PLOS Genetics, 2020, 16(9), pp. 1-32.
International Search Report and Written Opinion dated Aug. 9, 2021 for International Patent Application No. PCT/US2021/030669.

* cited by examiner

B) Position: 22:50549067:AG:A; cDNA: c.905delG; Amino acid: Gly302fs (truncates at aa 335)

| Study | Cases | Controls | AAF | | OR | p-value |
|---|---|---|---|---|---|---|
| UKB 300K Exome | 63,267 \| 117 \| 0 | 147,884 \| 133 \| 0 | 0.0006 | | 2.06 | 2.9E-09 |
| GHS 85K IDT Exome | 1,861 \| 5 \| 0 | 58,150 \| 38 \| 0 | 0.0004 | | 4.46 | 1.0E-02 |
| GHS 60K VCRome Exome | 3,142 \| 3 \| 0 | 44,797 \| 19 \| 0 | 0.0002 | | 2.56 | 1.8E-01 |
| Sinai Freeze Two Exome | 20 \| 1 \| 0 | 10,171 \| 9 \| 0 | 0.0005 | | 7.96 | 4.3E-02 |
| Meta | 68,471 \| 126 \| 0 | 261,002 \| 199 \| 0 | 0.0005 | | 2.13 | 4.6E-11 |

| Study | Cases | Controls | AAF | | OR | p-value |
|---|---|---|---|---|---|---|
| UKB Freeze 300 | 65,969 \| 120 \| 0 | 129,868 \| 113 \| 0 | 0.0006 | | 2.09 | 1.0E-09 |
| GHS Freeze 145 IDT | 3,796 \| 7 \| 0 | 56,125 \| 35 \| 0 | 0.0004 | | 3.12 | 1.6E-02 |
| GHS Freeze 145 VCRome | 5,594 \| 5 \| 0 | 42,424 \| 17 \| 0 | 0.0002 | | 2.38 | 1.1E-01 |
| Sinai Freeze Two | 313 \| 1 \| 0 | 10,013 \| 9 \| 0 | 0.0005 | | 5.04 | 7.6E-02 |
| Meta | 75,672 \| 133 \| 0 | 238,430 \| 174 \| 0 | 0.0005 | | 2.15 | 9.2E-12 |

C) Position: 22:50549676:G:A; cDNA: c.1510G>A; Amino acid: Val504Met

| Study | Cases | Controls | AAF | | OR | p-value |
|---|---|---|---|---|---|---|
| UKB 300K Imputed | 92,019 | 9,039 | 283 | 221,108 | 19,348 | 371 | 0.0434 | | 1.14 | 1.9E-27 |
| GHS 85K IDT Imputed | 1,711 | 156 | 2 | 53,828 | 4,324 | 103 | 0.0410 | | 1.11 | 1.2E-01 |
| GHS 80K VCRome Imputed | 2,915 | 238 | 12 | 41,580 | 3,370 | 162 | 0.0391 | | 1.07 | 1.1E-01 |
| Malmo Freeze Two Imputed | 305 | 20 | 1 | 25,624 | 1,813 | 37 | 0.0356 | | 1.00 | 7.1E-01 |
| Sinai Freeze Two Imputed | 189 | 13 | 0 | 9,504 | 667 | 10 | 0.0385 | | 0.99 | 4.9E-01 |
| Meta | 97,129 | 9,466 | 298 | 351,644 | 29,522 | 681 | 0.0417 | | 1.17 | 3.3E-28 |

KELCH DOMAIN CONTAINING 7B (KLHDC7B) VARIANTS AND USES THEREOF

REFERENCE TO SEQUENCE LISTING

This application includes a Sequence Listing submitted electronically as a text file named 18923804001SEQ, created on May 1, 2021, with a size of 246 kilobytes. The Sequence Listing is incorporated herein by reference.

FIELD

The present disclosure relates generally to the treatment of subjects having hearing loss, methods of identifying subjects having an increased risk of developing hearing loss, and methods of detecting KLHDC7B variant nucleic acid molecules and variant polypeptides.

BACKGROUND

Auditory dysfunction in humans is an ongoing problem in the medical fields of otology and audiology. About 300 million people worldwide currently suffer from moderate to severe hearing loss, and this number is expected to increase to 700 million by the year 2015. Auditory dysfunction is a common consequence of aging in Western societies. Approximately 17 percent of Americans have hearing loss and half of that number are under the age of 65. It is predicted that the number of Americans with hearing loss will exceed 70 million by the year 2030.

Auditory dysfunctions typically arise from both acute and chronic exposures to loud sounds, ototoxic chemicals, and aging. Hearing impairments can be attributed to a wide variety of causes, including infections (e.g., otitis media), genetic predisposition, mechanical injury, tumors, loud sounds or prolonged exposure to noise, aging, and chemical-induced ototoxicity (e.g., antibiotics or platin drugs) that damages neurons and/or hair cells of the peripheral auditory system. This can be caused by acute noise or can be progressive over time. Sounds exceeding 85 decibels can cause hearing loss and is generated by sound sources such as, gun shots, exploding bombs, jet engines, power tools, and musical concerts. Other common everyday activities and products also give rise to high intensity noise such as use of hair dryers, MP3 players, lawn mowers, and blenders. Military personnel are particularly at risk for noise induced hearing loss due to typical military noise exposures. Side effects of noise-induced hearing loss include tinnitus (ringing in the ears), diminished speech understanding, hyperacusis, and various types of auditory processing impairments. Exposures to commonly used medications may also induce auditory dysfunctions. For instance, subjects treated with anticancer therapies, antibiotics, and other medications often develop hearing loss as a side effect. Furthermore, exposure to industrial chemicals and gasses may induce auditory impairments.

The prevalence of hearing loss after damage to the mammalian cochlea has been thought to be due to a lack of spontaneous regeneration of hair cells and/or neurons, the primary components to detect sound. Humans are born with about 15,000 inner ear hair cells and hair cells do not regenerate after birth. Supporting cells, which surround hair cells in the normal cochlear epithelium, have potential to differentiate into new hair cells in the neonatal mouse following ototoxic damage. Using lineage tracing, the new hair cells, predominantly outer hair cells, have been shown to arise from Lgr5-expressing inner pillar and third Deiters cells, and new hair cell generation has been shown to incrementally be increased by pharmacological inhibition of Notch.

Permanent damage to the hair cells of the inner ear results in sensorineural hearing loss, leading to communication difficulties in a large percentage of the population. Hair cells are the receptor cells that transduce the acoustic stimulus. Regeneration of damaged hair cells provide an avenue for the treatment of a condition that currently has no therapies other than prosthetic devices. Although hair cells do not regenerate in the mammalian cochlea, new hair cells in lower vertebrates are generated from epithelial cells, called supporting cells, that surround hair cells.

Currently, very few cases of hearing loss can actually be cured. Audiological devices such as hearing aids have limitations including the inability to improve speech intelligibility. Of those impacted by hearing impairments, less than 20 percent presently use hearing instruments. In cases of age-related, noise- or drug-induced auditory dysfunctions, often the only effective way to currently "treat" the disorder or reduce its severity is prevention, such as by avoiding excessive noise and using ear protectors, practicing a healthy lifestyle, and avoiding exposure to ototoxic drugs and substances if possible.

Thus, there remains a long felt need to protect auditory cells before injury and preserve/promote the function of existing cells after injury.

Kelch Domain Containing 7B (KLHDC7B) is a protein member of the Kelch superfamily, proteins involved in cellular processes such as cytoskeletal rearrangement and protein degradation, and also have roles in extracellular communication, cell morphology, gene expression and actin binding. In addition, members of this superfamily can be co-opted by a virus after an infection. Alterations in this protein superfamily have been associated with various types of cancer, including leukemia, lung, prostate, brain, and Hodgkin's disease. KLHDC7B was identified as being hypermethylated, yet upregulated, in breast cancer cells. Moderate levels of KLHDC7B expression were observed in hair cells of the ear, while outer hair cells seem to show slightly higher expression (gEAR portal).

SUMMARY

The present disclosure provides methods of identifying a subject having an increased risk for developing hearing loss, wherein the methods comprise: determining or having determined the presence or absence of a KLHDC7B missense variant nucleic acid molecule encoding a KLHDC7B predicted loss-of-function polypeptide in a biological sample obtained from the subject; wherein: i) when the subject is KLHDC7B reference, then the subject does not have an increased risk for developing hearing loss; and ii) when the subject is heterozygous or homozygous for a KLHDC7B missense variant nucleic acid molecule encoding a KLHDC7B predicted loss-of-function polypeptide, then the subject has an increased risk for developing hearing loss.

The present disclosure also provides methods of treating a subject with a therapeutic agent that treats or inhibits hearing loss, wherein the subject has hearing loss, the methods comprising the steps of: determining whether the subject has a KLHDC7B missense variant nucleic acid molecule encoding a KLHDC7B predicted loss-of-function polypeptide by: i) obtaining or having obtained a biological sample from the subject; and ii) performing or having performed a sequence analysis on the biological sample to determine if the subject has a genotype comprising the KLHDC7B missense variant nucleic acid molecule encoding a KLHDC7B predicted loss-of-function polypeptide; and administering or continuing to administer the therapeutic agent that treats or inhibits hearing loss in a standard dosage amount to a subject that is KLHDC7B reference; and administering or continuing to administer the therapeutic agent that treats or inhibits hearing loss in an amount that is the same as or greater than a standard dosage amount to a subject that is heterozygous or homozygous for the KLHDC7B missense variant nucleic acid molecule; wherein the presence of a genotype having the a KLHDC7B missense variant nucleic acid molecule encoding a KLHDC7B predicted loss-of-function polypeptide indicates the subject has an increased risk of developing hearing loss.

The present disclosure also provides methods of detecting a KLHDC7B missense variant nucleic acid molecule encoding a KLHDC7B predicted loss-of-function polypeptide in a subject comprising assaying a sample obtained from the subject to determine whether a nucleic acid molecule in the sample is: i) a genomic nucleic acid molecule comprising a nucleotide sequence: comprising an adenine at a position corresponding to position 3,778 according to SEQ ID NO:2, or the complement thereof; lacking a guanine at a position corresponding to position 2,807 according to SEQ ID NO:1, or the complement thereof; or lacking a guanine at a position corresponding to position 3,170 according to SEQ ID NO:1, or the complement thereof; ii) an mRNA molecule comprising a nucleotide sequence: comprising an adenine at a position corresponding to position 3,778 according to SEQ ID NO:7, or the complement thereof; comprising an adenine at a position corresponding to position 1,644 according to SEQ ID NO:8, or the complement thereof; comprising an adenine at a position corresponding to position 3,474 according to SEQ ID NO:9, or the complement thereof; comprising an adenine at a position corresponding to position 1,644 according to SEQ ID NO:10, or the complement thereof; lacking a guanine at a position corresponding to position 2,807 according to SEQ ID NO:3, or the complement thereof; lacking a guanine at a position corresponding to position 673 according to SEQ ID NO:4, or the complement thereof; lacking a guanine at a position corresponding to position 2,503 according to SEQ ID NO:5, or the complement thereof; lacking a guanine at a position corresponding to position 673 according to SEQ ID NO:6, or the complement thereof; lacking a guanine at a position corresponding to position 3,170 according to SEQ ID NO:3, or the complement thereof; lacking a guanine at a position corresponding to position 1,036 according to SEQ ID NO:4, or the complement thereof; lacking a guanine at a position corresponding to position 2,866 according to SEQ ID NO:5, or the complement thereof; or lacking a guanine at a position corresponding to position 1,036 according to SEQ ID NO:6, or the complement thereof; or iii) a cDNA molecule comprising a nucleotide sequence: comprising an adenine at a position corresponding to position 3,778 according to SEQ ID NO:15, or the complement thereof; comprising an adenine at a position corresponding to position 1,644 according to SEQ ID NO:16, or the complement thereof; comprising an adenine at a position corresponding to position 3,474 according to SEQ ID NO:17, or the complement thereof; comprising an adenine at a position corresponding to position 1,644 according to SEQ ID NO:18, or the complement thereof; lacking a guanine at a position corresponding to position 2,807 according to SEQ ID NO:11, or the complement thereof; lacking a guanine at a position corresponding to position 673 according to SEQ ID NO:12, or the complement thereof; lacking a guanine at a position corresponding to position 2,503 according to SEQ ID NO:13, or the complement thereof; lacking a guanine at a position corresponding to position 673 according to SEQ ID NO:14, or the complement thereof; lacking a guanine at a position corresponding to position 3,170 according to SEQ ID NO:11, or the complement thereof; lacking a guanine at a position corresponding to position 1,036 according to SEQ ID NO:12, or the complement thereof; lacking a guanine at a position corresponding to position 2,866 according to SEQ ID NO:13, or the complement thereof; or lacking a guanine at a position corresponding to position 1,036 according to SEQ ID NO:14, or the complement thereof.

The present disclosure also provides methods of detecting the presence of a KLHDC7B V1145M, V504M, V405M, K822fs, K181fs, K82fs, G943fs, G302fs, or G203fs variant polypeptide, comprising performing an assay on a sample obtained from a subject to determine whether a KLHDC7B protein in the sample: comprises a methionine at a position corresponding to position 1,145 according to SEQ ID NO:22, comprises a methionine at a position corresponding to position 504 according to SEQ ID NO:23, comprises a methionine at a position corresponding to position 405 according to SEQ ID NO:24, terminates at a position corresponding to position 885 according to SEQ ID NO:43 and lacks amino acids at positions corresponding to positions 886 to 1,235 of SEQ ID NO:19, terminates at a position corresponding to position 244 according to SEQ ID NO:44 and lacks amino acids at positions corresponding to positions 245 to 594 of SEQ ID NO:20, terminates at a position corresponding to position 145 according to SEQ ID NO:45 and lacks amino acids at positions corresponding to positions 146 to 495 of SEQ ID NO:21, terminates at a position corresponding to position 975 according to SEQ ID NO:46 and lacks amino acids at positions corresponding to positions 976 to 1,235 of SEQ ID NO:19, terminates at a position corresponding to position 334 according to SEQ ID NO:47 and lacks amino acids at positions corresponding to positions 335 to 594 of SEQ ID NO:20, and terminates at a position corresponding to position 235 according to SEQ ID NO:48 and lacks amino acids at positions corresponding to positions 236 to 495 of SEQ ID NO:21.

The present disclosure also provides therapeutic agents that treat or inhibit hearing loss for use in the treatment of hearing loss in a subject having: i) a genomic nucleic acid molecule having a nucleotide sequence encoding a KLHDC7B polypeptide, wherein the nucleotide sequence: comprises an adenine at a position corresponding to position 3,778 according to SEQ ID NO:2, or the complement thereof; lacks a guanine at a position corresponding to position 2,807 according to SEQ ID NO:1, or the complement thereof; or lacks a guanine at a position corresponding to position 3,170 according to SEQ ID NO:1, or the complement thereof; ii) an mRNA molecule having a nucleotide sequence encoding a KLHDC7B polypeptide, wherein the nucleotide sequence comprises: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; or iii) a cDNA molecule having a nucleotide sequence encoding a KLHDC7B polypeptide, wherein the nucleotide sequence comprises: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof.

DESCRIPTION

Figure 1:
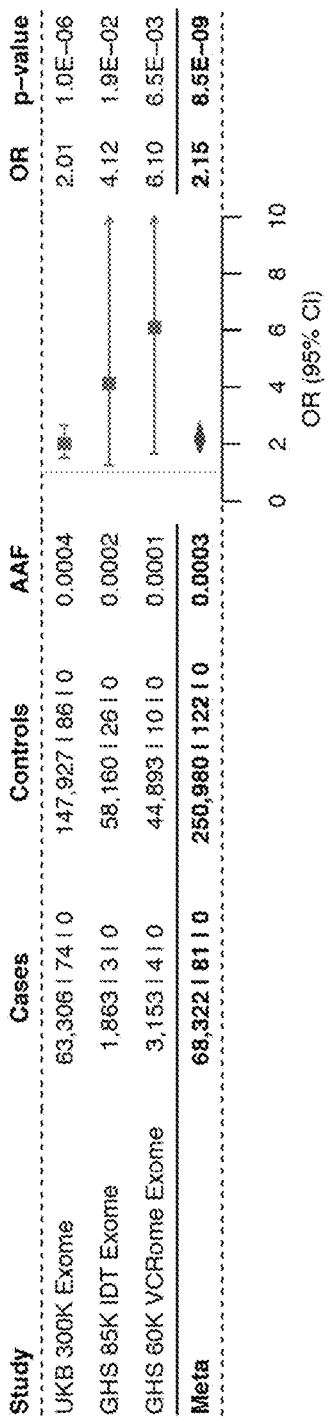
FIG. 1 (Panels A, B, and C) shows that a common missense variant, and rare, predicted loss-of-function (pLOF) variants in KLHDC7B are associated with increased risk for hearing loss. The association with the pLOF variants suggest that the missense is likely to be loss or of reduced function, and that reduction in KLHDC7B confers an increase in the risk for hearing loss.
Figure 1:
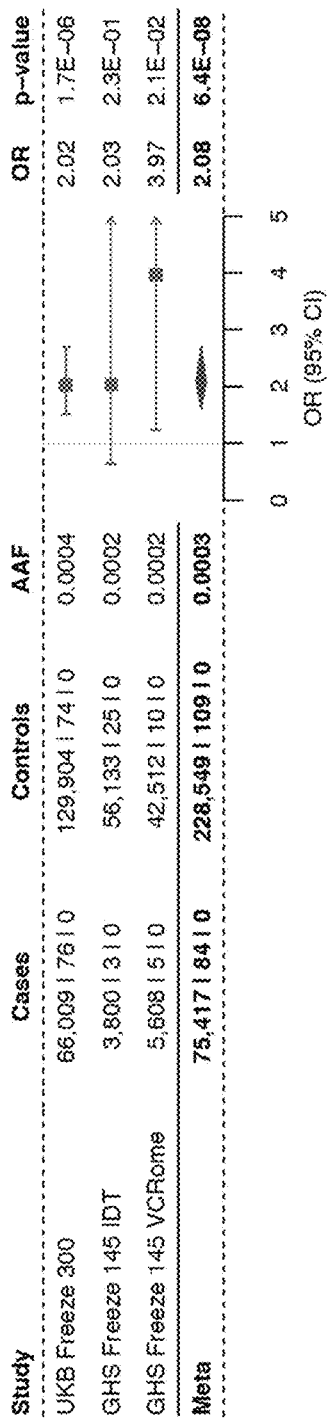
Figure 1:
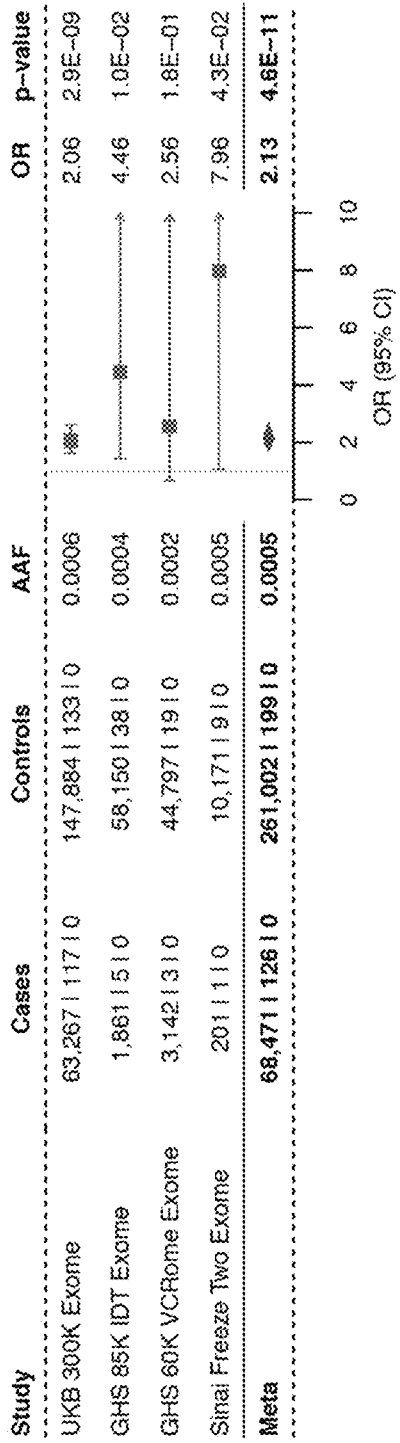
Figure 1:
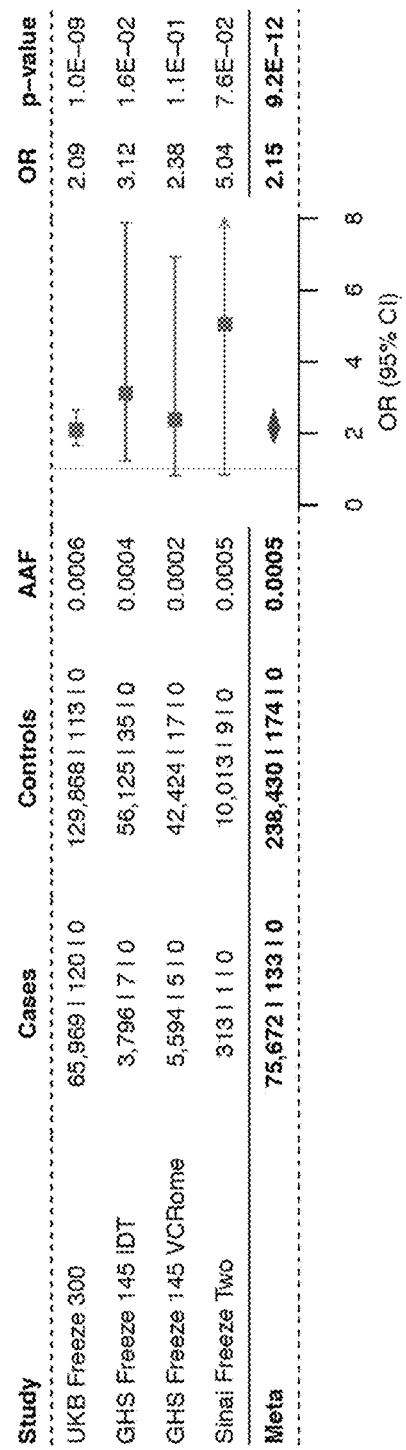

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

A rare variant in the KLHDC7B gene associated with an increased risk of developing hearing loss, such as conductive hearing loss, sensorineural hearing loss, or neural hearing loss, in humans has been identified in accordance with the present disclosure. For example, a genetic alteration that changes the guanine nucleotide of position 3,778 in the human KLHDC7B reference (see, SEQ ID NO:1) to adenine has been observed to indicate that the human having such an alteration may have an increased risk of developing hearing loss, such as conductive hearing loss, sensorineural hearing loss, or neural hearing loss. It is believed that no rare (minor allele frequency <1%) and predicted loss-of-function variants of the KLHDC7B gene or protein have any known association with hearing loss, such as conductive hearing loss, sensorineural hearing loss, or neural hearing loss. Altogether, the genetic analyses described herein surprisingly indicate that the KLHDC7B gene and, in particular, a variant in the KLHDC7B gene, associates with an increased risk of developing hearing loss, such as conductive hearing loss, sensorineural hearing loss, or neural hearing loss. Therefore, subjects that have a KLHDC7B variant nucleic acid molecule or polypeptide that associates with an increased risk of developing hearing loss, such as conductive hearing loss, sensorineural hearing loss, or neural hearing loss, may be treated such that hearing loss is prevented, the symptoms thereof are reduced, and/or development of symptoms is repressed. Accordingly, the present disclosure provides methods of leveraging the identification of such variants in subjects to identify or stratify risk in such subjects of developing hearing loss, such as conductive hearing loss, sensorineural hearing loss, or neural hearing loss, or to diagnose subjects as having an increased risk of developing hearing loss, such as conductive hearing loss, sensorineural hearing loss, or neural hearing loss, such that subjects at risk or subjects with active disease may be treated accordingly.

For purposes of the present disclosure, any particular subject can be categorized as having one of three KLHDC7B genotypes: i) KLHDC7B reference; ii) heterozygous for a KLHDC7B missense variant nucleic acid molecule encoding a KLHDC7B predicted loss-of-function polypeptide; or iii) homozygous for a KLHDC7B missense variant nucleic acid molecule encoding a KLHDC7B predicted loss-of-function polypeptide. A subject is KLHDC7B reference when the subject does not have a copy of a KLHDC7B missense variant nucleic acid molecule encoding a KLHDC7B predicted loss-of-function polypeptide. A subject is heterozygous for a KLHDC7B missense variant nucleic acid molecule encoding a KLHDC7B predicted loss-of-function polypeptide when the subject has a single copy of a KLHDC7B missense variant nucleic acid molecule encoding a KLHDC7B predicted loss-of-function polypeptide. A KLHDC7B missense variant nucleic acid molecule encoding a KLHDC7B predicted loss-of-function polypeptide is any KLHDC7B nucleic acid molecule (such as, a genomic nucleic acid molecule, an mRNA molecule, or a cDNA molecule) encoding a KLHDC7B polypeptide having a partial loss-of-function, a complete loss-of-function, a predicted partial loss-of-function, or a predicted complete loss-of-function. A subject who has a KLHDC7B polypeptide having a partial loss-of-function (or predicted partial loss-of-function) is hypomorphic for KLHDC7B. The KLHDC7B missense variant nucleic acid molecule encoding a KLHDC7B predicted loss-of-function polypeptide can be any nucleic acid molecule encoding KLHDC7B V1145M, V504M, V405M, K822fs, K181fs, K82fs, G943fs, G302fs, or G203fs. A subject is homozygous for a KLHDC7B missense variant nucleic acid molecule encoding a KLHDC7B predicted loss-of-function polypeptide when the subject has two copies of a KLHDC7B missense variant nucleic acid molecule encoding a KLHDC7B predicted loss-of-function polypeptide.

For subjects that are genotyped or determined to be heterozygous or homozygous for a KLHDC7B missense variant nucleic acid molecule encoding a KLHDC7B predicted loss-of-function polypeptide, such subjects have an increased risk of developing hearing loss, such as conductive hearing loss, sensorineural hearing loss, or neural hearing loss. For subjects that are genotyped or determined to be heterozygous or homozygous for a KLHDC7B missense variant nucleic acid molecule encoding a KLHDC7B predicted loss-of-function polypeptide, such subjects can be treated with an agent effective to treat hearing loss, such as conductive hearing loss, sensorineural hearing loss, or neural hearing loss.

In any of the embodiments described herein, the KLHDC7B missense variant nucleic acid molecule encoding a KLHDC7B predicted loss-of-function polypeptide can be any KLHDC7B nucleic acid molecule (such as, for example, genomic nucleic acid molecule, mRNA molecule, or cDNA molecule) encoding a KLHDC7B polypeptide having a partial loss-of-function, a complete loss-of-function, a predicted partial loss-of-function, or a predicted complete loss-of-function. For example, the KLHDC7B missense variant nucleic acid molecule encoding a KLHDC7B predicted loss-of-function polypeptide can be any nucleic acid molecule encoding KLHDC7B V1145M, V504M, V405M, K822fs, K181fs, K82fs, G943fs, G302fs, or G203fs. In some embodiments, the KLHDC7B missense variant nucleic acid molecule encodes KLHDC7B V1145M. In some embodiments, the KLHDC7B missense variant nucleic acid molecule encodes KLHDC7B V504M. In some embodiments, the KLHDC7B missense variant nucleic acid molecule encodes KLHDC7B V405M. In some embodiments, the KLHDC7B missense variant nucleic acid molecule encodes KLHDC7B K822fs. In some embodiments, the KLHDC7B missense variant nucleic acid molecule encodes KLHDC7B K181fs. In some embodiments, the KLHDC7B missense variant nucleic acid molecule encodes KLHDC7B K82fs. In some embodiments, the KLHDC7B missense variant nucleic acid molecule encodes KLHDC7B G943fs. In some embodiments, the KLHDC7B missense variant nucleic acid molecule encodes KLHDC7B G302fs. In some embodiments, the KLHDC7B missense variant nucleic acid molecule encodes KLHDC7B G203fs.

In any of the embodiments described herein, the KLHDC7B predicted loss-of-function polypeptide can be any KLHDC7B polypeptide having a partial loss-of-function, a complete loss-of-function, a predicted partial loss-of-function, or a predicted complete loss-of-function. In any of the embodiments described herein, the KLHDC7B predicted loss-of-function polypeptide can be any of the KLHDC7B polypeptides described herein including, for example, KLHDC7B V1145M, V504M, V405M, K822fs, K181fs, K82fs, G943fs, G302fs, or G203fs. In some embodiments, the KLHDC7B predicted loss-of-function polypeptide is KLHDC7B V1145M. In some embodiments, the KLHDC7B predicted loss-of-function polypeptide is KLHDC7B V504M. In some embodiments, the KLHDC7B predicted loss-of-function polypeptide is KLHDC7B V405M. In some embodiments, the KLHDC7B predicted loss-of-function polypeptide is KLHDC7B K822fs. In some embodiments, the KLHDC7B predicted loss-of-function polypeptide is KLHDC7B K181fs. In some embodiments, the KLHDC7B predicted loss-of-function polypeptide is KLHDC7B K82fs. In some embodiments, the KLHDC7B predicted loss-of-function polypeptide is KLHDC7B G943fs. In some embodiments, the KLHDC7B predicted loss-of-function polypeptide is KLHDC7B G302fs. In some embodiments, the KLHDC7B predicted loss-of-function polypeptide is KLHDC7B G203fs.

In any of the embodiments described herein, hearing loss is conductive hearing loss, sensorineural hearing loss, or neural hearing loss. In any of the embodiments described herein, hearing loss is conductive hearing loss. In any of the embodiments described herein, hearing loss is sensorineural hearing loss. In any of the embodiments described herein, hearing loss is neural hearing loss.

Symptoms of hearing loss include, but are not limited to, hearing problem (muffling of speech and other sounds, difficulty understanding words, especially against background noise or in a crowd, or trouble hearing consonants), ringing in the ears, sensitivity to sound, and speech delay in a child.

The present disclosure also provides methods of treating a subject with a therapeutic agent that treats or inhibits hearing loss, wherein the subject has hearing loss. In some embodiments, the methods comprise determining whether the subject has a KLHDC7B missense variant nucleic acid molecule encoding a KLHDC7B predicted loss-of-function polypeptide by obtaining or having obtained a biological sample from the subject, and performing or having performed a sequence analysis on the biological sample to determine if the subject has a genotype comprising the KLHDC7B missense variant nucleic acid molecule encoding a KLHDC7B predicted loss-of-function polypeptide. The methods comprise administering or continuing to administer the therapeutic agent that treats or inhibits hearing loss in a standard dosage amount to a subject that is KLHDC7B reference. The methods further comprise administering or continuing to administer the therapeutic agent that treats or inhibits hearing loss in an amount that is the same as or greater than a standard dosage amount to a subject that is heterozygous or homozygous for the KLHDC7B missense variant nucleic acid molecule. The presence of a genotype having the KLHDC7B missense variant nucleic acid molecule encoding a KLHDC7B predicted loss-of-function polypeptide indicates the subject has an increased risk of developing hearing loss. In some embodiments, the subject is KLHDC7B reference. In some embodiments, the subject is heterozygous for a KLHDC7B missense variant nucleic acid molecule encoding a KLHDC7B predicted loss-of-function polypeptide. In some embodiments, the subject is homozygous for a KLHDC7B missense variant nucleic acid molecule encoding a KLHDC7B predicted loss-of-function polypeptide.

In some embodiments, the methods of treatment further comprise detecting the presence or absence of a KLHDC7B missense variant nucleic acid molecule encoding a KLHDC7B predicted loss-of-function polypeptide in a biological sample from the subject. As used throughout the present disclosure, a "KLHDC7B missense variant nucleic acid molecule encoding a KLHDC7B predicted loss-of-function polypeptide" is any KLHDC7B nucleic acid molecule (such as, for example, genomic nucleic acid molecule, mRNA molecule, or cDNA molecule) encoding a KLHDC7B polypeptide having a partial loss-of-function, a complete loss-of-function, a predicted partial loss-of-function, or a predicted complete loss-of-function.

Detecting the presence or absence of a KLHDC7B missense variant nucleic acid molecule encoding a KLHDC7B predicted loss-of-function polypeptide in a biological sample from a subject and/or determining whether a subject has a KLHDC7B missense variant nucleic acid molecule encoding a KLHDC7B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of treating a subject with a therapeutic agent that treats or inhibits hearing loss, wherein the subject has hearing loss. In some embodiments, the method comprises determining whether the subject has a KLHDC7B predicted loss-of-function polypeptide by obtaining or having obtained a biological sample from the subject, and performing or having performed an assay on the biological sample to determine if the subject has a KLHDC7B predicted loss-of-function polypeptide. The methods comprise administering or continuing to administer the therapeutic agent that treats or inhibits hearing loss in a standard dosage amount to a subject that is KLHDC7B reference. The methods further comprise administering or continuing to administer the therapeutic agent that treats or inhibits hearing loss in an amount that is the same as or greater than a standard dosage amount to a subject that has a KLHDC7B predicted loss-of-function polypeptide. The presence of a KLHDC7B predicted loss-of-function polypeptide indicates the subject has an increased risk of developing hearing loss. In some embodiments, the subject has a KLHDC7B predicted loss-of-function polypeptide. In some embodiments, the subject does not have a KLHDC7B predicted loss-of-function polypeptide.

Detecting the presence or absence of a KLHDC7B predicted loss-of-function polypeptide in a biological sample from a subject and/or determining whether a subject has a KLHDC7B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit hearing loss include, but are not limited to: antioxidants, calcium-channel blockers, anti-inflammatory drugs (such as steroids), apoptosis inhibitors, D-methionine, ebselen, N-acetylcysteine, lipoic acid, combination of ebselen and allopurinol, resveratrol, neurotrophic factors (such as T-817MA), caspase inhibitors (such as z-DEVD-fmk), copper transport inhibitors (such as cimetidine and copper sulphate), and micronutrients with antioxidant vitamins.

In some embodiments, the dose of the therapeutic agents that treat or inhibit hearing loss can be increased by about 10%, by about 20%, by about 30%, by about 40%, by about 50%, by about 60%, by about 70%, by about 80%, or by about 90% for subjects that are heterozygous or homozygous for a KLHDC7B predicted loss-of-function variant (i.e., a greater amount than the standard dosage amount) compared to subjects that are KLHDC7B reference (who may receive a standard dosage amount). In some embodiments, the dose of the therapeutic agents that treat or inhibit hearing loss can be increased by about 10%, by about 20%, by about 30%, by about 40%, or by about 50%. In addition, the dose of therapeutic agents that treat or inhibit hearing loss in subjects that are heterozygous or homozygous for a KLHDC7B predicted loss-of-function variant can be administered more frequently compared to subjects that are KLHDC7B reference.

In some embodiments, the dose of the therapeutic agents that treat or inhibit hearing loss can be increased by about 10%, by about 20%, by about 30%, by about 40%, by about 50%, by about 60%, by about 70%, by about 80%, or by about 90% for subjects that are homozygous for a KLHDC7B predicted loss-of-function variant compared to subjects that are heterozygous for a KLHDC7B predicted loss-of-function variant. In some embodiments, the dose of the therapeutic agents that treat or inhibit hearing loss can be increased by about 10%, by about 20%, by about 30%, by about 40%, or by about 50%. In addition, the dose of therapeutic agents that treat or inhibit hearing loss in subjects that are homozygous for a KLHDC7B predicted loss-of-function variant can be administered more frequently compared to subjects that are heterozygous for a KLHDC7B predicted loss-of-function variant.

Administration of the therapeutic agents that treat or inhibit hearing loss can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit hearing loss can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in hearing loss, a decrease/reduction in the severity of hearing loss (such as, for example, a reduction or inhibition of development or hearing loss), a decrease/reduction in symptoms and hearing loss-related effects, delaying the onset of symptoms and hearing loss-related effects, reducing the severity of symptoms of hearing loss-related effects, reducing the severity of an acute episode, reducing the number of symptoms and hearing loss-related effects, reducing the latency of symptoms and hearing loss-related effects, an amelioration of symptoms and hearing loss-related effects, reducing secondary symptoms, preventing relapse to hearing loss, decreasing the number or frequency of relapse episodes, increasing latency between symptomatic episodes, increasing time to sustained progression, speeding recovery, and/or increasing efficacy of or decreasing resistance to alternative therapeutics, following administration of the agent or composition comprising the agent. A prophylactic effect may comprise a complete or partial avoidance/inhibition or a delay of hearing loss development/progression (such as, for example, a complete or partial avoidance/inhibition or a delay) following administration of a therapeutic protocol. Treatment of hearing loss encompasses the treatment of subjects already diagnosed as having any form of hearing loss at any clinical stage or manifestation, the delay of the onset or evolution or aggravation or deterioration of the symptoms or signs of hearing loss, and/or preventing and/or reducing the severity of hearing loss.

The present disclosure also provides methods of identifying a subject having an increased risk for developing hearing loss. In some embodiments, the method comprises determining or having determined in a biological sample obtained from the subject the presence or absence of a KLHDC7B missense variant nucleic acid molecule (such as a genomic nucleic acid molecule, mRNA molecule, and/or cDNA molecule) encoding a KLHDC7B predicted loss-of-function polypeptide. When the subject lacks a KLHDC7B missense variant nucleic acid molecule encoding a KLHDC7B predicted loss-of-function polypeptide (i.e., the subject is genotypically categorized as a KLHDC7B reference), then the subject does not have an increased risk for developing hearing loss. When the subject has a KLHDC7B missense variant nucleic acid molecule encoding a KLHDC7B predicted loss-of-function polypeptide (i.e., the subject is heterozygous or homozygous for a KLHDC7B missense variant nucleic acid molecule encoding a KLHDC7B predicted loss-of-function polypeptide), then the subject has an increased risk for developing hearing loss.

Determining whether a subject has a KLHDC7B missense variant nucleic acid molecule encoding a KLHDC7B predicted loss-of-function polypeptide in a biological sample from a subject and/or determining whether a subject has a KLHDC7B missense variant nucleic acid molecule encoding a KLHDC7B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing hearing loss, the subject is further treated with a therapeutic agent that treats or inhibits hearing loss, as described herein. In some embodiments, when the subject is heterozygous or homozygous for a KLHDC7B missense variant nucleic acid molecule encoding a KLHDC7B predicted loss-of-function polypeptide, the subject is administered the therapeutic agent that treats or inhibits hearing loss in a dosage amount that is the same as or greater than a standard dosage amount. In some embodiments, when the subject is homozygous for a KLHDC7B missense variant nucleic acid molecule encoding a KLHDC7B predicted loss-of-function polypeptide, the subject is administered the therapeutic agent that treats or inhibits hearing loss in a dosage amount that is the same as or greater than the dosage amount administered to a subject that is heterozygous for a KLHDC7B missense variant nucleic acid molecule encoding a KLHDC7B predicted loss-of-function polypeptide. In some embodiments, the subject is KLHDC7B reference. In some embodiments, the subject is heterozygous for a KLHDC7B missense variant nucleic acid molecule encoding a KLHDC7B predicted loss-of-function polypeptide. In some embodiments, the subject is homozygous for a KLHDC7B missense variant nucleic acid molecule encoding a KLHDC7B predicted loss-of-function polypeptide.

The present disclosure also provides methods of detecting the presence or absence of a KLHDC7B missense variant genomic nucleic acid molecule encoding a KLHDC7B predicted loss-of-function polypeptide in a biological sample from a subject, and/or a KLHDC7B missense variant mRNA molecule encoding a KLHDC7B predicted loss-of-function polypeptide in a biological sample from a subject, and/or a KLHDC7B missense variant cDNA molecule encoding a KLHDC7B predicted loss-of-function polypeptide produced from an mRNA molecule in a biological sample from a subject. It is understood that gene sequences within a population and mRNA molecules encoded by such genes can vary due to polymorphisms such as single-nucleotide polymorphisms. The sequences provided herein for the KLHDC7B variant genomic nucleic acid molecule, KLHDC7B variant mRNA molecule, and KLHDC7B variant cDNA molecule are only exemplary sequences. Other sequences for the KLHDC7B variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any KLHDC7B variant nucleic acid molecule, preliminary processing designed to isolate or enrich the sample for the genomic DNA can be employed. A variety of techniques may be used for this purpose. When detecting the level of any KLHDC7B variant mRNA, different techniques can be used enrich the biological sample with mRNA. Various methods to detect the presence or level of an mRNA or the presence of a particular variant genomic DNA locus can be used.

In some embodiments, detecting a KLHDC7B missense variant nucleic acid molecule encoding a KLHDC7B predicted loss-of-function polypeptide in a subject comprises assaying or genotyping a biological sample obtained from the subject to determine whether a KLHDC7B genomic nucleic acid molecule in the biological sample, and/or a KLHDC7B mRNA molecule in the biological sample, and/or a KLHDC7B cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a KLHDC7B missense variant nucleic acid molecule encoding a KLHDC7B predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the nucleotide sequence comprises: an adenine at a position corresponding to position 3,778 according to SEQ ID NO:2 (for genomic nucleic acid molecules), an adenine at a position corresponding to position 3,778 according to SEQ ID NO:7 (for mRNA molecules), or an adenine at a position corresponding to position 3,778 according to SEQ ID NO:15 (for cDNA molecules obtained from mRNA molecules).

In some embodiments, the nucleotide sequence comprises: an adenine at a position corresponding to position 1,644 according to SEQ ID NO:8 (for mRNA molecules), or an adenine at a position corresponding to position 1,644 according to SEQ ID NO:16 (for cDNA molecules obtained from mRNA molecules).

In some embodiments, the nucleotide sequence comprises: an adenine at a position corresponding to position 3,474 according to SEQ ID NO:9 (for mRNA molecules), or an adenine at a position corresponding to position 3,474 according to SEQ ID NO:17 (for cDNA molecules obtained from mRNA molecules).

In some embodiments, the nucleotide sequence comprises: an adenine at a position corresponding to position 1,644 according to SEQ ID NO:10 (for mRNA molecules), or an adenine at a position corresponding to position 1,644 according to SEQ ID NO:18 (for cDNA molecules obtained from mRNA molecules).

In some embodiments, the nucleotide sequence: lacks a guanine at a position corresponding to position 2,807 according to SEQ ID NO:1 (for genomic nucleic acid molecules), lacks a guanine at a position corresponding to position 2,807 according to SEQ ID NO:3 (for mRNA molecules), or lacks a guanine at a position corresponding to position 2,807 according to SEQ ID NO:11 (for cDNA molecules obtained from mRNA molecules).

In some embodiments, the nucleotide sequence: lacks a guanine at a position corresponding to position 673 according to SEQ ID NO:4 (for mRNA molecules), or lacks a guanine at a position corresponding to position 673 according to SEQ ID NO:12 (for cDNA molecules obtained from mRNA molecules).

In some embodiments, the nucleotide sequence: lacks a guanine at a position corresponding to position 2,503 according to SEQ ID NO:5 (for mRNA molecules), or lacks a guanine at a position corresponding to position 2,503 according to SEQ ID NO:13 (for cDNA molecules obtained from mRNA molecules).

In some embodiments, the nucleotide sequence: lacks a guanine at a position corresponding to position 673 according to SEQ ID NO:6 (for mRNA molecules), or lacks a guanine at a position corresponding to position 673 according to SEQ ID NO:14 (for cDNA molecules obtained from mRNA molecules).

In some embodiments, the nucleotide sequence: lacks a guanine at a position corresponding to position 3,170 according to SEQ ID NO:1 (for genomic nucleic acid molecules), lacks a guanine at a position corresponding to position 3,170 according to SEQ ID NO:3 (for mRNA molecules), or lacks a guanine at a position corresponding to position 3,170 according to SEQ ID NO:11 (for cDNA molecules obtained from mRNA molecules).

In some embodiments, the nucleotide sequence: lacks a guanine at a position corresponding to position 1,036 according to SEQ ID NO:4 (for mRNA molecules), or lacks a guanine at a position corresponding to position 1,036 according to SEQ ID NO:12 (for cDNA molecules obtained from mRNA molecules).

In some embodiments, the nucleotide sequence: lacks a guanine at a position corresponding to position 2,866 according to SEQ ID NO:5 (for mRNA molecules), or lacks a guanine at a position corresponding to position 2,866 according to SEQ ID NO:13 (for cDNA molecules obtained from mRNA molecules).

In some embodiments, the nucleotide sequence: lacks a guanine at a position corresponding to position 1,036 according to SEQ ID NO:6 (for mRNA molecules), or lacks a guanine at a position corresponding to position 1,036 according to SEQ ID NO:14 (for cDNA molecules obtained from mRNA molecules).

In some embodiments, the nucleotide sequence: comprises an adenine at a position corresponding to position 3,778 according to SEQ ID NO:2, or the complement thereof; lacks a guanine at a position corresponding to position 2,807 according to SEQ ID NO:1, or the complement thereof; or lacks a guanine at a position corresponding to position 3,170 according to SEQ ID NO:1, or the complement thereof.

In some embodiments, the nucleotide sequence: comprises an adenine at a position corresponding to position 3,778 according to SEQ ID NO:7, or the complement thereof; comprises an adenine at a position corresponding to position 1,644 according to SEQ ID NO:8, or the complement thereof; comprises an adenine at a position corresponding to position 3,474 according to SEQ ID NO:9, or the complement thereof; comprises an adenine at a position corresponding to position 1,644 according to SEQ ID NO:10, or the complement thereof; lacks a guanine at a position corresponding to position 2,807 according to SEQ ID NO:3, or the complement thereof; lacks a guanine at a position corresponding to position 673 according to SEQ ID NO:4, or the complement thereof; lacks a guanine at a position corresponding to position 2,503 according to SEQ ID NO:5, or the complement thereof; lacks a guanine at a position corresponding to position 673 according to SEQ ID NO:6, or the complement thereof; lacks a guanine at a position corresponding to position 3,170 according to SEQ ID NO:3, or the complement thereof; lacks a guanine at a position corresponding to position 1,036 according to SEQ ID NO:4, or the complement thereof; lacks a guanine at a position corresponding to position 2,866 according to SEQ ID NO:5, or the complement thereof; or lacks a guanine at a position corresponding to position 1,036 according to SEQ ID NO:6, or the complement thereof.

In some embodiments, the nucleotide sequence: comprises an adenine at a position corresponding to position 3,778 according to SEQ ID NO:15, or the complement thereof; comprises an adenine at a position corresponding to position 1,644 according to SEQ ID NO:16, or the complement thereof; comprises an adenine at a position corresponding to position 3,474 according to SEQ ID NO:17, or the complement thereof; comprises an adenine at a position corresponding to position 1,644 according to SEQ ID NO:18, or the complement thereof; lacks a guanine at a position corresponding to position 2,807 according to SEQ ID NO:11, or the complement thereof; lacks a guanine at a position corresponding to position 673 according to SEQ ID NO:12, or the complement thereof; lacks a guanine at a position corresponding to position 2,503 according to SEQ ID NO:13, or the complement thereof; lacks a guanine at a position corresponding to position 673 according to SEQ ID NO:14, or the complement thereof; lacks a guanine at a position corresponding to position 3,170 according to SEQ ID NO:11, or the complement thereof; lacks a guanine at a position corresponding to position 1,036 according to SEQ ID NO:12, or the complement thereof; lacks a guanine at a position corresponding to position 2,866 according to SEQ ID NO:13, or the complement thereof; or lacks a guanine at a position corresponding to position 1,036 according to SEQ ID NO:14, or the complement thereof.

In some embodiments, the biological sample comprises a cell or cell lysate. Such methods can further comprise, for example, obtaining a biological sample from the subject comprising a KLHDC7B genomic nucleic acid molecule or mRNA molecule, and if mRNA, optionally reverse transcribing the mRNA into cDNA. Such assays can comprise, for example determining the identity of these positions of the particular KLHDC7B nucleic acid molecule. In some embodiments, the method is an in vitro method.

In some embodiments, the determining step, detecting step, or sequence analysis comprises sequencing at least a portion of the nucleotide sequence of the KLHDC7B genomic nucleic acid molecule, the KLHDC7B mRNA molecule, or the KLHDC7B cDNA molecule in the biological sample, wherein the sequenced portion comprises one or more variations that cause a loss-of-function (partial or complete) or are predicted to cause a loss-of-function (partial or complete).

In some embodiments, the determining step, detecting step, or sequence analysis comprises sequencing at least a portion of: the nucleotide sequence of the KLHDC7B genomic nucleic acid molecule in the biological sample, wherein the sequenced portion comprises a position corresponding to position 3,778 according to SEQ ID NO:2, or the complement thereof; the nucleotide sequence of the KLHDC7B mRNA molecule in the biological sample, wherein the sequenced portion comprises a position corresponding to position 3,778 according to SEQ ID NO:7, or the complement thereof; and/or the nucleotide sequence of the KLHDC7B cDNA molecule produced from the mRNA in the biological sample, wherein the sequenced portion comprises a position corresponding to position 3,778 according to SEQ ID NO:15, or the complement thereof. When the sequenced portion of the KLHDC7B nucleic acid molecule in the biological sample comprises an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises a position corresponding to position 1,644 according to SEQ ID NO:8, or the complement thereof; and/or the nucleotide sequence of the KLHDC7B cDNA molecule produced from the mRNA in the biological sample, wherein the sequenced portion comprises a position corresponding to position 1,644 according to SEQ ID NO:16, or the complement thereof. When the sequenced portion of the KLHDC7B nucleic acid molecule in the biological sample comprises an adenine at a position corresponding to position 1,644 according to SEQ ID NO:8, or an adenine at a position corresponding to position 1,644 according to SEQ ID NO:16, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises a position corresponding to position 3,474 according to SEQ ID NO:9, or the complement thereof; and/or the nucleotide sequence of the KLHDC7B cDNA molecule produced from the mRNA in the biological sample, wherein the sequenced portion comprises a position corresponding to position 3,474 according to SEQ ID NO:17, or the complement thereof. When the sequenced portion of the KLHDC7B nucleic acid molecule in the biological sample comprises an adenine at a position corresponding to position 3,474 according to SEQ ID NO:9, or an adenine at a position corresponding to position 3,474 according to SEQ ID NO:17, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises a position corresponding to position 1,644 according to SEQ ID NO:10, or the complement thereof; and/or the nucleotide sequence of the KLHDC7B cDNA molecule produced from the mRNA in the biological sample, wherein the sequenced portion comprises a position corresponding to position 1,644 according to SEQ ID NO:18, or the complement thereof. When the sequenced portion of the KLHDC7B nucleic acid molecule in the biological sample comprises an adenine at a position corresponding to position 1,644 according to SEQ ID NO:10, or an adenine at a position corresponding to position 1,644 according to SEQ ID NO:18, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises positions corresponding to positions 2,806-2,807 according to SEQ ID NO:25, or the complement thereof; the nucleotide sequence of the KLHDC7B mRNA molecule in the biological sample, wherein the sequenced portion comprises positions corresponding to positions 2,806-2,807 according to SEQ ID NO:27, or the complement thereof; and/or the nucleotide sequence of the KLHDC7B cDNA molecule produced from the mRNA in the biological sample, wherein the sequenced portion comprises positions corresponding to positions 2,806-2,807 according to SEQ ID NO:35, or the complement thereof. When the sequenced portion of the KLHDC7B nucleic acid molecule in the biological sample comprises a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises positions corresponding to positions 672-673 according to SEQ ID NO:28, or the complement thereof; and/or the nucleotide sequence of the KLHDC7B cDNA molecule produced from the mRNA in the biological sample, wherein the sequenced portion comprises positions corresponding to positions 672-673 according to SEQ ID NO:36, or the complement thereof. When the sequenced portion of the KLHDC7B nucleic acid molecule in the biological sample comprises a CG dinucleotide at positions corresponding to positions 672-673 according to SEQ ID NO:28, or a CG dinucleotide at positions corresponding to positions 672-673 according to SEQ ID NO:36, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises positions corresponding to positions 2,502-2,503 according to SEQ ID NO:29, or the complement thereof; and/or the nucleotide sequence of the KLHDC7B cDNA molecule produced from the mRNA in the biological sample, wherein the sequenced portion comprises positions corresponding to positions 2,502-2,503 according to SEQ ID NO:37, or the complement thereof. When the sequenced portion of the KLHDC7B nucleic acid molecule in the biological sample comprises a CG dinucleotide at positions corresponding to positions 2,502-2,503 according to SEQ ID NO:29, or a CG dinucleotide at positions corresponding to positions 2,502-2,503 according to SEQ ID NO:37, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises positions corresponding to positions 672-673 according to SEQ ID NO:30, or the complement thereof; and/or the nucleotide sequence of the KLHDC7B cDNA molecule produced from the mRNA in the biological sample, wherein the sequenced portion comprises positions corresponding to positions 672-673 according to SEQ ID NO:38, or the complement thereof. When the sequenced portion of the KLHDC7B nucleic acid molecule in the biological sample comprises a CG dinucleotide at positions corresponding to positions 672-673 according to SEQ ID NO:30, or a CG dinucleotide at positions corresponding to positions 672-673 according to SEQ ID NO:38, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises positions corresponding to positions 3,169-3,170 according to SEQ ID NO:26, or the complement thereof; the nucleotide sequence of the KLHDC7B mRNA molecule in the biological sample, wherein the sequenced portion comprises positions corresponding to positions 3,169-3,170 according to SEQ ID NO:31, or the complement thereof; and/or the nucleotide sequence of the KLHDC7B cDNA molecule produced from the mRNA in the biological sample, wherein the sequenced portion comprises positions corresponding to positions 3,169-3,170 according to SEQ ID NO:39, or the complement thereof. When the sequenced portion of the KLHDC7B nucleic acid molecule in the biological sample comprises an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises the nucleotide sequence of the KLHDC7B mRNA molecule in the biological sample, wherein the sequenced portion comprises positions corresponding to positions 1,035-1,036 according to SEQ ID NO:32, or the complement thereof; and/or the nucleotide sequence of the KLHDC7B cDNA molecule produced from the mRNA in the biological sample, wherein the sequenced portion comprises positions corresponding to positions 1,035-1,036 according to SEQ ID NO:40, or the complement thereof. When the sequenced portion of the KLHDC7B nucleic acid molecule in the biological sample comprises an AG dinucleotide at positions corresponding to positions 1,035-1,036 according to SEQ ID NO:32, or an AG dinucleotide at positions corresponding to positions 1,035-1,036 according to SEQ ID NO:40, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises the nucleotide sequence of the KLHDC7B mRNA molecule in the biological sample, wherein the sequenced portion comprises positions corresponding to positions 2,865-2,866 according to SEQ ID NO:33, or the complement thereof; and/or the nucleotide sequence of the KLHDC7B cDNA molecule produced from the mRNA in the biological sample, wherein the sequenced portion comprises positions corresponding to positions 2,865-2,866 according to SEQ ID NO:41, or the complement thereof. When the sequenced portion of the KLHDC7B nucleic acid molecule in the biological sample comprises an AG dinucleotide at positions corresponding to positions 2,865-2,866 according to SEQ ID NO:33, or an AG dinucleotide at positions corresponding to positions 2,865-2,866 according to SEQ ID NO:41, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises the nucleotide sequence of the KLHDC7B mRNA molecule in the biological sample, wherein the sequenced portion comprises positions corresponding to positions 1,035-1,036 according to SEQ ID NO:34, or the complement thereof; and/or the nucleotide sequence of the KLHDC7B cDNA molecule produced from the mRNA in the biological sample, wherein the sequenced portion comprises positions corresponding to positions 1,035-1,036 according to SEQ ID NO:42, or the complement thereof. When the sequenced portion of the KLHDC7B nucleic acid molecule in the biological sample comprises an AG dinucleotide at positions corresponding to positions 1,035-1,036 according to SEQ ID NO:34, or an AG dinucleotide at positions corresponding to positions 1,035-1,036 according to SEQ ID NO:42, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of the nucleotide sequence of the KLHDC7B genomic nucleic acid molecule in the biological sample, wherein the sequenced portion comprises: a position corresponding to position 3,778 according to SEQ ID NO:2, or the complement thereof; positions corresponding to positions 2,806-2,807 according to SEQ ID NO:25, or the complement thereof; or positions corresponding to positions 3,169-3,170 according to SEQ ID NO:26, or the complement thereof. When the sequenced portion of the KLHDC7B nucleic acid molecule in the biological sample comprises: an adenine at a position corresponding to position 3,778 according to SEQ ID NO:2, a CG dinucleotide at positions corresponding to positions 2,806-2,807 according to SEQ ID NO:25, or an AG dinucleotide at positions corresponding to positions 3,169-3,170 according to SEQ ID NO:26, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of the nucleotide sequence of the KLHDC7B mRNA molecule in the biological sample, wherein the sequenced portion comprises: a position corresponding to position 3,778 according to SEQ ID NO:7, or the complement thereof; a position corresponding to position 1,644 according to SEQ ID NO:8, or the complement thereof; a position corresponding to position 3,474 according to SEQ ID NO:9, or the complement thereof; a position corresponding to position 1,644 according to SEQ ID NO:10, or the complement thereof; positions corresponding to positions 2,806-2,807 according to SEQ ID NO:27, or the complement thereof; positions corresponding to positions 672-673 according to SEQ ID NO:28, or the complement thereof; positions corresponding to positions 2,502-2,503 according to SEQ ID NO:29, or the complement thereof; positions corresponding to positions 672-673 according to SEQ ID NO:30, or the complement thereof; positions corresponding to positions 3,169-3,170 according to SEQ ID NO:31, or the complement thereof; positions corresponding to positions 1,035-1,036 according to SEQ ID NO:32, or the complement thereof; positions corresponding to positions 2,865-2,866 according to SEQ ID NO:33, or the complement thereof; or positions corresponding to positions 1,035-1,036 according to SEQ ID NO:34, or the complement thereof. When the sequenced portion of the KLHDC7B nucleic acid molecule in the biological sample comprises: an adenine at a position corresponding to position 3,778 according to SEQ ID NO:7, an adenine at a position corresponding to position 1,644 according to SEQ ID NO:8, an adenine at a position corresponding to position 3,474 according to SEQ ID NO:9, an adenine at a position corresponding to position 1,644 according to SEQ ID NO:10, a CG dinucleotide at positions corresponding to positions 2,806-2,807 to SEQ ID NO:27, a CG dinucleotide at positions corresponding to positions 672-673 according to SEQ ID NO:28, a CG dinucleotide at positions corresponding to positions 2,502-2,503 according to SEQ ID NO:29, a CG dinucleotide at positions corresponding to positions 672-673 according to SEQ ID NO:30, an AG dinucleotide at positions corresponding to positions 3,169-3,170 according to SEQ ID NO:31, an AG dinucleotide at positions corresponding to positions 1,035-1,036 according to SEQ ID NO:32, an AG dinucleotide at positions corresponding to positions 2,865-2,866 according to SEQ ID NO:33, or an AG dinucleotide at positions corresponding to positions 1,035-1,036 according to SEQ ID NO:34, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of the nucleotide sequence of the KLHDC7B cDNA molecule in the biological sample, wherein the sequenced portion comprises: a position corresponding to position 3,778 according to SEQ ID NO:15, or the complement thereof; a position corresponding to position 1,644 according to SEQ ID NO:16, or the complement thereof; a position corresponding to position 3,474 according to SEQ ID NO:17, or the complement thereof; a position corresponding to position 1,644 according to SEQ ID NO:18, or the complement thereof; positions corresponding to positions 2,806-2,807 according to SEQ ID NO:35, or the complement thereof; positions corresponding to positions 672-673 according to SEQ ID NO:36, or the complement thereof; positions corresponding to positions 2,502-2,503 according to SEQ ID NO:37, or the complement thereof; positions corresponding to positions 672-673 according to SEQ ID NO:38, or the complement thereof; positions corresponding to positions 3,169-3,170 according to SEQ ID NO:39, or the complement thereof; positions corresponding to positions 1,035-1,036 according to SEQ ID NO:40, or the complement thereof; positions corresponding to positions 2,865-2,866 according to SEQ ID NO:41, or the complement thereof; or positions corresponding to positions 1,035-1,036 according to SEQ ID NO:42, or the complement thereof. When the sequenced portion of the KLHDC7B nucleic acid molecule in the biological sample comprises: an adenine at a position corresponding to position 3,778 according to SEQ ID NO:15, an adenine at a position corresponding to position 1,644 according to SEQ ID NO:16, an adenine at a position corresponding to position 3,474 according to SEQ ID NO:17, an adenine at a position corresponding to position 1,644 according to SEQ ID NO:18, a CG dinucleotide at positions corresponding to positions 2,806-2,807 to SEQ ID NO:35, a CG dinucleotide at positions corresponding to positions 672-673 according to SEQ ID NO:36, a CG dinucleotide at positions corresponding to positions 2,502-2,503 according to SEQ ID NO:37, a CG dinucleotide at positions corresponding to positions 672-673 according to SEQ ID NO:38, an AG dinucleotide at positions corresponding to positions 3,169-3,170 according to SEQ ID NO:39, an AG dinucleotide at positions corresponding to positions 1,035-1,036 according to SEQ ID NO:40, an AG dinucleotide at positions corresponding to positions 2,865-2,866 according to SEQ ID NO:41, or an AG dinucleotide at positions corresponding to positions 1,035-1,036 according to SEQ ID NO:42, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises: a) contacting the biological sample with a primer hybridizing to a portion of the nucleotide sequence of the KLHDC7B: genomic nucleic acid molecule that is proximate to a position corresponding to position 3,778 according to SEQ ID NO:2; mRNA molecule that is proximate to a position corresponding to position 3,778 according to SEQ ID NO:7; and/or cDNA molecule that is proximate to a position corresponding to position 3,778 according to SEQ ID NO:15; b) extending the primer at least through the position of the nucleotide sequence of the KLHDC7B: genomic nucleic acid molecule corresponding to position 3,778 according to SEQ ID NO:2; mRNA molecule corresponding to position 3,778 according to SEQ ID NO:7; and/or cDNA molecule corresponding to position 3,778 according to SEQ ID NO:15; and c) determining whether the extension product of the primer comprises an adenine at a position corresponding to position 3,778 according to SEQ ID NO:2, an adenine at a position corresponding to position 3,778 according to SEQ ID NO:7, and/or an adenine at a position corresponding to position 3,778 according to SEQ ID NO:15.

In some embodiments, the determining step, detecting step, or sequence analysis comprises: a) contacting the biological sample with a primer hybridizing to a portion of the nucleotide sequence of the KLHDC7B mRNA molecule that is proximate to a position corresponding to position 1,644 according to SEQ ID NO:8, and/or cDNA molecule that is proximate to a position corresponding to position 1,644 according to SEQ ID NO:16; b) extending the primer at least through the position of the nucleotide sequence of the KLHDC7B mRNA molecule corresponding to position 1,644 according to SEQ ID NO:8, and/or cDNA molecule corresponding to position 1,644 according to SEQ ID NO:16; and c) determining whether the extension product of the primer comprises an adenine at a position corresponding to position 1,644 according to SEQ ID NO:8, and/or an adenine at a position corresponding to position 1,644 according to SEQ ID NO:16.

In some embodiments, the determining step, detecting step, or sequence analysis comprises: a) contacting the biological sample with a primer hybridizing to a portion of the nucleotide sequence of the KLHDC7B mRNA molecule that is proximate to a position corresponding to position 3,474 according to SEQ ID NO:9, and/or cDNA molecule that is proximate to a position corresponding to position 3,474 according to SEQ ID NO:17; b) extending the primer at least through the position of the nucleotide sequence of the KLHDC7B mRNA molecule corresponding to position 3,474 according to SEQ ID NO:9, and/or cDNA molecule corresponding to position 3,474 according to SEQ ID NO:17; and c) determining whether the extension product of the primer comprises an adenine at a position corresponding to position 3,474 according to SEQ ID NO:9, and/or an adenine at a position corresponding to position 3,474 according to SEQ ID NO:17.

In some embodiments, the determining step, detecting step, or sequence analysis comprises: a) contacting the biological sample with a primer hybridizing to a portion of the nucleotide sequence of the KLHDC7B mRNA molecule that is proximate to a position corresponding to position 1,644 according to SEQ ID NO:10, and/or cDNA molecule that is proximate to a position corresponding to position 1,644 according to SEQ ID NO:18; b) extending the primer at least through the position of the nucleotide sequence of the KLHDC7B mRNA molecule corresponding to position 1,644 according to SEQ ID NO:10, and/or cDNA molecule corresponding to position 1,644 according to SEQ ID NO:18; and c) determining whether the extension product of the primer comprises an adenine at a position corresponding to position 1,644 according to SEQ ID NO:10, and/or an adenine at a position corresponding to position 1,644 according to SEQ ID NO:18.

In some embodiments, the determining step, detecting step, or sequence analysis comprises: a) contacting the biological sample with a primer hybridizing to a portion of the nucleotide sequence of the KLHDC7B: genomic nucleic acid molecule that is proximate to positions corresponding to positions 2,806-2,807 according to SEQ ID NO:25; mRNA molecule that is proximate to positions corresponding to positions 2,806-2,807 according to SEQ ID NO:27; and/or cDNA molecule that is proximate to positions corresponding to positions 2,806-2,807 according to SEQ ID NO:35; b) extending the primer at least through the position of the nucleotide sequence of the KLHDC7B: genomic nucleic acid molecule that is proximate to positions corresponding to positions 2,806-2,807 according to SEQ ID NO:25; mRNA molecule that is proximate to positions corresponding to positions 2,806-2,807 according to SEQ ID NO:27; and/or cDNA molecule that is proximate to positions corresponding to positions 2,806-2,807 according to SEQ ID NO:35; and c) determining whether the extension product of the primer comprises a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 672-673 according to SEQ ID NO:28; and/or cDNA molecule that is proximate to positions corresponding to positions 672-673 according to SEQ ID NO:36; b) extending the primer at least through the position of the nucleotide sequence of the KLHDC7B: mRNA molecule that is proximate to positions corresponding to positions 672-673 according to SEQ ID NO:28; and/or cDNA molecule that is proximate to positions corresponding to positions 672-673 according to SEQ ID NO:36; and c) determining whether the extension product of the primer comprises a CG dinucleotide at positions corresponding to positions 672-673 according to SEQ ID NO:28, or a CG dinucleotide at positions corresponding to positions 672-673 according to SEQ ID NO:36.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 2,502-2,503 according to SEQ ID NO:29; and/or cDNA molecule that is proximate to positions corresponding to positions 2,502-2,503 according to SEQ ID NO:37; b) extending the primer at least through the position of the nucleotide sequence of the KLHDC7B: mRNA molecule that is proximate to positions corresponding to positions 2,502-2,503 according to SEQ ID NO:29; and/or cDNA molecule that is proximate to positions corresponding to positions 2,502-2,503 according to SEQ ID NO:37; and c) determining whether the extension product of the primer comprises a CG dinucleotide at positions corresponding to positions 2,502-2,503 according to SEQ ID NO:29, or a CG dinucleotide at positions corresponding to positions 2,502-2,503 according to SEQ ID NO:37.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 672-673 according to SEQ ID NO:30; and/or cDNA molecule that is proximate to positions corresponding to positions 672-673 according to SEQ ID NO:38; b) extending the primer at least through the position of the nucleotide sequence of the KLHDC7B: mRNA molecule that is proximate to positions corresponding to positions 672-673 according to SEQ ID NO:30; and/or cDNA molecule that is proximate to positions corresponding to positions 672-673 according to SEQ ID NO:38; and c) determining whether the extension product of the primer comprises a CG dinucleotide at positions corresponding to positions 672-673 according to SEQ ID NO:30, or a CG dinucleotide at positions corresponding to positions 672-673 according to SEQ ID NO:38.

In some embodiments, the determining step, detecting step, or sequence analysis comprises: a) contacting the biological sample with a primer hybridizing to a portion of the nucleotide sequence of the KLHDC7B: genomic nucleic acid molecule that is proximate to positions corresponding to positions 3,169-3,170 according to SEQ ID NO:26; mRNA molecule that is proximate to positions corresponding to positions 3,169-3,170 according to SEQ ID NO:31; and/or cDNA molecule that is proximate to positions corresponding to positions 3,169-3,170 according to SEQ ID NO:39; b) extending the primer at least through the position of the nucleotide sequence of the KLHDC7B: genomic nucleic acid molecule that is proximate to positions corresponding to positions 3,169-3,170 according to SEQ ID NO:26; mRNA molecule that is proximate to positions corresponding to positions 3,169-3,170 according to SEQ ID NO:31; and/or cDNA molecule that is proximate to positions corresponding to positions 3,169-3,170 according to SEQ ID NO:39; and c) determining whether the extension product of the primer comprises: an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 1,035-1,036 according to SEQ ID NO:32; and/or cDNA molecule that is proximate to positions corresponding to positions 1,035-1,036 according to SEQ ID NO:40; b) extending the primer at least through the position of the nucleotide sequence of the KLHDC7B: mRNA molecule that is proximate to positions corresponding to positions 1,035-1,036 according to SEQ ID NO:32; and/or cDNA molecule that is proximate to positions corresponding to positions 1,035-1,036 according to SEQ ID NO:40; and c) determining whether the extension product of the primer comprises an AG dinucleotide at positions corresponding to positions 1,035-1,036 according to SEQ ID NO:32, or an AG dinucleotide at positions corresponding to positions 1,035-1,036 according to SEQ ID NO:40.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 2,865-2,866 according to SEQ ID NO:33; and/or cDNA molecule that is proximate to positions corresponding to positions 2,865-2,866 according to SEQ ID NO:41; b)

extending the primer at least through the position of the nucleotide sequence of the KLHDC7B: mRNA molecule that is proximate to positions corresponding to positions 2,865-2,866 according to SEQ ID NO:33; and/or cDNA molecule that is proximate to positions corresponding to positions 2,865-2,866 according to SEQ ID NO:41; and c) determining whether the extension product of the primer comprises an AG dinucleotide at positions corresponding to positions 2,865-2,866 according to SEQ ID NO:33, or an AG dinucleotide at positions corresponding to positions 2,865-2,866 according to SEQ ID NO:41.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 1,035-1,036 according to SEQ ID NO:34; and/or cDNA molecule that is proximate to positions corresponding to positions 1,035-1,036 according to SEQ ID NO:42; b) extending the primer at least through the position of the nucleotide sequence of the KLHDC7B: mRNA molecule that is proximate to positions corresponding to positions 1,035-1,036 according to SEQ ID NO:34; and/or cDNA molecule that is proximate to positions corresponding to positions 1,035-1,036 according to SEQ ID NO:42; and c) determining whether the extension product of the primer comprises an AG dinucleotide at positions corresponding to positions 1,035-1,036 according to SEQ ID NO:34, or an AG dinucleotide at positions corresponding to positions 1,035-1,036 according to SEQ ID NO:42.

In some embodiments, the determining step, detecting step, or sequence analysis comprises: a) contacting the biological sample with a primer hybridizing to a portion of the nucleotide sequence of the KLHDC7B genomic nucleic acid molecule that is proximate to a position corresponding to position 3,778 according to SEQ ID NO:2, positions corresponding to positions 2,806-2,807 according to SEQ ID NO:25, or positions corresponding to positions 3,169-3,170 according to SEQ ID NO:26; b) extending the primer at least through the position of the nucleotide sequence of the KLHDC7B genomic nucleic acid molecule corresponding to position 3,778 according to SEQ ID NO:2, positions corresponding to positions 2,806-2,807 according to SEQ ID NO:25, or positions corresponding to positions 3,169-3,170 according to SEQ ID NO:26; and c) determining whether the extension product of the primer comprises: an adenine at a position corresponding to position 3,778 according to SEQ ID NO:2, a CG dinucleotide at positions corresponding to positions 2,806-2,807 according to SEQ ID NO:25, or an AG dinucleotide at positions corresponding to positions 3,169-3,170 according to SEQ ID NO:26.

In some embodiments, the determining step, detecting step, or sequence analysis comprises: a) contacting the biological sample with a primer hybridizing to a portion of the nucleotide sequence of the KLHDC7B mRNA molecule that is proximate to: a position corresponding to position 3,778 according to SEQ ID NO:7, a position corresponding to position 1,644 according to SEQ ID NO:8, a position corresponding to position 3,474 according to SEQ ID NO:9, a position corresponding to position 1,644 according to SEQ ID NO:10, positions corresponding to positions 2,806-2,807 according to SEQ ID NO:27, positions corresponding to positions 672-673 according to SEQ ID NO:28, positions corresponding to positions 2,502-2,503 according to SEQ ID NO:29, positions corresponding to positions 672-673 according to SEQ ID NO:30, positions corresponding to positions 3,169-3,170 according to SEQ ID NO:31, positions corresponding to positions 1,035-1,036 according to SEQ ID NO:32, positions corresponding to positions 2,865-2,866 according to SEQ ID NO:33, or positions corresponding to positions 1,035-1,036 according to SEQ ID NO:34; b) extending the primer at least through the position of the nucleotide sequence of the KLHDC7B mRNA molecule corresponding to: position 3,778 according to SEQ ID NO:7, position 1,644 according to SEQ ID NO:8, position 3,474 according to SEQ ID NO:9, position 1,644 according to SEQ ID NO:10, positions 2,806-2,807 according to SEQ ID NO:27, positions 672-673 according to SEQ ID NO:28, positions 2,502-2,503 according to SEQ ID NO:29, positions 672-673 according to SEQ ID NO:30, positions 3,169-3,170 according to SEQ ID NO:31, positions 1,035-1,036 according to SEQ ID NO:32, positions 2,865-2,866 according to SEQ ID NO:33, or positions 1,035-1,036 according to SEQ ID NO:34; and c) determining whether the extension product of the primer comprises: an adenine at a position corresponding to position 3,778 according to SEQ ID NO:7, an adenine at a position corresponding to position 1,644 according to SEQ ID NO:8, an adenine at a position corresponding to position 3,474 according to SEQ ID NO:9, an adenine at a position corresponding to position 1,644 according to SEQ ID NO:10, a CG dinucleotide at positions corresponding to positions 2,806-2,807 to SEQ ID NO:27, a CG dinucleotide at positions corresponding to positions 672-673 according to SEQ ID NO:28, a CG dinucleotide at positions corresponding to positions 2,502-2,503 according to SEQ ID NO:29, a CG dinucleotide at positions corresponding to positions 672-673 according to SEQ ID NO:30, an AG dinucleotide at positions corresponding to positions 3,169-3,170 according to SEQ ID NO:31, an AG dinucleotide at positions corresponding to positions 1,035-1,036 according to SEQ ID NO:32, an AG dinucleotide at positions corresponding to positions 2,865-2,866 according to SEQ ID NO:33, or an AG dinucleotide at positions corresponding to positions 1,035-1,036 according to SEQ ID NO:34.

In some embodiments, the determining step, detecting step, or sequence analysis comprises: a) contacting the biological sample with a primer hybridizing to a portion of the nucleotide sequence of the KLHDC7B cDNA molecule that is proximate to: a position corresponding to position 3,778 according to SEQ ID NO:15, a position corresponding to position 1,644 according to SEQ ID NO:16, a position corresponding to position 3,474 according to SEQ ID NO:17, a position corresponding to position 1,644 according to SEQ ID NO:18, positions corresponding to positions 2,806-2,807 according to SEQ ID NO:35, positions corresponding to positions 672-673 according to SEQ ID NO:36, positions corresponding to positions 2,502-2,503 according to SEQ ID NO:37, positions corresponding to positions 672-673 according to SEQ ID NO:38, positions corresponding to positions 3,169-3,170 according to SEQ ID NO:39, positions corresponding to positions 1,035-1,036 according to SEQ ID NO:40, positions corresponding to positions 2,865-2,866 according to SEQ ID NO:41, or positions corresponding to positions 1,035-1,036 according to SEQ ID NO:42; b) extending the primer at least through the position of the nucleotide sequence of the KLHDC7B cDNA molecule corresponding to: position 3,778 according to SEQ ID NO:15, position 1,644 according to SEQ ID NO:16, position 3,474 according to SEQ ID NO:17, position 1,644 according to SEQ ID NO:18, positions 2,806-2,807 according to SEQ ID NO:35, positions 672-673 according to SEQ ID NO:36, positions 2,502-2,503 according to SEQ ID NO:37, positions 672-673 according to SEQ ID NO:38, positions 3,169-3,170 according to SEQ ID NO:39, positions 1,035-1,036 according to SEQ ID NO:40, positions 2,865-2,866 according to SEQ ID NO:41, or positions 1,035-1,036 according to SEQ ID NO:42; and c) determining whether the extension product of the primer comprises: an adenine at a position corresponding to position 3,778 according to SEQ ID NO:15, an adenine at a position corresponding to position 1,644 according to SEQ ID NO:16, an adenine at a position corresponding to position 3,474 according to SEQ ID NO:17, an adenine at a position corresponding to position 1,644 according to SEQ ID NO:18, a CG dinucleotide at positions corresponding to positions 2,806-2,807 to SEQ ID NO:35, a CG dinucleotide at positions corresponding to positions 672-673 according to SEQ ID NO:36, a CG dinucleotide at positions corresponding to positions 2,502-2,503 according to SEQ ID NO:37, a CG dinucleotide at positions corresponding to positions 672-673 according to SEQ ID NO:38, an AG dinucleotide at positions corresponding to positions 3,169-3,170 according to SEQ ID NO:39, an AG dinucleotide at positions corresponding to positions 1,035-1,036 according to SEQ ID NO:40, an AG dinucleotide at positions corresponding to positions 2,865-2,866 according to SEQ ID NO:41, or an AG dinucleotide at positions corresponding to positions 1,035-1,036 according to SEQ ID NO:42.

In some embodiments, the assay comprises sequencing the entire nucleic acid molecule. In some embodiments, only a KLHDC7B genomic nucleic acid molecule is analyzed. In some embodiments, only a KLHDC7B mRNA is analyzed. In some embodiments, only a KLHDC7B cDNA obtained from KLHDC7B mRNA is analyzed.

In some embodiments, the determining step, detecting step, or sequence analysis comprises: a) amplifying at least a portion of the nucleic acid molecule that encodes the KLHDC7B polypeptide, wherein the amplified portion comprises: i) an adenine at a position corresponding to position 3,778 according to SEQ ID NO:2, or the complement thereof; ii) an adenine at a position corresponding to position 3,778 according to SEQ ID NO:7, or the complement thereof; and/or iii) an adenine at a position corresponding to position 3,778 according to SEQ ID NO:15, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an adenine at a position corresponding to position 3,778 according to SEQ ID NO:2, or the complement thereof; ii) an adenine at a position corresponding to position 3,778 according to SEQ ID NO:7, or the complement thereof; and/or iii) an adenine at a position corresponding to position 3,778 according to SEQ ID NO:15, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 1,644 according to SEQ ID NO:8, or the complement thereof; and/or an adenine at a position corresponding to position 1,644 according to SEQ ID NO:16, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 1,644 according to SEQ ID NO:8, or the complement thereof; and/or an adenine at a position corresponding to position 1,644 according to SEQ ID NO:16, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,474 according to SEQ ID NO:9, or the complement thereof; and/or an adenine at a position corresponding to position 3,474 according to SEQ ID NO:17, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,474 according to SEQ ID NO:9, or the complement thereof; and/or an adenine at a position corresponding to position 3,474 according to SEQ ID NO:17, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 1,644 according to SEQ ID NO:10, or the complement thereof; and/an adenine at a position corresponding to position 1,644 according to SEQ ID NO:18, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 1,644 according to SEQ ID NO:10, or the complement thereof; and/an adenine at a position corresponding to position 1,644 according to SEQ ID NO:18, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 2,806-2,807 according to SEQ ID NO:25, or the complement thereof; ii) a CG dinucleotide at positions corresponding to positions 2,806-2,807 to SEQ ID NO:27, or the complement thereof; and/or iii) a CG dinucleotide at positions corresponding to positions 2,806-2,807 to SEQ ID NO:35, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 2,806-2,807 according to SEQ ID NO:25, or the complement thereof; ii) a CG dinucleotide at positions corresponding to positions 2,806-2,807 to SEQ ID NO:27, or the complement thereof; and/or iii) a CG dinucleotide at positions corresponding to positions 2,806-2,807 to SEQ ID NO:35; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 672-673 according to SEQ ID NO:28, or the complement thereof; and/or ii) a CG dinucleotide at positions corresponding to positions 672-673 according to SEQ ID NO:36, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 672-673 according to SEQ ID NO:28, or the complement thereof; and/or ii) a CG dinucleotide at positions corresponding to positions 672-673 according to SEQ ID NO:36; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 2,502-2,503 according to SEQ ID NO:29, or the complement thereof; and/or ii) a CG dinucleotide at positions corresponding to positions 2,502-2,503 according to SEQ ID NO:37, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 2,502-2,503 according to SEQ ID NO:29, or the complement thereof; and/or ii) a CG dinucleotide at positions corresponding to positions 2,502-2,503 according to SEQ ID NO:37; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 672-673 according to SEQ ID NO:30, or the complement thereof; and/or ii) a CG dinucleotide at positions corresponding to positions 672-673 according to SEQ ID NO:38, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 672-673 according to SEQ ID NO:30, or the complement thereof; and/or ii) a CG dinucleotide at positions corresponding to positions 672-673 according to SEQ ID NO:38; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 3,169-3,170 according to SEQ ID NO:26, or the complement thereof; ii) an AG dinucleotide at positions corresponding to positions 3,169-3,170 according to SEQ ID NO:31, or the complement thereof; and/or iii) an AG dinucleotide at positions corresponding to positions 3,169-3,170 according to SEQ ID NO:39, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 3,169-3,170 according to SEQ ID NO:26, or the complement thereof; ii) an AG dinucleotide at positions corresponding to positions 3,169-3,170 according to SEQ ID NO:31, or the complement thereof; and/or iii) an AG dinucleotide at positions corresponding to positions 3,169-3,170 according to SEQ ID NO:39; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 1,035-1,036 according to SEQ ID NO:32, or the complement thereof; and/or ii) an AG dinucleotide at positions corresponding to positions 1,035-1,036 according to SEQ ID NO:40, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 1,035-1,036 according to SEQ ID NO:32, or the complement thereof; and/or ii) an AG dinucleotide at positions corresponding to positions 1,035-1,036 according to SEQ ID NO:40; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 2,865-2,866 according to SEQ ID NO:33, or the complement thereof; and/or ii) an AG dinucleotide at positions corresponding to positions 2,865-2,866 according to SEQ ID NO:41, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 2,865-2,866 according to SEQ ID NO:33, or the complement thereof; and/or ii) an AG dinucleotide at positions corresponding to positions 2,865-2,866 according to SEQ ID NO:41; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 1,035-1,036 according to SEQ ID NO:34, or the complement thereof; and/or ii) an AG dinucleotide at positions corresponding to positions 1,035-1,036 according to SEQ ID NO:42, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 1,035-1,036 according to SEQ ID NO:34, or the complement thereof; and/or ii) an AG dinucleotide at positions corresponding to positions 1,035-1,036 according to SEQ ID NO:42; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,778 according to SEQ ID NO:2, or the complement thereof; a CG dinucleotide at positions corresponding to positions 2,806-2,807 according to SEQ ID NO:25, or the complement thereof; or an AG dinucleotide at positions corresponding to positions 3,169-3,170 according to SEQ ID NO:26, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,778 according to SEQ ID NO:2, or the complement thereof; a CG dinucleotide at positions corresponding to positions 2,806-2,807 according to SEQ ID NO:25, or the complement thereof; or an AG dinucleotide at positions corresponding to positions 3,169-3,170 according to SEQ ID NO:26, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 according to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 according to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof; b) labeling the amplified nucleic acid molecule with a detectable label; c)

contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:2, or the complement thereof; an adenine at a position corresponding to position 3,778 according to SEQ ID NO:7, or the complement thereof; and/or an adenine at a position corresponding to position 3,778 according to SEQ ID NO:15, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 1,644 according to SEQ ID NO:8, or the complement thereof, and/or an adenine at a position corresponding to position 1,644 according to SEQ ID NO:16, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,474 according to SEQ ID NO:9, or the complement thereof, and/or an adenine at a position corresponding to position 3,474 according to SEQ ID NO:17, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 1,644 according to SEQ ID NO:10, or the complement thereof, and/or an adenine at a position corresponding to position 1,644 according to SEQ ID NO:18, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 2,806-2,807 according to SEQ ID NO:25, or the complement thereof; a CG dinucleotide at positions corresponding to positions 2,806-2,807 to SEQ ID NO:27, or the complement thereof; or a CG dinucleotide at positions corresponding to positions 2,806-2,807 to SEQ ID NO:35, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 672-673 according to SEQ ID NO:28, or the complement thereof; or a CG dinucleotide at positions corresponding to positions 672-673 according to SEQ ID NO:36, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 2,502-2,503 according to SEQ ID NO:29, or the complement thereof; or a CG dinucleotide at positions corresponding to positions 2,502-2,503 according to SEQ ID NO:37, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 672-673 according to SEQ ID NO:30, or the complement thereof; or a CG dinucleotide at positions corresponding to positions 672-673 according to SEQ ID NO:38, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 3,169-3,170 according to SEQ ID NO:26, or the complement thereof; an AG dinucleotide at positions corresponding to positions 3,169-3,170 according to SEQ ID NO:31, or the complement thereof; or an AG dinucleotide at positions corresponding to positions 3,169-3,170 according to SEQ ID NO:39, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 1,035-1,036 according to SEQ ID NO:32, or the complement thereof; or an AG dinucleotide at positions corresponding to positions 1,035-1,036 according to SEQ ID NO:40, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 2,865-2,866 according to SEQ ID NO:33, or the complement thereof; or an AG dinucleotide at positions corresponding to positions 2,865-2,866 according to SEQ ID NO:41, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 1,035-1,036 according to SEQ ID NO:34, or the complement thereof; or an AG dinucleotide at positions corresponding to positions 1,035-1,036 according to SEQ ID NO:42, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:2, or the complement thereof; a CG dinucleotide at positions corresponding to positions 2,806-2,807 according to SEQ ID NO:25, or the complement thereof; or an AG dinucleotide at positions corresponding to positions 3,169-3,170 according to SEQ ID NO:26, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a KLHDC7B variant genomic sequence, variant mRNA sequence, or variant cDNA sequence and not the corresponding KLHDC7B reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a KLHDC7B variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 3,778 according to SEQ ID NO:2 (genomic nucleic acid molecule), an adenine at a position corresponding to position 3,778 according to SEQ ID NO:7 (mRNA molecule), or an adenine at a position corresponding to position 3,778 according to SEQ ID NO:15 (cDNA molecule), the biological sample can be subjected to an amplification method using a primer pair that includes a first primer derived from the 5' flanking sequence adjacent to an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15, and a second primer derived from the 3' flanking sequence adjacent to an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15 to produce an amplicon that is indicative of the presence of the SNP at positions encoding an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15, and at least 1, 2, 3, 4, 5, 6, 7, 8, 9, 10, or more nucleotides on each side of positions comprising an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 1,644 according to SEQ ID NO:8 (mRNA molecule), or an adenine at a position corresponding to position 1,644 according to SEQ ID NO:16 (cDNA molecule), the biological sample can be subjected to an amplification method using a primer pair that includes a first primer derived from the 5' flanking sequence adjacent to an adenine at a position corresponding to position 1,644 according to SEQ ID NO:8, or an adenine at a position corresponding to position 1,644 according to SEQ ID NO:16, and a second primer derived from the 3' flanking sequence adjacent to an adenine at a position corresponding to position 1,644 according to SEQ ID NO:8, or an adenine at a position corresponding to position 1,644 according to SEQ ID NO:16 to produce an amplicon that is indicative of the presence of the SNP at positions encoding an adenine at a position corresponding to position 1,644 according to SEQ ID NO:8, or an adenine at a position corresponding to position 1,644 according to SEQ ID NO:16. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 1,644 according to SEQ ID NO:8, or an adenine at a position corresponding to position 1,644 according to SEQ ID NO:16, and at least 1, 2, 3, 4, 5, 6, 7, 8, 9, 10, or more nucleotides on each side of positions comprising an adenine at a position corresponding to position 1,644 according to SEQ ID NO:8, or an adenine at a position corresponding to position 1,644 according to SEQ ID NO:16.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 3,474 according to SEQ ID NO:9 (mRNA molecule), or an adenine at a position corresponding to position 3,474 according to SEQ ID NO:17 (cDNA molecule), the biological sample can be subjected to an amplification method using a primer pair that includes a first primer derived from the 5' flanking sequence adjacent to an adenine at a position corresponding to position 3,474 according to SEQ ID NO:9, or an adenine at a position corresponding to position 3,474 according to SEQ ID NO:17, and a second primer derived from the 3' flanking sequence adjacent to an adenine at a position corresponding to position 3,474 according to SEQ ID NO:9, or an adenine at a position corresponding to position 3,474 according to SEQ ID NO:17 to produce an amplicon that is indicative of the presence of the SNP at positions encoding an adenine at a position corresponding to position 3,474 according to SEQ ID NO:9, or an adenine at a position corresponding to position 3,474 according to SEQ ID NO:17. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 3,474 according to SEQ ID NO:9, or an adenine at a position corresponding to position 3,474 according to SEQ ID NO:17, and at least 1, 2, 3, 4, 5, 6, 7, 8, 9, 10, or more nucleotides on each side of positions comprising an adenine at a position corresponding to position 3,474 according to SEQ ID NO:9, or an adenine at a position corresponding to position 3,474 according to SEQ ID NO:17.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 1,644 according to SEQ ID NO:10 (mRNA molecule), or an adenine at a position corresponding to position 1,644 according to SEQ ID NO:18 (cDNA molecule), the biological sample can be subjected to an amplification method using a primer pair that includes a first primer derived from the 5' flanking sequence adjacent to an adenine at a position corresponding to position 1,644 according to SEQ ID NO:10, or an adenine at a position corresponding to position 1,644 according to SEQ ID NO:18, and a second primer derived from the 3' flanking sequence adjacent to an adenine at a position corresponding to position 1,644 according to SEQ ID NO:10, or an adenine at a position corresponding to position 1,644 according to SEQ ID NO:18 to produce an amplicon that is indicative of the presence of the SNP at positions encoding an adenine at a position corresponding to position 1,644 according to SEQ ID NO:10, or an adenine at a position corresponding to position 1,644 according to SEQ ID NO:18. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 1,644 according to SEQ ID NO:10, or an adenine at a position corresponding to position 1,644 according to SEQ ID NO:18, and at least 1, 2, 3, 4, 5, 6, 7, 8, 9, 10, or more nucleotides on each side of positions comprising an adenine at a position corresponding to position 1,644 according to SEQ ID NO:10, or an adenine at a position corresponding to position 1,644 according to SEQ ID NO:18.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 2,806-2,807 according to SEQ ID NO:25 (genomic nucleic acid molecule), a CG dinucleotide at positions corresponding to positions 2,806-2,807 to SEQ ID NO:27 (mRNA molecule), or a CG dinucleotide at positions corresponding to positions 2,806-2,807 to SEQ ID NO:35 (cDNA molecule), the biological sample can be subjected to an amplification method using a primer pair that includes a first primer derived from the 5' flanking sequence adjacent to a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35, and a second primer derived from the 3' flanking sequence adjacent to a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35 to produce an amplicon that is indicative of the presence of the SNP at positions encoding a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35, and at least 1, 2, 3, 4, 5, 6, 7, 8, 9, 10, or more nucleotides on each side of positions comprising a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 672-673 according to SEQ ID NO:28 (mRNA molecule), or a CG dinucleotide at positions corresponding to positions 672-673 according to SEQ ID NO:36 (cDNA molecule), the biological sample can be subjected to an amplification method using a primer pair that includes a first primer derived from the 5' flanking sequence adjacent to a CG dinucleotide at positions corresponding to positions 672-673 according to SEQ ID NO:28, or a CG dinucleotide at positions corresponding to positions 672-673 according to SEQ ID NO:36 and a second primer derived from the 3' flanking sequence adjacent to a CG dinucleotide at positions corresponding to positions 672-673 according to SEQ ID NO:28, or a CG dinucleotide at positions corresponding to positions 672-673 according to SEQ ID NO:36 to produce an amplicon that is indicative of the presence of the SNP at positions encoding a CG dinucleotide at positions corresponding to positions 672-673 according to SEQ ID NO:28, or a CG dinucleotide at positions corresponding to positions 672-673 according to SEQ ID NO:36. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 672-673 according to SEQ ID NO:28, or a CG dinucleotide at positions corresponding to positions 672-673 according to SEQ ID NO:36, and at least 1, 2, 3, 4, 5, 6, 7, 8, 9, 10, or more nucleotides on each side of positions comprising a CG dinucleotide at positions corresponding to positions 672-673 according to SEQ ID NO:28, or a CG dinucleotide at positions corresponding to positions 672-673 according to SEQ ID NO:36.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 2,502-2,503 according to SEQ ID NO:29 (mRNA molecule), or a CG dinucleotide at positions corresponding to positions 2,502-2,503 according to SEQ ID NO:37 (cDNA molecule), the biological sample can be subjected to an amplification method using a primer pair that includes a first primer derived from the 5' flanking sequence adjacent to a CG dinucleotide at positions corresponding to positions 2,502-2,503 according to SEQ ID NO:29, or a CG dinucleotide at positions corresponding to positions 2,502-2,503 according to SEQ ID NO:37 and a second primer derived from the 3' flanking sequence adjacent to a CG dinucleotide at positions corresponding to positions 2,502-2,503 according to SEQ ID NO:29, or a CG dinucleotide at positions corresponding to positions 2,502-2,503 according to SEQ ID NO:37 to produce an amplicon that is indicative of the presence of the SNP at positions encoding a CG dinucleotide at positions corresponding to positions 2,502-2,503 according to SEQ ID NO:29, or a CG dinucleotide at positions corresponding to positions 2,502-2,503 according to SEQ ID NO:37. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 2,502-2,503 according to SEQ ID NO:29, or a CG dinucleotide at positions corresponding to positions 2,502-2,503 according to SEQ ID NO:37, and at least 1, 2, 3, 4, 5, 6, 7, 8, 9, 10, or more nucleotides on each side of positions comprising a CG dinucleotide at positions corresponding to positions 2,502-2,503 according to SEQ ID NO:29, or a CG dinucleotide at positions corresponding to positions 2,502-2,503 according to SEQ ID NO:37.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 672-673 according to SEQ ID NO:30 (mRNA molecule), or a CG dinucleotide at positions corresponding to positions 672-673 according to SEQ ID NO:38 (cDNA molecule), the biological sample can be subjected to an amplification method using a primer pair that includes a first primer derived from the 5' flanking sequence adjacent to a CG dinucleotide at positions corresponding to positions 672-673 according to SEQ ID NO:30, or a CG dinucleotide at positions corresponding to positions 672-673 according to SEQ ID NO:38 and a second primer derived from the 3' flanking sequence adjacent to a CG dinucleotide at positions corresponding to positions 672-673 according to SEQ ID NO:30, or a CG dinucleotide at positions corresponding to positions 672-673 according to SEQ ID NO:38 to produce an amplicon that is indicative of the presence of the SNP at positions encoding a CG dinucleotide at positions corresponding to positions 672-673 according to SEQ ID NO:30, or a CG dinucleotide at positions corresponding to positions 672-673 according to SEQ ID NO:38. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 672-673 according to SEQ ID NO:30, or a CG dinucleotide at positions corresponding to positions 672-673 according to SEQ ID NO:38, and at least 1, 2, 3, 4, 5, 6, 7, 8, 9, 10, or more nucleotides on each side of positions comprising a CG dinucleotide at positions corresponding to positions 672-673 according to SEQ ID NO:30, or a CG dinucleotide at positions corresponding to positions 672-673 according to SEQ ID NO:38.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 3,169-3,170 according to SEQ ID NO:26 (genomic nucleic acid molecule), an AG dinucleotide at positions corresponding to positions 3,169-3,170 according to SEQ ID NO:31 (mRNA molecule), or an AG dinucleotide at positions corresponding to positions 3,169-3,170 according to SEQ ID NO:39 (cDNA molecule), the biological sample can be subjected to an amplification method using a primer pair that includes a first primer derived from the 5' flanking sequence adjacent to an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39, and a second primer derived from the 3' flanking sequence adjacent to an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39 to produce an amplicon that is indicative of the presence of the SNP at positions encoding an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39, and at least 1, 2, 3, 4, 5, 6, 7, 8, 9, 10, or more nucleotides on each side of positions comprising an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 1,035-1,036 according to SEQ ID NO:32 (mRNA molecule), or an AG dinucleotide at positions corresponding to positions 1,035-1,036 according to SEQ ID NO:40 (cDNA molecule), the biological sample can be subjected to an amplification method using a primer pair that includes a first primer derived from the 5' flanking sequence adjacent to an AG dinucleotide at positions corresponding to positions 1,035-1,036 according to SEQ ID NO:32, or an AG dinucleotide at positions corresponding to positions 1,035-1,036 according to SEQ ID NO:40 and a second primer derived from the 3' flanking sequence adjacent to an AG dinucleotide at positions corresponding to positions 1,035-1,036 according to SEQ ID NO:32, or an AG dinucleotide at positions corresponding to positions 1,035-1,036 according to SEQ ID NO:40 to produce an amplicon that is indicative of the presence of the SNP at positions encoding an AG dinucleotide at positions corresponding to positions 1,035-1,036 according to SEQ ID NO:32, or an AG dinucleotide at positions corresponding to positions 1,035-1,036 according to SEQ ID NO:40. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 1,035-1,036 according to SEQ ID NO:32, or an AG dinucleotide at positions corresponding to positions 1,035-1,036 according to SEQ ID NO:40, and at least 1, 2, 3, 4, 5, 6, 7, 8, 9, 10, or more nucleotides on each side of positions comprising an AG dinucleotide at positions corresponding to positions 1,035-1,036 according to SEQ ID NO:32, or an AG dinucleotide at positions corresponding to positions 1,035-1,036 according to SEQ ID NO:40.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 2,865-2,866 according to SEQ ID NO:33 (mRNA molecule), or an AG dinucleotide at positions corresponding to positions 2,865-2,866 according to SEQ ID NO:41 (cDNA molecule), the biological sample can be subjected to an amplification method using a primer pair that includes a first primer derived from the 5' flanking sequence adjacent to an AG dinucleotide at positions corresponding to positions 2,865-2,866 according to SEQ ID NO:33, or an AG dinucleotide at positions corresponding to positions 2,865-2,866 according to SEQ ID NO:41 and a second primer derived from the 3' flanking sequence adjacent to an AG dinucleotide at positions corresponding to positions 2,865-2,866 according to SEQ ID NO:33, or an AG dinucleotide at positions corresponding to positions 2,865-2,866 according to SEQ ID NO:41 to produce an amplicon that is indicative of the presence of the SNP at positions encoding an AG dinucleotide at positions corresponding to positions 2,865-2,866 according to SEQ ID NO:33, or an AG dinucleotide at positions corresponding to positions 2,865-2,866 according to SEQ ID NO:41. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 2,865-2,866 according to SEQ ID NO:33, or an AG dinucleotide at positions corresponding to positions 2,865-2,866 according to SEQ ID NO:41, and at least 1, 2, 3, 4, 5, 6, 7, 8, 9, 10, or more nucleotides on each side of positions comprising an AG dinucleotide at positions corresponding to positions 2,865-2,866 according to SEQ ID NO:33, or an AG dinucleotide at positions corresponding to positions 2,865-2,866 according to SEQ ID NO:41.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 1,035-1,036 according to SEQ ID NO:34 (mRNA molecule), or an AG dinucleotide at positions corresponding to positions 1,035-1,036 according to SEQ ID NO:42 (cDNA molecule), the biological sample can be subjected to an amplification method using a primer pair that includes a first primer derived from the 5' flanking sequence adjacent to an AG dinucleotide at positions corresponding to positions 1,035-1,036 according to SEQ ID NO:34, or an AG dinucleotide at positions corresponding to positions 1,035-1,036 according to SEQ ID NO:42 and a second primer derived from the 3' flanking sequence adjacent to an AG dinucleotide at positions corresponding to positions 1,035-1,036 according to SEQ ID NO:34, or an AG dinucleotide at positions corresponding to positions 1,035-1,036 according to SEQ ID NO:42 to produce an amplicon that is indicative of the presence of the SNP at positions encoding an AG dinucleotide at positions corresponding to positions 1,035-1,036 according to SEQ ID NO:34, or an AG dinucleotide at positions corresponding to positions 1,035-1,036 according to SEQ ID NO:42. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 1,035-1,036 according to SEQ ID NO:34, or an AG dinucleotide at positions corresponding to positions 1,035-1,036 according to SEQ ID NO:42, and at least 1, 2, 3, 4, 5, 6, 7, 8, 9, 10, or more nucleotides on each side of positions comprising an AG dinucleotide at positions corresponding to positions 1,035-1,036 according to SEQ ID NO:34, or an AG dinucleotide at positions corresponding to positions 1,035-1,036 according to SEQ ID NO:42.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a KLHDC7B predicted loss-of-function polypeptide comprising performing an assay on a sample obtained from a subject to determine whether a KLHDC7B polypeptide in the subject contains one or more variations that causes the polypeptide to have a loss-of-function (partial or complete) or predicted loss-of-function (partial or complete). The KLHDC7B predicted loss-of-function polypeptide can be any of the KLHDC7B truncated variant polypeptides described herein. In some embodiments, the methods detect the presence of KLHDC7B V1145M, V504M, V405M, K822fs, K181fs, K82fs, G943fs, G302fs, or G203fs. In some embodiments, the methods detect the presence of KLHDC7B V1145M. In some embodiments, the methods detect the presence of KLHDC7B V504M. In some embodiments, the methods detect the presence of KLHDC7B V405M. In some embodiments, the methods detect the presence of KLHDC7B K822fs. In some embodiments, the methods detect the presence of KLHDC7B K181fs. In some embodiments, the methods detect the presence of KLHDC7B K82fs. In some embodiments, the methods detect the presence of KLHDC7B G943fs. In some embodiments, the methods detect the presence of KLHDC7B G302fs. In some embodiments, the methods detect the presence of KLHDC7B G203fs.

In some embodiments, the methods comprise performing an assay on a sample obtained from a subject to determine whether a KLHDC7B polypeptide in the sample comprises a methionine at a position corresponding to position 1,145 according to SEQ ID NO:22. In some embodiments, the methods comprise performing an assay on a sample obtained from a subject to determine whether a KLHDC7B polypeptide in the sample comprises a methionine at a position corresponding to position 504 according to SEQ ID NO:23. In some embodiments, the methods comprise performing an assay on a sample obtained from a subject to determine whether a KLHDC7B polypeptide in the sample comprises a methionine at a position corresponding to position 405 according to SEQ ID NO:24.

In some embodiments, the methods comprise performing an assay on a sample obtained from a subject to determine whether the sample contains a KLHDC7B truncated variant polypeptide terminating at a position corresponding to position 885 according to SEQ ID NO:43. In some embodiments, the KLHDC7B truncated variant polypeptide lacks amino acids at positions corresponding to positions 886 to 1,235 of SEQ ID NO:19. In some embodiments, the KLHDC7B truncated variant polypeptide comprises or consists of SEQ ID NO:43.

In some embodiments, the methods comprise performing an assay on a sample obtained from a subject to determine whether the sample contains a KLHDC7B truncated variant polypeptide terminating at a position corresponding to position 244 according to SEQ ID NO:44. In some embodiments, the KLHDC7B truncated variant polypeptide lacks amino acids at positions corresponding to positions 245 to 594 of SEQ ID NO:20. In some embodiments, the KLHDC7B truncated variant polypeptide comprises or consists of SEQ ID NO:44.

In some embodiments, the methods comprise performing an assay on a sample obtained from a subject to determine whether the sample contains a KLHDC7B truncated variant polypeptide terminating at a position corresponding to position 145 according to SEQ ID NO:45. In some embodiments, the KLHDC7B truncated variant polypeptide lacks amino acids at positions corresponding to positions 146 to 495 of SEQ ID NO:21. In some embodiments, the KLHDC7B truncated variant polypeptide comprises or consists of SEQ ID NO:45.

In some embodiments, the methods comprise performing an assay on a sample obtained from a subject to determine whether the sample contains a KLHDC7B truncated variant polypeptide terminating at a position corresponding to position 975 according to SEQ ID NO:46. In some embodiments, the KLHDC7B truncated variant polypeptide lacks amino acids at positions corresponding to positions 976 to 1,235 of SEQ ID NO:19. In some embodiments, the KLHDC7B truncated variant polypeptide comprises or consists of SEQ ID NO:46.

In some embodiments, the methods comprise performing an assay on a sample obtained from a subject to determine whether the sample contains a KLHDC7B truncated variant polypeptide terminating at a position corresponding to position 334 according to SEQ ID NO:47. In some embodiments, the KLHDC7B truncated variant polypeptide lacks amino acids at positions corresponding to positions 335 to 594 of SEQ ID NO:20. In some embodiments, the KLHDC7B truncated variant polypeptide comprises or consists of SEQ ID NO:47.

In some embodiments, the methods comprise performing an assay on a sample obtained from a subject to determine whether the sample contains a KLHDC7B truncated variant polypeptide terminating at a position corresponding to position 235 according to SEQ ID NO:48. In some embodiments, the KLHDC7B truncated variant polypeptide lacks amino acids at positions corresponding to positions 236 to 495 of SEQ ID NO:21. In some embodiments, the KLHDC7B truncated variant polypeptide comprises or consists of SEQ ID NO:48.

In some embodiments, the detecting step comprises sequencing at least a portion of the polypeptide that comprises a position corresponding to position 1,145 according to SEQ ID NO:22 or SEQ ID NO:19. In some embodiments, the detecting step comprises sequencing at least a portion of the polypeptide that comprises a position corresponding to position 504 according to SEQ ID NO:23 or SEQ ID NO:20.

In some embodiments, the detecting step comprises sequencing at least a portion of the polypeptide that comprises a position corresponding to position 405 according to SEQ ID NO:24 or SEQ ID NO:21.

In some embodiments, the detecting step comprises sequencing at least a portion of a KLHDC7B polypeptide that may comprise positions corresponding to any positions that are C-terminal to position 885 according to SEQ ID NO:43. If amino acids are detected in the KLHDC7B polypeptide at positions corresponding to positions 886 to 1,235 according to SEQ ID NO:19, then such KLHDC7B polypeptide is a KLHDC7B reference polypeptide. An absence of positions 886 to 1,235 according to SEQ ID NO:19 in the KLHDC7B polypeptide indicates that the KLHDC7B polypeptide terminates at position 885 according to SEQ ID NO:43 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 244 according to SEQ ID NO:44. If amino acids are detected in the KLHDC7B polypeptide at positions corresponding to positions 245 to 594 according to SEQ ID NO:20, then such KLHDC7B polypeptide is a KLHDC7B reference polypeptide. An absence of positions 245 to 594 according to SEQ ID NO:20 in the KLHDC7B polypeptide indicates that the KLHDC7B polypeptide terminates at position 244 according to SEQ ID NO:44 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 145 according to SEQ ID NO:45. If amino acids are detected in the KLHDC7B polypeptide at positions corresponding to positions 146 to 495 according to SEQ ID NO:21, then such KLHDC7B polypeptide is a KLHDC7B reference polypeptide. An absence of positions 146 to 495 according to SEQ ID NO:21 in the KLHDC7B polypeptide indicates that the KLHDC7B polypeptide terminates at position 145 according to SEQ ID NO:45 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 975 according to SEQ ID NO:46. If amino acids are detected in the KLHDC7B polypeptide at positions corresponding to positions 976 to 1,235 according to SEQ ID NO:19, then such KLHDC7B polypeptide is a KLHDC7B reference polypeptide. An absence of positions 976 to 1,235 according to SEQ ID NO:19 in the KLHDC7B polypeptide indicates that the KLHDC7B polypeptide terminates at position 975 according to SEQ ID NO:46 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 334 according to SEQ ID NO:47. If amino acids are detected in the KLHDC7B polypeptide at positions corresponding to positions 335 to 594 according to SEQ ID NO:20, then such KLHDC7B polypeptide is a KLHDC7B reference polypeptide. An absence of positions 335 to 594 according to SEQ ID NO:20 in the KLHDC7B polypeptide indicates that the KLHDC7B polypeptide terminates at position 334 according to SEQ ID NO:47 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 235 according to SEQ ID NO:48. If amino acids are detected in the KLHDC7B polypeptide at positions corresponding to positions 236 to 495 according to SEQ ID NO:21, then such KLHDC7B polypeptide is a KLHDC7B reference polypeptide. An absence of positions 236 to 495 according to SEQ ID NO:21 in the KLHDC7B polypeptide indicates that the KLHDC7B polypeptide terminates at position 235 according to SEQ ID NO:48 and is a KLHDC7B predicted loss-of-function polypeptide.

In some embodiments, the detecting step comprises an immunoassay for detecting the presence of a polypeptide that comprises a position corresponding to position 1,145 according to SEQ ID NO:22 or SEQ ID NO:19. In some embodiments, the detecting step comprises an immunoassay for detecting the presence of a polypeptide that comprises a position corresponding to position 504 according to SEQ ID NO:23 or SEQ ID NO:20. In some embodiments, the detecting step comprises an immunoassay for detecting the presence of a polypeptide that comprises a position corresponding to position 405 according to SEQ ID NO:24 or SEQ ID NO:21.

In some embodiments, the detecting step comprises an immunoassay for detecting the presence of a KLHDC7B polypeptide that comprises or consists of SEQ ID NO:43. In some embodiments, the KLHDC7B polypeptide consists of SEQ ID NO:43. In some embodiments, the detecting step comprises detecting at least a portion of a KLHDC7B polypeptide that may comprise positions corresponding to any positions that are C-terminal to position 885 according to SEQ ID NO:43. If amino acids are detected in the KLHDC7B polypeptide at positions corresponding to positions 886 to 1,235 according to SEQ ID NO:19, then such KLHDC7B polypeptide is a KLHDC7B reference polypeptide. A lack of detection of positions 886 to 1,235 according to SEQ ID NO:19 in the KLHDC7B polypeptide indicates that the KLHDC7B polypeptide terminates at position 885 according to SEQ ID NO:43 and is a KLHDC7B predicted loss-of-function polypeptide.

In some embodiments, the detecting step comprises an immunoassay for detecting the presence of a KLHDC7B polypeptide that comprises or consists of SEQ ID NO:44. In some embodiments, the KLHDC7B polypeptide consists of SEQ ID NO:44. In some embodiments, the detecting step comprises detecting at least a portion of a KLHDC7B polypeptide that may comprise positions corresponding to any positions that are C-terminal to position 244 according to SEQ ID NO:44. If amino acids are detected in the KLHDC7B polypeptide at positions corresponding to positions 245 to 594 according to SEQ ID NO:20, then such KLHDC7B polypeptide is a KLHDC7B reference polypeptide. A lack of detection of positions 245 to 594 according to SEQ ID NO:20 in the KLHDC7B polypeptide indicates that the KLHDC7B polypeptide terminates at position 244 according to SEQ ID NO:44 and is a KLHDC7B predicted loss-of-function polypeptide.

In some embodiments, the detecting step comprises an immunoassay for detecting the presence of a KLHDC7B polypeptide that comprises or consists of SEQ ID NO:45. In some embodiments, the KLHDC7B polypeptide consists of SEQ ID NO:45. In some embodiments, the detecting step comprises detecting at least a portion of a KLHDC7B polypeptide that may comprise positions corresponding to any positions that are C-terminal to position 145 according to SEQ ID NO:45. If amino acids are detected in the KLHDC7B polypeptide at positions corresponding to positions 146 to 495 according to SEQ ID NO:21, then such KLHDC7B polypeptide is a KLHDC7B reference polypeptide. A lack of detection of positions 146 to 495 according to SEQ ID NO:21 in the KLHDC7B polypeptide indicates that the KLHDC7B polypeptide terminates at position 145 according to SEQ ID NO:45 and is a KLHDC7B predicted loss-of-function polypeptide.

In some embodiments, the detecting step comprises an immunoassay for detecting the presence of a KLHDC7B polypeptide that comprises or consists of SEQ ID NO:46. In some embodiments, the KLHDC7B polypeptide consists of SEQ ID NO:46. In some embodiments, the detecting step comprises detecting at least a portion of a KLHDC7B polypeptide that may comprise positions corresponding to any positions that are C-terminal to position 975 according to SEQ ID NO:46. If amino acids are detected in the KLHDC7B polypeptide at positions corresponding to positions 976 to 1,235 according to SEQ ID NO:19, then such KLHDC7B polypeptide is a KLHDC7B reference polypeptide. A lack of detection of positions 976 to 1,235 according to SEQ ID NO:19 in the KLHDC7B polypeptide indicates that the KLHDC7B polypeptide terminates at position 975 according to SEQ ID NO:46 and is a KLHDC7B predicted loss-of-function polypeptide.

In some embodiments, the detecting step comprises an immunoassay for detecting the presence of a KLHDC7B polypeptide that comprises or consists of SEQ ID NO:47. In some embodiments, the KLHDC7B polypeptide consists of SEQ ID NO:47. In some embodiments, the detecting step comprises detecting at least a portion of a KLHDC7B polypeptide that may comprise positions corresponding to any positions that are C-terminal to position 334 according to SEQ ID NO:47. If amino acids are detected in the KLHDC7B polypeptide at positions corresponding to positions 335 to 594 according to SEQ ID NO:20, then such KLHDC7B polypeptide is a KLHDC7B reference polypeptide. A lack of detection of positions 335 to 594 according to SEQ ID NO:20 in the KLHDC7B polypeptide indicates that the KLHDC7B polypeptide terminates at position 334 according to SEQ ID NO:47 and is a KLHDC7B predicted loss-of-function polypeptide.

In some embodiments, the detecting step comprises an immunoassay for detecting the presence of a KLHDC7B polypeptide that comprises or consists of SEQ ID NO:48. In some embodiments, the KLHDC7B polypeptide consists of SEQ ID NO:48. In some embodiments, the detecting step comprises detecting at least a portion of a KLHDC7B polypeptide that may comprise positions corresponding to any positions that are C-terminal to position 235 according to SEQ ID NO:48. If amino acids are detected in the KLHDC7B polypeptide at positions corresponding to positions 236 to 495 according to SEQ ID NO:21, then such KLHDC7B polypeptide is a KLHDC7B reference polypeptide. A lack of detection of positions 236 to 495 according to SEQ ID NO:21 in the KLHDC7B polypeptide indicates that the KLHDC7B polypeptide terminates at position 235 according to SEQ ID NO:48 and is a KLHDC7B predicted loss-of-function polypeptide.

In some embodiments, when the subject does not have a KLHDC7B predicted loss-of-function polypeptide, then the subject does not have an increased risk for developing hearing loss or any of conductive hearing loss, sensorineural hearing loss, or neural hearing loss. In some embodiments, when the subject has a KLHDC7B predicted loss-of-function polypeptide, then the subject has an increased risk for developing hearing loss or any of conductive hearing loss, sensorineural hearing loss, or neural hearing loss.

The present disclosure also provides isolated nucleic acid molecules that hybridize to KLHDC7B variant genomic nucleic acid molecules, KLHDC7B variant mRNA molecules, and/or KLHDC7B variant cDNA molecules (such as any of the genomic variant nucleic acid molecules, mRNA variant molecules, and cDNA variant molecules disclosed herein). In some embodiments, the isolated nucleic acid molecules hybridize to a portion of the KLHDC7B nucleic acid molecule that includes a position corresponding to position 3,778 according to SEQ ID NO:2, position 3,778 according to SEQ ID NO:7, or position 3,778 according to SEQ ID NO:15. In some embodiments, the isolated nucleic acid molecules hybridize to a portion of the KLHDC7B nucleic acid molecule that includes a position corresponding to position 1,644 according to SEQ ID NO:8, or position 1,644 according to SEQ ID NO:16. In some embodiments, the isolated nucleic acid molecules hybridize to a portion of the KLHDC7B nucleic acid molecule that includes a position corresponding to position 3,474 according to SEQ ID NO:9, or position 3,474 according to SEQ ID NO:17. In some embodiments, the isolated nucleic acid molecules hybridize to a portion of the KLHDC7B nucleic acid molecule that includes a position corresponding to position 1,644 according to SEQ ID NO:10, or position 1,644 according to SEQ ID NO:18. In some embodiments, the isolated nucleic acid molecules hybridize to a portion of the KLHDC7B nucleic acid molecule that includes positions corresponding to positions 2,806-2,807 according to SEQ ID NO:25, positions corresponding to positions 2,806-2,807 according to SEQ ID NO:27, or positions corresponding to positions 2,806-2,807 according to SEQ ID NO:35. In some embodiments, the isolated nucleic acid molecules hybridize to a portion of the KLHDC7B nucleic acid molecule that includes positions corresponding to positions 672-673 according to SEQ ID NO:28, or positions corresponding to positions 672-673 according to SEQ ID NO:36. In some embodiments, the isolated nucleic acid molecules hybridize to a portion of the KLHDC7B nucleic acid molecule that includes positions corresponding to positions 2,502-2,503 according to SEQ ID NO:29, or positions corresponding to positions 2,502-2,503 according to SEQ ID NO:37. In some embodiments, the isolated nucleic acid molecules hybridize to a portion of the KLHDC7B nucleic acid molecule that includes positions corresponding to positions 672-673 according to SEQ ID NO:30, or positions corresponding to positions 672-673 according to SEQ ID NO:38. In some embodiments, the isolated nucleic acid molecules hybridize to a portion of the KLHDC7B nucleic acid molecule that includes positions corresponding to positions 3,169-3,170 according to SEQ ID NO:26; positions corresponding to positions 3,169-3,170 according to SEQ ID NO:31, or positions corresponding to positions 3,169-3,170 according to SEQ ID NO:39. In some embodiments, the isolated nucleic acid molecules hybridize to a portion of the KLHDC7B nucleic acid molecule that includes positions corresponding to positions 1,035-1,036 according to SEQ ID NO:32, or positions corresponding to positions 1,035-1,036 according to SEQ ID NO:40. In some embodiments, the isolated nucleic acid molecules hybridize to a portion of the KLHDC7B nucleic acid molecule that includes positions corresponding to positions 2,865-2,866 according to SEQ ID NO:33, or positions corresponding to positions 2,865-2,866 according to SEQ ID NO:41. In some embodiments, the isolated nucleic acid molecules hybridize to a portion of the KLHDC7B nucleic acid molecule that includes positions corresponding to positions 1,035-1,036 according to SEQ ID NO:34, or positions corresponding to positions 1,035-1,036 according to SEQ ID NO:42.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to KLHDC7B variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to KLHDC7B variant genomic nucleic acid molecules, KLHDC7B variant mRNA molecules, and/or KLHDC7B variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 3,778 according to SEQ ID NO:2, or the complement thereof; position 3,778 according to SEQ ID NO:7, or the complement thereof; or position 3,778 according to SEQ ID NO:15, or the complement thereof. In some embodiments, the alteration-specific probe or alteration-specific primer comprises a nucleotide sequence which is complementary to a portion of a nucleotide sequence comprising positions corresponding to: positions 3,778-3,780 according to SEQ ID NO:2, or the complement thereof; positions 3,778-3,780 according to SEQ ID NO:7, or the complement thereof; and/or positions 3,778-3,780 according to SEQ ID NO:15, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 1,644 according to SEQ ID NO:8, or the complement thereof; or position 1,644 according to SEQ ID NO:16, or the complement thereof. In some embodiments, the alteration-specific probe or alteration-specific primer comprises a nucleotide sequence which is complementary to a portion of a nucleotide sequence comprising positions corresponding to: positions 1,644-1,646 according to SEQ ID NO:8, or the complement thereof and/or positions 1,644-1,646 according to SEQ ID NO:16, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 3,474 according to SEQ ID NO:9, or the complement thereof; or position 3,474 according to SEQ ID NO:17, or the complement thereof. In some embodiments, the alteration-specific probe or alteration-specific primer comprises a nucleotide sequence which is complementary to a portion of a nucleotide sequence comprising positions corresponding to: positions 3,474-3,476 according to SEQ ID NO:9, or the complement thereof; and/or positions 3,474-3,476 according to SEQ ID NO:17, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 1,644 according to SEQ ID NO:10, or the complement thereof; or position 1,644 according to SEQ ID NO:18, or the complement thereof. In some embodiments, the alteration-specific probe or alteration-specific primer comprises a nucleotide sequence which is complementary to a portion of a nucleotide sequence comprising positions corresponding to: positions 1,644-1,646 according to SEQ ID NO:10, or the complement thereof; and/or positions 1,644-1,646 according to SEQ ID NO:18, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 2,806-2,807 according to SEQ ID NO:25, or the complement thereof; a CG dinucleotide at positions corresponding to positions 2,806-2,807 to SEQ ID NO:27, or the complement thereof; or a CG dinucleotide at positions corresponding to positions 2,806-2,807 to SEQ ID NO:35, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 2,806-2,807 according to SEQ ID NO:25, or the complement thereof; a CG dinucleotide at positions corresponding to positions 2,806-2,807 to SEQ ID NO:27, or the complement thereof; or a CG dinucleotide at positions corresponding to positions 2,806-2,807 to SEQ ID NO:35, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 672-673 according to SEQ ID NO:28, or the complement thereof, or a CG dinucleotide at positions corresponding to positions 672-673 according to SEQ ID NO:36, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 672-673 according to SEQ ID NO:28, or the complement thereof, or a CG dinucleotide at positions corresponding to positions 672-673 according to SEQ ID NO:36, or the complement thereof In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 2,502-2,503 according to SEQ ID NO:29, or the complement thereof, or a CG dinucleotide at positions corresponding to positions 2,502-2,503 according to SEQ ID NO:37, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 2,502-2,503 according to SEQ ID NO:29, or the complement thereof, or a CG dinucleotide at positions corresponding to positions 2,502-2,503 according to SEQ ID NO:37, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 672-673 according to SEQ ID NO:30, or the complement thereof, or a CG dinucleotide at positions corresponding to positions 672-673 according to SEQ ID NO:38, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 672-673 according to SEQ ID NO:30, or the complement thereof, or a CG dinucleotide at positions corresponding to positions 672-673 according to SEQ ID NO:38, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 3,169-3,170 according to SEQ ID NO:26, or the complement thereof; an AG dinucleotide at positions corresponding to positions 3,169-3,170 according to SEQ ID NO:31, or the complement thereof; or an AG dinucleotide at positions corresponding to positions 3,169-3,170 according to SEQ ID NO:39, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 3,169-3,170 according to SEQ ID NO:26, or the complement thereof; an AG dinucleotide at positions corresponding to positions 3,169-3,170 according to SEQ ID NO:31, or the complement thereof; or an AG dinucleotide at positions corresponding to positions 3,169-3,170 according to SEQ ID NO:39, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 1,035-1,036 according to SEQ ID NO:32, or the complement thereof, or an AG dinucleotide at positions corresponding to positions 1,035-1,036 according to SEQ ID NO:40, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 1,035-1,036 according to SEQ ID NO:32, or the complement thereof, or an AG dinucleotide at positions corresponding to positions 1,035-1,036 according to SEQ ID NO:40, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 2,865-2,866 according to SEQ ID NO:33, or the complement thereof, or an AG dinucleotide at positions corresponding to positions 2,865-2,866 according to SEQ ID NO:41, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 2,865-2,866 according to SEQ ID NO:33, or the complement thereof, or an AG dinucleotide at positions corresponding to positions 2,865-2,866 according to SEQ ID NO:41, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 1,035-1,036 according to SEQ ID NO:34, or the complement thereof, or an AG dinucleotide at positions corresponding to positions 1,035-1,036 according to SEQ ID NO:42, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 1,035-1,036 according to SEQ ID NO:34, or the complement thereof, or an AG dinucleotide at positions corresponding to positions 1,035-1,036 according to SEQ ID NO:42, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the KLHDC7B variant genomic nucleic acid molecules, KLHDC7B variant mRNA molecules, and/or KLHDC7B variant cDNA molecules disclosed herein. The primers described herein can be used to amplify KLHDC7B variant genomic nucleic acid molecules, KLHDC7B variant mRNA molecules, or KLHDC7B variant cDNA molecules, or a fragment thereof.

The present disclosure also provides pairs of primers comprising any of the primers described above. For example, if one of the primers' 3'-ends hybridizes to a guanine at a position corresponding to position 3,778 according to SEQ ID NO:1 (rather than adenine) in a particular KLHDC7B nucleic acid molecule, then the presence of the amplified fragment would indicate the presence of a KLHDC7B reference genomic nucleic acid molecule. Conversely, if one of the primers' 3'-ends hybridizes to an adenine at a position corresponding to position 3,778 according to SEQ ID NO:2 (rather than guanine) in a particular KLHDC7B nucleic acid molecule, then the presence of the amplified fragment would indicate the presence of the KLHDC7B variant genomic nucleic acid molecule. In some embodiments, the nucleotide of the primer complementary to the adenine at a position corresponding to position 3,778 according to SEQ ID NO:2 can be at the 3' end of the primer. In addition, if one of the primers' 3'-ends hybridizes to a guanine at a position corresponding to position 3,778 according to SEQ ID NO:3 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 3,778 according to SEQ ID NO:7 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 3,778 according to SEQ ID NO:7 can be at the 3' end of the primer. In addition, if one of the primers' 3'-ends hybridizes to a guanine at a position corresponding to position 3,778 according to SEQ ID NO:11 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 3,778 according to SEQ ID NO:15 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 3,778 according to SEQ ID NO:15 can be at the 3' end of the primer.

If, for example, one of the primers' 3'-ends hybridizes to a guanine at a position corresponding to position 1,644 according to SEQ ID NO:4 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 1,644 according to SEQ ID NO:8 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 1,644 according to SEQ ID NO:8 can be at the 3' end of the primer. In addition, if one of the primers' 3'-ends hybridizes to a guanine at a position corresponding to position 1,644 according to SEQ ID NO:12 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 1,644 according to SEQ ID NO:16 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 1,644 according to SEQ ID NO:16 can be at the 3' end of the primer.

If, for example, one of the primers' 3'-ends hybridizes to a guanine at a position corresponding to position 3,474 according to SEQ ID NO:5 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 3,474 according to SEQ ID NO:9 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 3,474 according to SEQ ID NO:9 can be at the 3' end of the primer. In addition, if one of the primers' 3'-ends hybridizes to a guanine at a position corresponding to position 3,474 according to SEQ ID NO:13 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 3,474 according to SEQ ID NO:17 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 3,474 according to SEQ ID NO:17 can be at the 3' end of the primer.

If, for example, one of the primers' 3'-ends hybridizes to a guanine at a position corresponding to position 1,644 according to SEQ ID NO:6 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 1,644 according to SEQ ID NO:10 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 1,644 according to SEQ ID NO:10 can be at the 3' end of the primer. In addition, if one of the primers' 3'-ends hybridizes to a guanine at a position corresponding to position 1,644 according to SEQ ID NO:14 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 1,644 according to SEQ ID NO:18 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 1,644 according to SEQ ID NO:18 can be at the 3' end of the primer.

If, for example, one of the primers' 3'-ends hybridizes to a CGG trinucleotide at positions corresponding to positions 2,806-2,808 according to SEQ ID NO:1 (rather than a CG dinucleotide at positions corresponding to positions 2,806-2,807 according to SEQ ID NO:25) in a particular KLHDC7B nucleic acid molecule, then the presence of the amplified fragment would indicate the presence of a KLHDC7B reference genomic nucleic acid molecule. Conversely, if one of the primers' 3'-ends hybridizes to a CG dinucleotide at positions corresponding to positions 2,806-2,807 according to SEQ ID NO:25 (rather than a CGG trinucleotide at positions corresponding to positions 2,806-2,808 according to SEQ ID NO:1) in a particular KLHDC7B nucleic acid molecule, then the presence of the amplified fragment would indicate the presence of the KLHDC7B variant genomic nucleic acid molecule. In some embodiments, the nucleotide of the primer complementary to the CG dinucleotide at positions corresponding to positions 2,806-2,807 according to SEQ ID NO:25 can be at the 3' end of the primer. In addition, if one of the primers' 3'-ends hybridizes to a CGG trinucleotide at positions corresponding to positions 2,806-2,808 according to SEQ ID NO:3 (rather than a CG dinucleotide at positions corresponding to positions 2,806-2,807 to SEQ ID NO:27) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 2,806-2,807 to SEQ ID NO:27 (rather than CGG trinucleotide at positions corresponding to positions 2,806-2,808 according to SEQ ID NO:3) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 2,806-2,807 to SEQ ID NO:27 can be at the 3' end of the primer. In addition, if one of the primers' 3'-ends hybridizes to a CGG trinucleotide at positions corresponding to positions 2,806-2,808 according to SEQ ID NO:11 (rather than a CG dinucleotide at positions corresponding to positions 2,806-2,807 to SEQ ID NO:35) in a particular KLHDC7B nucleic acid molecule, then the presence of the amplified fragment would indicate the presence of a KLHDC7B reference cDNA molecule. Conversely, if one of the primers' 3'-ends hybridizes to a CG dinucleotide at positions corresponding to positions 2,806-2,807 to SEQ ID NO:35 (rather than CGG trinucleotide at positions corresponding to positions 2,806-2,808 according to SEQ ID NO:11) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 2,806-2,807 to SEQ ID NO:35 can be at the 3' end of the primer.

If, for example, if one of the primers' 3'-ends hybridizes to a CGG trinucleotide at positions corresponding to positions 672-674 according to SEQ ID NO:4 (rather than a CG dinucleotide at positions corresponding to positions 672-673 according to SEQ ID NO:28) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 672-673 according to SEQ ID NO:28 (rather than CGG trinucleotide at positions corresponding to positions 672-674 according to SEQ ID NO:4) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 672-673 according to SEQ ID NO:28 can be at the 3' end of the primer. In addition, if one of the primers' 3'-ends hybridizes to a CGG trinucleotide at positions corresponding to positions 672-674 according to SEQ ID NO:12 (rather than a CG dinucleotide at positions corresponding to positions 672-673 according to SEQ ID NO:36) in a particular KLHDC7B nucleic acid molecule, then the presence of the amplified fragment would indicate the presence of a KLHDC7B reference cDNA molecule. Conversely, if one of the primers' 3'-ends hybridizes to a CG dinucleotide at positions corresponding to positions 672-673 according to SEQ ID NO:36 (rather than CGG trinucleotide at positions corresponding to positions 672-674 according to SEQ ID NO:12) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 672-673 according to SEQ ID NO:36 can be at the 3' end of the primer.

If, for example, if one of the primers' 3'-ends hybridizes to a CGG trinucleotide at positions corresponding to positions 2,502-2,504 according to SEQ ID NO:5 (rather than a CG dinucleotide at positions corresponding to positions 2,502-2,503 according to SEQ ID NO:29) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 2,502-2,503 according to SEQ ID NO:29 (rather than CGG trinucleotide at positions corresponding to positions 2,502-2,504 according to SEQ ID NO:5) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 2,502-2,503 according to SEQ ID NO:29 can be at the 3' end of the primer. In addition, if one of the primers' 3'-ends hybridizes to a CGG trinucleotide at positions corresponding to positions 2,502-2,504 according to SEQ ID NO:13 (rather than a CG dinucleotide at positions corresponding to positions 2,502-2,503 according to SEQ ID NO:37) in a particular KLHDC7B nucleic acid molecule, then the presence of the amplified fragment would indicate the presence of a KLHDC7B reference cDNA molecule. Conversely, if one of the primers' 3'-ends hybridizes to CG dinucleotide at positions corresponding to positions 2,502-2,503 according to SEQ ID NO:37 (rather than CGG trinucleotide at positions corresponding to positions 2,502-2,504 according to SEQ ID NO:13) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 2,502-2,503 according to SEQ ID NO:37 can be at the 3' end of the primer.

If, for example, if one of the primers' 3'-ends hybridizes to a CGG trinucleotide at positions corresponding to positions 672-674 according to SEQ ID NO:6 (rather than a CG dinucleotide at positions corresponding to positions 672-673 according to SEQ ID NO:30) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 672-673 according to SEQ ID NO:30 (rather than CGG trinucleotide at positions corresponding to positions 672-674 according to SEQ ID NO:6) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 672-673 according to SEQ ID NO:30 can be at the 3' end of the primer. In addition, if one of the primers' 3'-ends hybridizes to a CGG trinucleotide at positions corresponding to positions 672-674 according to SEQ ID NO:14 (rather than a CG dinucleotide at positions corresponding to positions 672-673 according to SEQ ID NO:38) in a particular KLHDC7B nucleic acid molecule, then the presence of the amplified fragment would indicate the presence of a KLHDC7B reference cDNA molecule. Conversely, if one of the primers' 3'-ends hybridizes to a CG dinucleotide at positions corresponding to positions 672-673 according to SEQ ID NO:38 (rather than CGG trinucleotide at positions corresponding to positions 672-674 according to SEQ ID NO:14) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 672-673 according to SEQ ID NO:38 can be at the 3' end of the primer.

If, for example, one of the primers' 3'-ends hybridizes to an AGG trinucleotide at positions corresponding to positions 3,169-3,171 according to SEQ ID NO:1 (rather than an AG dinucleotide at positions corresponding to positions 3,169-3,170 according to SEQ ID NO:26) in a particular KLHDC7B nucleic acid molecule, then the presence of the amplified fragment would indicate the presence of a KLHDC7B reference genomic nucleic acid molecule. Conversely, if one of the primers' 3'-ends hybridizes to an AG dinucleotide at positions corresponding to positions 3,169-3,170 according to SEQ ID NO:26 (rather than an AGG trinucleotide at positions corresponding to positions 3,169-3,171 according to SEQ ID NO:1) in a particular KLHDC7B nucleic acid molecule, then the presence of the amplified fragment would indicate the presence of the KLHDC7B variant genomic nucleic acid molecule. In some embodiments, the nucleotide of the primer complementary to the AG dinucleotide at positions corresponding to positions 3,169-3,170 according to SEQ ID NO:26 can be at the 3' end of the primer. In addition, if one of the primers' 3'-ends hybridizes to an AGG trinucleotide at positions corresponding to positions 3,169-3,171 according to SEQ ID NO:3 (rather than an AG dinucleotide at positions corresponding to positions 3,169-3,170 according to SEQ ID NO:31) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 3,169-3,170 according to SEQ ID NO:31 (rather than AGG trinucleotide at positions corresponding to positions 3,169-3,171 according to SEQ ID NO:3) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 3,169-3,170 according to SEQ ID NO:31 can be at the 3' end of the primer. In addition, if one of the primers' 3'-ends hybridizes to an AGG trinucleotide at positions corresponding to positions 3,169-3,171 according to SEQ ID NO:11 (rather than an AG dinucleotide at positions corresponding to positions 3,169-3,170 according to SEQ ID NO:39) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 3,169-3,170 according to SEQ ID NO:39 (rather than AGG trinucleotide at positions corresponding to positions 3,169-3,171 according to SEQ ID NO:11) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 3,169-3,170 according to SEQ ID NO:39 can be at the 3' end of the primer.

If, for example, one of the primers' 3'-ends hybridizes to an AGG trinucleotide at positions corresponding to positions 1,035-1,037 according to SEQ ID NO:4 (rather than an AG dinucleotide at positions corresponding to positions 1,035-1,036 according to SEQ ID NO:32) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 1,035-1,036 according to SEQ ID NO:32 (rather than AGG trinucleotide at positions corresponding to positions 1,035-1,037 according to SEQ ID NO:4) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 1,035-1,036 according to SEQ ID NO:32 can be at the 3' end of the primer. In addition, if one of the primers' 3'-ends hybridizes to an AGG trinucleotide at positions corresponding to positions 1,035-1,037 according to SEQ ID NO:12 (rather than an AG dinucleotide at positions corresponding to positions 1,035-1,036 according to SEQ ID NO:40) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 1,035-1,036 according to SEQ ID NO:40 (rather than AGG trinucleotide at positions corresponding to positions 1,035-

1,037 according to SEQ ID NO:12) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 1,035-1,036 according to SEQ ID NO:40 can be at the 3' end of the primer.

If, for example, one of the primers' 3'-ends hybridizes to an AGG trinucleotide at positions corresponding to positions 2,865-2,867 according to SEQ ID NO:5 (rather than an AG dinucleotide at positions corresponding to positions 2,865-2,866 according to SEQ ID NO:33) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 2,865-2,866 according to SEQ ID NO:33 (rather than AGG trinucleotide at positions corresponding to positions 2,865-2,867 according to SEQ ID NO:5) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 2,865-2,866 according to SEQ ID NO:33 can be at the 3' end of the primer. In addition, if one of the primers' 3'-ends hybridizes to an AGG trinucleotide at positions corresponding to positions 2,865-2,867 according to SEQ ID NO:13 (rather than an AG dinucleotide at positions corresponding to positions 2,865-2,866 according to SEQ ID NO:41) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 2,865-2,866 according to SEQ ID NO:41 (rather than AGG trinucleotide at positions corresponding to positions 2,865-2,867 according to SEQ ID NO:13) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 2,865-2,866 according to SEQ ID NO:41 can be at the 3' end of the primer.

If, for example, one of the primers' 3'-ends hybridizes to an AGG trinucleotide at positions corresponding to positions 1,035-1,037 according to SEQ ID NO:6 (rather than an AG dinucleotide at positions corresponding to positions 1,035-1,036 according to SEQ ID NO:34) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 1,035-1,036 according to SEQ ID NO:34 (rather than AGG trinucleotide at positions corresponding to positions 1,035-1,037 according to SEQ ID NO:6) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 1,035-1,036 according to SEQ ID NO:34 can be at the 3' end of the primer. In addition, if one of the primers' 3'-ends hybridizes to an AGG trinucleotide at positions corresponding to positions 1,035-1,037 according to SEQ ID NO:14 (rather than an AG dinucleotide at positions corresponding to positions 1,035-1,036 according to SEQ ID NO:42) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 1,035-1,036 according to SEQ ID NO:42 (rather than AGG trinucleotide at positions corresponding to positions 1,035-1,037 according to SEQ ID NO:14) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 1,035-1,036 according to SEQ ID NO:42 can be at the 3' end of the primer.

In the context of the disclosure "specifically hybridizes" means that the probe or primer (such as, for example, the alteration-specific probe or alteration-specific primer) does not hybridize to a nucleic acid sequence encoding a KLHDC7B reference genomic nucleic acid molecule, a KLHDC7B reference mRNA molecule, and/or a KLHDC7B reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the KLHDC7B nucleic acid molecules (genomic nucleic acid molecules, mRNA molecules, or cDNA molecules), or complement thereof, described herein and any of the alteration-specific primers or alteration-specific probes described herein. In some embodiments, the KLHDC7B nucleic acid molecules (genomic nucleic acid molecules, mRNA molecules, or cDNA molecules), or complement thereof, in the molecular complexes are single-stranded. In some embodiments, the KLHDC7B nucleic acid molecule is any of the genomic nucleic acid molecules described herein. In some embodiments, the KLHDC7B nucleic acid molecule is any of the mRNA molecules described herein. In some embodiments, the KLHDC7B nucleic acid molecule is any of the cDNA molecules described herein. In some embodiments, the molecular complex comprises or consists of any of the KLHDC7B nucleic acid molecules (genomic nucleic acid molecules, mRNA molecules, or cDNA molecules), or complement thereof, described herein and any of the alteration-specific primers described herein. In some embodiments, the molecular complex comprises or consists of any of the KLHDC7B nucleic acid molecules (genomic nucleic acid molecules, mRNA molecules, or cDNA molecules), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a KLHDC7B polypeptide, wherein the alteration-specific primer or the alteration-specific probe is hybridized to an adenine at a position corresponding to position 3,778 according to SEQ ID NO:2, or the complement thereof.

In some embodiments, the molecular complex comprises or consists of an alteration-specific primer or an alteration-specific probe that is hybridized to an ATG codon at positions corresponding to positions 3,778-3,780 according to SEQ ID NO:2.

In some embodiments, the molecular complex comprises or consists of a genomic nucleic acid molecule that comprises SEQ ID NO:2.

In some embodiments, the molecular complex comprises or consists of an alteration-specific primer or an alteration-specific probe hybridized to an mRNA molecule comprising a nucleotide sequence encoding a KLHDC7B polypeptide, wherein the alteration-specific primer or the alteration-specific probe is hybridized to: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 according to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof.

In some embodiments, the molecular complex comprises or consists of an alteration-specific primer or an alteration-specific probe that is hybridized to: an AUG codon at positions corresponding to positions 3,778-3,780 according to SEQ ID NO:7, an AUG codon at positions corresponding to positions 1,644-1,646 according to SEQ ID NO:8, an AUG codon at positions corresponding to positions 3,474-3,476 according to SEQ ID NO:9, or an AUG codon at positions corresponding to positions 1,644-1,646 according to SEQ ID NO:10.

In some embodiments, the molecular complex comprises or consists of an mRNA molecule that comprises SEQ ID NO:7, SEQ ID NO:8, SEQ ID NO:9, SEQ ID NO:10, SEQ ID NO:27, SEQ ID NO:28, SEQ ID NO:29, SEQ ID NO:30, SEQ ID NO:31, SEQ ID NO:32, SEQ ID NO:33, or SEQ ID NO:34.

In some embodiments, the molecular complex comprises or consists of an alteration-specific primer or an alteration-specific probe hybridized to a cDNA molecule comprising a nucleotide sequence encoding a KLHDC7B polypeptide, wherein the alteration-specific primer or the alteration-specific probe is hybridized to: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof.

In some embodiments, the molecular complex comprises or consists of an alteration-specific primer or an alteration-specific probe that is hybridized to: an ATG codon at positions corresponding to positions 3,778-3,780 according to SEQ ID NO:15, an ATG codon at positions corresponding to positions 1,644-1,646 according to SEQ ID NO:16, an ATG codon at positions corresponding to positions 3,474-3,476 according to SEQ ID NO:17, or an ATG codon at positions corresponding to positions 1,644-1,646 according to SEQ ID NO:18.

In some embodiments, the molecular complex comprises or consists of a cDNA molecule that comprises SEQ ID NO:15, SEQ ID NO:16, SEQ ID NO:17, SEQ ID NO:18, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The nucleotide sequence of a KLHDC7B reference genomic nucleic acid molecule (hg38 chr22:50,545,899-50,551,023; ENST00000648057.3) is set forth in SEQ ID NO:1. Referring to SEQ ID NO:1, position 3,778 is a guanine.

A variant genomic nucleic acid molecule of KLHDC7B exists, wherein the guanine at position 3,778 (referring to SEQ ID NO:1) is replaced with an adenine. The nucleotide sequence of this KLHDC7B variant genomic nucleic acid molecule is set forth in SEQ ID NO:2 (rs36062310).

Another variant genomic nucleic acid molecule of KLHDC7B exists, wherein a guanine at position 2,807 (referring to SEQ ID NO:1) is deleted. The nucleotide sequence of this KLHDC7B variant genomic nucleic acid molecule is set forth in SEQ ID NO:25 (rs746113253).

Another variant genomic nucleic acid molecule of KLHDC7B exists, wherein a guanine at position 3,170 (referring to SEQ ID NO:1) is deleted. The nucleotide sequence of this KLHDC7B variant genomic nucleic acid molecule is set forth in SEQ ID NO:26 (rs749405486).

The nucleotide sequence of a KLHDC7B reference mRNA molecule is set forth in SEQ ID NO:3 (ENST00000648057.3). Referring to SEQ ID NO:3, position 3,778 is a guanine.

The nucleotide sequence of another KLHDC7B reference mRNA molecule is set forth in SEQ ID NO:4 (ENST00000395676.4). Referring to SEQ ID NO:4, position 1,644 is a guanine.

The nucleotide sequence of another KLHDC7B reference mRNA molecule is set forth in SEQ ID NO:5 (NM_138433.4). Referring to SEQ ID NO:5, position 3,474 is a guanine.

The nucleotide sequence of another KLHDC7B reference mRNA molecule is set forth in SEQ ID NO:6 (BC009980). Referring to SEQ ID NO:6, position 1,644 is a guanine.

A variant mRNA molecule of KLHDC7B exists, wherein the guanine at position 3,778 (referring to SEQ ID NO:3) is replaced with an adenine. The nucleotide sequence of this KLHDC7B variant mRNA molecule is set forth in SEQ ID NO:7 (ENST00000648057.3).

Another variant mRNA molecule of KLHDC7B exists, wherein the guanine at position 1,644 (referring to SEQ ID NO:4) is replaced with an adenine. The nucleotide sequence of this KLHDC7B variant mRNA molecule is set forth in SEQ ID NO:8 (ENST00000395676.4).

Another variant mRNA molecule of KLHDC7B exists, wherein the guanine at position 3,474 (referring to SEQ ID NO:5) is replaced with an adenine. The nucleotide sequence of this KLHDC7B variant mRNA molecule is set forth in SEQ ID NO:9 (NM_138433.4).

Another variant mRNA molecule of KLHDC7B exists, wherein the guanine at position 1,644 (referring to SEQ ID NO:6) is replaced with an adenine. The nucleotide sequence of this KLHDC7B variant mRNA molecule is set forth in SEQ ID NO:10 (BC009980).

Another variant mRNA molecule of KLHDC7B exists, wherein the guanine at position 2,807 (referring to SEQ ID NO:3) is deleted. The nucleotide sequence of this KLHDC7B variant mRNA molecule is set forth in SEQ ID NO:27 (ENST00000648057.3).

Another variant mRNA molecule of KLHDC7B exists, wherein the guanine at position 673 (referring to SEQ ID NO:4) is deleted. The nucleotide sequence of this KLHDC7B variant mRNA molecule is set forth in SEQ ID NO:28 (ENST00000395676.4).

Another variant mRNA molecule of KLHDC7B exists, wherein the guanine at position 2,503 (referring to SEQ ID NO:5) is deleted. The nucleotide sequence of this KLHDC7B variant mRNA molecule is set forth in SEQ ID NO:29 (NM_138433.4).

Another variant mRNA molecule of KLHDC7B exists, wherein the guanine at position 673 (referring to SEQ ID NO:6) is deleted. The nucleotide sequence of this KLHDC7B variant mRNA molecule is set forth in SEQ ID NO:30 (BC009980).

Another variant mRNA molecule of KLHDC7B exists, wherein the guanine at position 3,170 (referring to SEQ ID NO:3) is deleted. The nucleotide sequence of this KLHDC7B variant mRNA molecule is set forth in SEQ ID NO:31 (ENST00000648057.3).

Another variant mRNA molecule of KLHDC7B exists, wherein the guanine at position 1,036 (referring to SEQ ID NO:4) is deleted. The nucleotide sequence of this KLHDC7B variant mRNA molecule is set forth in SEQ ID NO:32 (ENST00000395676.4).

Another variant mRNA molecule of KLHDC7B exists, wherein the guanine at position 2,866 (referring to SEQ ID NO:5) is deleted. The nucleotide sequence of this KLHDC7B variant mRNA molecule is set forth in SEQ ID NO:33 (NM_138433.4).

Another variant mRNA molecule of KLHDC7B exists, wherein the guanine at position 1,036 (referring to SEQ ID NO:6) is deleted. The nucleotide sequence of this KLHDC7B variant mRNA molecule is set forth in SEQ ID NO:34 (BC009980).

The nucleotide sequence of a KLHDC7B reference cDNA molecule is set forth in SEQ ID NO:11 (ENST00000648057.3). Referring to SEQ ID NO:11, position 3,778 is a guanine.

The nucleotide sequence of another KLHDC7B reference cDNA molecule is set forth in SEQ ID NO:12 (ENST00000395676.4). Referring to SEQ ID NO:12, position 1,644 is a guanine.

The nucleotide sequence of another KLHDC7B reference cDNA molecule is set forth in SEQ ID NO:13 (NM_138433.4). Referring to SEQ ID NO:13, position 3,474 is a guanine.

The nucleotide sequence of another KLHDC7B reference cDNA molecule is set forth in SEQ ID NO:14 (BC009980). Referring to SEQ ID NO:14, position 1,644 is a guanine.

A variant cDNA molecule of KLHDC7B exists, wherein the guanine at position 3,778 (referring to SEQ ID NO:11) is replaced with an adenine. The nucleotide sequence of this KLHDC7B variant cDNA molecule is set forth in SEQ ID NO:15 (ENST00000648057.3).

Another variant cDNA molecule of KLHDC7B exists, wherein the guanine at position 1,644 (referring to SEQ ID NO:12) is replaced with an adenine. The nucleotide sequence of this KLHDC7B variant cDNA molecule is set forth in SEQ ID NO:16 (ENST00000395676.4).

Another variant cDNA molecule of KLHDC7B exists, wherein the guanine at position 3,474 (referring to SEQ ID NO:13) is replaced with an adenine. The nucleotide sequence of this KLHDC7B variant cDNA molecule is set forth in SEQ ID NO:17 (NM_138433.4).

Another variant cDNA molecule of KLHDC7B exists, wherein the guanine at position 1,644 (referring to SEQ ID NO:14) is replaced with an adenine. The nucleotide sequence of this KLHDC7B variant cDNA molecule is set forth in SEQ ID NO:18 (BC009980).

Another variant cDNA molecule of KLHDC7B exists, wherein the guanine at position 2,807 (referring to SEQ ID NO:11) is deleted. The nucleotide sequence of this KLHDC7B variant cDNA molecule is set forth in SEQ ID NO:35 (ENST00000648057.3).

Another variant cDNA molecule of KLHDC7B exists, wherein the guanine at position 673 (referring to SEQ ID NO:12) is deleted. The nucleotide sequence of this KLHDC7B variant cDNA molecule is set forth in SEQ ID NO:36 (ENST00000395676.4).

Another variant cDNA molecule of KLHDC7B exists, wherein the guanine at position 2,503 (referring to SEQ ID NO:13) is deleted. The nucleotide sequence of this KLHDC7B variant cDNA molecule is set forth in SEQ ID NO:37 (NM_138433.4).

Another variant cDNA molecule of KLHDC7B exists, wherein the guanine at position 673 (referring to SEQ ID NO:14) is deleted. The nucleotide sequence of this KLHDC7B variant cDNA molecule is set forth in SEQ ID NO:38 (BC009980).

Another variant cDNA molecule of KLHDC7B exists, wherein the guanine at position 3,170 (referring to SEQ ID NO:11) is deleted. The nucleotide sequence of this KLHDC7B variant cDNA molecule is set forth in SEQ ID NO:39 (ENST00000648057.3).

Another variant cDNA molecule of KLHDC7B exists, wherein the guanine at position 1,036 (referring to SEQ ID NO:12) is deleted. The nucleotide sequence of this KLHDC7B variant cDNA molecule is set forth in SEQ ID NO:40 (ENST00000395676.4).

Another variant cDNA molecule of KLHDC7B exists, wherein the guanine at position 2,866 (referring to SEQ ID NO:13) is deleted. The nucleotide sequence of this KLHDC7B variant cDNA molecule is set forth in SEQ ID NO:41 (NM_138433.4).

Another variant cDNA molecule of KLHDC7B exists, wherein the guanine at position 1,036 (referring to SEQ ID NO:14) is deleted. The nucleotide sequence of this KLHDC7B variant cDNA molecule is set forth in SEQ ID NO:42 (BC009980).

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, gluta-thione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH₂ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:3, or SEQ ID NO:11). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a KLHDC7B polypeptide, wherein the nucleotide sequence comprises an adenine at a position corresponding to position 3,778 according to SEQ ID NO:2 means that if the nucleotide sequence of the KLHDC7B genomic nucleic acid molecule is aligned to the sequence of SEQ ID NO:2, the KLHDC7B sequence has an adenine residue at the position that corresponds to position 3,778 of SEQ ID NO:2. The same applies for mRNA molecules comprising a nucleotide sequence encoding a KLHDC7B polypeptide, wherein the nucleotide sequence comprises an adenine at a position corresponding to position 3,778 according to SEQ ID NO:7, and cDNA molecules comprising a nucleotide sequence encoding a KLHDC7B polypeptide, wherein the nucleotide sequence comprises an adenine at a position corresponding to position 3,778 according to SEQ ID NO:15. In other words, these phrases refer to a nucleic acid molecule encoding a KLHDC7B polypeptide, wherein the genomic nucleic acid molecule has a nucleotide sequence that comprises an adenine residue that is homologous to the adenine residue at position 3,778 of SEQ ID NO:2 (or wherein the mRNA molecule has a nucleotide sequence that comprises an adenine residue that is homologous to the adenine residue at position 3,778 of SEQ ID NO:7, or wherein the cDNA molecule has a nucleotide sequence that comprises an adenine residue that is homologous to the adenine residue at position 3,778 of SEQ ID NO:15).

As described herein, a position within a KLHDC7B genomic nucleic acid molecule that corresponds to position 3,778 according to SEQ ID NO:2, for example, can be identified by performing a sequence alignment between the nucleotide sequence of a particular KLHDC7B nucleic acid molecule and the nucleotide sequence of SEQ ID NO:2. A variety of computational algorithms exist that can be used for performing a sequence alignment to identify a nucleotide position that corresponds to, for example, position 3,778 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of a KLHDC7B reference polypeptide is set forth in SEQ ID NO:19. Referring to SEQ ID NO:19, the KLHDC7B reference polypeptide is 1,235 amino acids in length. Referring to SEQ ID NO:19, position 1,145 is valine, position 822 is lysine, and position 943 is glycine.

The amino acid sequence of another KLHDC7B reference polypeptide is set forth in SEQ ID NO:20. Referring to SEQ ID NO:20, the KLHDC7B reference polypeptide is 594 amino acids in length. Referring to SEQ ID NO:20, position 504 is valine, position 181 is lysine, and position 302 is glycine.

The amino acid sequence of another KLHDC7B reference polypeptide is set forth in SEQ ID NO:21. Referring to SEQ ID NO:21, the KLHDC7B reference polypeptide is 495 amino acids in length. Referring to SEQ ID NO:21, position 405 is valine, position 82 is lysine, and position 203 is glycine.

A KLHDC7B variant polypeptide exists (V1145M or Val1145Met), the amino acid sequence of which is set forth in SEQ ID NO:22. Referring to SEQ ID NO:22, the KLHDC7B variant polypeptide is 1,235 amino acids in length. Referring to SEQ ID NO:22, position 1,145 is methionine.

Another KLHDC7B variant polypeptide exists (V504M or Val504Met), the amino acid sequence of which is set forth in SEQ ID NO:23. Referring to SEQ ID NO:23, the KLHDC7B variant polypeptide is 594 amino acids in length. Referring to SEQ ID NO:23, position 504 is methionine.

Another KLHDC7B variant polypeptide exists (V405M or Val405Met), the amino acid sequence of which is set forth in SEQ ID NO:24. Referring to SEQ ID NO:24, the KLHDC7B variant polypeptide is 495 amino acids in length. Referring to SEQ ID NO:24, position 405 is methionine.

A KLHDC7B truncated variant polypeptide exists (K822fs or Lys822fs), the amino acid sequence of which is set forth in SEQ ID NO:43. Referring to SEQ ID NO:43, the KLHDC7B variant polypeptide is 885 amino acids in length. Referring to SEQ ID NO:43, the KLHDC7B variant polypeptide is truncated at position 885 and does not contain amino acids at positions corresponding to positions 886 to 1,235 of SEQ ID NO:19. Referring to SEQ ID NO:43, position 822 is serine.

Another KLHDC7B truncated variant polypeptide exists (K181fs or Lys181fs), the amino acid sequence of which is set forth in SEQ ID NO:44. Referring to SEQ ID NO:44, the KLHDC7B variant polypeptide is 244 amino acids in length. Referring to SEQ ID NO:44, the KLHDC7B variant polypeptide is truncated at position 244 and does not contain amino acids at positions corresponding to positions 245 to 594 of SEQ ID NO:20. Referring to SEQ ID NO:44, position 181 is serine.

Another KLHDC7B truncated variant polypeptide exists (K82fs or Lys82fs), the amino acid sequence of which is set forth in SEQ ID NO:45. Referring to SEQ ID NO:45, the KLHDC7B variant polypeptide is 145 amino acids in length. Referring to SEQ ID NO:45, the KLHDC7B variant polypeptide is truncated at position 145 and does not contain amino acids at positions corresponding to positions 146 to 495 of SEQ ID NO:21. Referring to SEQ ID NO:45, position 82 is serine.

Another KLHDC7B truncated variant polypeptide exists (G943fs or Gly943fs), the amino acid sequence of which is set forth in SEQ ID NO:46. Referring to SEQ ID NO:46, the KLHDC7B variant polypeptide is 975 amino acids in length. Referring to SEQ ID NO:46, the KLHDC7B variant polypeptide is truncated at position 975 and does not contain amino acids at positions corresponding to positions 976 to 1,235 of SEQ ID NO:19. Referring to SEQ ID NO:46, position 943 is arginine.

Another KLHDC7B truncated variant polypeptide exists (G302fs or Gly302fs), the amino acid sequence of which is set forth in SEQ ID NO:47. Referring to SEQ ID NO:47, the KLHDC7B variant polypeptide is 334 amino acids in length. Referring to SEQ ID NO:47, the KLHDC7B variant polypeptide is truncated at position 334 and does not contain amino acids at positions corresponding to positions 335 to 594 of SEQ ID NO:20. Referring to SEQ ID NO:47, position 302 is arginine.

Another KLHDC7B truncated variant polypeptide exists (G203fs or Gly203fs), the amino acid sequence of which is set forth in SEQ ID NO:48. Referring to SEQ ID NO:48, the KLHDC7B variant polypeptide is 235 amino acids in length. Referring to SEQ ID NO:48, the KLHDC7B variant polypeptide is truncated at position 235 and does not contain amino acids at positions corresponding to positions 236 to 495 of SEQ ID NO:21. Referring to SEQ ID NO:48, position 203 is arginine.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit hearing loss for use in the treatment of hearing loss (or for use in the preparation of a medicament for treating hearing loss) in a subject, wherein the subject has any of the genomic nucleic acid molecules, mRNA molecules, and/or cDNA molecules encoding a KLHDC7B polypeptide described herein. The therapeutic agents that treat or inhibit hearing loss can be any of the therapeutic agents that treat or inhibit hearing loss described herein.

In some embodiments, the subject comprises: a genomic nucleic acid molecule having a nucleotide sequence encoding a KLHDC7B polypeptide, wherein the nucleotide sequence comprises: an adenine at a position corresponding to position 3,778 according to SEQ ID NO:2, or the complement thereof; an mRNA molecule having a nucleotide sequence encoding a KLHDC7B polypeptide, wherein the nucleotide sequence comprises an adenine at a position corresponding to position 3,778 according to SEQ ID NO:7, or the complement thereof; a cDNA molecule having a nucleotide sequence encoding a KLHDC7B polypeptide, wherein the nucleotide sequence comprises an adenine at a position corresponding to position 3,778 according to SEQ ID NO:15, or the complement thereof; or a KLHDC7B polypeptide that comprises a methionine at a position corresponding to position 1,145 according to SEQ ID NO:22.

In some embodiments, the subject comprises: an mRNA molecule having a nucleotide sequence encoding a KLHDC7B polypeptide, wherein the nucleotide sequence comprises an adenine at a position corresponding to position 1,644 according to SEQ ID NO:8, or the complement thereof; a cDNA molecule having a nucleotide sequence encoding a KLHDC7B polypeptide, wherein the nucleotide sequence comprises an adenine at a position corresponding to position 1,644 according to SEQ ID NO:16, or the complement thereof; or a KLHDC7B polypeptide that comprises a methionine at a position corresponding to position 504 according to SEQ ID NO:23.

In some embodiments, the subject comprises: an mRNA molecule having a nucleotide sequence encoding a KLHDC7B polypeptide, wherein the nucleotide sequence comprises an adenine at a position corresponding to position 3,474 according to SEQ ID NO:9, or the complement thereof; a cDNA molecule having a nucleotide sequence encoding a KLHDC7B polypeptide, wherein the nucleotide sequence comprises an adenine at a position corresponding to position 3,474 according to SEQ ID NO:17, or the complement thereof; or a KLHDC7B polypeptide that comprises a methionine at a position corresponding to position 405 according to SEQ ID NO:24.

In some embodiments, the subject comprises: an mRNA molecule having a nucleotide sequence encoding a KLHDC7B polypeptide, wherein the nucleotide sequence comprises an adenine at a position corresponding to position 1,644 according to SEQ ID NO:10, or the complement thereof; a cDNA molecule having a nucleotide sequence encoding a KLHDC7B polypeptide, wherein the nucleotide sequence comprises an adenine at a position corresponding to position 1,644 according to SEQ ID NO:18, or the complement thereof.

In some embodiments, the subject comprises: a genomic nucleic acid molecule having a nucleotide sequence encoding a KLHDC7B polypeptide, wherein the nucleotide sequence comprises: a CG dinucleotide at positions corresponding to positions 2,806-2,807 according to SEQ ID NO:25, or the complement thereof; an mRNA molecule having a nucleotide sequence encoding a KLHDC7B polypeptide, wherein the nucleotide sequence comprises a CG dinucleotide at positions corresponding to positions 2,806-2,807 to SEQ ID NO:27, or the complement thereof; a cDNA molecule having a nucleotide sequence encoding a KLHDC7B polypeptide, wherein the nucleotide sequence comprises a CG dinucleotide at positions corresponding to positions 2,806-2,807 to SEQ ID NO:35, or the complement thereof; or a KLHDC7B polypeptide that comprises a serine at a position corresponding to position 822 according to SEQ ID NO:43.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises a CG dinucleotide at positions corresponding to positions 672-673 according to SEQ ID NO:28, or the complement thereof; a cDNA molecule having a nucleotide sequence encoding a KLHDC7B polypeptide, wherein the nucleotide sequence comprises a CG dinucleotide at positions corresponding to positions 672-673 according to SEQ ID NO:36, or the complement thereof; or a KLHDC7B polypeptide that comprises a serine at a position corresponding to position 181 according to SEQ ID NO:44.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises a CG dinucleotide at positions corresponding to positions 2,502-2,503 according to SEQ ID NO:29, or the complement thereof; a cDNA molecule having a nucleotide sequence encoding a KLHDC7B polypeptide, wherein the nucleotide sequence comprises a CG dinucleotide at positions corresponding to positions 2,502-2,503 according to SEQ ID NO:37, or the complement thereof; or a KLHDC7B polypeptide that comprises a serine at a position corresponding to position 82 according to SEQ ID NO:45.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises a CG dinucleotide at positions corresponding to positions 672-673 according to SEQ ID NO:30, or the complement thereof; or a cDNA molecule having a nucleotide sequence encoding a KLHDC7B polypeptide, wherein the nucleotide sequence comprises a CG dinucleotide at positions corresponding to positions 672-673 according to SEQ ID NO:38, or the complement thereof.

In some embodiments, the subject comprises: a genomic nucleic acid molecule having a nucleotide sequence encoding a KLHDC7B polypeptide, wherein the nucleotide sequence comprises: an AG dinucleotide at positions corresponding to positions 3,169-3,170 according to SEQ ID NO:26, or the complement thereof; an mRNA molecule having a nucleotide sequence encoding a KLHDC7B polypeptide, wherein the nucleotide sequence comprises an AG dinucleotide at positions corresponding to positions 3,169-3,170 according to SEQ ID NO:31, or the complement thereof; a cDNA molecule having a nucleotide sequence encoding a KLHDC7B polypeptide, wherein the nucleotide sequence comprises an AG dinucleotide at positions corresponding to positions 3,169-3,170 according to SEQ ID NO:39, or the complement thereof; or a KLHDC7B polypeptide that comprises an arginine at a position corresponding to position 943 according to SEQ ID NO:46.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises an AG dinucleotide at positions corresponding to positions 1,035-1,036 according to SEQ ID NO:32, or the complement thereof; a cDNA molecule having a nucleotide sequence encoding a KLHDC7B polypeptide, wherein the nucleotide sequence comprises an AG dinucleotide at positions corresponding to positions 1,035-1,036 according to SEQ ID NO:40, or the complement thereof; or a KLHDC7B polypeptide that comprises an arginine at a position corresponding to position 302 according to SEQ ID NO:47.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises an AG dinucleotide at positions corresponding to positions 2,865-2,866 according to SEQ ID NO:33, or the complement thereof; a cDNA molecule having a nucleotide sequence encoding a KLHDC7B polypeptide, wherein the nucleotide sequence comprises an AG dinucleotide at positions corresponding to positions 2,865-2,866 according to SEQ ID NO:41, or the complement thereof; or a KLHDC7B polypeptide that comprises an arginine at a position corresponding to position 203 according to SEQ ID NO:48.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises an AG dinucleotide at positions corresponding to positions 1,035-1,036 according to SEQ ID NO:34, or the complement thereof; or a cDNA molecule having a nucleotide sequence encoding a KLHDC7B polypeptide, wherein the nucleotide sequence comprises an AG dinucleotide at positions corresponding to positions 1,035-1,036 according to SEQ ID NO:42, or the complement thereof.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Figure 2:
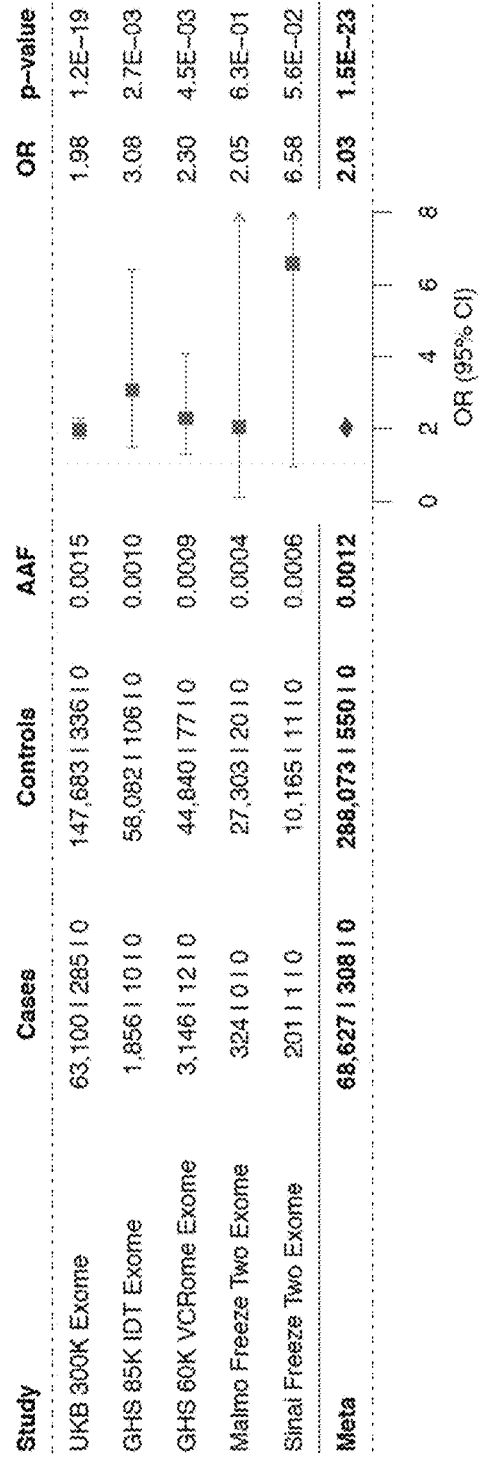
FIG. 2 shows an aggregate of rare (minor allele frequency <1%), pLOF variants in KLHDC7B is associated with hearing loss. This suggests that there are additional loss of function variants that increase the risk for hearing loss in carriers.
Figure 2:
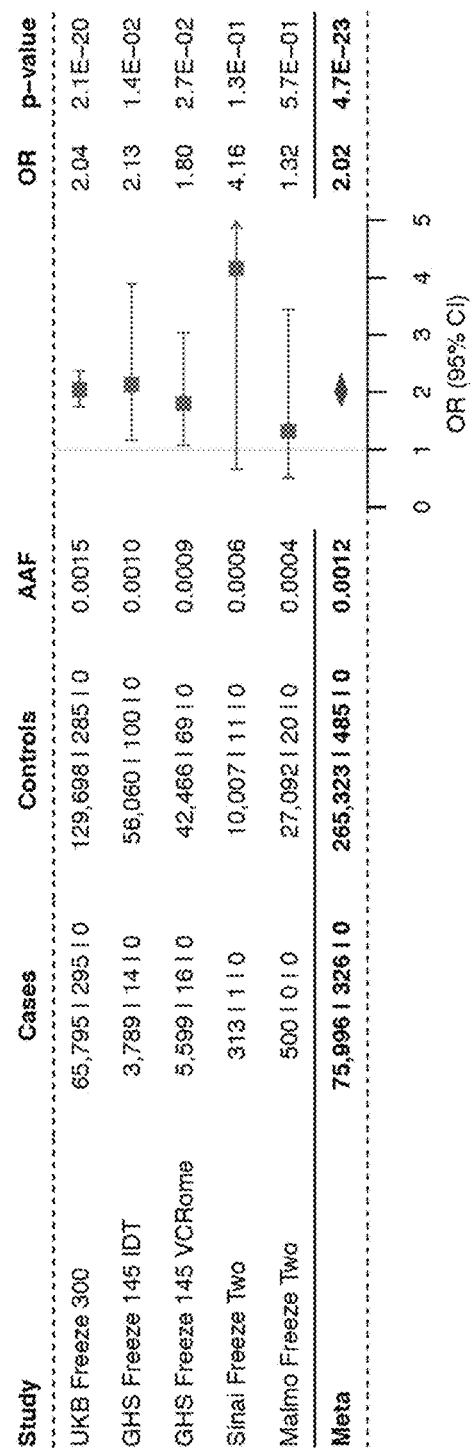

Example 1: A Missense Variant and Predicted Loss-of-Function Variants in KLHDC7B are Associated with Increased Risk for Hearing Loss A genome-wide and exome-wide analysis of self-reported and ICD code based hearing loss was carried out in UK Biobank, Geisinger (GHS) and other datasets. A common missense variant (FIG. 1, Panel C) and two rare, predicted loss-of-function (pLOF) variants (FIG. 1, Panels A and B) in KLHDC7B were associated with increased risk for hearing loss in meta-analysis of UK Biobank and 3 other cohorts. In addition, an aggregate of rare (minor allele frequency of less than 1%), pLOF variants in KLHDC7B also show an association with increased risk for hearing loss in the meta-analysis (FIG. 2) suggesting that KLHDC7B loss of function variants in addition to the two described in FIG. 1 confer an increased risk for hearing loss in carriers. The association with loss of function variants further suggests that reduced function of KLHDC7B is detrimental to hearing ability.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

SEQUENCE LISTING

```
<160> NUMBER OF SEQ ID NOS: 48

<210> SEQ ID NO 1
<211> LENGTH: 5125
<212> TYPE: DNA
<213> ORGANISM: homo sapien

<400> SEQUENCE: 1
agaagcaggt tggctgtgat gacagcacag agctcaggaa cgctgcctga ggaccctggg      60
gcctacgagg aggagaagag ggcaggagct ggtggggtgc ttgcagagac cctgggctcc     120
tatcctgcca taagcctcgc tgtctcctga tatctgcagc caggccctac tgacaccccc     180
aggcctgagt gcaagcagag accccaccat tcccaggccc tggaggactg gtccaccta     240 actgggcagc ccttggggca ggcgctggcc ggtgcctcag cccaggcctc tgtgctctgc     300
```

```
atgcactgcc agcctgccat caggcctcta ttgcagccct gaaccatgat ccagggcacc    360
ttggagccag atggtcccct ctggggctgg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctggcc ctgcaaccga agtctaaggt cagtgatggc    600
agcgaggggc agagcccagg gcaggggaaa ccagagcccc aggacgcggg ccagcagagc    660
cctgtccctg ctgcagcgcc gggcggggc ctggccgcca tgcccggct ccactcaag    720 acggctgtcg aggaggcccg cagagaggca ttaggacagc aacgggcag tgccacccc    780 gcggccccc gagcggaagg aaaggagcct cccaggccag cactgccct cctgggcagg    840 agcgaagcag gggggatgtc cgcccccctc ctgatccact tcactcctcg gagccctggc    900
agcgaagcgg aggcggagac aggtggtgtc agggcgtcct ctcgccaggc cgcaggcccc    960
gcggggcaac aggacactgg cccctggcag gcgggcgcgg ggcctcgg ctcgatgggg   1020 agaggccggg gccggcggcg gcggatggac gctggctcgg gagacagagc ccgccgcccc   1080
cggaaactgg acccgctccg cctgggcgcc gcggggagcg tgtgggacgc ggtggacggg   1140
gccgccgccc tggacgccca cgcgcgcggc ctccccacag acccccact cgcccaggag   1200 cccgcactcc cggcgctgcc cgctccccgc gccctgcagc ctgggtctca gacggaaggc   1260
tctggggcca agggtggctg gagcagggag gcctcggggg tccctgcccc cggaggaggc   1320
tggccctggg tcagcaggga ggtcccgggc accggagct ttggcccagc ccagactcc   1380 acgcgcccct ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tggggcccac ccggccccg gagcaagcaa agccggctgc agccggccac   1560
agccgcgcgc cctccccgag ccgtgagcct cgcccgcgct ccgctccccc gcccgcagct   1620
cccgccccgg ggttcccacc tgaagccctg actctcccct ctccttcaga cttttttgccc   1680 ctggaggtta cccaggatcc ttccgtgggc gaaaatctca gagcggcgcc agccccaagt   1740
tcagcctcag cccaagtctt aacttcagct ccagcctcag tcctagcccc agccctggct   1800
tcatccccca gctcagcacc aacctcagcc accacctcaa cctcatcccc cacctcagcc   1860 ccagcccag ctccaacctc agctccaact tcaaccccag ccccagcccc aagtccagct   1920
gcagccgcaa ctccagcccc agcccagtc ccagtcccaa ccctcacacc cccatcccca   1980
gccctaaccc cagtcccaac cccagcccta agcccagctc caactccagc ctaaccccca   2040
gccgcatccc cagccctaac cccagtccca accccagccc taagcccagc tccaactcca   2100
gccccaaccc cagccgcatc ccctgcccca gcccccacct cagccccaac cccaacccca   2160
gccgcatccc ctgcccccagc tgacgggtca agcctcagg agagtgtggc tctccccagg   2220
cgctaccagg agggggcaggt tcagccagc tggggaaacc ttattgccat ggttcttaga   2280
agccacccct tccccaggca agacaggccc caagggagtg tcccgagggc ggttcccggg   2340 agcccccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctcccccagg cctaagagga   2520
gagggaacca gggagaaaag tctagacccg ctgccccaag ccgcgatgcc caggggcccc   2580
gcacagcccc ccgcgcagag gccgcctggc cccgcggcct cctcctctgc gaggcgctca   2640
cagccggtac cccagctacg gaaacgcagc aggtgcgaaa tcgccccgag ctcggagcag   2700
```

```
gaggtcaggc cggccgcctc gggggaccct caaggggagg cgccggggga gggggggcagc    2760 cctgccggcc gcagcggggc gctcacggaa aagcaggagg aggcccggaa gctcatggtg    2820
tttctgcaga ggcccggggg ttgggggggtg gtggagggggc cccggaagcc cagctcccgg   2880
gccctggagc ccgccacggc ggcagccctg cggcggcggc tggacctggg cagttgcctg    2940
gacgtgctgg cctttgccca gcagcacgga gagcccggcc tggcgcagga gacctacgcg    3000
ctgatgagcg acaacctgct gcgagtgctg ggagacccgt gcctctaccg ccggctgagc    3060
gcggccgacc gcgagcgcat cctcagcctg cggaccggcc ggggccgggc ggtgctgggc    3120
gtcctcgtac tgcccagcct ctaccagggg ggccgctcag ggctccccag gggccctcgt    3180
ggcgaggagc ctcctgcggc ggcccctgtg tccctgcctc tacctgcgca cctgcatgtg    3240
ttcaaccccc gggagaacac ctggcggccc ctgacccagg tgcccgagga ggccccgctt    3300
cggggctgcg gtctctgcac catgcacaac tacctgtttc tggcgggggg catccgtggc    3360
tccggtgcca aggccgtctg ctccaacgag gtcttctgct acaaccctct gaccaacatc    3420
tggagccagg ttcggcccat gcagcaggcc cgagcccagc tcaagctggt ggccctggac    3480
gggctgctct atgccatcgg tggcgaatgc ctgtacagca tggagtgcta cgacccgcga    3540
acagacgcct ggaccccacg cgcgccactc cccgcaggca ccttccctgt ggcccacgag    3600
gctgtggcct gccgtgggga catctacgtc accgggggtc acctcttcta ccgcctgctc    3660
aggtacagcc ccgtgaagga tgcttgggac gagtgcccat acagtgccag ccaccggcgt    3720
tccagcgaca tcgtggcact ggggggcttc ctgtaccgct tcgacctgct gcggggcgtg    3780
ggcgccgccg tgatgcgcta caacacagtg accggctcct ggagcagggc tgcctccctg    3840
cccctgcccg cccccgcccc actgcactgc accaccctgg gcaacaccat ttactgcctc    3900 aaccccagg tcactgccac cttcacggtc tctgggggga ctgcccagtt ccaggccaag    3960
gagctgcagc ccttcccctt ggggagcacc ggggtcctca gtccattcat cctgactctg    4020 cccccctgagg accggctgca gacctcactc tgagtggcag gcagagaacc aaagctgctt    4080
cgctgctctc cagggagacc ctcctgggat gggcctgaga ggccggggct cagggaaggg    4140
gctgggatcg gaacttcctg ctcttgtttc tggacaactt tccccttctg ctttaaaggt    4200
tgtcgattat tttgaagccc agactccctc agcctctttc tgcccctcac tccacaccca    4260 gactgttttcc tgactcaatt ccgtacctac ttacagaccc tctcagcttg ctgacacccc    4320
cctgtctgtg ggactcccta ttccctagag ccagggactg atgcgtctcc acagacaagg    4380
acttggctcg ctggagctct gctgagccga gagaggaggg ggtagaaaac attcacactt    4440
cctatgctct gtcagcagga cagggagcaa aaacgtcccc aggcaacgcc ctcgcctctg    4500
ggactttctg cctgtcctaa ggcctcccca ggtaccaacc ccgtagctat ctgggtctgt    4560
ttggcactgt ggattctcaa gggcctagaa cccttgcctc tgaaactggt ccgctggtgc    4620
agccctgctg tctgcagctc ctgccccatac ccccagccca caccaggcca ggcccactcc    4680
gggctcacca ccctctgcag ccttgtgggg ctctcccagc cctccagaa gcccacccca    4740 cttctcgcca accccgatc tctaaatgag gcctgagcgt cacccctagtt ctgccccttt    4800 ttagctgtgt agacttggac gagacatttg acttcccttt ctccttgtct ataaaatgtg    4860
gacagtggac gtctgtcacc caagagagtt gtgggagaca agatcacagc tatgagcacc    4920
tcgcacggtg tccaggatgc acagcacaat ccatgatgcg ttttctcccc ttacgcactt    4980
tgaaacccat gctagaaaag tgaatacatc tgactgtgct ccactccaac ctccagcctg    5040
```

```
gatgtccctg tctgggccct ttttctgttt tttattctat gttcagcacc actggcacca    5100
aatacatttt aattcaccga aagca                                          5125

<210> SEQ ID NO 2
<211> LENGTH: 5125
<212> TYPE: DNA
<213> ORGANISM: homo sapien

<400> SEQUENCE: 2
agaagcaggt tggctgtgat gacagcacag agctcaggaa cgctgcctga ggaccctggg      60
gcctacgagg aggagaagag ggcaggagct ggtggggtgc ttgcagagac cctgggctcc     120
tatcctgcca taagcctcgc tgtctcctga tatctgcagc caggccctac tgacaccccc     180
aggcctgagt gcaagcagag accccaccat tcccaggccc tggaggactg gtccacctta    240
actgggcagc ccttggggca ggcgctggcc ggtgcctcag cccaggcctc tgtgctctgc     300
atgcactgcc agcctgccat caggcctcta ttgcagccct gaaccatgat ccagggcacc     360
ttggagccag atggtcccct ctggggctgg gactgggaca gtgacaatga ctgggatagt     420
gctgtgctgg ccctcctggc gctggctgtg gtggctgcca cagcgctggc cttacactgg     480
tttggctccg ggcacgatca agaggcggca gaaccggtgt ccacagccct cggggctcaa     540
cctcatcagg caggaggagc tgagctggcc ctgcaaccga agtctaaggt cagtgatggc     600
agcgaggggc agagcccagg gcaggggaaa ccagagcccc caggacgcgg ccagcagagc     660
cctgtccctg ctgcagcgcc gggcgggggc ctggccgcca tgcccggct tccactcaag     720 acggctgtcg aggaggcccg cagagaggca ttaggacagc aacggggcag tgccaccccc     780
gcggcccccc gagcggaagg aaaggagcct cccaggccag gcactgccct cctgggcagg     840
agcgaagcag gggggatgtc cgcccccctc ctgatccact tcactcctcg gagccctggc     900
agcgaagcgg aggcggagac aggtggtgtc agggcgtcct ctcgccaggc cgcaggcccc     960
gcggggcaac aggacactgg cccctggcag gcgggcgcgg ggccctcggg ctcgatgggg    1020
agaggccggg gccggcggcg gcggatggac gctggctcgg gagacagagc ccgccgcccc    1080
cggaaactgg acccgctccg cctgggcgcc gcggggagcg tgtgggacgc ggtgacgggg    1140
gccgccgccc tggacgccca cgcgcgcggc ctccccacag gacccccact cgcccaggag    1200
cccgcactcc cggcgctgcc cgctcccccgc gccctgcagc ctgggtctca dcgaaggc     1260 tctggggcca agggtggctg gagcagggag gcctcggggg tccctgcccc cggaggaggc    1320
tggccctggg tcagcaggga ggtcccgggc accggagct ttggcccagc ccagactcc     1380 acgcgcccct ggctagagag tccgcctcaa ggtcgcccac tctcgtccca agggccgggt    1440
gccacagggg cctacgatgc cggcgaggcc ggggctgaca gctcccgaga taacagtcct    1500
gccgctgacc tggggcccac ccggccccccg gagcaagcaa agccggctgc agccggccac    1560
agccgcgcgc cctcccggag ccgtgagcct cgcccgcgct ccgcctcccc gcccgcagct    1620
cccggcccgg ggttcccacc tgaagccctg actctcccct tccttcaga cttttttgccc     1680 ctggaggtta cccaggatcc ttccgtgggc gaaaatctca gagcggcgcc agccccaagt    1740
tcagcctcag cccaagtctt aacttcagct ccagcctcag tcctagcccc agccctggct    1800
tcatccccca gctcagcacc aacctcagcc accacctcaa cctcatcccc cacctcagcc    1860 ccagcccag ctccaacctc agctccaact tcaaccccag cccagcccc aagtccagct      1920 gcagccgcaa ctccagcccc agcccagtc ccagtcccaa cctcacacc cccatccca       1980 gccctaaccc cagtcccaac cccagccta agcccagctc caactccagc cctaacccca    2040
```

```
gccgcatccc cagccctaac cccagtccca accccagccc taagcccagc tccaactcca    2100
gccccaaccc cagccgcatc ccctgcccca gcccccacct cagccccaac cccaaccccca   2160 gccgcatccc ctgccccagc tgacgggtca aagcctcagg agagtgtggc tctcccagg     2220 cgctaccagg aggggcaggt ctcagccagc tggggaaacc ttattgccat ggttcttaga    2280
agccacccct tccccaggca agacaggccc caagggagtg tcccgagggc ggttcccggg    2340
agccccgtgg gtcccagcac ttccacacac tctgaggaca gacacggccc ctcttcttca    2400
gtggggacag tcatagggac aggtacaggg ggcctggttg aggctggagg tcagccacag    2460
ccaagaagct ccgagaccaa cggatcgccc agcccagacc ctcccccagg cctaagagga    2520
gagggaacca gggagaaaag tctagacccg ctgccccaag ccgcgatgcc caggggcccc    2580
gcacagcccc ccgcgcagag gccgcctggc cccgcggcct cctcctctgc gaggcgctca    2640
cagccggtac cccagctacg aaacgcagc aggtgcgaaa tcgccccgag ctcggagcag     2700
gaggtcaggc cggccgcctc gggggaccct caagggagg cgccggggga ggggggcagc    2760
cctgccggcc gcagcggggc gctcacggaa aagcaggagg aggcccggaa gctcatggtg    2820
tttctgcaga ggcccggggg ttgggggtg gtggaggggc cccggaagcc cagctcccgg    2880
gccctggagc ccgccacggc ggcagccctg cggcggcggc tggacctggg cagttgcctg    2940
gacgtgctgg cctttgccca gcagcacgga gagcccggcc tggcgcagga gacctacgcg    3000
ctgatgagcg acaacctgct gcgagtgctg ggagacccgt gcctctaccg ccggctgagc    3060
gcggccgacc gcgagcgcat cctcagcctg cggaccggcc ggggccgggc ggtgctgggc    3120
gtcctcgtac tgcccagcct ctaccagggg ggccgctcag ggctccccag gggccctcgt    3180
ggcgaggagc ctcctgcggc ggcccctgtg tccctgcctc tacctgcgca cctgcatgtg    3240
ttcaaccccc gggagaacac ctggcggccc ctgacccagg tgcccgagga ggccccgctt    3300
cggggctgcg gtctctgcac catgcacaac tacctgtttc tggcgggggg catccgtggc    3360
tccggtgcca aggccgtctg ctccaacgag gtcttctgct acaaccctct gaccaacatc    3420
tggagccagg ttcggcccat gcagcaggcc cgagcccagc tcaagctggt ggccctggac    3480
gggctgctct atgccatcgg tggcgaatgc ctgtacagca tggagtgcta cgacccgcga    3540
acagacgcct ggaccccacg cgcgccactc cccgcaggca ccttccctgt ggcccacgag    3600
gctgtggcct gccgtgggga catctacgtc accggggggtc acctcttcta ccgcctgctc    3660
aggtacagcc ccgtgaagga tgcttgggac gagtgcccat acagtgccag ccaccggcgt    3720
tccagcgaca tcgtggcact ggggggcttc ctgtaccgct tcgacctgct gcggggcatg    3780
ggcgccgccg tgatgcgcta caacacagtg accggctcct ggagcagggc tgcctccctg    3840
cccctgcccg ccccgcccc actgcactgc accaccctgg gcaacaccat ttactgcctc    3900 aaccccccagg tcactgccac cttcacggtc tctgggggga ctgcccagtt ccaggccaag    3960
gagctgcagc ccttcccctt ggggagcacc ggggtcctca gtccattcat cctgactctg    4020 cccccctgagg accggctgca gacctcactc tgagtggcag gcagagaacc aaagctgctt    4080
cgctgctctc cagggagacc ctcctgggat gggcctgaga ggccggggct cagggaaggg    4140
gctgggatcg gaacttcctg ctcttgtttc tggacaactt tccccttctg ctttaaaggt    4200
tgtcgattat tttgaagccc agactccctc agcctctttc tgcccctcac tccacaccca    4260
gactgtttcc tgactcaatt ccgtacctac ttacagaccc tctcagcttg ctgacacccc    4320
cctgtctgtg ggactcccta ttccctagag ccagggactg atgcgtctcc acagacaagg    4380
```

-continued

| | |
|---|---|
| acttggctcg ctggagctct gctgagccga gagaggaggg ggtagaaaac attcacactt | 4440 |
| cctatgctct gtcagcagga cagggagcaa aaacgtcccc aggcaacgcc ctcgcctctg | 4500 |
| ggactttctg cctgtcctaa ggcctcccca ggtaccaacc ccgtagctat ctgggtctgt | 4560 |
| ttggcactgt ggattctcaa gggcctagaa cccttgcctc tgaaactggt ccgctggtgc | 4620 |
| agccctgctg tctgcagctc ctgcccatac ccccagccca caccaggcca ggcccactcc | 4680 |
| gggctcacca ccctctgcag ccttgtgggg ctctcccagc cctccagaa gcccacccca | 4740 |
| cttctcgcca accccgatc tctaaatgag gcctgagcgt caccctagtt ctgccccttt | 4800 |
| ttagctgtgt agacttggac gagacatttg acttcccttt ctccttgtct ataaaatgtg | 4860 |
| gacagtggac gtctgtcacc caagagagtt gtgggagaca agatcacagc tatgagcacc | 4920 |
| tcgcacggtg tccaggatgc acagcacaat ccatgatgcg ttttctcccc ttacgcactt | 4980 |
| tgaaacccat gctagaaaag tgaatacatc tgactgtgct ccactccaac ctccagcctg | 5040 |
| gatgtccctg tctgggccct ttttctgttt tttattctat gttcagcacc actggcacca | 5100 |
| aatacatttt aattcaccga aagca | 5125 |

```
<210> SEQ ID NO 3
<211> LENGTH: 5125
<212> TYPE: DNA
<213> ORGANISM: homo sapien

<400> SEQUENCE: 3
```

| | |
|---|---|
| agaagcaggu uggcugugau gacagcacag agcucaggaa cgcugccuga ggacccuggg | 60 |
| gccuacgagg aggagaagag ggcaggagcu gguggguguc uugcagagac ccugggcucc | 120 |
| uauccugcca uaagccucgc ugucuccuga uaucugcagc caggcccuac ugacaccccc | 180 |
| aggccugagu gcaagcagag accccaccau ucccaggccc uggaggacug guccaccuua | 240 |
| acugggcagc ccuuggggca ggcgcuggcc ggugccucag cccaggccuc ugugcucugc | 300 |
| augcacugcc agccugccau caggcccucua uugcagcccu gaaccaugau ccagggcacc | 360 |
| uuggagccag augguccccu cuggggcugg acugggaca gugacaauga cuggauagu | 420 |
| gcugugcugg ccccuccugg cgcuggcugu ggcugccca cagcgcuggc cuuacacugg | 480 |
| uuugcuccg ggcacgauca agaggcggca gaaccggugu ccacagcccu cggggcucaa | 540 |
| ccucaucagg caggaggagc ugagcuggcc cugcaaccga agucuaaggu cagugauggc | 600 |
| agcgaggggc agagcccagg gcagggggaaa ccagagcccc caggacgcgg ccagcagagc | 660 |
| ccuguccug cugcagcgcc gggcgggggc cuggccgcca uggcccggcu uccacucaag | 720 |
| acggcugucg aggaggcccg cagagaggca uuaggacagc aacggggcag ugccaccccc | 780 |
| gcggcccccc gagcggaagg aaaggagccu cccaggccag gcacugcccu ccugggcagg | 840 |
| agcgaagcag gggggauguc cgcccccuc cugauccacu ucacuccucg gagcccuggc | 900 |
| agcgaagcgg aggcggagac agguggugc agggcgucuu cucgccaggc cgcaggcccc | 960 |
| gcggggcaac aggacacugg ccccugguag gcggcgcgg ggcccucggg ucgauggggg | 1020 |
| agaggccggg gccggcggcg gcggauggac gcuggcucgg gagacagagc ccgccgcccc | 1080 |
| cggaaacugg acccgcuccg ccugggcgcc gcggggagcg uguggacgc ggugacgggg | 1140 |
| gccgccgccc uggacgccca cgcgcgcggc cuccccacag gaccccacu cgcccaggag | 1200 |
| cccgcacucc cggccugcc cgcucccgc gccugcagc cugggucuca gacgaaggc | 1260 |
| ucuggggcca aggguggcug gagcaggggag gccucggggg uccugccccc ggaggaggc | 1320 |
| uggcccuggg ucagcaggga gguccggggc accggagcu uuggcccagc cccagacucc | 1380 |

```
acgcgcsccu ggcuagagag uccgccucaa ggucgsccac ucucguscca agggscgggu    1440
gccacagggg ccuacgaugc cggcgaggcc ggggcugaca gccccgaga uaacaguccu    1500 gccgcugacc uggggcccac ccggcccccg gagcaagcaa agccggcugc agccggccac    1560
agccgcgcgc ccucccggag ccgugagccu cgcccgcgcu ccgccucccc gcccgcagcu    1620
cccggcccgg gguccsacc ugaagcccug acucuscccu cuccuucaga cuuuuugccc     1680
cuggagguua cccaggaucc uuccgugggc gaaaaucuca gagcggcgcc agccccaagu    1740
ucagccucag cccaagucuu aacuucagcu ccagccucag uccuagccscc agcccuggcu   1800 ucauccccca gcagcacc aaccucagcc accaccucaa ccuauccccc caccucagcc      1860
ccagccccag cuccaaccuc agcuccaacu ucaaccscag cccscagcccc aaguccagcu   1920 gcagccgcaa cuccagcccc agcccsagucc cagucccaa cccucacacc cccauccccca   1980 gcccuaaccc cagucscaac cccagcccuas agcccagcuc caacuccagc ccuaaccscca  2040 gccgcaucscc cagcccuaac cccsagucsca accscagccc uaagcccsagc uscaacuscca 2100 gccccaaccc cagccgcauc cccugcccca gccccaccu cagccccaac cccaaccccca   2160 gccgcaucscc cugcccsagc ugacggguca aagccucagg agagugusggc ucucccscagg 2220 cgcuaccagg aggsgcaggu cucagccagc ugggsgaaacc uuauugccau ggusucuuaga 2280 agccacccscu ucccscaggca agacaggscc caagggagug ucccgagggsc gsguuscscggg 2340 agccscgugg guccscagcac usuccacacac ucugaggaca gacacggscccc cucuuscuuca 2400 gugsgggacag ucauagsggac agguacaggsg gggcugguug aggcsuggagg ucagsccacag 2460 ccaagaagcu ccgagaccaa cggaucgccc agcccagacc cuccccscagg ccuaagagsga  2520 gagggaacca gggagaaaag ucuagacccg cugccccaag ccgcgaugcc caggggcccc   2580
gcacagcccc ccgcgcagag gccgccuggc cccgcgcscu cuscusugc gsaggcsgcuca  2640 cagccsgguac cccagcuacg gaaacgcsagc agguscgaaa ucgsccsgag ucsggagscag  2700 gaggucaggc cggccgccuc gggsggacscscu caaggsggagg cgccsggggsga gssggsggcsagc 2760 ccugccsggcc gcagsgsgggc gcucacgaaa aagcaggagsg aggsccsggaa gcucaugsgug 2820 uuucsugcaga ggcccggsggsg uugggsggsgug ugsgagsgsgsgc cscsggaagscc cagscuscsccgsg 2880 gcscsuggagsc cscgscsacsgsg gscsagsccssssgg cgsgscsgsgscsgsgc uggsaccsuggssg cagsuusgccssug 2940 gscsacsgsugscsussg cscssuusgsccsca gcagcsacsggsa gsagscscscgsgcc usggcsgcsagsga gsaccsuasccgsg 3000
```



```
acgcgccccu ggcuagagag uccgccucaa ggucgcccac ucucgsccca agggccgggu    1440
gccacagggg ccuacgaugc cggcgaggcc ggggcugaca gccccgaga  uaacaguccu    1500
gccgcugacc uggggcccac ccggcccccg gagcaagcaa agccggcugc agccggccac    1560
agccgcgcgc ccucccggag ccgugagccu cgcccgcgcu ccgccucccc gcccgcagcu    1620
cccggcccgg gguccsacc  ugaagcccug acucuscccu cuccuucaga cuuuuugccc    1680
cuggagguua cccaggaucc uuccgugggc gaaaaucuca gagcggcgcc agccccaagu    1740
ucagccucag cccaagucuu aacuucagcu ccagccucag uccuagcccc agcccuggcu    1800
ucauccccca gcagcacc   aaccucagcc accaccucaa ccuauccccc caccucagcc    1860
ccagccccag cuccaaccuc agcuccaacu ucaaccccag cccsagcccc aaguccagcu    1920
gcagccgcaa cuccagcccc agcccagucc cagucccaa  cccucacacc cccaucccca    1980
gcccuaaccc cagucccaac cccagcccua agcccagcuc caacuccagc cuaacccca     2040
gccgcauccc cagcccuaac cccsagucsca accccagccc uaagcccagc uccaacucca   2100
gccccaaccc cagccgcauc cccugcccca gccccaccu  cagccccaac cccaacccca   2160
gccgcauccc cugcccsagc ugacggguca aagccucagg agagugugsgc ucucccsagg   2220
cgcuaccagg aggsgcaggu cucagccagc ugggsgaaacc uuauugccau ggusucuuaga  2280
agccacccsu  ucccscaggca agacaggscc caagggagug cccgaggsgc gsuucsggsgg  2340
agccscgugg guccsagcac usuccacacac ucugaggaca gacacggcccc cucusucusca 2400
```

This OCR appears garbled.

[The image shows a continuation of a nucleotide sequence listing in RNA (u instead of t) with position numbers 1440–3720 at the right margin. The sequence consists of lower-case letters a, c, g, u arranged in 10-character groups, 6 groups per line.]

| | |
|---|---:|
| uccagcgaca ucguggcacu gggggggcuuc cuguaccgcu ucgaccugcu gcggggcgug | 3780 |
| ggcgccgccg ugaugcgcua caacacagug accggcuccu ggagcagggc ugccucccug | 3840 |
| ccccugcccg ccccgccccc acugcacugc accacccugg gcaacaccau uuacugccuc | 3900 |
| aaccccagg ucacugccac cuucacgguc ucgggggga cugcccaguu ccaggccaag | 3960 |
| gagcugcagc ccuuccccuu ggggagcacc ggggguccuca guccauucau ccugacucug | 4020 |
| cccccugagg accggcugca gaccucacuc ugaguggcag gcagagaacc aaagcugcuu | 4080 |
| cgcugcucuc cagggagacc cuccugggau gggccugaga ggccgggggcu cagggaaggg | 4140 |
| gcugggaucg gaacuuccug ucucuuguuuc uggacaacuu uccccuucug cuuuaaaggu | 4200 |
| ugucgauuau uuugaagccc agacccccuc agccucuuuc ugcccucac uccacaccca | 4260 |
| gacuguuucc ugacucaauu ccguaccuac uuacagaccc cucagccuug cugacacccc | 4320 |
| ccugucugug ggacucccua uucccuagag ccagggacug augcgucucc acagacaagg | 4380 |
| acuuggcucg cuggagcucu gcugagccga gagaggaggg gguagaaaac auucacacuu | 4440 |
| ccuaugcucu gucagcagga cagggagcaa aaacguccccc aggcaacgcc cucgccucug | 4500 |
| ggacuuucug ccuguccuaa ggccuccccca gguaccaacc ccguagcuau cugggucugu | 4560 |
| uuggcacugu ggauucucaa gggccuagaa cccuugccuc ugaaacuggu ccgcuggugc | 4620 |
| agcccugcug ucugcagcuc cugcccauac ccccagccca caccaggcca ggcccacucc | 4680 |
| gggcucacca cccucugcag ccuuguggggg cucuccccagc cccuccagaa gcccaccccca | 4740 |
| cuucucgcca accccccgauc ucuaaaugag gccugagcgu cacccuaguu cugcccccuuu | 4800 |
| uuagcugugu agacuuggac gagacauuug acuucccuuu cuccuugucu auaaaaugug | 4860 |
| gacaguggac gucugucacc caagagaguu gugggagaca agaucacagc uaugagcacc | 4920 |
| ucgcacggug uccaggaugc acagcacaau ccaugaugcg uuuucccccc uuacgcacuu | 4980 |
| ugaaacccau gcuagaaaag ugaauacauc ugacugugcu ccacuccaac cuccagccug | 5040 |
| gaugucccug ucugggcccu uuuucuguuu uuuauucuau guucagcacc acuggcacca | 5100 |
| aauacauuuu aauucaccga aagca | 5125 |

<210> SEQ ID NO 4
<211> LENGTH: 2990
<212> TYPE: DNA
<213> ORGANISM: homo sapien

<400> SEQUENCE: 4

| | |
|---|---:|
| ccaccucagc cccaaccccca accccagccg caucccccugc cccagcugac gggucaaagc | 60 |
| cucaggagag uguggcucuc cccaggcgcu accaggaggg gcaggucuca gccagcuggg | 120 |
| gaaaccuuau ugccaugguu cuuagaagcc accccuuccc caggcaagac aggcccaag | 180 |
| ggagugucccc gagggcgguu cccggagcc ccguggucc cagcacuucc acacacucug | 240 |
| aggacagaca cggccccucu ucuucagugg ggacagucau agggacaggu caggggggcc | 300 |
| ugguugaggc uggaggucag ccacagccaa gaagcuccga gaccaacgga ucgcccagcc | 360 |
| cagacccucc cccaggccua agaggagagg gaaccaggga gaaaagucua gacccgcugc | 420 |
| cccaagccgc gaugcccagg ggccccgcac agccccccgc gcagaggccg ccuggccccg | 480 |
| cggccuccuc cucugcgagg cgcucacagc cgguaccccca gcuacggaaa cgcagcaggu | 540 |
| gcgaaaucgc cccgagcucg gagcaggagg ucaggccggc cgccucgggg gacccucaag | 600 |
| gggaggcgcc gggggagggg ggcagcccug ccggccgcag cggggcgcuc acggaaaagc | 660 |
| aggaggaggc ccggaagcuc auggugutuuc ugcagaggcc cggggguugg ggggugugg | 720 |

```
aggggcccccg gaagcccagc ucccgggccc uggagcccgc cacggcggca gcccugcggc    780
ggcggcugga ccugggcagu ugccuggacg ugcuggccuu ugcccagcag cacggagagc    840
ccggccuggc gcaggagacc uacgcgcuga ugagcgacaa ccugcugcga gugcugggag    900
acccgugccu cuaccgccgg cugagcgcgg ccgaccgcga cgcauccuc agccugcgga     960 ccggccgggg ccgggcggug cugggcgucc ucguacugcc cagccucuac caggggggcc   1020
gcucagggcu cccagggggc ccucguggcg aggagccucc ugcggcggcc ccugugubccc   1080 ugccucuacc ugcgcaccug caugguguuca accccccggga gaacaccugg cggcccbbuga   1140 cccaggugcc cgaggaggcc ccgcuucggg gcugcggucu cugcaccaug cacaacuacc   1200
uguuucuggc gggggggcauc cguggcuccg gugccaaggc cgucugcucc aacgaggucu   1260
ucugcuacaa cccucugacc aacaucugga gccagguucg gcccaugcag caggcccgag   1320
cccagcucaa gcugguggcc cuggacgggc ugcucuaugc caucggauggc gaaugccugu   1380 acagcaugga gugcuacgac ccgcgaacag acgccuggac cccacgcgcg ccacucccccg   1440 caggcaccuu cccuguggcc cacgaggcug uggccugccg uggggacauc uacgucaccg   1500
ggggucaccu cuuucaccgc cugcucaggu acagccccgu gaaggaugcu ugggacgagu   1560
gcccauacag ugccagccac cggcguucca gcgacaucgu ggcacugggg ggcuuccugu   1620
accgcuucga ccugcugcgg ggcgugggcg ccgccgugau cgcuacaac acagugaccg   1680 gcuccuggag cagggcugcc ucccugcccc ugcccgcccc cgccccacug cacugcacca   1740
cccugggcaa caccauuuac ugccucaacc cccaggucac ugccaccuuc acggucucug   1800
gggggacugc ccaguuccag gccaaggagc ugcagcccuu ccccuugggg agcaccgggg   1860 uccucaguce auucauccug acucugcccc cugaggaccg gcugcagacc ucacucugag   1920
uggcaggcag agaaccaaag cugcuucgcu gcucuccagg gagacccuccc ugggaugggc   1980 cugagaggcc ggggcucagg gaaggggcug ggaucggaac uuccugcucu uguuucgga    2040 caacuuccc cuucugcuuu aaagguuguc gauuauuuug aagcccagac ucccucagcc    2100
ucuuucugcc cccacucca cccccagacu guuccugac ucaauuccgu accuacuuac     2160
agacccucuc agcuugcuga caccccccug ucuguggac ucccuauucc cuagagccag    2220
ggacugaugc gucuccacag acaaggacuu ggcucgcugg agcucugcug agccgagaga    2280 ggaggggggua gaaaacauuc acacuuccua ugcucuguca gcaggacagg gagcaaaaac    2340
guccccaggc aacgcccucg ccucugggac uuucugccug uccuaaggcc uccccaggua    2400
ccaaccccgu agcuaucugg gucuguuugg cacuguggau ucucaagggc cuagaacccu    2460
ugccucugaa acuggucecgc uggugcagcc cugcugucug cagcuccugc ccauaccccc    2520
agcccacacc aggccaggcc cacuccgggc ucaccacccu cugcagccuu gggggcucu     2580 cccagcccccu ccagaagccc accccacuuc ucgccaaccc ccgaucucua aaugaggccu    2640
gagcgucacc cuaguucugc cccuuuuuag cuguguagac uuggacgaga cauuugacuu    2700
cccuuucucc uugucuauaa aaugugggaca guggacgucu gucacccaag agaguugugg    2760
gagacaagau cacagcuaug agccaccucgc acggugucca ggaugcacag cacaauccau    2820
gaugcguuuu cuccccuuac gcacuuugaa acccaugcua gaaaagugaa uacaucugac    2880
ugugcuccac uccaaccucc agccuggaug ucccugucug ggcccuuuuu cuguuuuuua   2940
uucuauguuc agcaccacug gcaccaaaua cauuuuaauu caccgaaagc                2990
```

<210> SEQ ID NO 5

<211> LENGTH: 4837
<212> TYPE: DNA
<213> ORGANISM: homo sapien

<400> SEQUENCE: 5

```
acugccagcc ugccaucagg ccucuauugc agcccugaac caugauccag ggcaccuugg      60
agccagaugg uccccucugg ggcugggacu gggacaguga caaugacugg gauagugcug     120
ugcuggcccu ccuggcgcug gcugugguug cugccacagc gcuggccuua cacugguuug     180
gcuccgggca cgaucaagag gcggcagaac cggugccac agcccucggg gcucaaccuc      240
aucaggcagg aggagcugag cuggcccugc aaccgaaguc uaaggucagu gauggcagcg     300
aggggcagag cccagggcag gggaaaccag agccccagg acgcggccag cagagcccug      360
ucccugcugc agcgccgggc gggggccugg ccgccauggc ccggcuucca cucaagacgg     420
cugucgagga ggcccgcaga gaggcauuag gacagcaacg gggcagugcc acccccgcgg     480 cccccgagc ggaaggaaag gagccuccca ggccaggcac ugccuccug ggcaggagcg       540 aagcagggg gauguccgcc ccccuccuga uccacuucac uccucggagc ccuggcagcg      600
aagcggaggc ggagacaggu ggugucaggg cguccucucg ccaggccgca ggccccgcgg     660
ggcaacagga cacuggcccc uggcaggcgg gcgcggggcc cucgggcucg auggggagag     720
gccggggccg gcggcggcgg auggacgcug gcucgggaga cagagcccgc cgcccccgga     780
aacuggaccc gcuccgccug ggccgcgcgg ggagcgugug ggacgcggug gacggggccg     840
ccgcccugga cgcccacgcg cgcggccucc ccacaggacc ccacucgcc caggagcccg      900 cacuccggc gcugcccgcu ccccgcgccc ugcagccugg gucucagacg gaaggcucug     960
gggccaaggg uggcuggagc agggaggccu cggggguccc ugcccccgga ggaggcuggc    1020 ccuggucag cagggagguc ccgggcaccc ggagcuuugg cccagcccca gacuccacgc     1080
gccccuggcu agagaguccg ccucaagguc gcccacucuc gucccaaggg ccgggugcca    1140
caggggccua cgaugccggc gaggccgggg cugacagcuc ccgagauaac aguccugccg    1200
cugaccuggg gccaccccgg cccccggagc aagcaaagcc ggcugcagcc ggccacagcc    1260
gcgcgcccuc ccggagccgu gagccucgcc cgcgcuccgc cucccgcccc gcagcucccg    1320
gcccgggguu cccaccugaa gcccugacuc uccccucucc uucagacuuu uugcccuugg    1380
agguuaccca ggauccuucc gugggcgaaa aucucagagc ggcgccagcc ccaaguucag    1440
ccucagccca agucuuaacu ucagcuccag ccucagccca gcccccagcc cuggcuucau    1500 ccccccagcuc agcaccaacc ucagccacca ccucaaccuc auccccacc ucagcccag     1560 ccccagcucc aaccucagcu ccaacuucaa ccccagcccc agcccaagu ccagcugcag    1620 ccgcaacucc agcccccagcc ccaguccag ucccaacccu cacaccccca ucccccagccc   1680 uaaccccagu cccaaccccca gcccuaagcc cagcccaac uccagcccua accccagccg    1740 caucccagc ccuaacccca gucccaaccc cagcccuaag cccagcucca acuccagccc     1800
caaccccagc cgcauccccu gcccagcccc caccucagc cccaaccccca ccccagccg    1860 caucccugc cccagcugac gggucaaagc ucaggagag uguggcucuc cccaggcgcu     1920
accaggaggg gcaggucuca gccagcuggg gaaaccuuau ugccaugguu cuuagaagcc    1980
accccuuccc caggcaagac aggcccccaag ggaguguccc gagggcgguu cccgggagcc   2040
ccgugggucc cagcacuucc acacacucug aggacagaca cggccccucu ucuucagugg   2100
ggacagucau agggacaggu acaggggccu gguugaggg uggaggucag ccacagccaa    2160
gaagcuccga gaccaacgga ucgcccagcc cagacccucc cccaggccua agaggagagg    2220
```

```
gaaccaggga gaaaagucua gacccgcugc cccaagccgc gaugcccagg ggccccgcac   2280
agccccccgc gcagaggccg ccuggccccg cggccuccuc cucugcgagg cgcucacagc   2340
cgguacccca gcuacggaaa cgcagcaggu gcgaaaucgc cccgagcucg gagcaggagg   2400
ucaggccggc cgccucgggg gacccucaag ggaggcgcc ggggggaggg ggcagcccug    2460
ccggccgcag cggggcgcuc acggaaaagc aggaggaggc ccggaagcuc augugcuuuc   2520
ugcagaggcc cggggguugg gggguggugg aggggccccg gaagcccagc ccccgggccc   2580
uggagcccgc cacggcggca gcccugcggc ggcggcugga ccugggcagu ugccuggacg   2640
ugcuggccuu ugcccagcag cacgagagcc ccggccuggc gcaggagacc uacgcgcuga   2700
ugagcgacaa ccugcugcga gugcuggagg acccgugccu cuaccgccgg cugagcgcgg   2760
ccgaccgcga gcgcauccuc agccugcgga ccggccgggg ccgggcggug cugggcgucc   2820
ucguacugcc cagccucuac cagggggggcc gcucagggcu cccagggggc ccucguggcg   2880
aggagccucc ugcggcggcc ccugugucc ugccucuacc ugcgcaccug caugucuuca    2940
acccccggga gaacaccugg cggccccuga cccaggugcc cgaggaggcc ccgcuucggg   3000
gcugcggucu cugcaccaug cacaacuacc uguuucuggc ggggggcauc cguggcuccg   3060
gugccaaggc cgucugcucc aacgaggucu ucugcuacaa cccucugacc aacaucugga   3120
gccagguucg gcccaugcag caggcccgag cccagcucaa gcugguggcc cuggacgggc   3180
ugcucuaugc caucggugggc gaaugccugu acagcaugga gugcuacgac ccgcgaacag   3240
acgccuggac cccacgcgcg ccacucccccg caggcaccuu cccugugggcc cacgaggcug   3300 uggccugccg ugggggacauc uacgucaccg ggggucaccu cuucuaccgc cugcucaggu   3360
acagccccgu gaaggaugcu ugggacgagu gcccauacag ugccagccac cggcguucca    3420
gcgacaucgu ggcacugggg ggcuuccugu accgcuucga ccugcugcgg ggcguggggcg   3480 ccgccgugau gcgcuacaac acagugaccg gcuccuggag cagggcugcc uccccugccc   3540 ugccccgcccc cgccccacug cacugcacca cccugggcaa caccauuuac ugccucaacc   3600
cccaggucac ugccaccuuc acggucucug ggggacugc ccaguccag gccaaggagc    3660 ugcagcccuu cccuuuggggg agcaccgggg uccagucu auucauccug acucugcccc   3720
cugaggaccg gcugcagacc ucacucugag uggcaggcag agaaccaaag cugcuucgcu   3780
gcucuccagg gagacccucc uggggauggc cugagaggcc ggggcucagg gaagggcug    3840 ggaucggaac uuccugcucu uguuucugga caacuuccc cuucugcuuu aaagguuguc    3900
gauuauuuug aagcccagac uccccagccc ucuuucugcc ccuacuccca cacccagacu   3960
guuuccugac ucaauuccgu accacuuac agacccucuc agcuugcuga caccccccug   4020
ucugugggac ucccuauucc cuagagccag ggacugaugc gucuccacag acaaggacuu   4080
ggcucgcugg agcucugcug agccgagaga ggagggggua gaaaacauuc acacuuccua   4140
ugcucuguca gcaggacagg gagcaaaaac gucccccaggc aacgcccucg ccucugggac   4200
uuucugccug uccuaaggcc uccccaggua ccaaccccgu agcuaucugg gucuguuugg   4260
cacuguggau ucucaagggc cuagaacccu ugccucugaa acuggccgc uggugcagcc    4320 cugcugcugu cagcuccugc ccauacccc agcccacacc aggccaggcc cacuccgggc   4380
ucaccacccu cugcagccuu gugggggcucu cccagcccccu ccagaagccc accccacuuc   4440
ucgccaaccc ccgaucucua aaugaggccu gagcgucacc cuaguucugc cccuuuuuag   4500
cuguguagac uuggacgaga cauuugacuu cccuuucucc uugcuauaa aaugguggaca   4560
```

| | |
|---|---:|
| guggacgucu gucacccaag agaguugugg gagacaagau cacagcuaug agcaccucgc | 4620 |
| acgguguccagg augcacag cacaauccau gaugcguuuu cuccccuuac gcacuuugaa | 4680 |
| acccaugcua gaaaagugaa uacaucugac ugugcuccac uccaaccucc agccuggaug | 4740 |
| ucccugucug ggcccuuuuu cuguuuuuua uucuauguuc agcaccacug gcaccaaaua | 4800 |
| cauuuuaauu caccgaaagc aaaaaaaaaa aaaaaaa | 4837 |

<210> SEQ ID NO 6
<211> LENGTH: 2099
<212> TYPE: DNA
<213> ORGANISM: homo sapien

<400> SEQUENCE: 6

| | |
|---|---:|
| ccaccucagc cccaaccccca accccagccg caucccccugc cccagcugac gggucaaagc | 60 |
| cucaggagag uguggcucuc cccaggcgcu accaggaggg gcaggucuca gccagcuggg | 120 |
| gaaaccuuau ugccaugguu cuuagaagcc accccuuccc caggcaagac aggcccccaag | 180 |
| ggaguguccc gagggcgguu cccggagccc cguggguucc cagcacuucc acacacucug | 240 |
| aggacagaca cggccccucu ucuucagugg ggacagucau agggacaggu acagggggcc | 300 |
| ugguugaggc uggaggucag ccacagccaa gaagcuccga gaccaacgga ucgcccagcc | 360 |
| cagacccucc cccaggccua agaggagagg gaaccaggga gaaaagucua gacccgcugc | 420 |
| cccaagccgc gaugcccagg ggccccgcac agccccccgc gcagaggccg ccuggccccg | 480 |
| cggccuccuc cucugcgagg cgcucacagc cgguacccca gcuacggaaa cgcagcaggu | 540 |
| gcgaaaucgc cccgagcucg gagcaggagg ucaggccggc cgccucgggg gacccucaag | 600 |
| gggaggcgcc gggggagggg ggcagcccug ccggccgcag cggggcgcuc acggaaaagc | 660 |
| aggaggaggc ccggaagcuc augguguuuc ugcagaggcc cggggguugg ggggugggug | 720 |
| aggggccccg gaagcccagc ucccgggccc uggagcccgc cacggcggca gcccugcggc | 780 |
| ggcggcugga ccugggcagu ugccuggacg ugcuggccuu ugcccagcag cacgagagc | 840 |
| ccggccuggc gcaggagacc uacgcgcuga ugagcgacaa ccugcugcga gugcugggag | 900 |
| acccgugccu cuaccgccgg cugagcgcgg ccgaccgcga gcgcauccuc agccugcgga | 960 |
| ccggccgggg ccgggcggug cugggcgucc ucguacugcc cagccucuac caggggggcc | 1020 |
| gcucagggcu cccagggggc ccucguggcg aggagccucc ugcggcggcc ccuguguccc | 1080 |
| ugccucuacc ugcgcaccug caugguguuca accccgggga gaacaccugg cggcccucuga | 1140 |
| cccaggugcc cgaggaggcc ccgcuucggg gcucgggucu cugcaccaug cacaacuacc | 1200 |
| uguuucuggc gggggggcauc cguggcuccg gugccaaggc cgucugcucc aacgaggucu | 1260 |
| ucugcuacaa cccucugacc aacaucugga gccagguucg gcccaugcag caggcccgag | 1320 |
| cccagcucaa gcugguggcc cuggacgggc ugcucuaugc caucgguggc gaaugccugu | 1380 |
| acagcaugga gugcuacgac ccgcgaacag acgccuggac cccacgcgcg ccacuccccg | 1440 |
| caggcaccuu cccugugggcc cacgaggcug uggccugccg uggggacauc uacgucaccg | 1500 |
| gggucaccu cuucuaccgc cugcucaggu acagccccgu gaaggaugcu ugggacgagu | 1560 |
| gcccauacag ugccagccac cggcguucca gcgacaucgu ggcacugggg ggcuuccugu | 1620 |
| accgcuucga ccugcugcgg ggcguggcg ccgccgugau gcgcuacaac acagugaccg | 1680 |
| gcuccuggag cagggcugcc ucccagcccc ugccgccccc cgccccacug cacugcacca | 1740 |
| cccugggcaa caccauuuac ugccucaacc cccaggcac ugccaccuuc acggucucug | 1800 |
| ggggacugc ccaguuccag gccaaggagc ugcagcccuu ccccuugggg agcaccgggg | 1860 |

```
uccucaguec auucauccug acucugcccc cugaggaccg gcugcagacc ucacucugag    1920
uggcaggcag agaaccaaag cugcuucgcu gcucuccagg gagacccucc ugggauggc    1980 cugagaggcc ggggcucagg aaggggcug ggaucggaac uuccugcucu uguuucugga    2040 caacuuccc cuucugcuuu aaagguuguc gauuauuuug aaaaaaaaaa aaaaaaaa      2099
```

<210> SEQ ID NO 7
<211> LENGTH: 5125
<212> TYPE: DNA
<213> ORGANISM: homo sapien

<400> SEQUENCE: 7

```
agaagcaggu uggcugugau gacagcacag agcucaggaa cgcugccuga ggacccuggg    60
gccuacgagg aggagaagag ggcaggagcu gguggggugc uugcagagac ccugggcucc   120
uauccugcca uaagccucgc ugucuccuga uaucugcagc caggcccuac ugacaccccc   180
aggccugagu gcaagcagag accccaccau ucccaggccc uggaggacug guccaccuua   240
acugggcagc ccuuggggca ggcgcuggcc ggugccucag cccaggccuc ugugcucugc   300
augcacugcc agccugccau caggccucua uugcagcccu gaaccaugau ccagggcacc   360
uuggagccag auggucccu cuggggcugg gacugggaca gugacaauga cuggggauagu   420 gcugugcugg cccuccuggc gcuggcugug guggcugcca cagcgcuggc cuuacacugg   480
uuuggcuccg ggcacgauca agaggcggca gaaccggugu ccacagcccu cggggcucaa   540
ccucaucagg caggaggagc ugagcuggcc cugcaaccga agucuaaggu cagugauggc   600 agcgagggc agagcccagg gcaggggaaa ccagagcccc caggacgcgg ccagcagagc   660 ccuguccug cugcagcgcc gggcgggggc cuggccgcca uggcccggcu uccacucaag   720
acggcugucg aggaggcccg cagagaggca uuaggacagc aacggggcag ugccaccccc   780
gcggcccccc gagcggaagg aaaggagcc cccaggccag gcacugcccu ccugggcagg   840
agcgaagcag ggggggauguc cgcccccuc cugauccacu ucacuccucg gagcccuggc   900
agcgaagcgg aggcggagac aggugguguc agggcguccu cucgccaggc cgcaggccc    960 gcggggcaac aggacacugg ccccuggcag gcggcgcgg ggccucggg cucgauggg     1020 agaggccggg gccggcggcg gcggauggac gcuggcucgg gagacagagc ccgccgcccc  1080
cggaaacugg acccgcuccg ccugggcgcc gcggggagcg uguggacgc gguggacggg   1140 gccgccgccc uggacgccca cgcgcgcggc cuccccacag accccccacu cgcccaggag  1200
cccgcacucc cggcgcugcc cgcucccccgc gcccugcagc cugggucuca gacggaaggc  1260
ucuggggcca agggguggcug gagcaggag gccucggggg uccugccccc cggaggagcc  1320
uggcccuggu cagcaggga ggucccgggc accggagcu uggcccagc ccagacucc      1380 acgcgcccu ggcuagagag uccgccucaa ggucgccac ucucguccca agggccgggu    1440
gccacagggg ccuacgaugc cggcgaggcc ggggcugaca gccccgaga uaacaguccu    1500 gccgcugacc ugggccccac ccggccccg gagcaagcaa agccggcugc agccggccac    1560
agccgcgcgc ccucccggag ccgugagccu cgcccgcgcu ccgccucccc gcccgcagcu   1620
ccccgcccgg gguucccacc ugaagcccug acucucccu cuccuucaga cuuuuugccc    1680
cuggagguua cccaggaucc uuccguggc gaaaaucuca gagcggcgcc agcccaagu    1740 ucagccucag cccaagucuu aacuucagcu ccagccucag uccuagcccc agcccuggcu   1800
ucauccccca gcucagcacc aacccugagc caccaccucaa ccuauccccc caccucagcc   1860
```

```
ccagccccag cuccaaccuc agcuccaacu ucaaccccag ccccagcccc aaguccagcu    1920
gcagccgcaa cuccagcccc agcccagguc ccaguccaa cccucacacc cccauccca      1980 gcccuaaccc caguccaac cccagcccua agcccagcuc caacuccagc ccuaaccca      2040 gccgcauccc cagcccuaac cccaguccca accccagccc uaagcccagc uccaacucca    2100
gccccaaccc cagccgcauc cccugcccca gccccaccu cagccccaac cccaaccca      2160 gccgcauccc cugcccagc ugacggguca aagccucagg agagugggc ucccccagg       2220 cgcuaccagg aggggcaggu ucagccagc uggggaaacc uuauugccau gguucuuaga     2280
agccaccccu uccccaggca agacaggccc aagggagug ucccgagggc gguucccggg     2340
agccccgugg gucccagcac uuccacacac ucugaggaca gacacggccc cucuucuuca    2400 gugggacag ucauagggac agguacaggg ggccugguug aggcuggagg ucagccacag     2460
ccaagaagcu ccgagaccaa cggaucgccc agccagacc cuccccagg ccuaagagga      2520 gagggaacca gggagaaaag ucuagaccg cugccccaag ccgcgaugcc caggggcccc     2580
gcacagcccc ccgcgcagag gccgccuggc cccgcgccu ccuccucugc gaggcgcuca    2640
cagccgguac cccagcuacg gaaacgcagc aggugcgaaa ucgccccgag cucggagcag   2700
gaggucaggc cggccgccuc gggggacccu caaggggagg cgccggggga ggggggcagc   2760
ccugccggcc gcagcggggc gcucacgaaa aagcaggagg aggcccggaa gcucauggug   2820
uuucugcaga ggcccggggg uuggggggug guggaggggc cccggaagcc cagcucccgg   2880
gcccuggagc ccgccacggc ggcagcccug cggcggcggc uggaccuggg caguugccug   2940
gacgugcugg ccuuugccca gcagcacgga gagcccggcc uggcgcagga gaccuacgcg   3000
cugaugagcg acaaccugcu gcgagugcug ggagacccgu gccucuaccg ccggcugagc   3060
gcggccgacc gcgagcgcau ccucagccug cggaccggcc ggggccgggc ggugcugggc   3120
guccucguac ugcccagccu cuaccagggg ggccgcucag ggcuccccag ggccccucgu   3180
ggcgaggagc cuccugcggc ggccccugug ucccugccuc uaccgcgca ccugcaugug    3240 uucaaccccc gggagaacac cuggcggccc cugacccagg ugcccgagga ggccccgcuu   3300
cggggcugcg gucucugcac caugcacaac uaccuguuuc ggcggggg cauccgguggc    3360 uccggugcca aggccgucug cuccaacgag gucuucugcu acaacccucu gaccaacauc   3420
uggagccagg uucggcccau gcagcaggcc cgagcccagc ucaagcuggu ggcccuggac   3480
gggcugcucu augccaucgg uggcgaaugc cuguacagca uggagugcua cgaccgcgca   3540
acagacgccu ggaccccacg cgcgccacuc cccgcaggca ccuucccgu ggcccacgag    3600 gcuguggccu gccgugggga caucuacguc accgggggc accucuucua ccgccugcuc   3660
agguacagcc ccgugaagga ugcuugggac gagugcccau acagugccag ccaccggcgu   3720
uccagcgaca ucguggcacu gggggcuuc cuguaccgcu ucgaccugcu gcggggcaug   3780
ggcgccgccg ugaugcgcua caacacagug accggucu ggagcagggc ugccucccug    3840
ccccugcccg ccccgcccc acugcacugc accacccugg gcaacaccau uuacugccuc   3900 aaccccagg ucacugccac cuucacgguc ucuggggga cugcccaguu ccaggccaag    3960
gagcugcagc ccuucccuu ggggagcacc gggguccuca guccauucau ccugacucug   4020 ccccugagg accggcugca gaccucacuc ugaguggcag gcagagaacc aaagcugcuu   4080
cgcugcucuc cagggagacc cuccugggau gggccuagaa ggccggggcu cagggaaggg   4140
gcugggaucg gaacuuccug cucuuguuuc uggacaacuu ccccuucug cuuuaaaggu    4200 ugucgauuau uuugaagccc agacuccucu agccucuuuc ugccccucac uccacaccca   4260
```

```
gacuguuucc ugacucaauu ccguaccuac uuacagaccc ucucagcuug cugacacccc    4320
ccugucugug ggacucccua uucccuagag ccagggacug augcgucucc acagacaagg    4380
acuuggcucg cuggagcucu gcugagccga gagaggaggg gguagaaaac auucacacuu    4440
ccuaugcucu ucagcagga cagggagcaa aaacgucccc aggcaacgcc cucgccucug    4500
ggacuuucug ccuguccuaa ggccuccca gguaccaacc ccguagcuau cugggucugu    4560
uuggcacugu ggauucucaa gggccuagaa cccuugccuc ugaaacuggu ccgcuggugc    4620
agcccugcug ucugcagcuc cugcccauac cccagccca caccaggcca ggcccacucc    4680
gggcucacca cccucugcag ccuuguggg cucuccagc cccuccagaa gcccacccca    4740
cuucucgcca accccgauc ucuaaaugag gccugagcgu cacccuaguu cugcccuuu    4800 uuagcugugu agacuuggac gagacauuug acuucccuuu uccuugucu auaaaaugug    4860 gacaguggac gucugucacc caagagaguu gugggagaca agaucacagc uaugagcacc    4920
ucgcacggug uccaggaugc acagcacaau ccaugaugcg uuuucucccc uuacgcacuu    4980
ugaaacccau gcuagaaaag ugaauacauc ugacugugcu ccacuccaac cuccagccug    5040
gaugucccug ucugggcccu uuuucuguuu uuuauucuau guucagcacc acuggcacca    5100
aauacauuuu aauucaccga aagca                                         5125
```

```
<210> SEQ ID NO 8
<211> LENGTH: 2990
<212> TYPE: DNA
<213> ORGANISM: homo sapien

<400> SEQUENCE: 8
```

```
ccaccucagc cccaacccca accccagccg cauccccugc cccagcugac gggucaaagc      60
cucaggagag uguggcucuc cccaggcgcu accaggaggg gcaggucuca gccagcuggg     120
gaaaccuuau ugccaugguu cuuagaagcc accccuuccc caggcaagac aggcccaag     180 ggagugucccc gagggcgguu cccggagccc ccgugggucc cagcacuucc acacacucug    240
aggacagaca cggccccucu ucuucagugg ggacagucau agggacaggu cagggggcc     300 ugguugaggc uggaggucag ccacagccaa gaagcuccga gaccaacgga ucgcccagcc    360
cagacccucc cccaggccua agaggagagg gaaccaggga gaaaagucua gaccgcugc    420 cccaagccgc gaugcccagg ggccccgcac agccccgc gcagaggccg ccuggccccg     480
cggccuccuc ucucgcgagg cgcucacagc cgguacccca gcuacggaaa cgcagcaggu    540
gcgaaaucgc cccgagcucg gagcaggagg ucaggccggc cgccucgggg gacccucaag    600
gggaggcgcc gggggagggg ggcagcccug ccggccgcag cggggcgcuc acggaaaagc    660
aggaggaggc ccggaagcuc augguguuuc ugcagaggcc cggggguugg ggggugguugg   720 aggggccccg gaagcccagc ucccgggccc uggagcccgc cacggcggca gcccugcggc    780
ggcggcugga ccugggcagu ugccuggacg ugcuggccuu ugcccagcag cacgagagc    840 ccggccuggc gcaggagacc uacgcgcuga ugagcgacaa ccugcugcga gugcugggag    900
acccgugccu cuaccgccgg cugagcgcgcg ccgaccgcga gcgcauccuc agccugcgga    960
ccggccgggg ccggccggug cugggcgucc ucguacugcc cagccucuac caggggggcc   1020
gcucagggcu cccaggggc ccucguggcg aggagccucc ugcggcggcc ccuguccc    1080 ugccucuacc ugcgcaccug caugugucca cccccgggga gaacaccugg cggcccuga    1140 cccaggugcc cgaggaggcc ccgcuucggg gcugcggucu cugcaccaug cacaacuacc    1200
```

| | |
|---|---|
| uguuucuggc gggggcauc cguggcuccg ugccaaggc cgucugcucc aacgaggucu | 1260 |
| ucugcuacaa cccucugacc aacaucugga gccagguucg gcccaugcag caggcccgag | 1320 |
| cccagcucaa gcugguggcc cuggacgggc ugcucuaugc caucggugg gaaugccgu | 1380 |
| acagcaugga gugcuacgac ccgcgaacag acgccuggac cccacgcgcg ccacuccccg | 1440 |
| caggcaccuu cccuguggcc cacgaggcug uggccugccg uggggacauc uacgucaccg | 1500 |
| ggggucaccu cuucuaccgc cugcucaggu acagccccgu gaaggaugcu ugggacgagu | 1560 |
| gcccauacag ugccagccac cggcguucca gcgacaucgu ggcacggggg ggcuuccugu | 1620 |
| accgcuucga ccugcugcgg ggcauggcg ccgccgugau gcgcuacaac acagugaccg | 1680 |
| gcuccuggag cagggcugcc uccugcccc ugcccgcccc cgcccacug cacugcacca | 1740 |
| cccugggcaa caccauuuac ugccucaacc ccaggucac ugccaccuuc acggucucug | 1800 |
| gggggacugc ccaguccag gccaaggagc ugcagcccuu ccccuugggg agcaccgggg | 1860 |
| uccucaguc auucauccug acucugcccc cugaggaccg gcugcagacc ucacucugag | 1920 |
| uggcaggcag agaaccaaag cugcuucgcu gcucuccagg gagacccucc ugggaugggc | 1980 |
| cugagaggcc ggggcucagg gaaggggcug ggaucggaac uuccugcucu uguuucugga | 2040 |
| caacuuuccc cuucugcuuu aaagguuguc gauuauuuug aagcccagac ucccucagcc | 2100 |
| ucuuucugcc cccacucca cacccagacu guuccugac ucaauuccgu accuacuuac | 2160 |
| agacccucuc agcuugcuga caccccccug ucuguggac ucccuauucc cuagagccag | 2220 |
| ggacugaugc gucuccacag acaaggacuu ggcucgcugg agcucugcug agccgagaga | 2280 |
| ggagggggua gaaaacauuc acacuuccua ugcucuguca gcaggacagg gagcaaaaac | 2340 |
| guccccaggc aacgcccucg ccucugggac uuucugccug uccuaaggcc uccccaggua | 2400 |
| ccaaccccgu agcuaucugg gucuguuugg cacuguggau ucucaagggc cuagaacccu | 2460 |
| ugccucugaa acuggucgc uggugcagcc cugcugucug cagcuccugc ccauaccccc | 2520 |
| agcccacacc aggccaggcc cacuccgggc ucaccacccu cugcagccuu guggggcucu | 2580 |
| cccagcccu ccagaagccc accccacuuc ucgccaaccc ccgaucucua aaugaggccu | 2640 |
| gagcgucacc cuaguucgc cccuuuuuag cuguguagac uuggacgaga cauuugacuu | 2700 |
| cccuuucucc uugucuauaa aauguggaca guggacgucu gucacccaag agaguugugg | 2760 |
| gagacaagau cacagcuaug agcaccucgc acguguccca ggaugcacag cacaauccau | 2820 |
| gaugcguuuu ucccccuuac gcacuuugaa acccaugcua gaaagugaa uacaucugac | 2880 |
| ugugcuccac uccaacccuc agccuggaug cccugucug ggcccuuuuu cuguuuuua | 2940 |
| uucuauguuc agcaccacug gcaccaaaua cauuuaauu caccgaaagc | 2990 |

<210> SEQ ID NO 9
<211> LENGTH: 4837
<212> TYPE: DNA
<213> ORGANISM: homo sapien

<400> SEQUENCE: 9

| | |
|---|---|
| acugccagcc ugccaucagg cccucuauugc agcccugaac caugauccag ggcaccuugg | 60 |
| agccagaugg uccccucugg ggcugggacu gggacaguga caaugacugg gauagugcug | 120 |
| ugcuggcccu ccuggcgcug gcuguggugg cugccacagc gcuggccuua cacugguuug | 180 |
| gcuccgggca cgaucaagag gcggcagaac cggugccac agcccucggg gcucaaccuc | 240 |
| aucaggcagg aggagcugag cuggcccugc aaccgaaguc uaaggucagu gauggcagcg | 300 |
| aggggcagag cccagggcag gggaaaccag agccccagg acgcggccag cagagcccug | 360 |

```
ucccugcugc agcgccgggc gggggccugg ccgccauggc ccggcuucca cucaagacgg    420
cugucgagga ggcccgcaga gaggcauuag gacagcaacg gggcagugcc accccgcgg    480 cccccgagc ggaaggaaag gagccuccca ggccaggcac ugccuccug gcaggagcg    540 aagcagggg gaugucgcc ccccuccuga uccacuucac uccucggagc ccuggcagcg    600
aagcggaggc ggagacaggu ggugucaggg cguccucucg ccaggccgca ggccccgcgg    660
ggcaacagga cacuggcccc uggcaggcgg gcgcggggcc cucgggcucg auggggagag    720
gccggggccg gcggcggcgg auggacgcug gcucgggaga cagagcccgc cgcccccgga    780
aacuggaccc gcuccgccug ggcgccgcgg ggagcgugug ggacgcggug gacggggccg    840
ccgcccugga cgcccacgcg cgcggccucc ccacaggacc cccacucgcc caggagcccg    900
cacucccggc gcugcccgcu ccccgcgccc ugcagccugg gucucagacg gaaggcucug    960
gggccaaggg uggcuggagc agggaggccu cggggguccc ugccccggga ggaggcuggc    1020 ccuggucag cagggagguc ccgggcaccc ggagcuuugg cccagcccca gacuccacgc    1080
gccccuggcu agagaguccg ccucaagguc gcccacucuc gucccaaggg ccgggugcca    1140
caggggccua cgaugccggc gaggccgggg cugacagcuc ccgagauaac aguccugccg    1200
cugaccuggg gccacccgg ccccggagc aagcaaagcc ggcugcagcc ggccacagcc    1260
gcgcgcccuc ccggagccgu gagccucgcc cgcgcuccgc cuccccgccc gcagcucccg    1320 gcccggggu cccaccugaa gcccugacuc uccccucucc uucagacuuu uugcccuugg    1380
agguuaccca ggauccuucc gugggcgaaa aucucagagc ggcgcagcc ccaaguucag    1440 ccucagccca agucuuaacu ucagcuccag ccucagccu agcccagcc cuggcuucau    1500 cccccagcuc agcaccaacc ucagccacca ccucaaccuc auccccacc ucagccccag    1560 ccccagcucc aaccucagcu ccaacuucaa ccccagcccc agcccaagu ccagcugcag    1620 ccgcaacucc agcccagcc ccaguccag ucccaaccu cacaccccca ucccagccc    1680 uaaccccagu cccaaccca gcccuaagcc cagcccaac uccagcccua ccccagccg    1740 caucccagc ccuaaccccca guccaaccc cagcccuaag cccagcucca acuccagccc    1800
caaccccagc cgcaucccu gcccagccc ccaccucagc cccaaccca accccagccg    1860 caucccugc cccagcugac gggucaaagc ucaggagag uguggcucuc cccaggcgcu    1920
accaggaggg gcaggucuca gccagcuggg gaaaccuuau ugccaugguu cuuagaagcc    1980
acccuucccc caggcaagac aggccccaag ggagugucccc gagggcgguu cccgggagcc    2040
ccgugggucc cagcacuucc acacacucug aggacagaca cggccccucu ucuucagugg    2100
ggacagucau agggacaggu acaggggcc ugguugaggc uggaggucag ccacagccaa    2160
gaagcuccga ccaacggga ucgccagcc cagacccucc ccaggccua agaggagagg    2220 gaaccaggga gaaaagucua gacccgcugc cccaagccgc gaugcccagg ggccccgcac    2280 agcccccgc gcagaggccg ccuggccccg cggccuccuc cucugcgagg cgcucacagc    2340
cgguacccca gcuacggaaa cgcagcaggu gcgaaaucgc cccgagcucg gagcaggagg    2400
ucaggccggc cgccucgggg gacccucaag ggaggcgcc gggggagggg ggcagcccug    2460
ccggccgcag cggggcgcuc acggaaaagc aggaggagcc ccggaagcuc auggugguuuc    2520 ugcagaggcc cggggguugg ggggugugug aggggccccg gaagcccagc ucccgggccc    2580
uggagcccgc cacggcggca gcccugcggc ggcggcugga ccuggcagu ugccuggacg    2640 ugcuggccuu ugcccagcag cacgagagc ccggccuggc gcaggagacc uacgcgcuga    2700
```

| | | | | |
|---|---|---|---|---|
| ugagcgacaa | ccugcugcga | gugcuggag | acccgugccu | cuaccgccgg cugagcgcgg | 2760 |
| ccgaccgcga | gcgcauccuc | agccugcgga | ccggccgggg | ccgggcggug cugggcgucc | 2820 |
| ucguacugcc | cagccucuac | caggggggcc | gcucagggcu | ccccaggggc ccucguggcg | 2880 |
| aggagccucc | ugcggcggcc | ccuguguccc | ugcucuacc | ugcgcaccug caugguuca | 2940 |
| acccccggga | gaacaccugg | cggccccuga | cccaggugcc | cgaggaggcc ccgcuucggg | 3000 |
| gcugcggucu | cugcaccaug | cacaacuacc | uguuucuggc | gggggcauc cguggcuccg | 3060 |
| gugccaaggc | cgucugcucc | aacgaggucu | ucugcuacaa | cccucugacc aacaucugga | 3120 |
| gccagguucg | gcccaugcag | caggcccgag | cccagcucaa | gcugguggcc cuggacgggc | 3180 |
| ugcucuaugc | caucggugcc | gaaugccugu | acagcaugga | gugcuacgac ccgcgaacag | 3240 |
| acgccuggac | cccacgcgcg | ccacccccg | caggcaccuu | cccugugcc cacgaggcug | 3300 |
| uggccugccg | uggggacauc | uacgucaccg | ggggucaccu | cuucuaccgc cugcucaggu | 3360 |
| acagccccgu | gaaggaugcu | ugggacgagu | gcccauacag | ugccagccac cggcguucca | 3420 |
| gcgacaucgu | ggcacugggg | ggcuuccugu | accgcuucga | ccugcugcgg ggcaugggcg | 3480 |
| ccgccgugau | gcgcuacaac | acagugaccg | gcuccuggag | cagggcugcc ucccugcccc | 3540 |
| ugcccgcccc | cgccccacug | cacugcacca | cccugggcaa | caccauuuac ugcccaaccc | 3600 |
| cccaggucac | ugccaccuuc | acggucucug | ggggacugc | ccaguccag gccaaggagc | 3660 |
| ugcagcccuu | cccccugggg | agcaccgggg | uccucaguccc | auucauccug acucugcccc | 3720 |
| cugaggaccg | gcugcagacc | ucacucugag | uggcaggcag | agaaccaaag cugcuucgcu | 3780 |
| gcucuccagg | gagacccucc | ugggauggc | cugagaggcc | ggggcucagg gaaggggcug | 3840 |
| ggaucggaac | uuccugcucu | uguuucugga | caacuuccc | cuucugcuuu aaagguuguc | 3900 |
| gauuauuug | aagcccagac | ucccucagcc | ucuuucugcc | ccucacucca cacccagacu | 3960 |
| guuccugac | ucaauuccgu | accacuuac | agacccucuc | agcugcuga caccccccug | 4020 |
| ucugugggac | ucccuauucc | cuagagccag | ggacugaugc | gucuccacag acaaggacuu | 4080 |
| ggcucgcugg | agcucugcug | agccgagaga | ggaggggua | gaaaacauuc acacuuccua | 4140 |
| ugcucuguca | gcaggacagg | gagcaaaaac | guccccaggc | aacgcccucg ccucugggac | 4200 |
| uuucugccug | uccuaaggcc | uccccaggua | ccaaccccgu | agcuaucugg gucuguuugg | 4260 |
| cacuguggau | ucucaagggc | cuagaacccu | ugcucugaa | acuggccgc uggugcagcc | 4320 |
| cugcugucug | cagcuccugc | ccauaccccc | agcccacacc | aggccaggcc cacuccgggc | 4380 |
| ucaccacccu | cugcagccuu | guggggcucu | cccagcccu | ccagaagccc acccacuuc | 4440 |
| ucgccaaccc | ccgaucucua | aaugaggccu | gagcgucacc | cuaguucugc cccuuuuag | 4500 |
| cuguguagac | uuggacgaga | cauuugacuu | cccuuucucc | uugcuauaa aauguggaca | 4560 |
| guggacgucu | gucacccaag | agaguugugg | gagacaagau | cacagcuaug agcaccucgc | 4620 |
| acggugucca | ggaugcacag | cacaauccau | gaugcguuuu | ucccccuuac gcacuuugaa | 4680 |
| acccaugcua | gaaaagugaa | uacaucugac | ugugcuccac | ccaacccucc agccuggaug | 4740 |
| ucccugucug | ggcccuuuuu | cuguuuuua | uucuauguuc | agcaccacug gcaccaaaua | 4800 |
| cauuuaauu | caccgaaagc | aaaaaaaaaa | aaaaaaa | | 4837 |

<210> SEQ ID NO 10
<211> LENGTH: 2099
<212> TYPE: DNA
<213> ORGANISM: homo sapien

<400> SEQUENCE: 10

```
ccaccucagc cccaacccca accccagccg caucccccugc cccagcugac gggucaaagc      60
cucaggagag uguggcucuc cccaggcgcu accaggaggg caggucuca gccagcuggg       120 gaaaccuuau ugccaugguu cuuagaagcc accccuuccc caggcaagac aggcccaag       180 ggaguguccc gagggcgguu cccgggagcc ccguggaguc cagcacuucc acacacucug      240
aggacagaca cggcccccucu ucuucagugg ggacagucau agggacaggu acaggggcc     300 ugguugaggc uggaggucag ccacagccaa gaagcuccga gaccaacgga ucgcccagcc    360
cagacccucc cccaggccua agaggagagg gaaccaggga gaaaagucua gacccgcugc    420
cccaagccgc gaugcccagg ggccccgcac agcccccgc gcagaggccg ccuggccccg     480
cggccuccuc cucugcgagg cgcucacagc cgguacccca gcuacggaaa cgcagcaggu     540
gcgaaaucgc cccgagcucg gagcaggagg ucaggccggc cgccucgggg gacccucaag    600
gggaggcgcc ggggggagggg ggcagcccug ccggccgcag cggggcgcuc acggaaaagc   660
aggaggaggc ccggaagcuc auggguguuuc ugcagaggcc cggggguugg ggggugugug   720
aggggccccg gaagcccagc ucccgggccc uggagcccgc cacggcggca gcccugcggc    780
ggcggcugga ccugggcagu ugccuggacg ugcuggccuu ugcccagcag cacgagagac    840
ccggccuggc gcaggagacc uacgcgcuga ugagcgacaa ccugcugcga gugcugggag    900
acccgugccu cuaccgccgg cugagcgcgg ccgaccgcga gcgcauccuc agccugcgga    960
ccggccgggg ccgggcggug cugggcgucc ucguacugcc cagccucuac caggggggcc   1020
gcucagggcu cccagggggc ccucguggcg aggagccucc ucggcggcc ccugugucc     1080 ugccucuacc ugcgcaccug cauguguuca accccgggga gaacaccugg cggcccccuga  1140 cccaggugcc cgaggaggcc ccgcuucggg gcugcggucu cugcaccaug cacaacuacc   1200
uguuucuggc ggggggcauc cguggcuccg gugccaaggc cgucugcucc aacgaggucu   1260
ucugcuacaa cccucugacc aacaucugga gccagguucg gcccaugcag caggcccgag   1320
cccagcucaa gcuggguggcc cuggacgggc ugcucuaugc caucggguggc gaaugccugu   1380 acagcaugga gugcuacgac ccgcgaacag acgccuggac cccacgcgcg ccacuccccg   1440
caggcaccuu cccugugggcc cacgaggcug uggccugccg uggggacauc uacgucaccg   1500
ggggucaccu cuucuaccgc cugcucaggu acagccccgu gaaggaugcu ugggacgagu   1560
gcccauacag ugccagccac cggcguucca gcgacaucgu ggcacugggg ggcuuccugu   1620
accgcuucga ccugcugcgg ggcaugggcg ccgccgugau gcgcuacaac acagugaccg   1680
gcuccuggag cagggcugcc ucccugcccc ugcccgcccc cgcccacugu cacugcacca   1740
cccugggcaa caccauuuac ugccucaacc cccaggucac ugccaccuuc acggucucug   1800 ggggacugc ccaguccag gccaaggagc ugcagcccuu cccuugggg agcaccgggg    1860 uccucaguccc auucauccug acucugcccc cugaggaccg gcugcagacc ucacucugag   1920
uggcaggcag agaaccaaag cugcuucgcu gcucuccagg gagacccucc ugggaugggc   1980
cugagaggcc ggggcucagg aaggggcug ggaucggaac uuccugcucu uguuucugga    2040
caacuucccc cuucugcuuu aaagguugu gauuauuug aaaaaaaaaa aaaaaaaa       2099
```

<210> SEQ ID NO 11
<211> LENGTH: 5125
<212> TYPE: DNA
<213> ORGANISM: homo sapien

<400> SEQUENCE: 11

-continued

```
agaagcaggt tggctgtgat gacagcacag agctcaggaa cgctgcctga ggaccctggg      60
gcctacgagg aggagaagag ggcaggagct ggtggggtgc ttgcagagac cctgggctcc     120
tatcctgcca taagcctcgc tgtctcctga tatctgcagc caggccctac tgacaccccc     180
aggcctgagt gcaagcagag accccaccat tcccaggccc tggaggactg gtccacctta     240
actgggcagc ccttggggca ggcgctggcc ggtgcctcag cccaggcctc tgtgctctgc     300
atgcactgcc agcctgccat caggcctcta ttgcagccct gaaccatgat ccagggcacc     360
ttggagccag atggtcccct ctggggctgg gactgggaca gtgacaatga ctgggatagt     420
gctgtgctgg ccctcctggc gctggctgtg gtggctgcca cagcgctggc cttacactgg     480
tttggctccg ggcacgatca agaggcggca gaaccggtgt ccacagccct cggggctcaa     540
cctcatcagg caggaggagc tgagctggcc ctgcaaccga agtctaaggt cagtgatggc     600
agcgaggggc agagcccagg gcaggggaaa ccagagcccc caggacgcgg ccagcagagc     660
cctgtccctg ctgcagcgcc gggcgggggc ctggccgcca tggcccggct tccactcaag     720
acggctgtcg aggaggcccg cagagaggca ttaggacagc aacggggcag tgccaccccc     780
gcggcccccc gagcggaagg aaaggagcct cccaggccag gcactgccct cctgggcagg     840
agcgaagcag gggggatgtc cgcccccctc ctgatccact tcactcctcg gagccctggc     900
agcgaagcgg aggcggagac aggtggtgtc agggcgtcct ctcgccaggc cgcaggcccc     960
gcggggcaac aggacactgg cccctggcag gcgggcgcgg ggcctcgggg ctcgatgggg    1020
agaggccggg gccggcggcg gcggatggac gctggctcgg gagacagagc cgccgccccc    1080
cggaaactgg acccgctccg cctgggcgcc gcggggagcg tgtgggacgc ggtggacggg    1140
gccgccgccc tggacgccca cgcgcgcggc ctccccacag accccccact cgcccaggag    1200
cccgcactcc cggcgctgcc cgctccccgc gccctgcagc ctgggtctca gacgaaggc    1260 tctggggcca agggtggctg gagcaggag gcctcggggg tccctgcccc cggaggaggc    1320
tggccctggg tcagcaggga ggtcccggcc accggagct ttggcccagc ccagactcc    1380 acgcgcccct ggctagagag tccgcctcaa ggtcgcccac tctcgtccca agggccgggt    1440
gccacagggg cctacgatgc cggcgaggcc ggggctgaca gctcccgaga taacagtcct    1500
gccgctgacc tggggcccac ccggcccccg gagcaagcaa agccggctgc agccggccac    1560
agccgcgcgc cctcccggag ccgtgagcct cgcccgcgct ccgcctcccc gcccgcagct    1620
cccggcccgg ggttcccacc tgaagccctg actctccct ctccttcaga cttttgccc     1680 ctggaggtta cccaggatcc ttccgtgggc gaaaatctca gagcggcgcc agccccaagt    1740
tcagcctcag cccaagtctt aacttcagct ccagcctcag tcctagcccc agccctggct    1800
tcatccccca gctcagcacc aacctcagcc accacctcaa cctcatcccc cacctcagcc    1860
ccagccccag ctccaacctc agctccaact tcaaccccag ccccagcccc aagtccagct    1920
gcagccgcaa ctccagcccc agcccagtc ccagtcccaa cctcacacc ccatcccca      1980 gccctaaccc cagtcccaac cccagcccta agcccagctc caactccagc cctaacccca    2040
gccgcatccc cagccctaac cccagtccca accccagccc taagcccagc tccaactcca    2100
gccccaaccc cagccgcatc cctgccccca gcccccacct cagccccaac cccaacccca    2160
gccgcatccc ctgccccagc tgacgggtca agcctcagg agagtgtggc tctccccagg    2220
cgctaccagg aggggcaggt ctcagccagc tggggaaacc ttattgccat ggttcttaga    2280
agccaccctt tccccaggca agacaggccc caagggagtg tcccgagggc ggttcccggg    2340
agccccgtgg gtcccagcac ttccacacac tctgaggaca gacacggccc ctcttcttca    2400
```

```
gtggggacag tcatagggac aggtacaggg ggcctggttg aggctggagg tcagccacag    2460
ccaagaagct ccgagaccaa cggatcgccc agcccagacc ctcccccagg cctaagagga    2520
gaggaaacca gggagaaaag tctagacccg ctgccccaag ccgcgatgcc caggggcccc    2580
gcacagcccc ccgcgcagag gccgcctggc cccgcggcct cctcctctgc gaggcgctca    2640
cagccggtac cccagctacg aaacgcagc aggtgcgaaa tcgccccgag ctcggagcag     2700
gaggtcaggc cggccgcctc ggggaccct caaggggagg cgccggggga ggggggcagc    2760
cctgccggcc gcagcggggc gctcacggaa aagcaggagg aggcccggaa gctcatggtg    2820
tttctgcaga ggcccggggg ttgggggtg gtggaggggc cccggaagcc cagctcccgg     2880
gccctggagc ccgccacggc ggcagccctg cggcggcggc tggacctggg cagttgcctg    2940
gacgtgctgg cctttgccca gcagcacgga gagcccggcc tggcgcagga gacctacgcg    3000
ctgatgagcg acaacctgct gcgagtgctg ggagacccgt gcctctaccg ccggctgagc    3060
gcggccgacc gcgagcgcat cctcagcctg cggaccggcc ggggccgggc ggtgctgggc    3120
gtcctcgtac tgcccagcct ctaccagggg ggccgctcag ggctccccag ggccctcgt    3180 ggcgaggagc ctcctgcggc ggcccctgtg tccctgcctc tacctgcgca cctgcatgtg    3240
ttcaaccccc gggagaacac ctggcggccc ctgacccagg tgcccgagga ggccccgctt    3300
cggggctgcg gtctctgcac catgcacaac tacctgtttc tggcgggggg catccgtggc    3360
tccggtgcca aggccgtctg ctccaacgag gtcttctgct acaaccctct gaccaacatc    3420
tggagccagt tcggcccat gcagcaggcc cgagcccagc tcaagctggt ggccctggac    3480
gggctgctct atgccatcgg tggcgaatgc ctgtacagca tggagtgcta cgacccgcga    3540
acagacgcct ggaccccacg cgcgccactc cccgcaggca ccttccctgt ggcccacgag    3600
gctgtggcct gccgtgggga catctacgtc accgggggtc acctcttcta ccgcctgctc    3660
aggtacagcc ccgtgaagga tgcttgggac gagtgcccat acagtgccag ccaccggcgt    3720
tccagcgaca tcgtggcact ggggggcttc ctgtaccgct tcgacctgct gcggggcgtg    3780
ggcgccgccg tgatgcgcta caacacagtg accggctcct ggagcagggc tgcctccctg    3840
cccctgcccg ccccgccc actgcactgc accaccctgg caacaccat ttactgcctc      3900 aaccccagg tcactgccac cttcacggtc tctggggga ctgcccagtt ccaggccaag      3960
gagctgcagc ccttcccctt ggggagcacc ggggtcctca gtccattcat cctgactctg    4020 cccccctgagg accggctgca gacctcactc tgagtggcag gcagagaacc aaagctgctt    4080
cgctgctctc cagggagacc ctcctgggat gggcctgaga ggccggggct cagggaaggg    4140
gctgggatcg gaacttcctg ctcttgtttc tggacaactt tccccttctg ctttaaaggt    4200
tgtcgattat tttgaagccc agactccctc agcctctttc tgcccctcac tccacaccca    4260
gactgtttcc tgactcaatt ccgtacctac ttacagaccc tctcagcttg ctgacacccc    4320
cctgtctgtg ggactcccta ttccctagag ccagggacta tgcgtctccc acagacaagg    4380
acttggctcg ctggagctct gctgagccga gagaggaggg ggtagaaaac attcacactt    4440
cctatgctct gtcagcagga cagggagcaa aaacgtcccc aggcaacgcc ctcgcctctg    4500
ggactttctg cctgtcctaa ggcctcccca ggtaccaacc ccgtagctat ctgggtctgt    4560
ttggcactgt ggattctcaa gggcctagaa cccttgcctc tgaaactggt ccgctggtgc    4620
agccctgctg tctgcagctc ctgcccatac ccccagccca caccaggcca ggcccactcc    4680
gggctcacca ccctctgcag ccttgtgggg ctctcccagc ccctccagaa gcccaccca    4740
```

| | |
|---|---|
| cttctcgcca accccgatc tctaaatgag gcctgagcgt caccctagtt ctgccccttt | 4800 |
| ttagctgtgt agacttggac gagacatttg acttcccttt ctccttgtct ataaaatgtg | 4860 |
| gacagtggac gtctgtcacc aagagagtt gtgggagaca agatcacagc tatgagcacc | 4920 |
| tcgcacggtg tccaggatgc acagcacaat ccatgatgcg ttttctcccc ttacgcactt | 4980 |
| tgaaacccat gctagaaaag tgaatacatc tgactgtgct ccactccaac ctccagcctg | 5040 |
| gatgtccctg tctgggccct ttttctgttt tttattctat gttcagcacc actggcacca | 5100 |
| aatacatttt aattcaccga aagca | 5125 |

<210> SEQ ID NO 12
<211> LENGTH: 2990
<212> TYPE: DNA
<213> ORGANISM: homo sapien

<400> SEQUENCE: 12

| | |
|---|---|
| ccacctcagc cccaacccca accccagccg catcccctgc cccagctgac gggtcaaagc | 60 |
| ctcaggagag tgtggctctc cccaggcgct accaggaggg gcaggtctca gccagctggg | 120 |
| gaaaccttat tgccatggtt cttagaagcc acccctcccc caggcaagac aggcccaag | 180 |
| ggagtgtccc gagggcggtt cccggagcc ccgtgggtcc cagcacttcc acacactctg | 240 |
| aggacagaca cggcccctct tcttcagtgg ggacagtcat agggacaggt acaggggcc | 300 |
| tggttgaggc tggaggtcag ccacagccaa gaagctccga gaccaacgga tcgcccagcc | 360 |
| cagaccctcc cccaggccta agaggagagg gaaccaggga gaaaagtcta gacccgctgc | 420 |
| cccaagccgc gatgcccagg ggccccgcac agccccccgc gcagaggccg cctggccccg | 480 |
| cggcctcctc ctctgcgagg cgctcacagc cggtacccca gctacggaaa cgcagcaggt | 540 |
| gcgaaatcgc cccgagctcg gagcaggagg tcaggcggc cgcctcgggg gacccctcaag | 600 |
| gggaggcgcc gggggagggg ggcagccctg ccggccgcag cggggcgctc acggaaaagc | 660 |
| aggaggaggc ccggaagctc atggtgtttc tgcagaggcc cggggggttgg ggggtggtgg | 720 |
| aggggccccg gaagcccagc tcccgggccc tggagcccgc cacggcggca gccctgcggc | 780 |
| ggcggctgga cctgggcagt tgcctggacg tgctggcctt tgcccagcag cacgagagc | 840 |
| ccggcctggc gcaggagacc tacgcgctga tgagcgacaa cctgctgcga gtgctgggag | 900 |
| acccgtgcct ctaccgccgg ctgagcgcgg ccgaccgcga gcgcatcctc agcctgcgga | 960 |
| ccggccgggg ccgggcggtg ctgggcgtcc tcgtactgcc cagcctctac cagggggggcc | 1020 |
| gctcagggct cccagggggc cctcgtggcg aggagcctcc tgcggcggcc cctgtgtccc | 1080 |
| tgcctctacc tgcgcacctg catgtgttca accccgggga gaacacctgg cggcccctga | 1140 |
| cccaggtgcc cgaggaggcc ccgcttcggg gctgcggtct ctgcaccatg cacaactacc | 1200 |
| tgtttctggc gggggggcatc cgtggctccg gtgccaaggc cgtctgctcc aacgaggtct | 1260 |
| tctgctacaa ccctctgacc aacatctgga gccaggttcg gcccatgcag caggcccgag | 1320 |
| cccagctcaa gctggtggcc ctggacgggc tgctctatgc catcggtggc gaatgcctgt | 1380 |
| acagcatgga gtgctacgac ccgcgaacag acgcctggac cccacgcgcg ccactccccg | 1440 |
| caggcacctt ccctgtggcc cacgaggctg tggcctgccg tggggacatc tacgtcaccg | 1500 |
| ggggtcacct cttctaccgc ctgctcaggt acagccccgt gaaggatgct tgggacgagt | 1560 |
| gcccatacag tgccagccac cggcgttcca gcgacatcgt ggcactgggg ggcttcctgt | 1620 |
| accgcttcga cctgctgcgg ggcgtgggcg ccgccgtgat gcgctacaac acagtgaccg | 1680 |
| gctcctggag cagggctgcc tccctgcccc tgcccgcccc cgccccactg cactgcacca | 1740 |

| | |
|---|---|
| ccctgggcaa caccatttac tgcctcaacc cccaggtcac tgccaccttc acggtctctg | 1800 |
| gggggactgc ccagttccag gccaaggagc tgcagcccct cccctggggg agcaccgggg | 1860 |
| tcctcagtcc attcatcctg actctgcccc ctgaggaccg gctgcagacc tcactctgag | 1920 |
| tggcaggcag agaaccaaag ctgcttcgct gctctccagg gagaccctcc tgggatgggc | 1980 |
| ctgagaggcc ggggctcagg gaaggggctg ggatcggaac ttcctgctct tgtttctgga | 2040 |
| caactttccc cttctgcttt aaaggttgtc gattattttg aagcccagac tccctcagcc | 2100 |
| tctttctgcc cctcactcca cacccagact gtttcctgac tcaattccgt acctacttac | 2160 |
| agaccctctc agcttgctga cacccccctg tctgtgggac tccctattcc ctagagccag | 2220 |
| ggactgatgc gtctccacag acaaggactt ggctcgctgg agctctgctg agccgagaga | 2280 |
| ggaggggta gaaaacattc acacttccta tgctctgtca gcaggacagg gagcaaaaac | 2340 |
| gtccccaggc aacgccctcg cctctgggac tttctgcctg tcctaaggcc tccccaggta | 2400 |
| ccaacccgt agctatctgg gtctgtttgg cactgtggat tctcaagggc ctagaaccct | 2460 |
| tgcctctgaa actggtccgc tggtgcagcc ctgctgtctg cagctcctgc ccatacccc | 2520 |
| agcccacacc aggccaggcc cactccgggc tcaccaccct ctgcagcctt gtggggctct | 2580 |
| cccagcccct ccagaagccc accccacttc tcgccaaccc ccgatctcta aatgaggcct | 2640 |
| gagcgtcacc ctagttctgc ccctttttag ctgtgtagac ttggacgaga catttgactt | 2700 |
| cccttttctcc ttgtctataa aatgtggaca gtggacgtct gtcacccaag agagttgtgg | 2760 |
| gagacaagat cacagctatg agcacctcgc acggtgtcca ggatgcacag cacaatccat | 2820 |
| gatgcgtttt ctccccttac gcactttgaa acccatgcta gaaaagtgaa tacatctgac | 2880 |
| tgtgctccac tccaacctcc agcctggatg tccctgtctg ggcccttttt ctgttttta | 2940 |
| ttctatgttc agcaccactg gcaccaaata cattttaatt caccgaaagc | 2990 |

<210> SEQ ID NO 13
<211> LENGTH: 4837
<212> TYPE: DNA
<213> ORGANISM: homo sapien

<400> SEQUENCE: 13

| | |
|---|---|
| actgccagcc tgccatcagg cctctattgc agccctgaac catgatccag ggcaccttgg | 60 |
| agccagatgg tccctctgg ggctgggact gggacagtga caatgactgg gatagtgctg | 120 |
| tgctggccct cctggcgctg ctgtggtgg ctgccacagc gctggcctta cactggtttg | 180 |
| gctccgggca cgatcaagag gcggcagaac cggtgtccac agccctcggg gctcaacctc | 240 |
| atcaggcagg aggagctgag ctggccctgc aaccgaagtc taaggtcagt gatggcagcg | 300 |
| aggggcagag cccagggcag gggaaaccag agccccagg acgcggccag cagagccctg | 360 |
| tccctgctgc agcgccgggc gggggcctgg ccgccatggc ccggcttcca ctcaagacgg | 420 |
| ctgtcgagga ggcccgcaga gaggcattag acagcaacg gggcagtgcc accccgcgg | 480 |
| ccccccgagc ggaaggaaag gagcctccca ggccaggcac tgccctcctg ggcaggagcg | 540 |
| aagcaggggg gatgtccgcc cccctcctga tccacttcac tcctcggagc cctggcagcg | 600 |
| aagcggaggc ggagacaggt ggtgtcaggg cgtcctctcg ccaggccgca ggccccgcgg | 660 |
| ggcaacagga cactggcccc tgcaggcgg gcgcggggcc ctcgggctcg atggggagag | 720 |
| gccggggccg gcgcggcgg atggacgctg gctcggagaa cagagcccgc cgcccccgga | 780 |
| aactggaccc gctccgcctg ggcgccgcgg ggagcgtgtg ggacgcggtg gacggggccg | 840 |

| | |
|---|---|
| ccgccctgga cgcccacgcg cgcggcctcc ccacaggacc cccactcgcc caggagcccg | 900 |
| cactcccggc gctgcccgct ccccgcgccc tgcagcctgg gtctcagacg gaaggctctg | 960 |
| gggccaaggg tggctggagc agggaggcct cgggggtccc tgcccccgga ggaggctggc | 1020 |
| cctgggtcag cagggaggtc ccgggcaccc ggagctttgg cccagcccca gactccacgc | 1080 |
| gcccctggct agagagtccg cctcaaggtc gcccactctc gtcccaaggg ccgggtgcca | 1140 |
| caggggccta cgatgccggc gaggccgggg ctgacagctc ccgagataac agtcctgccg | 1200 |
| ctgacctggg gcccacccgg cccccggagc aagcaaagcc ggctgcagcc ggccacagcc | 1260 |
| gcgcgccctc ccggagccgt gagcctcgcc cgcgctccgc ctcccgccc gcagctcccg | 1320 |
| gcccggggtt cccacctgaa gccctgactc tcccctctcc ttcagacttt ttgcccctgg | 1380 |
| aggttaccca ggatccttcc gtgggcgaaa atctcagagc ggcgccagcc ccaagttcag | 1440 |
| cctcagccca agtcttaact tcagctccag cctcagtcct agcccagcc ctggcttcat | 1500 |
| cccccagctc agcaccaacc tcagccacca cctcaacctc atccccacc tcagcccag | 1560 |
| ccccagctcc aacctcagct ccaacttcaa ccccagcccc agcccaagt ccagctgcag | 1620 |
| ccgcaactcc agcccagcc ccagtccag tcccaaccct cacaccccca tcccagccc | 1680 |
| taaccccagt cccaacccca gccctaagcc cagctccaac tccagcccta accccagccg | 1740 |
| catccccagc cctaaccca gtcccaaccc cagccctaag cccagctcca actccagccc | 1800 |
| caaccccagc cgcatcccct gccccagccc ccacctcagc cccaacccca accccagccg | 1860 |
| catcccctgc cccagctgac gggtcaaagc ctcaggagag tgtggctctc cccaggcgct | 1920 |
| accaggaggg gcaggtctca gccagctggg gaaaccttat tgccatggtt cttagaagcc | 1980 |
| acccccttccc caggcaagac aggcccaag ggagtgtccc gagggcggtt cccgggagcc | 2040 |
| ccgtgggtcc cagcacttcc acacactctg aggacagaca cggcccctct tcttcagtgg | 2100 |
| ggacagtcat agggacaggt acaggggggcc tggttgaggc tggaggtcag ccacagccaa | 2160 |
| gaagctccga gaccaacgga tcgcccagcc cagaccctcc cccaggccta agaggagagg | 2220 |
| gaaccaggga gaaaagtcta gacccgctgc cccaagccgc gatgcccagg ggccccgcac | 2280 |
| agccccccgc gcagaggccg cctggcccg cggcctcctc ctctgcgagg cgctcacagc | 2340 |
| cggtacccca gctacggaaa cgcagcaggt gcgaaatcgc cccgagctcg gagcaggagg | 2400 |
| tcaggccggc cgcctcgggg gaccctcaag gggaggcgcc gggggagggg ggcagccctg | 2460 |
| ccggccgcag cggggcgctc acggaaaagc aggaggaggc ccggaagctc atggtgtttc | 2520 |
| tgcagaggcc cggggttgg ggggtggtgg agggcccg gaagcccagc tcccgggccc | 2580 |
| tggagcccgc cacggcggca gccctgcggc ggcggctgga cctgggcagt tgcctggacg | 2640 |
| tgctggcctt tgcccagcag cacggagagc ccggcctggc gcaggagacc tacgcgctga | 2700 |
| tgagcgacaa cctgctgcga gtgctgggag accgtgcct ctaccgccgg ctgagcgcgg | 2760 |
| ccgaccgcga gcgcatcctc agcctgcgga cggccggg ccgggcggtg ctgggcgtcc | 2820 |
| tcgtactgcc cagcctctac caggggggcc gctcagggct cccagggc cctcgtggcg | 2880 |
| aggagcctcc tgcggcggcc cctgtgtccc tgcctctacc tgcgcacctg catgtgttca | 2940 |
| accccccggga gaacacctgg cggccccgtga cccaggtgcc cgaggaggcc ccgcttcggg | 3000 |
| gctgcggtct ctgcaccatg cacaactacc tgtttctggc gggggggcatc cgtggctccg | 3060 |
| gtgccaaggc cgtctgctcc aacgaggtct tctgctacaa ccctctgacc aacatctgga | 3120 |
| gccaggttcg gcccatgcag caggcccgag cccagctcaa gctggtggcc ctggacgggc | 3180 |
| tgctctatgc catcggtggc gaatgcctgt acagcatgga gtgctacgac ccgcgaacag | 3240 |

-continued

| | |
|---|---|
| acgcctggac cccacgcgcg ccactccccg caggcaccTT ccctgtggcc cacgaggctg | 3300 |
| tggcctgccg tggggacatc tacgtcaccg ggggtcacct cttctaccgc ctgctcaggt | 3360 |
| acagccccgt gaaggatgct tgggacgagt gcccatacag tgccagccac cggcgttcca | 3420 |
| gcgacatcgt ggcactgggg ggcttcctgt accgcttcga cctgctgcgg ggcgtgggcg | 3480 |
| ccgccgtgat gcgctacaac acagtgaccg gctcctggag cagggctgcc tccctgcccc | 3540 |
| tgcccgcccc cgccccactg cactgcacca ccctgggcaa caccatttac tgcctcaacc | 3600 |
| cccaggtcac tgccaccttc acggtctctg ggggactgcc ccagttccag gccaaggagc | 3660 |
| tgcagccctt cccttgggg agcaccgggg tcctcagtcc attcatcctg actctgcccc | 3720 |
| ctgaggaccg gctgcagacc tcactctgag tggcaggcag agaaccaaag ctgcttcgct | 3780 |
| gctctccagg gagaccctcc tgggatgggc ctgagaggcc ggggctcagg gaaggggctg | 3840 |
| ggatcggaac ttcctgctct tgtttctgga caactttccc cttctgcttt aaaggttgtc | 3900 |
| gattattttg aagcccagac tccctcagcc tctttctgcc cctcactcca cacccagact | 3960 |
| gtttcctgac tcaattccgt acctacttac agaccctctc agcttgctga cacccccctg | 4020 |
| tctgtggac tccctattcc ctagagccag ggactgatgc gtctccacag acaaggactt | 4080 |
| ggctcgctgg agctctgctg agccgagaga ggaggggggta gaaaacattc acacttccta | 4140 |
| tgctctgtca gcaggacagg gagcaaaaac gtccccaggc aacgccctcg cctctgggac | 4200 |
| tttctgcctg tcctaaggcc tccccaggta ccaaccccgt agctatctgg gtctgtttgg | 4260 |
| cactgtggat tctcaagggc ctagaaccct tgcctctgaa actggtccgc tggtgcagcc | 4320 |
| ctgctgtctg cagctcctgc ccatacccc agcccacacc aggccaggcc cactccgggc | 4380 |
| tcaccaccct ctgcagcctt gtggggctct cccagcccct ccagaagccc accccacttc | 4440 |
| tcgccaaccc ccgatctcta aatgaggcct gagcgtcacc ctagttctgc ccctttttag | 4500 |
| ctgtgtagac ttggacgaga catttgactt cccttctcc ttgtctataa aatgtggaca | 4560 |
| gtggacgtct gtcacccaag agagttgtgg gagacaagat cacagctatg agcacctcgc | 4620 |
| acggtgtcca ggatgcacag cacaatccat gatgcgtttt ctcccttac gcactttgaa | 4680 |
| acccatgcta gaaaagtgaa tacatctgac tgtgctccac tccaacctcc agcctggatg | 4740 |
| tccctgtctg ggcccttttt ctgttttta ttctatgttc agcaccactg gcaccaaata | 4800 |
| cattttaatt caccgaaagc aaaaaaaaaa aaaaaaa | 4837 |

<210> SEQ ID NO 14
<211> LENGTH: 2099
<212> TYPE: DNA
<213> ORGANISM: homo sapien

<400> SEQUENCE: 14

| | |
|---|---|
| ccacctcagc cccaaccccaa accccagccg catcccctgc cccagctgac gggtcaaagc | 60 |
| ctcaggagag tgtggctctc cccaggcgct accaggaggg gcaggtctca gccagctggg | 120 |
| gaaaccttat tgccatggtt cttagaagcc acccccttccc caggcaagac aggccccaag | 180 |
| ggagtgtccc gagggcggtt cccgggagcc ccgtgggtcc cagcacttcc acacactctg | 240 |
| aggacagaca cggcccctct tcttcagtgg ggacagtcat agggacaggt acaggggcc | 300 |
| tggttgaggc tggaggtcag ccacagccaa gaagctccga gaccaacgga tcgcccagcc | 360 |
| cagaccctcc cccaggccta agaggagagg gaaccaggga gaaagtctca gacccgctgc | 420 |
| cccaagccgc gatgcccagg ggccccgcac agccccccgc gcagaggccg cctggccccg | 480 |

```
cggcctcctc ctctgcgagg cgctcacagc cggtacccca gctacggaaa cgcagcaggt    540
gcgaaatcgc cccgagctcg gagcaggagg tcaggccggc cgcctcgggg gaccctcaag    600
gggaggcgcc gggggagggg ggcagccctg ccggccgcag cggggcgctc acggaaaagc    660
aggaggaggc ccggaagctc atggtgtttc tgcagaggcc cggggggttgg ggggtggtgg    720 aggggccccg gaagcccagc tcccgggccc tggagcccgc cacggcggca gccctgcggc    780
ggcggctgga cctgggcagt tgcctggacg tgctggcctt tgcccagcag cacggagagc    840
ccggcctggc gcaggagacc tacgcgctga tgagcgacaa cctgctgcga gtgctgggag    900
acccgtgcct ctaccgccgg ctgagcgcgg ccgaccgcga gcgcatcctc agcctgcgga    960
ccggccgggg ccgggcggtg ctgggcgtcc tcgtactgcc cagcctctac caggggggcc    1020
gctcagggct ccccagggc cctcgtggcg aggagcctcc tgcggcggcc cctgtgtccc    1080
tgcctctacc tgcgcacctg catgtgttca accccggga gaacacctgg cggcccctga    1140
cccaggtgcc cgaggaggcc ccgcttcggg gctgcggtct ctgcaccatg cacaactacc    1200
tgtttctggc gggggcatc cgtggctccg gtgccaaggc cgtctgctcc aacgaggtct    1260
tctgctacaa ccctctgacc aacatctgga gccaggttcg gcccatgcag caggcccgag    1320
cccagctcaa gctggtggcc ctggacgggc tgctctatgc catcggtggc gaatgcctgt    1380
acagcatgga gtgctacgac ccgcgaacag acgcctggac cccacgcgcg ccactccccg    1440
caggcacctt ccctgtggcc acgaggctg tggcctgccg tggggacatc tacgtcaccg    1500
ggggtcacct cttctaccgc ctgctcaggt acagccccgt gaaggatgct tgggacgagt    1560
gcccatacag tgccagccac cggcgttcca gcgacatcgt ggcactgggg ggcttcctgt    1620
accgcttcga cctgctgcgg ggcgtgggcg ccgccgtgat gcgctacaac acagtgaccg    1680
gctcctggag cagggctgcc tccctgcccc tgcccgcccc cgcccactg cactgcacca    1740 ccctgggcaa caccatttac tgcctcaacc cccaggtcac tgccaccttc acggtctctg    1800 ggggactgc ccagttccag gccaaggagc tgcagccctt ccccttgggg agcaccgggg    1860
tcctcagtcc attcatcctg actctgcccc ctgaggaccg gctgcagacc tcactctgag    1920
tggcaggcag agaaccaaag ctgcttcgct gctctccagg gagaccctcc tgggatgggc    1980
ctgagaggcc ggggctcagg gaaggggctg ggatcggaac ttcctgctct tgtttctgga    2040
caactttccc cttctgcttt aaaggttgtc gattattttg aaaaaaaaaa aaaaaaaaa    2099
```

<210> SEQ ID NO 15
<211> LENGTH: 5125
<212> TYPE: DNA
<213> ORGANISM: homo sapien

<400> SEQUENCE: 15

```
agaagcaggt tggctgtgat gacagcacag agctcaggaa cgctgcctga ggaccctggg    60
gcctacgagg aggagaagag ggcaggagct ggtggggtgc ttgcagagac cctgggctcc    120
tatcctgcca taagcctcgc tgtctcctga tatctgcagc caggcccttac tgacaccccc    180 aggcctgagt gcaagcagag accccaccat tcccaggccc tggaggactg gtccaccttta    240 actgggcagc ccttggggca ggcgctgccc ggtgcctcag cccaggcctc tgtgctctgc    300
atgcactgcc agcctgccat caggcctcta ttgcagccct gaaccatgat ccagggcacc    360
ttggagccag atggtcccct ctggggctgg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
```

```
cctcatcagg caggaggagc tgagctggcc ctgcaaccga agtctaaggt cagtgatggc    600
agcgaggggc agagcccagg gcagggaaaa ccagagcccc caggacgcgg ccagcagagc    660
cctgtccctg ctgcagcgcc gggcggggc ctggccgcca tggcccggct tccactcaag    720
acggctgtcg aggaggcccg cagagaggca ttaggacagc aacggggcag tgccaccccc    780 gcggccccc gagcggaagg aaaggagcct cccaggccag gcactgccct cctgggcagg    840
agcgaagcag gggggatgtc cgccccctc ctgatccact tcactcctcg gagccctggc    900
agcgaagcgg aggcggagac aggtggtgtc agggcgtcct ctcgccaggc cgcaggcccc    960
gcggggcaac aggacactgg cccctggcag gcgggcgcgg ggccctcggg ctcgatgggg   1020
agaggccggg gccggcggcg gcggatggac gctggctcgg gagacagagc ccgccgcccc   1080
cggaaactgg acccgctccg cctgggcgcc gcggggagcg tgtgggacgc ggtggacggg   1140
gccgccgccc tggacgccca cgcgcgcggc ctccccacag gaccccact cgcccaggag   1200 cccgcactcc cggcgctgcc cgctccccgc gccctgcagc ctgggtctca gacggaaggc   1260
tctggggcca agggtggctg gagcaggag gcctcggggg tccctgcccc cggaggaggc   1320
tggccctggg tcagcaggga ggtcccggc accggagct ttggcccagc cccagactcc   1380
acgcgcccct ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tggggcccac ccggccccg gagcaagcaa agccggctgc agccggccac   1560
agccgcgcgc cctcccggag ccgtgagcct cgcccgcgct ccgcctcccc gcccgcagct   1620
cccggcccgg ggttcccacc tgaagccctg actctcccct ctccttcaga cttttgccc   1680 ctggaggtta cccaggatcc ttccgtgggc gaaaatctca gagcggcgcc agccccaagt   1740
tcagcctcag cccaagtctt aacttcagct ccagcctcag tcctagcccc agccctggct   1800
tcatccccca gctcagcacc aacctcagcc accactcaa cctcatcccc cacctcagcc   1860
ccagccccag ctccaacctc agctccaact tcaaccccag ccccagcccc aagtccagct   1920
gcagccgcaa ctccagcccc agcccagtc ccagtcccaa ccctcacacc ccatccccca   1980
gccctaaccc cagtcccaac cccagcccta agcccagctc caactccagc ctaaccccca   2040
gccgcatccc cagccctaac cccagtccca accccagccc taagcccagc tccaactcca   2100
gccccaaccc cagccgcatc ccctgcccca gcccccacct cagccccaac cccaaccca   2160 gccgcatccc ctgccccagc tgacgggtca aagcctcagg agagtgtggc tctcccagg   2220 cgctaccagg aggggcaggt ctcagccagc tggggaaacc ttattgccat ggttcttaga   2280 agccaccct tccccaggca agacaggccc caagggagtg tcccgagggc ggttccgggg   2340
agccccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctcccccagg cctaagagga   2520
gagggaacca gggagaaaag tctagacccg ctgccccaag ccgcgatgcc cagggcccc   2580 gcacagcccc ccgcgcagag gccgcctggc cccgcggcct cctcctctgc gaggcgctca   2640
cagccggtac cccagctacg gaaacgcagc aggtgcgaaa tcgccccgag ctcggagcag   2700
gaggtcaggc cggccgcctc gggggaccct caagggagg cgccgggga gggggggcagc   2760 cctgccggcc gcagcgggc gctcacggaa aagcaggagg aggcccggaa gctcatggtg   2820
tttctgcaga ggcccggggg ttggggggtg gtggagggc cccggaagcc cagctcccgg   2880
```

-continued

```
gccctggagc cgccacggc ggcagccctg cggcggcggc tggacctggg cagttgcctg    2940
gacgtgctgg cctttgccca gcagcacgga gagcccggcc tggcgcagga gacctacgcg    3000
ctgatgagcg acaacctgct gcgagtgctg ggagacccgt gcctctaccg ccggctgagc    3060
gcggccgacc gcgagcgcat cctcagcctg cggaccggcc ggggccgggc ggtgctgggc    3120
gtcctcgtac tgcccagcct ctaccagggg ggccgctcag ggctccccag ggccctcgt     3180
ggcgaggagc ctcctgcggc ggccctgtg tccctgcctc tacctgcgca cctgcatgtg     3240
ttcaaccccc gggagaacac ctggcggccc ctgacccagg tgcccgagga ggccccgctt    3300
cggggctgcg gtctctgcac catgcacaac tacctgtttc tggcggggg catccgtggc    3360
tccggtgcca aggccgtctg ctccaacgag gtcttctgct acaaccctct gaccaacatc    3420
tggagccagg ttcggcccat gcagcaggcc cgagcccagc tcaagctggt ggccctggac    3480
gggctgctct atgccatcgg tggcgaatgc ctgtacagca tggagtgcta cgacccgcga    3540
acagacgcct ggaccccacg cgcgccactc cccgcaggca ccttccctgt ggcccacgag    3600
gctgtggcct gccgtgggga catctacgtc accgggggtc acctcttcta ccgctgctc    3660
aggtacagcc ccgtgaagga tgcttgggac gagtgcccat acagtgccag ccaccggcgt    3720
tccagcgaca tcgtggcact gggggggcttc ctgtaccgct tcgacctgct gcggggcatg    3780
ggcgccgccg tgatgcgcta caacacagtg accggctcct ggagcagggc tgcctccctg    3840
cccctgcccg ccccgccc actgcactgc accaccctgg caacaccat ttactgcctc      3900
aacccccagg tcactgccac cttcacggtc tctgggggga ctgcccagtt ccaggccaag    3960
gagctgcagc ccttcccctt ggggagcacc ggggtcctca gtccattcat cctgactctg    4020
cccctgagg accggctgca gacctcactc tgagtggcag gcagagaacc aaagctgctt     4080
cgctgctctc cagggagacc ctcctgggat gggcctgaga ggccggggct cagggaaggg    4140
gctgggatcg gaacttcctg ctcttgtttc tggacaactt tccccttctg ctttaaaggt    4200
tgtcgattat tttgaagccc agactccctc agcctcttc tgcccctcac tccacaccca    4260
gactgtttcc tgactcaatt ccgtacctac ttacagaccc tctcagcttg ctgacacccc    4320
cctgtctgtg ggactcccta ttccctagag ccagggactg atgcgtctcc acagacaagg    4380
acttggctcg ctggagctct gctgagccga gagaggaggg ggtagaaaac attcacactt    4440
cctatgctct gtcagcagga cagggagcaa aaacgtcccc aggcaacgcc ctcgcctctg    4500
ggactttctg cctgtcctaa ggcctcccca ggtaccaacc ccgtagctat ctgggtctgt    4560
ttggcactgt ggattctcaa gggcctagaa cccttgcctc tgaaactggt ccgctggtgc    4620
agccctgctg tctgcagctc ctgcccatac ccccagccca caccaggcca ggcccactcc    4680
gggctcacca ccctctgcag ccttgtgggg ctctcccagc ccctcagaa gcccacccca    4740
cttctcgcca accccgatc tctaaatgag gcctgagcgt caccctagtt ctgcccttt     4800
ttagctgtgt agacttggac gagacatttg acttcccttt ctccttgtct ataaaatgtg    4860
gacagtggac gtcgtcacc caagagagtt gtgggagaca agatcacagc tatgagcacc    4920
tcgcacggtg tccaggatgc acagcacaat ccatgatgcg ttttctcccc ttacgcactt    4980
tgaaacccat gctagaaaag tgaatacatc tgactgtgct ccactccaac ctccagcctg    5040
gatgtccctg tctgggccct ttttctgttt tttattctat gttcagcacc actggcacca    5100
aatacatttt aattcaccga aagca                                          5125
```

<210> SEQ ID NO 16
<211> LENGTH: 2990

```
<212> TYPE: DNA
<213> ORGANISM: homo sapien

<400> SEQUENCE: 16
ccacctcagc cccaacccca accccagccg catcccctgc ccagctgac gggtcaaagc      60 ctcaggagag tgtggctctc cccaggcgct accaggaggg gcaggtctca gccagctggg     120
gaaaccttat tgccatggtt cttagaagcc accccttccc caggcaagac aggcccaag      180 ggagtgtccc gagggcggtt cccgggagcc ccgtgggtcc cagcacttcc acacactctg     240
aggacagaca cggcccctct tcttcagtgg ggacagtcat agggacaggt acaggggggcc    300 tggttgaggc tggaggtcag ccacagccaa gaagctccga gaccaacgga tcgcccagcc     360
cagaccctcc cccaggccta agaggagagg gaaccaggga gaaaagtcta gacccgctgc     420
cccaagccgc gatgcccagg ggccccgcac agccccccgc gcagaggccg cctgcccccg     480
cggcctcctc ctctgcgagg cgctcacagc cggtacccca gctacggaaa cgcagcaggt     540
gcgaaatcgc cccgagctcg gagcaggagg tcaggccggc cgcctcgggg gaccctcaag    600
gggaggcgcc gggggagggg ggcagccctg ccggccgcag cggggcgctc acggaaaagc     660
aggaggaggc ccggaagctc atggtgtttc tgcagaggcc cggggggttgg ggggtggtgg    720 aggggccccg gaagcccagc tcccgggccc tggagcccgc cacggcggca gccctgcggc    780
ggcggctgga cctgggcagt tgcctggacg tgctggcctt tgcccagcag cacgagagc      840 ccggcctggc gcaggagacc tacgcgctga tgagcgacaa cctgctgcga gtgctgggag     900
acccgtgcct ctaccgccgg ctgagcgcgg ccgaccgcga gcgcatcctc agcctgcgga     960
ccggccgggg ccgggcggtg ctgggcgtcc tcgtactgcc cagcctctac caggggggcc    1020
gctcagggct cccagggggc cctcgtggcg aggagcctcc tgcggcggcc cctgtgtccc    1080
tgcctctacc tgcgcacctg catgtgttca accccgggga gaacacctgg cggcccctga    1140
cccaggtgcc cgaggaggcc ccgcttcggg gctgcggtct ctgcaccatg cacaactacc    1200
tgtttctggc gggggggcatc cgtggctccg gtgccaaggc cgtctgctcc aacgaggtct    1260
tctgctacaa ccctctgacc aacatctgga gccaggttcg gcccatgcag caggcccgag    1320
cccagctcaa gctggtggcc ctggacgggc tgctctatgc catcggtggc gaatgcctgt    1380
acagcatgga gtgctacgac ccgcgaacag acgcctggac cccacgcgcg ccactcccg     1440 caggcaccctt ccctgtggcc cacgaggctg tggcctgccg tggggacatc tacgtcaccg    1500
ggggtcacct cttctaccgc ctgctcaggt acagccccgt gaaggatgct tgggacgagt    1560
gcccatacag tgccagccac cggcgttcca gcgacatcgt ggcactgggg ggcttcctgt    1620
accgcttcga cctgctgcgg ggcatgggcg ccgccgtgat gcgctacaac acagtgaccg    1680
gctcctggag cagggctgcc tccctgcccc tgcccgcccc cgccccactg cactgcacca    1740
ccctgggcaa caccatttac tgcctcaacc cccaggtcac tgccaccttc acggtctctg    1800 ggggggactgc ccagttccag gccaaggagc tgcagccctt ccccttgggg agcaccgggg    1860
tcctcagtcc attcatcctg actctgcccc ctgaggaccg gctgcagacc tcactctgag    1920
tggcaggcag agaaccaaag ctgcttcgct gctctccagg gagaccctcc tgggatgggc    1980
ctgagaggcc ggggctcagg gaaggggctg ggatcggaac ttcctgctct tgtttctgga    2040
caactttccc cttctgcttt aaaggttgtc gattattttg aagcccagac tccctcagcc    2100
tctttctgcc cctcactcca cacccagact gtttcctgac tcaattccgt acctacttac    2160
agaccctctc agcttgctga caccccccctg tctgtgggac tccctattcc ctagagccag    2220
```

-continued

| | | |
|---|---|---|
| ggactgatgc gtctccacag acaaggactt ggctcgctgg agctctgctg agccgagaga | 2280 | |
| ggagggggta gaaaacattc acacttccta tgctctgtca gcaggacagg gagcaaaaac | 2340 | |
| gtccccaggc aacgccctcg cctctgggac tttctgcctg tcctaaggcc tccccaggta | 2400 | |
| ccaaccccgt agctatctgg gtctgtttgg cactgtggat tctcaagggc ctagaaccct | 2460 | |
| tgcctctgaa actggtccgc tggtgcagcc ctgctgtctg cagctcctgc ccatacccc | 2520 | |
| agcccacacc aggccaggcc cactccgggc tcaccaccct ctgcagcctt gtgggctct | 2580 | |
| cccagcccct ccagaagccc accccacttc tcgccaaccc ccgatctcta aatgaggcct | 2640 | |
| gagcgtcacc ctagttctgc ccctttttag ctgtgtagac ttggacgaga catttgactt | 2700 | |
| cccttctcc ttgtctataa aatgtggaca gtggacgtct gtcacccaag agagttgtgg | 2760 | |
| gagacaagat cacagctatg agcacctcgc acggtgtcca ggatgcacag cacaatccat | 2820 | |
| gatgcgtttt ctccccttac gcactttgaa acccatgcta gaaaagtgaa tacatctgac | 2880 | |
| tgtgctccac tccaacctcc agcctggatg tccctgtctg ggcccttttt ctgttttta | 2940 | |
| ttctatgttc agcaccactg gcaccaaata cattttaatt caccgaaagc | 2990 | |

<210> SEQ ID NO 17
<211> LENGTH: 4837
<212> TYPE: DNA
<213> ORGANISM: homo sapien

<400> SEQUENCE: 17

| | | |
|---|---|---|
| actgccagcc tgccatcagg cctctattgc agccctgaac catgatccag ggcaccttgg | 60 | |
| agccagatgg tccCctctgg ggctgggact gggacagtga caatgactgg gatagtgctg | 120 | |
| tgctggccct cctggcgctg ctgtggtgg ctgccacagc gctggcctta cactggtttg | 180 | |
| gctccgggca cgatcaagag gcggcagaac cggtgtccac agccctcggg gctcaacctc | 240 | |
| atcaggcagg aggagctgag ctggccctgc aaccgaagtc taaggtcagt gatggcagcg | 300 | |
| aggggcagag cccagggcag gggaaaccag agccccagg acgcggccag cagagccctg | 360 | |
| tccctgctgc agcgccgggc gggggcctgg ccgccatggc ccggcttcca ctcaagacgg | 420 | |
| ctgtcgagga ggcccgcaga gaggcattag acagcaacg gggcagtgcc accccccgcgg | 480 | |
| cccccgagc ggaaggaaag gagcctccca ggccaggcac tgccctcctg ggcaggagcg | 540 | |
| aagcaggggg gatgtccgcc ccctcctga tccacttcac tcctcggagc cctggcagcg | 600 | |
| aagcggaggc ggagacaggt ggtgtcaggg cgtcctctcg ccaggccgca ggccccgcgg | 660 | |
| ggcaacagga cactggcccc tgcaggcgg gcgcggggcc ctcgggctcg atggggagag | 720 | |
| gccggggccg gcggcggcgg atggacgctg gctcgggaga cagagcccgc cgcccccgga | 780 | |
| aactggaccc gctccgcctg ggcgccgcgg ggagcgtgtg ggacgcggtg gacgggggccg | 840 | |
| ccgccctgga cgcccacgcg cgcggcctcc ccacaggacc cccactcgcc caggagcccg | 900 | |
| cactcccggc gctgcccgct ccccgcgcc tgcagcctgg gtctcagacg gaaggctctg | 960 | |
| gggccaaggg tggctggagc agggaggcct cgggggtccc tgcccccgga ggaggctggc | 1020 | |
| cctgggtcag cagggaggtc ccgggcaccc ggagctttgg cccagcccca gactccacgc | 1080 | |
| gcccctggct agagagtccg cctcaaggtc gccactctc gtcccaaggg ccgggtgcca | 1140 | |
| caggggccta cgatgccggc gaggccgggg ctgacagctc ccgagataac agtcctgccg | 1200 | |
| ctgacctggg gccacccggg cccggagc aagcaaagcc ggctgcagcc ggccacagcc | 1260 | |
| gcgcgccctc ccggagccgt gagcctcgcc cgcgctccgc ctccccgccc gcagctcccg | 1320 | |
| gcccgggggtt cccacctgaa gccctgactc tcccctctcc ttcagacttt ttgccctgg | 1380 | |

```
aggttaccca ggatccttcc gtgggcgaaa atctcagagc ggcgccagcc ccaagttcag    1440
cctcagccca agtcttaact tcagctccag cctcagtcct agcccagcc ctggcttcat    1500 cccccagctc agcaccaacc tcagccacca cctcaacctc atccccacc tcagccccag    1560 ccccagctcc aacctcagct ccaacttcaa ccccagcccc agcccaagt ccagctgcag    1620 ccgcaactcc agcccagcc ccagtcccag tcccaaccct cacacccca tcccagccc    1680 taacccagt cccaacccca gccctaagcc cagctccaac tccagcccta ccccagccg    1740 catccccagc cctaacccca gtcccaaccc cagccctaag cccagctcca actccagccc    1800
caaccccagc cgcatcccct gccccagccc ccacctcagc ccaaccccca accccagccg    1860
catcccctgc cccagctgac gggtcaaagc ctcaggagag tgtggctctc cccaggcgct    1920
accaggaggg gcaggtctca gccagctggg gaaaccttat tgccatggtt cttagaagcc    1980
acccCttccc caggcaagac aggccccaag ggagtgtccc gagggcggtt cccgggagcc    2040
ccgtgggtcc cagcacttcc acacactctg aggacagaca cggcccctct tcttcagtgg    2100
ggacagtcat agggacaggt acaggggcc tggttgaggc tggaggtcag ccacagccaa    2160
gaagctccga gaccaacgga tcgcccagcc cagaccctcc cccaggccta agaggagagg    2220
gaaccaggga gaaaagtcta gacccgctgc cccaagccgc gatgcccagg ggccccgcac    2280 agccccgc gcagaggccg cctggccccg cggcctcctc ctctgcgagg cgctcacagc    2340
cggtacccca gctacggaaa cgcagcaggt gcgaaatcgc cccgagctcg gagcaggagg    2400
tcaggccggc cgcctcgggg gaccctcaag gggaggcgcc gggggagggg ggcagccctg    2460
ccggccgcag cggggcgctc acggaaaagc aggaggaggc ccggaagctc atggtgtttc    2520
tgcagaggcc cggggttgg ggggtggtgg aggggccccg gaagcccagc tcccgggccc    2580
tggagcccgc cacggcggca gccctgcggc ggcggctgga cctgggcagt tgcctggacg    2640
tgctggcctt tgcccagcag cacgagagc ccggcctggc gcaggagacc tacgcgctga    2700
tgagcgacaa cctgctgcga gtgctgggag acccgtgcct ctaccgccgg ctgagcgcgg    2760
ccgaccgcga gcgcatcctc agcctgcgga ccggccgggg ccgggcggtg ctgggcgtcc    2820
tcgtactgcc cagcctctac cagggggggcc gctcagggct cccagggggc cctcgtggcg    2880
aggagcctcc tgcggcggcc cctgtgtccc tgcctctacc tgcgcacctg catgtgttca    2940 accccccggga gaacacctgg cggccccctga cccaggtgcc cgaggaggcc ccgcttcggg    3000
gctgcggtct ctgcaccatg cacaactacc tgtttctggc gggggggcatc cgtggctccg    3060 gtgccaaggc cgtctgctcc aacgaggtct tctgctacaa ccctctgacc aacatctgga    3120
gccaggttcg gccatgcag cagccccgag cccagctcaa gctggtggcc ctggacgggc    3180
tgctctatgc catcggtggc gaatgcctgt acagcatgga gtgctacgac ccgcgaacag    3240
acgcctggac cccacgcgcg ccactccccg caggcacctt ccctgtggcc cacgaggctg    3300
tggcctgccg tggggacatc tacgtcaccg ggggtcacct cttctaccgc ctgctcaggt    3360
acagccccgt gaaggatgct tgggacgagt gcccatacag tgccagccac cggcgttcca    3420
gcgacatcgt ggcactgggg ggcttcctgt accgcttcga cctgctgcgg ggcatgggcg    3480
ccgccgtgat gcgctacaac acagtgaccg gctcctggag cagggctgcc tccctgcccc    3540
tgcccgcccc cgccccactg cactgcacca cctgggcaa caccatttac tgcctcaacc    3600
cccaggtcac tgccaccttc acggtctctg gggggactgc ccagttccag gccaaggagc    3660 tgcagcccctt cccctgggg agcaccgggg tcctcagtcc attcatcctg actctgcccc    3720
```

| | |
|---|---|
| ctgaggaccg gctgcagacc tcactctgag tggcaggcag agaaccaaag ctgcttcgct | 3780 |
| gctctccagg gagaccctcc tgggatgggc ctgagaggcc ggggctcagg gaaggggctg | 3840 |
| ggatcggaac ttcctgctct tgtttctgga caactttccc cttctgcttt aaaggttgtc | 3900 |
| gattattttg aagcccagac tccctcagcc tctttctgcc cctcactcca cacccagact | 3960 |
| gtttcctgac tcaattccgt acctacttac agaccctctc agcttgctga cacccccctg | 4020 |
| tctgtgggac tccctattcc ctagagccag ggactgatgc gtctccacag acaaggactt | 4080 |
| ggctcgctgg agctctgctg agccgagaga ggaggggggta gaaaacattc acacttccta | 4140 |
| tgctctgtca gcaggacagg gagcaaaaac gtccccaggc aacgccctcg cctctgggac | 4200 |
| tttctgcctg tcctaaggcc tccccaggta ccaacccccgt agctatctgg gtctgtttgg | 4260 |
| cactgtggat tctcaagggc ctagaaccct tgcctctgaa actggtccgc tggtgcagcc | 4320 |
| ctgctgtctg cagctcctgc ccatacccccc agcccacacc aggccaggcc cactccgggc | 4380 |
| tcaccaccct ctgcagcctt gtggggctct cccagcccct ccagaagccc accccacttc | 4440 |
| tcgccaaccc ccgatctcta aatgaggcct gagcgtcacc ctagttctgc ccctttttag | 4500 |
| ctgtgtagac ttggacgaga catttgactt ccctttctcc ttgtctataa aatgtggaca | 4560 |
| gtggacgtct gtcacccaag agagttgtgg gagacaagat cacagctatg agcacctcgc | 4620 |
| acggtgtcca ggatgcacag cacaatccat gatgcgtttt ctccccttac gcactttgaa | 4680 |
| acccatgcta gaaaagtgaa tacatctgac tgtgctccac tccaacctcc agcctggatg | 4740 |
| tccctgtctg ggccctttt ctgttttta ttctatgttc agcaccactg gcaccaaata | 4800 |
| cattttaatt caccgaaagc aaaaaaaaaa aaaaaaa | 4837 |

<210> SEQ ID NO 18
<211> LENGTH: 2099
<212> TYPE: DNA
<213> ORGANISM: homo sapien

<400> SEQUENCE: 18

| | |
|---|---|
| ccacctcagc cccaaccccca accccagccg catcccctgc cccagctgac gggtcaaagc | 60 |
| ctcaggagag tgtggctctc cccaggcgct accaggaggg gcaggtctca gccagctggg | 120 |
| gaaaccttat tgccatggtt cttagaagcc accccttccc caggcaagac aggccccaag | 180 |
| ggagtgtccc gagggcggtt cccgggagcc ccgtgggtcc cagcacttcc acacactctg | 240 |
| aggacagaca cggcccctct tcttcagtgg ggacagtcat agggacaggt acaggggcc | 300 |
| tggttgaggc tggaggtcag ccacagccaa gaagctccga gaccaacgga tcgcccagcc | 360 |
| cagaccctcc cccaggccta agaggagagg gaaccaggga gaaaagtcta gaccgctgc | 420 |
| cccaagccgc gatgcccagg ggccccgcac agccccccgc gcagaggccg cctggccccg | 480 |
| cggcctcctc ctctgcgagg cgctcacagc cggtacccca gctacggaaa cgcagcaggt | 540 |
| gcgaaatcgc cccgagctcg gagcaggagg tcaggccggc cgcctcgggg gaccctcaag | 600 |
| gggaggcgcc gggggagggg ggcagccctg ccggccgcag cggggcgctc acggaaaagc | 660 |
| aggaggaggc ccggaagctc atggtgtttc tgcagaggcc cggggggttgg ggggtggtgg | 720 |
| aggggccccg gaagcccagc tcccgggccc tggagcccgc cacggcggca gccctgcggc | 780 |
| ggcggctgga cctgggcagt tgcctggacg tgctggcctt tgcccagcag cacggagagc | 840 |
| ccggcctggc gcaggagacc tacgcgctga tgagcgacaa cctgctgcga gtgctgggag | 900 |
| acccgtgcct ctaccgccgg ctgagcgcgg ccgaccgcga gcgcatcctc agcctgcgga | 960 |
| ccggccgggg ccgggcggtg ctgggcgtcc tcgtactgcc cagcctctac caggggggcc | 1020 |

-continued

```
gctcagggct ccccaggggc cctcgtggcg aggagcctcc tgcggcggcc cctgtgtccc    1080
tgcctctacc tgcgcacctg catgtgttca accccgggga gaacacctgg cggcccctga    1140
cccaggtgcc cgaggaggcc ccgcttcggg gctgcggtct ctgcaccatg cacaactacc    1200
tgtttctggc ggggggcatc cgtggctccg gtgccaaggc cgtctgctcc aacgaggtct    1260
tctgctacaa ccctctgacc aacatctgga gccaggttcg gcccatgcag caggcccgag    1320
cccagctcaa gctggtggcc ctggacgggc tgctctatgc catcggtggc gaatgcctgt    1380
acagcatgga gtgctacgac ccgcgaacag acgcctggac cccacgcgcg ccactccccg    1440
caggcacctt ccctgtggcc cacgaggctg tggcctgccg tggggacatc tacgtcaccg    1500
ggggtcacct cttctaccgc ctgctcaggt acagccccgt gaaggatgct gggacgagt    1560 gcccatacag tgccagccac cggcgttcca cgacatcgt ggcactgggg ggcttcctgt    1620
accgcttcga cctgctgcgg ggcatgggcg ccgccgtgat cgctacaac acagtgaccg    1680 gctcctggag cagggctgcc tccctgcccc tgcccgcccc cgcccactg cactgcacca    1740 ccctgggcaa caccatttac tgcctcaacc cccaggtcac tgccaccttc acggtctctg    1800
gggggactgc ccagttccag gccaaggagc tgcagcccct tcccttgggg agcaccgggg    1860
tcctcagtcc attcatcctg actctgcccc ctgaggaccg gctgcagacc tcactctgag    1920 tgcaggcag agaaccaaag ctgcttcgct gctctccagg gagaccctcc tgggatgggc    1980
ctgagaggcc ggggctcagg gaaggggctg ggatcggaac ttcctgctct tgtttctgga    2040
caactttccc cttctgcttt aaaggttgtc gattattttg aaaaaaaaaa aaaaaaaaa    2099
```

```
<210> SEQ ID NO 19
<211> LENGTH: 1235
<212> TYPE: PRT
<213> ORGANISM: homo sapien

<400> SEQUENCE: 19

Met Ile Gln Gly Thr Leu Glu Pro Asp Gly Pro Leu Trp Gly Trp Asp
1               5                   10                  15

Trp Asp Ser Asp Asn Asp Trp Asp Ser Ala Val Leu Ala Leu Leu Ala
            20                  25                  30

Leu Ala Val Val Ala Ala Thr Ala Leu Ala Leu His Trp Phe Gly Ser
        35                  40                  45

Gly His Asp Gln Glu Ala Ala Glu Pro Val Ser Thr Ala Leu Gly Ala
    50                  55                  60

Gln Pro His Gln Ala Gly Gly Ala Glu Leu Ala Leu Gln Pro Lys Ser
65                  70                  75                  80

Lys Val Ser Asp Gly Ser Glu Gly Gln Ser Pro Gly Gln Gly Lys Pro
                85                  90                  95

Glu Pro Pro Gly Arg Gly Gln Gln Ser Pro Val Pro Ala Ala Ala Pro
            100                 105                 110

Gly Gly Gly Leu Ala Ala Met Ala Arg Leu Pro Leu Lys Thr Ala Val
        115                 120                 125

Glu Glu Ala Arg Arg Glu Ala Leu Gly Gln Gln Arg Gly Ser Ala Thr
    130                 135                 140

Pro Ala Ala Pro Arg Ala Glu Gly Lys Glu Pro Arg Pro Gly Thr
145                 150                 155                 160

Ala Leu Leu Gly Arg Ser Glu Ala Gly Gly Met Ser Ala Pro Leu Leu
                165                 170                 175

Ile His Phe Thr Pro Arg Ser Pro Gly Ser Glu Ala Glu Ala Glu Thr
```

```
            180                 185                 190
Gly Gly Val Arg Ala Ser Ser Arg Gln Ala Ala Gly Pro Ala Gly Gln
            195                 200                 205
Gln Asp Thr Gly Pro Trp Gln Ala Gly Ala Gly Pro Ser Gly Ser Met
            210                 215                 220
Gly Arg Gly Arg Gly Arg Arg Arg Met Asp Ala Gly Ser Gly Asp
225                 230                 235                 240
Arg Ala Arg Arg Pro Arg Lys Leu Asp Pro Leu Arg Leu Gly Ala Ala
                    245                 250                 255
Gly Ser Val Trp Asp Ala Val Asp Gly Ala Ala Leu Asp Ala His
            260                 265                 270
Ala Arg Gly Leu Pro Thr Gly Pro Leu Ala Gln Glu Pro Ala Leu
            275                 280                 285
Pro Ala Leu Pro Ala Pro Arg Ala Leu Gln Pro Gly Ser Gln Thr Glu
            290                 295                 300
Gly Ser Gly Ala Lys Gly Gly Trp Ser Arg Glu Ala Ser Gly Val Pro
305                 310                 315                 320
Ala Pro Gly Gly Gly Trp Pro Trp Val Ser Arg Glu Val Pro Gly Thr
                    325                 330                 335
Arg Ser Phe Gly Pro Ala Pro Asp Ser Thr Arg Pro Trp Leu Glu Ser
            340                 345                 350
Pro Pro Gln Gly Arg Pro Leu Ser Ser Gln Gly Pro Gly Ala Thr Gly
            355                 360                 365
Ala Tyr Asp Ala Gly Glu Ala Gly Ala Asp Ser Ser Arg Asp Asn Ser
            370                 375                 380
Pro Ala Ala Asp Leu Gly Pro Thr Arg Pro Pro Glu Gln Ala Lys Pro
385                 390                 395                 400
Ala Ala Ala Gly His Ser Arg Ala Pro Ser Arg Ser Arg Glu Pro Arg
                    405                 410                 415
Pro Arg Ser Ala Ser Pro Pro Ala Ala Pro Gly Pro Gly Phe Pro Pro
                    420                 425                 430
Glu Ala Leu Thr Leu Pro Ser Pro Ser Asp Phe Leu Pro Leu Glu Val
            435                 440                 445
Thr Gln Asp Pro Ser Val Gly Glu Asn Leu Arg Ala Ala Pro Ala Pro
            450                 455                 460
Ser Ser Ala Ser Ala Gln Val Leu Thr Ser Ala Pro Ala Ser Val Leu
465                 470                 475                 480
Ala Pro Ala Leu Ala Ser Ser Pro Ser Ser Ala Pro Thr Ser Ala Thr
                    485                 490                 495
Thr Ser Thr Ser Ser Pro Thr Ser Ala Pro Ala Pro Ala Pro Thr Ser
                    500                 505                 510
Ala Pro Thr Ser Thr Pro Ala Pro Ala Pro Ser Pro Ala Ala Ala
            515                 520                 525
Thr Pro Ala Pro Ala Pro Val Pro Val Pro Thr Leu Thr Pro Ser
            530                 535                 540
Pro Ala Leu Thr Pro Val Pro Thr Pro Ala Leu Ser Pro Ala Pro Thr
545                 550                 555                 560
Pro Ala Leu Thr Pro Ala Ala Ser Pro Ala Leu Thr Pro Val Pro Thr
                    565                 570                 575
Pro Ala Leu Ser Pro Ala Pro Thr Pro Ala Pro Thr Pro Ala Ala Ser
                    580                 585                 590
Pro Ala Pro Ala Pro Thr Ser Ala Pro Thr Pro Thr Pro Ala Ala Ser
                    595                 600                 605
```

```
Pro Ala Pro Ala Asp Gly Ser Lys Pro Gln Glu Ser Val Ala Leu Pro
    610                 615                 620
Arg Arg Tyr Gln Glu Gly Gln Val Ser Ala Ser Trp Gly Asn Leu Ile
625                 630                 635                 640
Ala Met Val Leu Arg Ser His Pro Phe Pro Arg Gln Asp Arg Pro Gln
                645                 650                 655
Gly Ser Val Pro Arg Ala Val Pro Gly Ser Pro Val Gly Pro Ser Thr
            660                 665                 670
Ser Thr His Ser Glu Asp Arg His Gly Pro Ser Ser Ser Val Gly Thr
        675                 680                 685
Val Ile Gly Thr Gly Thr Gly Gly Leu Val Glu Ala Gly Gly Gln Pro
    690                 695                 700
Gln Pro Arg Ser Ser Glu Thr Asn Gly Ser Pro Ser Pro Asp Pro Pro
705                 710                 715                 720
Pro Gly Leu Arg Gly Glu Gly Thr Arg Glu Lys Ser Leu Asp Pro Leu
                725                 730                 735
Pro Gln Ala Ala Met Pro Arg Gly Pro Ala Gln Pro Pro Ala Gln Arg
            740                 745                 750
Pro Pro Gly Pro Ala Ala Ser Ser Ser Ala Arg Arg Ser Gln Pro Val
        755                 760                 765
Pro Gln Leu Arg Lys Arg Ser Arg Cys Glu Ile Ala Pro Ser Ser Glu
    770                 775                 780
Gln Glu Val Arg Pro Ala Ala Ser Gly Asp Pro Gln Gly Glu Ala Pro
785                 790                 795                 800
Gly Glu Gly Gly Ser Pro Ala Gly Arg Ser Gly Ala Leu Thr Glu Lys
                805                 810                 815
Gln Glu Glu Ala Arg Lys Leu Met Val Phe Leu Gln Arg Pro Gly Gly
            820                 825                 830
Trp Gly Val Val Glu Gly Pro Arg Lys Pro Ser Ser Arg Ala Leu Glu
        835                 840                 845
Pro Ala Thr Ala Ala Ala Leu Arg Arg Arg Leu Asp Leu Gly Ser Cys
    850                 855                 860
Leu Asp Val Leu Ala Phe Ala Gln Gln His Gly Glu Pro Gly Leu Ala
865                 870                 875                 880
Gln Glu Thr Tyr Ala Leu Met Ser Asp Asn Leu Leu Arg Val Leu Gly
                885                 890                 895
Asp Pro Cys Leu Tyr Arg Arg Leu Ser Ala Ala Asp Arg Glu Arg Ile
            900                 905                 910
Leu Ser Leu Arg Thr Gly Arg Gly Arg Ala Val Leu Gly Val Leu Val
        915                 920                 925
Leu Pro Ser Leu Tyr Gln Gly Gly Arg Ser Gly Leu Pro Arg Gly Pro
    930                 935                 940
Arg Gly Glu Glu Pro Pro Ala Ala Ala Pro Val Ser Leu Pro Leu Pro
945                 950                 955                 960
Ala His Leu His Val Phe Asn Pro Arg Glu Asn Thr Trp Arg Pro Leu
                965                 970                 975
Thr Gln Val Pro Glu Glu Ala Pro Leu Arg Gly Cys Gly Leu Cys Thr
            980                 985                 990
Met His Asn Tyr Leu Phe Leu Ala  Gly Gly Ile Arg Gly  Ser Gly Ala
        995                 1000                1005
Lys Ala  Val Cys Ser Asn Glu  Val Phe Cys Tyr Asn  Pro Leu Thr
    1010                1015                1020
```

```
Asn Ile Trp Ser Gln Val Arg Pro Met Gln Gln Ala Arg Ala Gln
    1025                1030                1035

Leu Lys Leu Val Ala Leu Asp Gly Leu Leu Tyr Ala Ile Gly Gly
    1040                1045                1050

Glu Cys Leu Tyr Ser Met Glu Cys Tyr Asp Pro Arg Thr Asp Ala
    1055                1060                1065

Trp Thr Pro Arg Ala Pro Leu Pro Ala Gly Thr Phe Pro Val Ala
    1070                1075                1080

His Glu Ala Val Ala Cys Arg Gly Asp Ile Tyr Val Thr Gly Gly
    1085                1090                1095

His Leu Phe Tyr Arg Leu Leu Arg Tyr Ser Pro Val Lys Asp Ala
    1100                1105                1110

Trp Asp Glu Cys Pro Tyr Ser Ala Ser His Arg Ser Ser Asp
    1115                1120                1125

Ile Val Ala Leu Gly Gly Phe Leu Tyr Arg Phe Asp Leu Leu Arg
    1130                1135                1140

Gly Val Gly Ala Ala Val Met Arg Tyr Asn Thr Val Thr Gly Ser
    1145                1150                1155

Trp Ser Arg Ala Ala Ser Leu Pro Leu Pro Ala Pro Ala Pro Leu
    1160                1165                1170

His Cys Thr Thr Leu Gly Asn Thr Ile Tyr Cys Leu Asn Pro Gln
    1175                1180                1185

Val Thr Ala Thr Phe Thr Val Ser Gly Gly Thr Ala Gln Phe Gln
    1190                1195                1200

Ala Lys Glu Leu Gln Pro Phe Pro Leu Gly Ser Thr Gly Val Leu
    1205                1210                1215

Ser Pro Phe Ile Leu Thr Leu Pro Pro Glu Asp Arg Leu Gln Thr
    1220                1225                1230

Ser Leu
    1235

<210> SEQ ID NO 20
<211> LENGTH: 594
<212> TYPE: PRT
<213> ORGANISM: homo sapien

<400> SEQUENCE: 20

Met Val Leu Arg Ser His Pro Phe Pro Arg Gln Asp Arg Pro Gln Gly
1               5                   10                  15

Ser Val Pro Arg Ala Val Pro Gly Ser Pro Val Gly Pro Ser Thr Ser
                20                  25                  30

Thr His Ser Glu Asp Arg His Gly Pro Ser Ser Ser Val Gly Thr Val
            35                  40                  45

Ile Gly Thr Gly Thr Gly Gly Leu Val Glu Ala Gly Gly Gln Pro Gln
        50                  55                  60

Pro Arg Ser Ser Glu Thr Asn Gly Ser Pro Ser Asp Pro Pro
65                  70                  75                  80

Gly Leu Arg Gly Glu Gly Thr Arg Glu Lys Ser Leu Asp Pro Leu Pro
                85                  90                  95

Gln Ala Ala Met Pro Arg Gly Pro Ala Gln Pro Pro Ala Gln Arg Pro
            100                 105                 110

Pro Gly Pro Ala Ala Ser Ser Ser Ala Arg Ser Gln Pro Val Pro
        115                 120                 125

Gln Leu Arg Lys Arg Ser Arg Cys Glu Ile Ala Pro Ser Ser Glu Gln
    130                 135                 140
```

```
Glu Val Arg Pro Ala Ala Ser Gly Asp Pro Gln Gly Glu Ala Pro Gly
145                 150                 155                 160

Glu Gly Gly Ser Pro Ala Gly Arg Ser Gly Ala Leu Thr Glu Lys Gln
            165                 170                 175

Glu Glu Ala Arg Lys Leu Met Val Phe Leu Gln Arg Pro Gly Gly Trp
        180                 185                 190

Gly Val Val Glu Gly Pro Arg Lys Pro Ser Ser Arg Ala Leu Glu Pro
    195                 200                 205

Ala Thr Ala Ala Ala Leu Arg Arg Arg Leu Asp Leu Gly Ser Cys Leu
210                 215                 220

Asp Val Leu Ala Phe Ala Gln Gln His Gly Glu Pro Gly Leu Ala Gln
225                 230                 235                 240

Glu Thr Tyr Ala Leu Met Ser Asp Asn Leu Leu Arg Val Leu Gly Asp
            245                 250                 255

Pro Cys Leu Tyr Arg Arg Leu Ser Ala Ala Asp Arg Glu Arg Ile Leu
        260                 265                 270

Ser Leu Arg Thr Gly Arg Gly Arg Ala Val Leu Gly Val Leu Val Leu
    275                 280                 285

Pro Ser Leu Tyr Gln Gly Gly Arg Ser Gly Leu Pro Arg Gly Pro Arg
290                 295                 300

Gly Glu Glu Pro Pro Ala Ala Ala Pro Val Ser Leu Pro Leu Pro Ala
305                 310                 315                 320

His Leu His Val Phe Asn Pro Arg Glu Asn Thr Trp Arg Pro Leu Thr
            325                 330                 335

Gln Val Pro Glu Glu Ala Pro Leu Arg Gly Cys Gly Leu Cys Thr Met
        340                 345                 350

His Asn Tyr Leu Phe Leu Ala Gly Gly Ile Arg Gly Ser Gly Ala Lys
    355                 360                 365

Ala Val Cys Ser Asn Glu Val Phe Cys Tyr Asn Pro Leu Thr Asn Ile
370                 375                 380

Trp Ser Gln Val Arg Pro Met Gln Gln Ala Arg Ala Gln Leu Lys Leu
385                 390                 395                 400

Val Ala Leu Asp Gly Leu Leu Tyr Ala Ile Gly Gly Glu Cys Leu Tyr
            405                 410                 415

Ser Met Glu Cys Tyr Asp Pro Arg Thr Asp Ala Trp Thr Pro Arg Ala
        420                 425                 430

Pro Leu Pro Ala Gly Thr Phe Pro Val Ala His Glu Ala Val Ala Cys
    435                 440                 445

Arg Gly Asp Ile Tyr Val Thr Gly Gly His Leu Phe Tyr Arg Leu Leu
450                 455                 460

Arg Tyr Ser Pro Val Lys Asp Ala Trp Asp Glu Cys Pro Tyr Ser Ala
465                 470                 475                 480

Ser His Arg Arg Ser Ser Asp Ile Val Ala Leu Gly Gly Phe Leu Tyr
            485                 490                 495

Arg Phe Asp Leu Leu Arg Gly Val Gly Ala Ala Val Met Arg Tyr Asn
        500                 505                 510

Thr Val Thr Gly Ser Trp Ser Arg Ala Ala Ser Leu Pro Leu Pro Ala
    515                 520                 525

Pro Ala Pro Leu His Cys Thr Thr Leu Gly Asn Thr Ile Tyr Cys Leu
530                 535                 540

Asn Pro Gln Val Thr Ala Thr Phe Thr Val Ser Gly Gly Thr Ala Gln
545                 550                 555                 560
```

```
Phe Gln Ala Lys Glu Leu Gln Pro Phe Pro Leu Gly Ser Thr Gly Val
                565                 570                 575

Leu Ser Pro Phe Ile Leu Thr Leu Pro Pro Glu Asp Arg Leu Gln Thr
            580                 585                 590

Ser Leu

<210> SEQ ID NO 21
<211> LENGTH: 495
<212> TYPE: PRT
<213> ORGANISM: homo sapien

<400> SEQUENCE: 21

Met Pro Arg Gly Pro Ala Gln Pro Pro Ala Gln Arg Pro Pro Gly Pro
1               5                   10                  15

Ala Ala Ser Ser Ser Ala Arg Arg Ser Gln Pro Val Pro Gln Leu Arg
                20                  25                  30

Lys Arg Ser Arg Cys Glu Ile Ala Pro Ser Ser Glu Gln Glu Val Arg
            35                  40                  45

Pro Ala Ala Ser Gly Asp Pro Gln Gly Glu Ala Pro Gly Glu Gly Gly
        50                  55                  60

Ser Pro Ala Gly Arg Ser Gly Ala Leu Thr Glu Lys Gln Glu Glu Ala
65                  70                  75                  80

Arg Lys Leu Met Val Phe Leu Gln Arg Pro Gly Gly Trp Gly Val Val
                85                  90                  95

Glu Gly Pro Arg Lys Pro Ser Ser Arg Ala Leu Glu Pro Ala Thr Ala
            100                 105                 110

Ala Ala Leu Arg Arg Arg Leu Asp Leu Gly Ser Cys Leu Asp Val Leu
        115                 120                 125

Ala Phe Ala Gln Gln His Gly Glu Pro Gly Leu Ala Gln Glu Thr Tyr
    130                 135                 140

Ala Leu Met Ser Asp Asn Leu Leu Arg Val Leu Gly Asp Pro Cys Leu
145                 150                 155                 160

Tyr Arg Arg Leu Ser Ala Ala Asp Arg Glu Arg Ile Leu Ser Leu Arg
                165                 170                 175

Thr Gly Arg Gly Arg Ala Val Leu Gly Val Leu Val Leu Pro Ser Leu
            180                 185                 190

Tyr Gln Gly Gly Arg Ser Gly Leu Pro Arg Gly Pro Arg Gly Glu Glu
        195                 200                 205

Pro Pro Ala Ala Ala Pro Val Ser Leu Pro Leu Pro Ala His Leu His
    210                 215                 220

Val Phe Asn Pro Arg Glu Asn Thr Trp Arg Pro Leu Thr Gln Val Pro
225                 230                 235                 240

Glu Glu Ala Pro Leu Arg Gly Cys Gly Leu Cys Thr Met His Asn Tyr
                245                 250                 255

Leu Phe Leu Ala Gly Gly Ile Arg Gly Ser Gly Ala Lys Ala Val Cys
            260                 265                 270

Ser Asn Glu Val Phe Cys Tyr Asn Pro Leu Thr Asn Ile Trp Ser Gln
        275                 280                 285

Val Arg Pro Met Gln Gln Ala Arg Ala Gln Leu Lys Leu Val Ala Leu
    290                 295                 300

Asp Gly Leu Leu Tyr Ala Ile Gly Gly Glu Cys Leu Tyr Ser Met Glu
305                 310                 315                 320

Cys Tyr Asp Pro Arg Thr Asp Ala Trp Thr Pro Arg Ala Pro Leu Pro
                325                 330                 335
```

```
Ala Gly Thr Phe Pro Val Ala His Glu Ala Val Ala Cys Arg Gly Asp
                340                 345                 350

Ile Tyr Val Thr Gly Gly His Leu Phe Tyr Arg Leu Leu Arg Tyr Ser
            355                 360                 365

Pro Val Lys Asp Ala Trp Asp Glu Cys Pro Tyr Ser Ala Ser His Arg
        370                 375                 380

Arg Ser Ser Asp Ile Val Ala Leu Gly Gly Phe Leu Tyr Arg Phe Asp
385                 390                 395                 400

Leu Leu Arg Gly Val Gly Ala Ala Val Met Arg Tyr Asn Thr Val Thr
                405                 410                 415

Gly Ser Trp Ser Arg Ala Ala Ser Leu Pro Leu Pro Ala Pro Ala Pro
            420                 425                 430

Leu His Cys Thr Thr Leu Gly Asn Thr Ile Tyr Cys Leu Asn Pro Gln
        435                 440                 445

Val Thr Ala Thr Phe Thr Val Ser Gly Gly Thr Ala Gln Phe Gln Ala
    450                 455                 460

Lys Glu Leu Gln Pro Phe Pro Leu Gly Ser Thr Gly Val Leu Ser Pro
465                 470                 475                 480

Phe Ile Leu Thr Leu Pro Pro Glu Asp Arg Leu Gln Thr Ser Leu
                485                 490                 495

<210> SEQ ID NO 22
<211> LENGTH: 1235
<212> TYPE: PRT
<213> ORGANISM: homo sapien

<400> SEQUENCE: 22

Met Ile Gln Gly Thr Leu Glu Pro Asp Gly Pro Leu Trp Gly Trp Asp
1               5                   10                  15

Trp Asp Ser Asp Asn Asp Trp Asp Ser Ala Val Leu Ala Leu Leu Ala
                20                  25                  30

Leu Ala Val Val Ala Ala Thr Ala Leu Ala Leu His Trp Phe Gly Ser
            35                  40                  45

Gly His Asp Gln Glu Ala Ala Glu Pro Val Ser Thr Ala Leu Gly Ala
        50                  55                  60

Gln Pro His Gln Ala Gly Gly Ala Glu Leu Ala Leu Gln Pro Lys Ser
65                  70                  75                  80

Lys Val Ser Asp Gly Ser Glu Gly Gln Ser Pro Gly Gln Gly Lys Pro
                85                  90                  95

Glu Pro Pro Gly Arg Gly Gln Gln Ser Pro Val Pro Ala Ala Ala Pro
            100                 105                 110

Gly Gly Gly Leu Ala Ala Met Ala Arg Leu Pro Leu Lys Thr Ala Val
        115                 120                 125

Glu Glu Ala Arg Arg Glu Ala Leu Gly Gln Gln Arg Gly Ser Ala Thr
130                 135                 140

Pro Ala Ala Pro Arg Ala Glu Gly Lys Glu Pro Pro Arg Pro Gly Thr
                145                 150                 155                 160

Ala Leu Leu Gly Arg Ser Glu Ala Gly Met Ser Ala Pro Leu Leu
            165                 170                 175

Ile His Phe Thr Pro Arg Ser Pro Gly Ser Glu Ala Glu Ala Glu Thr
        180                 185                 190

Gly Gly Val Arg Ala Ser Ser Arg Gln Ala Ala Gly Pro Ala Gly Gln
    195                 200                 205

Gln Asp Thr Gly Pro Trp Gln Ala Gly Ala Gly Pro Ser Gly Ser Met
210                 215                 220
```

```
Gly Arg Gly Arg Gly Arg Arg Arg Met Asp Ala Gly Ser Gly Asp
225                 230                 235                 240

Arg Ala Arg Arg Pro Arg Lys Leu Asp Pro Leu Arg Leu Gly Ala Ala
            245                 250                 255

Gly Ser Val Trp Asp Ala Val Asp Gly Ala Ala Leu Asp Ala His
        260                 265                 270

Ala Arg Gly Leu Pro Thr Gly Pro Pro Leu Ala Gln Glu Pro Ala Leu
            275                 280                 285

Pro Ala Leu Pro Ala Pro Arg Ala Leu Gln Pro Gly Ser Gln Thr Glu
290                 295                 300

Gly Ser Gly Ala Lys Gly Gly Trp Ser Arg Glu Ala Ser Gly Val Pro
305                 310                 315                 320

Ala Pro Gly Gly Gly Trp Pro Trp Val Ser Arg Glu Val Pro Gly Thr
                325                 330                 335

Arg Ser Phe Gly Pro Ala Pro Asp Ser Thr Arg Pro Trp Leu Glu Ser
            340                 345                 350

Pro Pro Gln Gly Arg Pro Leu Ser Ser Gln Gly Pro Gly Ala Thr Gly
        355                 360                 365

Ala Tyr Asp Ala Gly Glu Ala Gly Ala Asp Ser Ser Arg Asp Asn Ser
370                 375                 380

Pro Ala Ala Asp Leu Gly Pro Thr Arg Pro Glu Gln Ala Lys Pro
385                 390                 395                 400

Ala Ala Ala Gly His Ser Arg Ala Pro Ser Arg Ser Arg Glu Pro Arg
                405                 410                 415

Pro Arg Ser Ala Ser Pro Pro Ala Ala Pro Gly Pro Gly Phe Pro Pro
            420                 425                 430

Glu Ala Leu Thr Leu Pro Ser Pro Ser Asp Phe Leu Pro Leu Glu Val
            435                 440                 445

Thr Gln Asp Pro Ser Val Gly Glu Asn Leu Arg Ala Ala Pro Ala Pro
450                 455                 460

Ser Ser Ala Ser Ala Gln Val Leu Thr Ser Ala Pro Ala Ser Val Leu
465                 470                 475                 480

Ala Pro Ala Leu Ala Ser Ser Pro Ser Ser Ala Pro Thr Ser Ala Thr
                485                 490                 495

Thr Ser Thr Ser Ser Pro Thr Ser Ala Pro Ala Pro Thr Ser
            500                 505                 510

Ala Pro Thr Ser Thr Pro Ala Pro Ala Pro Ser Pro Ala Ala Ala
            515                 520                 525

Thr Pro Ala Pro Ala Pro Val Pro Val Pro Thr Leu Thr Pro Pro Ser
530                 535                 540

Pro Ala Leu Thr Pro Val Pro Thr Pro Ala Leu Ser Pro Ala Pro Thr
545                 550                 555                 560

Pro Ala Leu Thr Pro Ala Ala Ser Pro Ala Leu Thr Pro Val Pro Thr
            565                 570                 575

Pro Ala Leu Ser Pro Ala Pro Thr Pro Ala Pro Thr Pro Ala Ala Ser
            580                 585                 590

Pro Ala Pro Ala Pro Thr Ser Ala Pro Thr Pro Thr Pro Ala Ala Ser
            595                 600                 605

Pro Ala Pro Ala Asp Gly Ser Lys Pro Gln Glu Ser Val Ala Leu Pro
            610                 615                 620

Arg Arg Tyr Gln Glu Gly Gln Val Ser Ala Ser Trp Gly Asn Leu Ile
625                 630                 635                 640
```

Ala Met Val Leu Arg Ser His Pro Phe Pro Arg Gln Asp Arg Pro Gln
                     645                 650                 655

Gly Ser Val Pro Arg Ala Val Pro Gly Ser Pro Val Gly Pro Ser Thr
            660                 665                 670

Ser Thr His Ser Glu Asp Arg His Gly Pro Ser Ser Val Gly Thr
        675                 680                 685

Val Ile Gly Thr Gly Thr Gly Leu Val Glu Ala Gly Gly Gln Pro
    690                 695                 700

Gln Pro Arg Ser Ser Glu Thr Asn Gly Ser Pro Ser Pro Asp Pro Pro
705                 710                 715                 720

Pro Gly Leu Arg Gly Glu Gly Thr Arg Glu Lys Ser Leu Asp Pro Leu
                725                 730                 735

Pro Gln Ala Ala Met Pro Arg Gly Pro Ala Gln Pro Pro Ala Gln Arg
            740                 745                 750

Pro Pro Gly Pro Ala Ala Ser Ser Ala Arg Arg Ser Gln Pro Val
        755                 760                 765

Pro Gln Leu Arg Lys Arg Ser Arg Cys Glu Ile Ala Pro Ser Ser Glu
    770                 775                 780

Gln Glu Val Arg Pro Ala Ala Ser Gly Asp Pro Gln Gly Glu Ala Pro
785                 790                 795                 800

Gly Glu Gly Gly Ser Pro Ala Gly Arg Ser Gly Ala Leu Thr Glu Lys
                805                 810                 815

Gln Glu Glu Ala Arg Lys Leu Met Val Phe Leu Gln Arg Pro Gly Gly
            820                 825                 830

Trp Gly Val Val Glu Gly Pro Arg Lys Pro Ser Ser Arg Ala Leu Glu
    835                 840                 845

Pro Ala Thr Ala Ala Ala Leu Arg Arg Arg Leu Asp Leu Gly Ser Cys
850                 855                 860

Leu Asp Val Leu Ala Phe Ala Gln Gln His Gly Glu Pro Gly Leu Ala
865                 870                 875                 880

Gln Glu Thr Tyr Ala Leu Met Ser Asp Asn Leu Leu Arg Val Leu Gly
                885                 890                 895

Asp Pro Cys Leu Tyr Arg Arg Leu Ser Ala Ala Asp Arg Glu Arg Ile
            900                 905                 910

Leu Ser Leu Arg Thr Gly Arg Gly Arg Ala Val Leu Gly Val Leu Val
        915                 920                 925

Leu Pro Ser Leu Tyr Gln Gly Gly Arg Ser Gly Leu Pro Arg Gly Pro
    930                 935                 940

Arg Gly Glu Glu Pro Pro Ala Ala Ala Pro Val Ser Leu Pro Leu Pro
945                 950                 955                 960

Ala His Leu His Val Phe Asn Pro Arg Glu Asn Thr Trp Arg Pro Leu
                965                 970                 975

Thr Gln Val Pro Glu Glu Ala Pro Leu Arg Gly Cys Gly Leu Cys Thr
            980                 985                 990

Met His Asn Tyr Leu Phe Leu Ala Gly Gly Ile Arg Gly Ser Gly Ala
        995                 1000                1005

Lys Ala Val Cys Ser Asn Glu Val Phe Cys Tyr Asn Pro Leu Thr
    1010                1015                1020

Asn Ile Trp Ser Gln Val Arg Pro Met Gln Gln Ala Arg Ala Gln
    1025                1030                1035

Leu Lys Leu Val Ala Leu Asp Gly Leu Leu Tyr Ala Ile Gly Gly
    1040                1045                1050

Glu Cys Leu Tyr Ser Met Glu Cys Tyr Asp Pro Arg Thr Asp Ala

```
                   1055                1060                1065

Trp Thr Pro Arg Ala Pro Leu Pro Ala Gly Thr Phe Pro Val Ala
        1070                1075                1080

His Glu Ala Val Ala Cys Arg Gly Asp Ile Tyr Val Thr Gly Gly
    1085                1090                1095

His Leu Phe Tyr Arg Leu Leu Arg Tyr Ser Pro Val Lys Asp Ala
    1100                1105                1110

Trp Asp Glu Cys Pro Tyr Ser Ala Ser His Arg Arg Ser Ser Asp
    1115                1120                1125

Ile Val Ala Leu Gly Gly Phe Leu Tyr Arg Phe Asp Leu Leu Arg
    1130                1135                1140

Gly Met Gly Ala Ala Val Met Arg Tyr Asn Thr Val Thr Gly Ser
    1145                1150                1155

Trp Ser Arg Ala Ala Ser Leu Pro Leu Pro Ala Pro Ala Pro Leu
    1160                1165                1170

His Cys Thr Thr Leu Gly Asn Thr Ile Tyr Cys Leu Asn Pro Gln
    1175                1180                1185

Val Thr Ala Thr Phe Thr Val Ser Gly Gly Thr Ala Gln Phe Gln
    1190                1195                1200

Ala Lys Glu Leu Gln Pro Phe Pro Leu Gly Ser Thr Gly Val Leu
    1205                1210                1215

Ser Pro Phe Ile Leu Thr Leu Pro Pro Glu Asp Arg Leu Gln Thr
    1220                1225                1230

Ser Leu
    1235

<210> SEQ ID NO 23
<211> LENGTH: 594
<212> TYPE: PRT
<213> ORGANISM: homo sapien

<400> SEQUENCE: 23

Met Val Leu Arg Ser His Pro Phe Pro Arg Gln Asp Arg Pro Gln Gly
1               5                   10                  15

Ser Val Pro Arg Ala Val Pro Gly Ser Pro Val Gly Pro Ser Thr Ser
            20                  25                  30

Thr His Ser Glu Asp Arg His Gly Pro Ser Ser Val Gly Thr Val
        35                  40                  45

Ile Gly Thr Gly Thr Gly Gly Leu Val Glu Ala Gly Gly Gln Pro Gln
    50                  55                  60

Pro Arg Ser Ser Glu Thr Asn Gly Ser Pro Ser Pro Asp Pro Pro
65                  70                  75                  80

Gly Leu Arg Gly Glu Gly Thr Arg Glu Lys Ser Leu Asp Pro Leu Pro
                85                  90                  95

Gln Ala Ala Met Pro Arg Gly Pro Ala Gln Pro Ala Gln Arg Pro
            100                 105                 110

Pro Gly Pro Ala Ala Ser Ser Ala Arg Arg Ser Gln Pro Val Pro
        115                 120                 125

Gln Leu Arg Lys Arg Ser Arg Cys Glu Ile Ala Pro Ser Ser Glu Gln
    130                 135                 140

Glu Val Arg Pro Ala Ala Ser Asp Pro Gln Gly Glu Ala Pro Gly
145                 150                 155                 160

Glu Gly Gly Ser Pro Ala Gly Arg Ser Gly Ala Leu Thr Glu Lys Gln
                165                 170                 175
```

```
Glu Glu Ala Arg Lys Leu Met Val Phe Leu Gln Arg Pro Gly Trp
            180                 185                 190
Gly Val Val Glu Gly Pro Arg Lys Pro Ser Ser Arg Ala Leu Glu Pro
        195                 200                 205
Ala Thr Ala Ala Ala Leu Arg Arg Arg Leu Asp Leu Gly Ser Cys Leu
210                 215                 220
Asp Val Leu Ala Phe Ala Gln Gln His Gly Glu Pro Gly Leu Ala Gln
225                 230                 235                 240
Glu Thr Tyr Ala Leu Met Ser Asp Asn Leu Leu Arg Val Leu Gly Asp
                245                 250                 255
Pro Cys Leu Tyr Arg Arg Leu Ser Ala Ala Asp Arg Glu Arg Ile Leu
            260                 265                 270
Ser Leu Arg Thr Gly Arg Gly Arg Ala Val Leu Gly Val Leu Val Leu
        275                 280                 285
Pro Ser Leu Tyr Gln Gly Gly Arg Ser Gly Leu Pro Arg Gly Pro Arg
    290                 295                 300
Gly Glu Glu Pro Pro Ala Ala Ala Pro Val Ser Leu Pro Leu Pro Ala
305                 310                 315                 320
His Leu His Val Phe Asn Pro Arg Glu Asn Thr Trp Arg Pro Leu Thr
                325                 330                 335
Gln Val Pro Glu Glu Ala Pro Leu Arg Gly Cys Gly Leu Cys Thr Met
            340                 345                 350
His Asn Tyr Leu Phe Leu Ala Gly Gly Ile Arg Gly Ser Gly Ala Lys
        355                 360                 365
Ala Val Cys Ser Asn Glu Val Phe Cys Tyr Asn Pro Leu Thr Asn Ile
    370                 375                 380
Trp Ser Gln Val Arg Pro Met Gln Gln Ala Arg Ala Gln Leu Lys Leu
385                 390                 395                 400
Val Ala Leu Asp Gly Leu Leu Tyr Ala Ile Gly Gly Glu Cys Leu Tyr
                405                 410                 415
Ser Met Glu Cys Tyr Asp Pro Arg Thr Asp Ala Trp Thr Pro Arg Ala
            420                 425                 430
Pro Leu Pro Ala Gly Thr Phe Pro Val Ala His Glu Ala Val Ala Cys
        435                 440                 445
Arg Gly Asp Ile Tyr Val Thr Gly Gly His Leu Phe Tyr Arg Leu Leu
    450                 455                 460
Arg Tyr Ser Pro Val Lys Asp Ala Trp Asp Glu Cys Pro Tyr Ser Ala
465                 470                 475                 480
Ser His Arg Arg Ser Ser Asp Ile Val Ala Leu Gly Gly Phe Leu Tyr
                485                 490                 495
Arg Phe Asp Leu Leu Arg Gly Met Gly Ala Ala Val Met Arg Tyr Asn
            500                 505                 510
Thr Val Thr Gly Ser Trp Ser Arg Ala Ala Ser Leu Pro Leu Pro Ala
        515                 520                 525
Pro Ala Pro Leu His Cys Thr Thr Leu Gly Asn Thr Ile Tyr Cys Leu
    530                 535                 540
Asn Pro Gln Val Thr Ala Thr Phe Thr Val Ser Gly Gly Thr Ala Gln
545                 550                 555                 560
Phe Gln Ala Lys Glu Leu Gln Pro Phe Pro Leu Gly Ser Thr Gly Val
                565                 570                 575
Leu Ser Pro Phe Ile Leu Thr Leu Pro Pro Glu Asp Arg Leu Gln Thr
            580                 585                 590
Ser Leu
```

```
<210> SEQ ID NO 24
<211> LENGTH: 495
<212> TYPE: PRT
<213> ORGANISM: homo sapien

<400> SEQUENCE: 24

Met Pro Arg Gly Pro Ala Gln Pro Ala Gln Arg Pro Pro Gly Pro
1               5                   10                  15

Ala Ala Ser Ser Ser Ala Arg Arg Ser Gln Pro Val Pro Gln Leu Arg
            20                  25                  30

Lys Arg Ser Arg Cys Glu Ile Ala Pro Ser Ser Glu Gln Glu Val Arg
        35                  40                  45

Pro Ala Ala Ser Gly Asp Pro Gln Gly Glu Ala Pro Gly Glu Gly Gly
50                  55                  60

Ser Pro Ala Gly Arg Ser Gly Ala Leu Thr Glu Lys Gln Glu Glu Ala
65                  70                  75                  80

Arg Lys Leu Met Val Phe Leu Gln Arg Pro Gly Gly Trp Gly Val Val
                85                  90                  95

Glu Gly Pro Arg Lys Pro Ser Ser Arg Ala Leu Glu Pro Ala Thr Ala
            100                 105                 110

Ala Ala Leu Arg Arg Arg Leu Asp Leu Gly Ser Cys Leu Asp Val Leu
        115                 120                 125

Ala Phe Ala Gln Gln His Gly Glu Pro Gly Leu Ala Gln Glu Thr Tyr
130                 135                 140

Ala Leu Met Ser Asp Asn Leu Leu Arg Val Leu Gly Asp Pro Cys Leu
145                 150                 155                 160

Tyr Arg Arg Leu Ser Ala Ala Asp Arg Glu Arg Ile Leu Ser Leu Arg
                165                 170                 175

Thr Gly Arg Gly Arg Ala Val Leu Gly Val Leu Val Leu Pro Ser Leu
            180                 185                 190

Tyr Gln Gly Gly Arg Ser Gly Leu Pro Arg Gly Pro Arg Gly Glu Glu
        195                 200                 205

Pro Pro Ala Ala Ala Pro Val Ser Leu Pro Leu Pro Ala His Leu His
210                 215                 220

Val Phe Asn Pro Arg Glu Asn Thr Trp Arg Pro Leu Thr Gln Val Pro
225                 230                 235                 240

Glu Glu Ala Pro Leu Arg Gly Cys Gly Leu Cys Thr Met His Asn Tyr
                245                 250                 255

Leu Phe Leu Ala Gly Gly Ile Arg Gly Ser Gly Ala Lys Ala Val Cys
            260                 265                 270

Ser Asn Glu Val Phe Cys Tyr Asn Pro Leu Thr Asn Ile Trp Ser Gln
        275                 280                 285

Val Arg Pro Met Gln Gln Ala Arg Ala Gln Leu Lys Leu Val Ala Leu
290                 295                 300

Asp Gly Leu Leu Tyr Ala Ile Gly Gly Glu Cys Leu Tyr Ser Met Glu
305                 310                 315                 320

Cys Tyr Asp Pro Arg Thr Asp Ala Trp Thr Pro Arg Ala Pro Leu Pro
                325                 330                 335

Ala Gly Thr Phe Pro Val Ala His Glu Ala Val Ala Cys Arg Gly Asp
            340                 345                 350

Ile Tyr Val Thr Gly Gly His Leu Phe Tyr Arg Leu Leu Arg Tyr Ser
        355                 360                 365

Pro Val Lys Asp Ala Trp Asp Glu Cys Pro Tyr Ser Ala Ser His Arg
```

```
                370                 375                 380
Arg Ser Ser Asp Ile Val Ala Leu Gly Gly Phe Leu Tyr Arg Phe Asp
385                 390                 395                 400

Leu Leu Arg Gly Met Gly Ala Ala Val Met Arg Tyr Asn Thr Val Thr
                405                 410                 415

Gly Ser Trp Ser Arg Ala Ala Ser Leu Pro Leu Pro Ala Pro Ala Pro
                420                 425                 430

Leu His Cys Thr Thr Leu Gly Asn Thr Ile Tyr Cys Leu Asn Pro Gln
                435                 440                 445

Val Thr Ala Thr Phe Thr Val Ser Gly Gly Thr Ala Gln Phe Gln Ala
                450                 455                 460

Lys Glu Leu Gln Pro Phe Pro Leu Gly Ser Thr Gly Val Leu Ser Pro
465                 470                 475                 480

Phe Ile Leu Thr Leu Pro Pro Glu Asp Arg Leu Gln Thr Ser Leu
                485                 490                 495

<210> SEQ ID NO 25
<211> LENGTH: 5124
<212> TYPE: DNA
<213> ORGANISM: homo sapien

<400> SEQUENCE: 25
```

| | | | | | |
|---|---|---|---|---|---|
| agaagcaggt | tggctgtgat | gacagcacag | agctcaggaa | cgctgcctga | ggaccctggg | 60 |
| gcctacgagg | aggagaagag | ggcaggagct | ggtggggtgc | ttgcagagac | cctgggctcc | 120 |
| tatcctgcca | taagcctcgc | tgtctcctga | tatctgcagc | caggccctac | tgacaccccc | 180 |
| aggcctgagt | gcaagcagag | accccaccat | tcccaggccc | tggaggactg | gtccaccta | 240 |
| actgggcagc | ccttggggca | ggcgctggcc | ggtgcctcag | cccaggcctc | tgtgctctgc | 300 |
| atgcactgcc | agcctgccat | caggcctcta | ttgcagccct | gaaccatgat | ccagggcacc | 360 |
| ttggagccag | atggtcccct | ctggggctgg | gactgggaca | gtgacaatga | ctgggatagt | 420 |
| gctgtgctgg | ccctcctggc | gctggctgtg | gtggctgcca | cagcgctggc | cttacactgg | 480 |
| tttggctccg | ggcacgatca | agaggcggca | gaaccggtgt | ccacagccct | cggggctcaa | 540 |
| cctcatcagg | caggaggagc | tgagctggcc | ctgcaaccga | agtctaaggt | cagtgatggc | 600 |
| agcgaggggc | agagcccagg | gcaggggaaa | ccagagcccc | caggacgcgg | ccagcagagc | 660 |
| cctgtccctg | ctgcagcgcc | gggcgggggc | ctggccgcca | tgcccggct | tccactcaag | 720 |
| acggctgtcg | aggaggcccg | cagagaggca | ttaggacagc | aacggggcag | tgccacccc | 780 |
| gcggcccccc | gagcggaagg | aaaggagcct | cccaggccag | gcactgccct | cctgggcagg | 840 |
| agcgaagcag | gggggatgtc | cgccccctc | ctgatccact | tcactcctcg | gagccctggc | 900 |
| agcgaagcgg | aggcggagac | aggtggtgtc | agggcgtcct | ctcgccaggc | gcaggcccc | 960 |
| gcgggcaac | aggacactgg | cccctggcag | gcgggcgcgg | ggcctcgggg | ctcgatgggg | 1020 |
| agaggccggg | gccggcggcg | gcggatggac | gctggctcgg | gagacagagc | ccgccgcccc | 1080 |
| cggaaactgg | acccgctccg | cctgggcgcc | gcggggagcg | tgtgggacgc | ggtggacggg | 1140 |
| gccgccgccc | tggacgccca | cgcgcgcggc | ctccccacag | gacccccact | cgcccaggag | 1200 |
| cccgcactcc | cggcgctgcc | cgctccccgc | gccctgcagc | ctgggtctca | gacgaaggc | 1260 |
| tctggggcca | aggtggctg | gagcaggag | gcctcggggg | tccctgcccc | cggaggaggc | 1320 |
| tggccctggg | tcagcaggga | ggtcccggc | accggagct | ttggcccagc | ccagactcc | 1380 |
| acgcgcccct | ggctagagag | tccgcctcaa | ggtcgcccac | tctcgtccca | agggccgggt | 1440 |

-continued

```
gccacagggg cctacgatgc cggcgaggcc ggggctgaca gctcccgaga taacagtcct    1500
gccgctgacc tggggcccac ccggcccccg gagcaagcaa agccggctgc agccggccac    1560
agccgcgcgc cctcccggag ccgtgagcct cgcccgcgct ccgcctcccc gcccgcagct    1620
cccgccccgg ggttcccacc tgaagccctg actctcccct ctccttcaga cttttttgccc    1680 ctggaggtta cccaggatcc ttccgtgggc gaaaatctca gagcggcgcc agccccaagt    1740
tcagcctcag cccaagtctt aacttcagct ccagcctcag tcctagcccc agccctggct    1800
tcatccccca gctcagcacc aacctcagcc accacctcaa cctcatcccc cacctcagcc    1860
ccagccccag ctccaacctc agctccaact tcaaccccag ccccagcccc aagtccagct    1920
gcagccgcaa ctccagcccc agcccagtc ccagtcccaa ccctcacacc cccatcccca     1980
gccctaaccc cagtcccaac cccagcccta agcccagctc caactccagc cctaacccca    2040
gccgcatccc cagccctaac cccagtccca acccagccc taagcccagc tccaactcca     2100
gccccaaccc cagccgcatc ccctgcccca gcccccacct cagccccaac cccaacccca    2160
gccgcatccc ctgcccagc tgacgggtca aagcctcagg agagtgtggc tctccccagg    2220
cgctaccagg aggggcaggt ctcagccagc tggggaaacc ttattgccat ggttcttaga    2280
agccacccct tccccaggca agacaggccc caagggagtg tcccgagggc ggttcccggg    2340
agccccgtgg gtcccagcac ttccacacac tctgaggaca gacacggccc ctcttcttca    2400
gtggggacag tcatagggac aggtacaggg ggcctggttg aggctggagg tcagccacag    2460
ccaagaagct ccgagaccaa cggatcgccc agcccagacc ctcccccagg cctaagagga    2520
gagggaacca gggagaaaag tctagacccg ctgccccaag ccgcgatgcc caggggcccc    2580
gcacagcccc ccgcgcagag gccgcctggc cccgcggcct cctcctctgc gaggcgctca    2640
cagccggtac cccagctacg gaaacgcagc aggtgcgaaa tcgccccgag ctcggagcag    2700
gaggtcaggc cggccgcctc gggggaccct caaggggagg cgccggggga gggggggcagc    2760 cctgccggcc gcagcggggc gctcacggaa aagcaggagg aggcccgaag ctcatggtgt    2820
ttctgcagag gcccgggggt tggggggtgg tggaggggcc ccggaagccc agctcccggg    2880
ccctggagcc cgccacggcg gcagccctgc ggcggcggct ggacctgggc agttgcctgg    2940
acgtgctggc ctttgcccag cagcacggag agcccggcct ggcgcaggag acctacgcgc    3000
tgatgagcga caacctgctg cgagtgctgg gagacccgtg cctctaccgc cggctgagcg    3060
cggccgaccg cgagcgcatc ctcagcctgc ggaccggccg gggccggggcg gtgctgggcg    3120 tcctcgtact gcccagcctc taccagggg gccgctcagg gctccccagg ggccctcgtg    3180
gcgaggagcc tcctgcggcg gcccctgtgt ccctgcctct acctgcgcac ctgcatgtgt    3240 tcaaccccg ggagaacacc tggcggcccc tgacccaggt gcccgaggag gccccgcttc    3300
ggggctgcgg tctctgcacc atgcacaact acctgtttct ggcggggggc atccgtggct    3360
ccggtgccaa ggccgtctgc tccaacgagg tcttctgcta caaccctctg accaacatct    3420
ggagccaggt tcggcccatg cagcaggccc gagcccagct caagctggtg gccctggacg    3480
ggctgctcta tgccatcggt ggcgaatgcc tgtacagcat ggagtgctac gacccgcgaa    3540
cagacgcctg gaccccacgc gcgccactcc ccgcaggcac cttccctgtg gcccacgagg    3600
ctgtggcctg ccgtggggac atctacgtca ccgggggtca cctcttctac cgcctgctca    3660
ggtacagccc cgtgaaggat gcttgggacg agtgcccata cagtgccagc caccggcgtt    3720
ccagcgacat cgtggcactg gggggcttcc tgtaccgctt cgacctgctg cggggcgtgg    3780
gcgccgccgt gatgcgctac aacacagtga ccggctcctg gagcagggct gcctcccctgc    3840
```

```
cccctgcccgc ccccgcccca ctgcactgca ccaccctggg caacaccatt tactgcctca   3900
acccccaggt cactgccacc ttcacggtct ctgggggac tgcccagttc caggccaagg     3960
agctgcagcc cttccccttg gggagcaccg gggtcctcag tccattcatc ctgactctgc   4020
cccctgagga ccggctgcag acctcactct gagtggcagg cagagaacca aagctgcttc   4080
gctgctctcc agggagaccc tcctgggatg ggcctgagag gccggggctc agggaagggg   4140
ctgggatcgg aacttcctgc tcttgtttct ggacaacttt ccccttctgc tttaaaggtt   4200
gtcgattatt ttgaagccca gactccctca gcctctttct gcccctcact ccacacccag   4260
actgtttcct gactcaattc cgtacctact tacagaccct ctcagcttgc tgacaccccc   4320
ctgtctgtgg gactccctat tccctagagc cagggactga tgcgtctcca cagacaagga   4380
cttggctcgc tggagctctg ctgagccgag agaggagggg gtagaaaaca ttcacacttc   4440
ctatgctctg tcagcaggac agggagcaaa aacgtcccca ggcaacgccc tcgcctctgg   4500
gactttctgc ctgtcctaag gcctccccag gtaccaaccc cgtagctatc tgggtctgtt   4560
tggcactgtg gattctcaag ggcctagaac ccttgcctct gaaactggtc cgctggtgca   4620
gccctgctgt ctgcagctcc tgcccatacc cccagcccac accaggccag cccactccg   4680 ggctcaccac cctctgcagc cttgtggggc tctcccagcc cctccagaag cccacccac   4740 ttctcgccaa ccccgatct ctaaatgagg cctgagcgtc accctagttc tgcccctttt    4800
tagctgtgta gacttggacg agacatttga cttcccttc tccttgtcta taaaatgtgg    4860
acagtggacg tctgtcaccc aagagagttg tgggagacaa gatcacagct atgagcacct   4920
cgcacggtgt ccaggatgca cagcacaatc catgatgcgt tttctcccct tacgcacttt   4980
gaaacccatg ctagaaaagt gaatacatct gactgtgctc cactccaacc tccagcctgg   5040
atgtccctgt ctgggcccctt tttctgtttt ttattctatg ttcagcacca ctggcaccaa   5100
atacatttta attcaccgaa agca                                            5124

<210> SEQ ID NO 26
<211> LENGTH: 5124
<212> TYPE: DNA
<213> ORGANISM: homo sapien

<400> SEQUENCE: 26
agaagcaggt tggctgtgat gacagcacag agctcaggaa cgctgcctga ggaccctggg     60
gcctacgagg aggagaagag ggcaggagct ggtggggtgc ttgcagagac cctgggctcc    120
tatcctgcca taagcctcgc tgtctcctga tatctgcagc caggccctac tgacaccccc    180
aggcctgagt gcaagcagag accccaccat tcccaggccc tggaggactg gtccacctta   240
actgggcagc ccttggggca ggcgctgcc ggtgcctcag cccaggcctc tgtgctctgc    300
atgcactgcc agcctgccat caggcctcta ttgcagccct gaaccatgat ccagggcacc    360
ttggagccag atggtcccct ctggggctgg gactgggaca gtgacaatga ctgggatagt    420
gctgtgctgg ccctcctggc gctggctgtg gtggctgcca cagcgctggc cttacactgg    480
tttggctccg gcacgatca agaggcggca gaaccggtgt ccacagccct cggggctcaa    540
cctcatcagg caggaggagc tgagctgcc ctgcaaccga agtctaaggt cagtgatggc    600
agcgaggggc agagcccagg gcagggaaa ccagagcccc caggacgcgg ccagcagagc    660
cctgtccctg ctgcagcgcc gggcgggggc ctggccgcca tggcccggct tccactcaag    720
acggctgtcg aggaggcccg cagagaggca ttaggacagc aacggggcag tgccacccc     780
```

```
gcggccccc  gagcggaagg  aaaggagcct  cccaggccag  gcactgccct  cctgggcagg   840
agcgaagcag  gggggatgtc  cgccccctc   ctgatccact  tcactcctcg  gagccctggc   900
agcgaagcgg  aggcggagac  aggtggtgtc  agggcgtcct  ctcgccaggc  cgcaggcccc   960
gcggggcaac  aggacactgg  cccctggcag  gcgggcgcgg  ggccctcggg  ctcgatgggg  1020
agaggccggg  gccggcggcg  gcggatggac  gctggctcgg  gagacagagc  ccgccgcccc  1080
cggaaactgg  acccgctccg  cctgggcgcc  gcggggagcg  tgtgggacgc  ggtgacgggg  1140
gccgccgccc  tggacgccca  cgcgcgcggc  ctccccacag  gaccccccact  cgcccaggag  1200 cccgcactcc  cggcgctgcc  cgctcccgc   gccctgcagc  ctgggtctca  gacgaaggc   1260 tctggggcca  agggtggctg  gagcagggag  gcctcggggg  tccctgcccc  cggaggaggc  1320
tggccctggg  tcagcaggga  ggtcccgggc  accggagct   ttggcccagc  cccagactcc  1380
acgcgcccct  ggctagagag  tccgcctcaa  ggtcgcccac  tctcgtccca  agggccgggt  1440
gccacagggg  cctacgatgc  cggcgaggcc  ggggctgaca  gctcccgaga  taacagtcct  1500
gccgctgacc  tgggggccccac  ccggccccg   gagcaagcaa  agccggctgc  agccggccac  1560
agccgcgcgc  cctcccggag  ccgtgagcct  cgccgcgcgt  ccgcctcccc  gcccgcagct  1620
cccggcccgg  ggttcccacc  tgaagccctg  actctcccct  ctccttcaga  cttttttgccc  1680 ctggaggtta  cccaggatcc  ttccgtgggc  gaaaatctca  gagcggcgcc  agccccaagt  1740
tcagcctcag  cccaagtctt  aacttcagct  ccagcctcag  tcctagcccc  agccctggct  1800
tcatccccca  gctcagcacc  aacctcagcc  accacctcaa  cctcatcccc  cacctcagcc  1860 ccagcccag   ctccaaccctc  agctccaact  tcaaccccag  cccagccccc  aagtccagct  1920
gcagccgcaa  ctccagcccc  agcccagtc   ccagtcccaa  ccctcacacc  cccatcccca  1980
gccctaaccc  cagtcccaac  cccagcccta  agcccagctc  caactccagc  cctaacccca  2040
gccgcatccc  cagccctaac  cccagtccca  accccagccc  taagcccagc  tccaactcca  2100
gccccaaccc  cagccgcatc  ccctgcccca  gcccccacct  cagccccaac  cccaaccccca  2160 gccgcatccc  ctgccccagc  tgacgggtca  aagcctcagg  agagtgtggc  tctccccagg  2220
cgctaccagg  aggggcaggt  ctcagccagc  tggggaaacc  ttattgccat  ggttcttaga  2280 agccaccct   tccccaggca  agacaggccc  caagggagtg  tcccgagggc  ggttcccggg  2340
agccccgtgg  gtcccagcac  ttccacacac  tctgaggaca  gacacggccc  ctcttcttca  2400
gtggggacag  tcatagggac  aggtacaggg  ggcctggttg  aggctggagg  tcagccacag  2460
ccaagaagct  ccgagaccaa  cggatcgccc  agcccagacc  ctcccccagg  cctaagagga  2520
gagggaacca  gggagaaaag  tctagacccg  ctgccccaag  ccgcgatgcc  cagggggccc  2580
gcacagcccc  ccgcgcagag  gccgcctggc  ccgcgcgcct  cctcctctgc  gaggcgctca  2640
cagccggtac  cccagctacg  gaaacgcagc  aggtgcgaaa  tcgccccgag  ctcggagcag  2700
gaggtcaggc  cggccgcctc  gggggaccct  caagggagg   cgccggggga  gggggggcagc  2760 cctgccggcc  gcagcggggc  gctcacggaa  aagcaggagg  aggcccggaa  gctcatggtg  2820
tttctgcaga  ggcccggggg  ttgggggggtg  gtggagggggc  cccggaagcc  cagctcccgg  2880
gccctggagc  ccgccacggc  ggcagccctg  cggcggcggc  tggacctggg  cagttgcctg  2940
gacgtgctgg  cctttgccca  gcagcacgga  gagcccggcc  tggcgcagga  gacctacgcg  3000
ctgatgagcg  acaacctgct  gcgagtgctg  ggagacccgt  gcctctaccg  ccggctgagc  3060
gcggccgacc  gcgagcgcat  cctcagcctg  cggaccggcc  ggggcggggc  ggtgctgggc  3120
gtcctcgtac  tgcccagcct  ctaccagggg  ggccgctcag  ggctccccag  ggccctcgtg  3180
```

| | |
|---|---|
| gcgaggagcc tcctgcggcg gcccctgtgt ccctgcctct acctgcgcac ctgcatgtgt | 3240 |
| tcaaccccg ggagaacacc tggcggcccc tgacccaggt gcccgaggag cccccgcttc | 3300 |
| ggggctgcgg tctctgcacc atgcacaact acctgtttct ggcgggggc atccgtggct | 3360 |
| ccggtgccaa ggccgtctgc tccaacgagg tcttctgcta caaccctctg accaacatct | 3420 |
| ggagccaggt tcggcccatg cagcaggccc gagcccagct caagctggtg ccctggacg | 3480 |
| ggctgctcta tgccatcggt ggcgaatgcc tgtacagcat ggagtgctac gacccgcgaa | 3540 |
| cagacgcctg gaccccacgc gcgccactcc ccgcaggcac cttccctgtg cccacgagg | 3600 |
| ctgtggcctg ccgtgggac atctacgtca ccggggtca cctcttctac cgcctgctca | 3660 |
| ggtacagccc cgtgaaggat gcttgggacg agtgcccata cagtgccagc caccggcgtt | 3720 |
| ccagcgacat cgtggcactg gggggcttcc tgtaccgctt cgacctgctg cggggcgtgg | 3780 |
| gcgccgccgt gatgcgctac aacacagtga ccggctcctg gagcagggct gcctccctgc | 3840 |
| ccctgcccgc ccccgcccca ctgcactgca ccaccctggg caacaccatt tactgcctca | 3900 |
| acccccaggt cactgccacc ttcacggtct ctgggggac tgcccagttc caggccaagg | 3960 |
| agctgcagcc cttcccttg gggagcaccg gggtcctcag tccattcatc ctgactctgc | 4020 |
| cccctgagga ccggctgcag acctcactct gagtggcagg cagagaacca aagctgcttc | 4080 |
| gctgctctcc agggagaccc tcctgggatg ggcctgagag gccggggctc agggaagggg | 4140 |
| ctgggatcgg aacttcctgc tcttgtttct ggacaacttt ccccttctgc tttaaaggtt | 4200 |
| gtcgattatt ttgaagccca gactcccctca gcctctttct gccctcact ccacacccag | 4260 |
| actgttcct gactcaattc cgtacctact tacagaccct ctcagcttgc tgacaccccc | 4320 |
| ctgtctgtgg gactccctat tccctagagc cagggactga tgcgtctcca cagacaagga | 4380 |
| cttggctcgc tggagctctg ctgagccgag agaggaggg gtagaaaaca ttcacacttc | 4440 |
| ctatgctctg tcagcaggac agggagcaaa aacgtcccca ggcaacgccc tcgcctctgg | 4500 |
| gactttctgc ctgtcctaag gcctccccag gtaccaaccc cgtagctatc tgggtctgtt | 4560 |
| tggcactgtg gattctcaag ggcctagaac ccttgcctct gaaactggtc cgctggtgca | 4620 |
| gccctgctgt ctgcagctcc tgcccatacc cccagcccac accaggccag gcccactccg | 4680 |
| ggctcaccac cctctgcagc cttgtggggc tctcccagcc cctccagaag cccacccac | 4740 |
| ttctcgccaa ccccgatct ctaaatgagg cctgagcgtc accctagttc tgcccctttt | 4800 |
| tagctgtgta gacttggacg agacatttga cttcccttc tccttgtcta taaaatgtgg | 4860 |
| acagtggacg tctgtcaccc aagagagttg tgggagacaa gatcacagct atgagcacct | 4920 |
| cgcacggtgt ccaggatgca cagcacaatc catgatgcgt tttctcccct tacgcacttt | 4980 |
| gaaacccatg ctagaaaagt gaatacatct gactgtgctc cactccaacc tccagcctgg | 5040 |
| atgtccctgt ctgggccctt tttctgtttt ttattctatg ttcagcacca ctggcaccaa | 5100 |
| atacatttta attcaccgaa agca | 5124 |

<210> SEQ ID NO 27
<211> LENGTH: 5124
<212> TYPE: DNA
<213> ORGANISM: homo sapien

<400> SEQUENCE: 27

| | |
|---|---|
| agaagcaggu uggcugugau gacagcacag agcucaggaa cgcugccuga ggacccuggg | 60 |
| gccuacgagg aggagaagag ggcaggagcu ggugggguggc uugcagagac ccugggcucc | 120 |

```
uauccugcca uaagccucgc ugucuccuga uaucugcagc caggcccuac ugacaccccc    180
aggccugagu gcaagcagag accccaccau ucccaggccc uggaggacug guccaccuua    240
acugggcagc ccuuggggca ggcgcuggcc ggugccucag cccaggccuc ugugcucugc    300
augcacugcc agccugccau caggccucua uugcagcccu gaaccaugau ccagggcacc    360
uuggagccag augguccccu cuggggcugg gacugggaca gugacaauga cugggauagu    420
gcugugcugg cccuccuggc gcuggcugug guggcugcca cagcgcuggc cuuacacugg    480
uuuggcuccg ggcacgauca agaggcggca gaaccggugu ccacagcccu cggggcucaa    540
ccucaucagg caggaggagc ugagcuggcc cugcaaccga agucuaaggu cagugauggc    600
agcgaggggc agagcccagg gcaggggaaa ccagagcccc caggacgcgg ccagcagagc    660
ccugucccug cugcagcgcc gggcggggc cuggccgcca uggcccggcu uccacucaag    720
acggcugucg aggaggcccg cagagaggca uuaggacagc aacggggcag ugccaccccc    780
gcggcccccc gagcggaagg aaaggagccu cccaggccag gcacugcccu ccugggcagg    840
agcgaagcag gggggauguc cgcccccuc cugauccacu ucacuccucg gagcccuggc    900
agcgaagcgg aggcggagac agguggugc agggcguccu cucgccaggc cgcaggcccc    960
gcggggcaac aggacacugg ccccuggcag gcggcgcgg ggcccucggg cucgaugggg   1020
agaggccggg gccggcggcg gcggauggac gcuggcucgg gagacagagc ccgccgcccc   1080
cggaaacugg acccgcuccg ccuggcgcc gcggggagcg uguggacgc gguggacggg   1140 gccgccgccc uggacgccca cgcgcgcggc cucccacag accccccacu cgcccaggag   1200
cccgcacucc cggcgcugcc cgcucccgc gcccugcagc cugggucuca gacggaaggc   1260
ucuggggcca agguggcug gagcaggag gccucggggg ucccugcccc cggaggaggc   1320
uggcccuggu ucagcaggga gguccggc accggagcu uuggcccagc cccagacucc   1380
acgcgccccu ggcuagagag uccgccucaa ggucgccac ucucguccca agggccgggu   1440
gccacagggg ccuacgaugc cggcgaggcc ggggcugaca gcccgagc uaacaguccu   1500 gccgcugacc ugggcccac ccggcccccg gagcaagcaa agccggcug agccggccac   1560 agccgcgcgc ccuccggag ccgugagccu cgccgcgcu ccgccuccc gcccgcagcu   1620 cccggcccgg gguucccacc ugaagcccug acucuccccu cuccuucaga cuuuugccc   1680 cuggagguua cccaggaucc uucgugggc gaaaaucuca gagcggcgcc agccccaagu   1740
ucagccucag cccaagucuu aacuucagcu ccagccucag uccuagcccc agcccuggcu   1800
ucauccccca gcucagcacc aaccucagcc accaccucaa ccuauccccc caccucagcc   1860 ccagcccag cuccaaccuc agcuccaacu ucaacccag cccagcccc aaguccagcu   1920 gcagccgcaa cuccagcccc agcccagu ccaguccaa cccucacacc cccauccca   1980 gcccuaaccc caguccaaac cccagcccua gcccagcuc caacuccagc ccuaacccca   2040 gccgcaucc cagcccuaac cccaguccca accccagccc uaagcccagc uccaaccucca   2100 gccccaaccc cagccgcauc cccugcccca gcccccaccu cagccccaac cccaaccccca   2160 gccgcauccc cugcccagc ugacggguca agccucagg agagugggc ucccccagg   2220 cgcuaccagg aggggcaggu ucagccagc ugggaaaac uuauugccau gguucuuaga   2280
agccaccccu uccccaggca agacaggccc caagggagug uccgagggc gguccccggg   2340 agccccgugg gucccagcac uuccacacac ucugaggaca gacacggccc cucuucuuca   2400 gugggggacag ucauagggac agguacaggg ggccugguug aggcuggagg ucagccacag   2460
ccaagaagcu ccgagaccaa cggaucgccc agcccagacc cuccccccagg ccuaagagga   2520
```

```
gagggaacca gggagaaaag ucuagacccg cugccccaag ccgcgaugcc caggggcccc    2580
gcacagcccc ccgcgcagag gccgccuggc cccgcggccu ccuccucugc gaggcgcuca    2640
cagccgguac cccagcuacg gaaacgcagc aggugcgaaa ucgccccgag cucggagcag    2700
gaggucaggc cggccgccuc gggggacccu caaggggagg cgccggggga gggggcagc    2760 ccugccggcc gcagcggggc gcucacggaa aagcaggagg aggcccgaag cucaugugu    2820 uucugcagag gcccggggu uggggggugg uggaggggcc ccggaagccc agcucccggg    2880
cccuggagcc cgccacggcg gcagcccugc ggcggcggcu ggaccugggc aguugccugg    2940
acgugcuggc cuuugcccag cagcacggag agcccgccu ggcgcaggag accuacgcgc    3000
ugaugagcga caaccugcug cgagugcugg agacccgug ccucuaccgc cggcugagcg    3060
cggccgaccg cgagcgcauc ucagccugc ggaccggccg gggccgggcg gugcugggcg    3120
uccucguacu gcccagccuc uaccaggggg gccgcucagg gcucccagg ggcccucgug    3180 gcgaggagcc uccugcggcg gcccugugu cccugccucu accgcgcac cugcaugugu    3240 ucaaccccg ggagaacacc uggcggcccc ugacccaggu gccgaggag gccccgcuuc    3300 ggggcugcgg ucucugcacc augcacaacu accuguuucu ggcggggc auccguggcu    3360 ccggugccaa ggccgucugc uccaacgagg ucuucugcua caaccccucug accaacaucu    3420 ggagccaggu ucggcccaug cagcaggccc gagcccagcu caagcuggug gcccuggacg    3480
ggcugcucua ugccaucggu ggcgaaugcc uguacagcau ggagugcuac gacccgcgaa    3540
cagacgccug gaccccacgc gcgccacucc ccgcaggcac cuucccugug gcccacgagg    3600
cuguggccug ccgugggac aucuacguca ccgggggguca ccucuucuac cgccugcuca    3660
gguacagccc cgugaaggau gcuugggacg agugcccaua cagugccagc caccggcguu    3720
ccagcgacau cguggcacug ggggcuucc uguaccgcuu cgaccugcug cggggcgugg    3780
gcgccgccgu gaugcgcuac aacacaguga ccggccccug gagcagggcu gccuccugc    3840 cccugcccgc ccccgcccca cugcacugca ccacccuggg caacaccauu uacugccuca    3900 accccaggu cacugccacc uucacgucu cuggggggac ugccaguuc caggccaagg    3960 agcugcagcc cuuccccuug gggagcaccg gguccucag uccauucauc cugacucugc    4020
ccccugagga ccggcugcag accucacucu gaguggcagg cagagaacca aagcugcuuc    4080
gcugcucucc agggagaccc uccugggaug ggccugagag gccggggcuc agggaagggg    4140
cugggaucgg aacuccugc ucuuguuucu ggacaacuuu ccccuucugc uuuaaagguu    4200
gucgauuauu uugaagccca gacucccuca gccucuuucu gccccucacu ccacacccag    4260 acuguuccu gacucaauuc cguaccuacu uacagacccu cucagcuugc ugacaccccc    4320 cugucugug gacucccuau ucccuagagc cagggacuga ugcgucucca cagacaagga    4380
cuuggcucgc uggagcucug cugagccgag agaggagggg guagaaaaca uucacacuuc    4440
cuaugcucug ucagcaggac agggagcaaa aacgucccca gcaacgcccc ucgccucugg    4500
gacuuucugc cugccuaag gccucccag guaccaaccc cguagcuauc uggucuguu    4560 uggcacugug gauucucaag ggccuagaac ccugccucu gaaacugguc cgcuggugca    4620
gcccugcugu cugcagcucc ugcccauacc cccagcccac accaggccag gcccacuccg    4680
ggcucaccac ccucugcagc cuugugggc ucccagcc ccuccagaag cccacccac    4740 uucucgccaa ccccgaucu cuaaaugagg ccugagcguc acccuaguuc ugccccuuuu    4800
uagcugugua gacuuggacg agacauuuga cuucccuuuc uccuugucua uaaaauguggg   4860
```

| | |
|---|---:|
| acaguggacg ucugucaccc aagagaguug ugggagacaa gaucacagcu augagcaccu | 4920 |
| cgcacggugu ccaggaugca cagcacaauc caugaugcgu uuucuccccu uacgcacuuu | 4980 |
| gaaacccaug cuagaaaagu gaauacaucu gacugugcuc cacuccaacc uccagccugg | 5040 |
| augucccugu cugggcccuu uuucuguuuu uuauucuaug uucagcacca cuggcaccaa | 5100 |
| auacauuuua auucaccgaa agca | 5124 |

<210> SEQ ID NO 28
<211> LENGTH: 2989
<212> TYPE: DNA
<213> ORGANISM: homo sapien

<400> SEQUENCE: 28

| | |
|---|---:|
| ccaccucagc cccaaccccca accccagccg caucccccugc cccagcugac gggucaaagc | 60 |
| cucaggagag uguggcucuc cccaggcgcu accaggaggg gcaggucuca gccagcuggg | 120 |
| gaaaccuuau ugccaugguu cuuagaagcc accccuuccc caggcaagac aggccccaag | 180 |
| ggaguguccc gagggcgguu cccggagccc cguggguccc cagcacuucc acacacucug | 240 |
| aggacagaca cggcccccucu ucuucagugg ggacagucau agggacaggu cagggggggcc | 300 |
| ugguugaggc uggaggucag ccacagccaa gaagcuccga gaccaacgga ucgcccagcc | 360 |
| cagacccucc cccaggccua agaggagagg gaaccaggga gaaaagucua gacccgcugc | 420 |
| cccaagccgc gaugcccagg ggccccgcac agccccccgc gcagaggccg ccuggccccg | 480 |
| cggccuccuc cucugcgagg cgcucacagc cgguacccca gcuacggaaa cgcagcaggu | 540 |
| gcgaaaucgc cccgagcucg gagcaggagg ucaggccggc cgccucgggg gacccucaag | 600 |
| gggaggcgcc gggggagggg ggcagcccug ccggccgcag cggggcgcuc acggaaaagc | 660 |
| aggaggaggc ccgaagcuca ugguguuucu gcagaggccc ggggguuggg ggguggugga | 720 |
| ggggcccccgg aagcccagcu cccgggcccu ggagcccgcc acggcggcag cccugcggcg | 780 |
| gcggcuggac cugggcaguu gccuggacgu gcuggccuuu gccagcagc acggagagcc | 840 |
| cggccuggcg caggagaccu acgcgcugau gagcgacaac cugcugcgag ugcugggaga | 900 |
| cccgugccuc uaccgccggc ugagcgcggc cgaccgcgag cgcauccuca gccgcggac | 960 |
| cggccggggc cgggcggugc ugggcguccu cguacugccc agccucuacc aggggggccg | 1020 |
| cucagggcuc cccaggggcc ucgguggcga ggagccuccu gcggcggccc cuguguccu | 1080 |
| gccucuaccu gcgcaccugc auguguucaa ccccccgggag aacaccuggc ggccccugac | 1140 |
| ccaggugccc gaggaggccc cgcuucgggg cugcggucuc ugcaccaugc acaacuaccu | 1200 |
| guuucuggcg gggggcaucc guggcuccgg ugccaaggcc gucugcucca acgaggucuu | 1260 |
| cugcuacaac ccucugacca acaucuggag ccagguucgg cccaugcagc aggcccgagc | 1320 |
| ccagcucaag cugguggccc uggacgggcu gcucuaugcc aucgguggcg aaugccugua | 1380 |
| cagcauggag ugcuacgacc cgcgaacaga cgccuggacc ccacgcgcgc cacuccccgc | 1440 |
| aggcaccuuc ccuguggccc acgaggcugu ggccugccgu ggggacaucu acgucaccgg | 1500 |
| gggucaccuc uuccaccgcc ugcucaggua cagccccgug aaggaugcuu gggacgagug | 1560 |
| cccauacagu gccagccacc ggcguuccag cgacaucgug cacuggggg cuuccugua | 1620 |
| ccgcuucgac cugcugcggg gcguggcgc cgccgugaug cgcuacaaca cagugaccgg | 1680 |
| cuccuggagc agggcugccu cccgcccccu gccgcccccu gcccacugc acugcaccac | 1740 |
| ccugggcaac accauuuacu gccucaaccc ccaggucacu gccaccuuca gucucucugg | 1800 |
| ggggacugcc caguuccagg ccaaggagcu gcagccccuuc cccuugggga gcaccgggu | 1860 |

| | |
|---|---|
| ccucagucca uucauccuga cucugccccc ugaggaccgg cugcagaccu cacucugagu | 1920 |
| ggcaggcaga gaaccaaagc ugcuucgcug cucuccaggg agacccuccu gggaugggcc | 1980 |
| ugagaggccg gggcucaggg aaggggcugg gaucggaacu uccugcucuu guuucuggac | 2040 |
| aacuuucccc uucugcuuua aagguugucg auuauuuuga agcccagacu cccucagccu | 2100 |
| cuuucugccc cucacuccac acccagacug uuccugacu caauuccgua ccuacuuaca | 2160 |
| gacccucuca gcuugcugac acccccugu cuguggacu cccuauuccc uagagccagg | 2220 |
| gacugaugcg ucuccacaga caaggacuug gcucgcugga gcucugcuga gccgagagag | 2280 |
| gaggggguag aaaacauuca cacuuccuau gcucugucag caggacaggg agcaaaaacg | 2340 |
| uccccaggca acgcccucgc cucugggacu uucugccugu ccuaaggccu ccccagguac | 2400 |
| caaccccgua gcuaucuggg ucuguuuggc acguggauu ucaagggcc uagaacccuu | 2460 |
| gccucugaaa cuggucccgcu ggugcagccc ugcugucugc agccugcc cauacccca | 2520 |
| gcccacacca ggccaggccc acuccgggcu caccacccuc ugcagccuug uggggcucuc | 2580 |
| ccagccccuc cagaagccca ccccacuucu cgccaacccc cgaucucuaa augaggccug | 2640 |
| agcgucaccc uaguucugcc ccuuuuuagc uguguagacu uggacgagac auuugacuuc | 2700 |
| ccuuucuccu ugucuauaaa augguggacag uggacgucug ucacccaaga gaguuguggg | 2760 |
| agacaagauc acagcuauga gcaccucgca cggugccag gaugcacagc acaauccaug | 2820 |
| augcguuuuc uccccuuacg cacuuugaaa cccaugcuag aaaagugaau acaucugacu | 2880 |
| gugcuccacu ccaaccucca gccuggaugu cccugucgg gcccuuuuuc uguuuuuau | 2940 |
| ucuauguuca gcaccacugg caccaaauac auuuuaauuc accgaaagc | 2989 |

<210> SEQ ID NO 29
<211> LENGTH: 4836
<212> TYPE: DNA
<213> ORGANISM: homo sapien

<400> SEQUENCE: 29

| | |
|---|---|
| acugccagcc ugccaucagg ccucuauugc agcccugaac caugauccag ggcaccuugg | 60 |
| agccagaugg uccccucugg ggcugggacu gggacaguga caaugacugg gauagugcug | 120 |
| ugcuggcccu ccuggcgcug gcuggguggug cugccacagc gcuggccuua cacugguuug | 180 |
| gcuccgggca cgaucaagag gcggcagaac cggugccac agcccucggg gcucaaccuc | 240 |
| aucaggcagg aggagcugag cuggcccugc aaccgaaguc uaaggucagu gauggcagcg | 300 |
| aggggcagag cccagggcag gggaaaccag agccccagg acgcggccag cagagcccug | 360 |
| ucccugcugc agcgccgggc gggggccugg ccgccauggc ccggcuucca cucaagacgg | 420 |
| cugucgagga ggcccgcaga gaggcauuag gacagcaacg gggcagugcc accccgcgg | 480 |
| cccccccgagc ggaaggaaag gagccucccca ggccaggcac ugcccuccug gcaggagcg | 540 |
| aagcaggggg gauguccgcc cccucccuga uccacuucac uccucggagc ccuggcagcg | 600 |
| aagcggaggc ggagacaggu gguguucaggg cguccucucg ccaggccgca ggccccgcgg | 660 |
| ggcaacagga cacuggcccc uggcaggcgg gcgcggggcc cucgggcucg auggggagag | 720 |
| gccggggccg gcggcggcgg auggacgcug gcucgggaga cagagcccgc cgccccgga | 780 |
| aacuggaccc gcuccgccug ggcgccgcg ggagcgugug ggacgcggug gacggggccg | 840 |
| ccgcccugga cgcccacgcg cgcggccucc cacaggacc cccacucgcc caggagcccg | 900 |
| cacucccggc gcugcccgcu ccccgcgccc ugcagccugg gucucagacg gaaggcucug | 960 |

-continued gggccaaggg uggcuggagc agggaggccu cgggggguccc ugcccccgga ggaggcuggc 1020
ccugggucag cagggagguc ccgggcaccc ggagcuuugg cccagcccca gacuccacgc 1080
gccccuggcu agagaguccg ccucaagguc gcccacucuc gucccaaggg ccgggugcca 1140
caggggccua cgaugccggc gaggccgggg cugacagcuc ccgagauaac aguccugccg 1200
cugaccuggg gcccacccgg cccccggagc aagcaaagcc ggcugcagcc ggccacagcc 1260
gcgcgcccuc ccggagccgu gagccucgcc cgcgcuccgc cuccccgccc gcagcucccg 1320
gcccgggguu cccaccugaa gcccugacuc uccccucucc uucagacuuu uugccccugg 1380
agguuaccca ggauccuucc gugggcgaaa aucucagagc ggcgccagcc ccaaguucag 1440
ccucagccca agucuuaacu ucagcuccag ccucaguccu agccccagcc cuggcuucau 1500
cccccagcuc agcaccaacc ucagccacca ccucaaccuc aucccccacc ucagccccag 1560
ccccagcucc aaccucagcu ccaacuucaa ccccagcccc agccccaagu ccagcugcag 1620
ccgcaacucc agccccagcc ccagucccag ucccaacccu cacaccccca uccccagccc 1680
uaaccccagu cccaacccca gcccuaagcc cagcuccaac uccagcccua accccagccg 1740
cauccccagc ccuaacccca gucccaaccc cagcccuaag cccagcucca acuccagccc 1800
caaccccagc cgcaucccu gccccagccc ccaccucagc cccaacccca accccagccg 1860
cauccccugc cccagcugac gggucaaagc cucaggagag uguggcucuc cccaggcgcu 1920
accaggaggg gcaggucuca gccagcuggg gaaaccuuau ugccaugguu cuuagaagcc 1980
accccuuccc caggcaagac aggccccaag ggagugucccc gagggcgguu cccgggagcc 2040
ccgugggucc cagcacuucc acacacucug aggacagaca cggccccucu ucuucagugg 2100
ggacagucau agggacaggu acagggggcc ugguugaggc uggaggucag ccacagccaa 2160
gaagcuccga gaccaacgga ucgcccagcc cagacccucc cccaggccua agaggagagg 2220
gaaccaggga gaaaagucua gacccgcugc cccaagccgc gaugcccagg ggccccgcac 2280
agccccccgc gcagaggccg ccuggccccg cggccuccuc cucugcgagg cgcucacagc 2340
cgguacccca gcuacggaaa cgcagcaggu gcgaaaucgc cccgagcucg gagcaggagg 2400
ucaggccggc cgccucgggg gacccucaag gggaggcgcc gggggagggg ggcagcccug 2460
ccggccgcag cggggcgcuc acggaaaagc aggaggaggc ccgaagcuca uggguguuucu 2520
gcagaggccc gggggguuggg ggguggugga ggggccccgg aagcccagcu cccgggcccu 2580
ggagcccgcc acggcggcag cccugcggcg gcggcuggac cugggcaguu gccuggacgu 2640
gcuggccuuu gcccagcagc acggagagcc cggccuggcg caggagaccu acgcgcugau 2700
gagcgacaac cugcugcgag ugcugggaga cccgugccuc uaccgccggc ugagcgcggc 2760
cgaccgcgag cgcauccuca gccugcggac cggccggggc cgggcggugc ugggcgucccu 2820
cguacugccc agccucuacc aggggggccg cucagggcuc cccaggggcc cucguggcga 2880
ggagccuccu gcggcggccc cuguguccccu gccucuaccu gcgcaccugc auguguucaa 2940
cccccgggag aacaccuggc ggccccugac ccaggugccc gaggaggccc cgcuucgggg 3000
cugcggucuc ugcaccaugc acaacuaccu guuucuggcg gggggcaucc guggcuccgg 3060
ugccaaggcc gucugcucca acgaggucuu cugcuacaac ccucugacca acaucuggag 3120
ccagguucgg cccaugcagc aggcccgagc ccagcucaag cugguggccc uggacgggcu 3180
gcucuaugcc aucgguggcg aaugccugua cagcauggag ugcuacgacc cgcgaacaga 3240
cgccuggacc ccacgcgcgc cacuccccgc aggcaccuuc ccuguggccc acgaggcugu 3300
ggccugccgu ggggacaucu acgucaccgg gggucaccuc uucuaccgcc ugcucaggua 3360


-continued

| | |
|---|---|
| cagccccgug aaggaugcuu gggacgagug cccauacagu gccagccacc ggcguuccag | 3420 |
| cgacaucgug gcacuggggg gcuuccugua ccgcuucgac cugcugcggg gcgugggcgc | 3480 |
| cgccgugaug cgcuacaaca cagugaccgg cuccuggagc agggcugccu cccugcccu | 3540 |
| gcccgccccc gccccacugc acugcaccac ccugggcaac accauuuacu gccucaaccc | 3600 |
| ccaggucacu gccaccuuca cggucucugg ggggacugcc caguuccagg ccaaggagcu | 3660 |
| gcagcccuuc cccuugggga gcaccggggu ccucagucca uucauccuga cucugccccc | 3720 |
| ugaggaccgg cugcagaccu cacucugagu ggcaggcaga gaaccaaagc ugcuucgcug | 3780 |
| cucuccaggg agacccuccu gggaugggcc ugagaggccg gggcucaggg aaggggcugg | 3840 |
| gaucggaacu uccugcucuu guuucggac aacuuccccc uucugcuuua aagguugucg | 3900 |
| auuauuuuga agcccagacu cccucagccu cuuucugccc cucaccccac acccagacug | 3960 |
| uuccugacu caauuccgua ccacuuaca gacccucuca gcuugcugac accccccugu | 4020 |
| cugugggacu cccuauuccc uagagccagg gacugaugcg ucuccacaga caaggacuug | 4080 |
| gcucgcugga gcucugcuga gccgagagag gaggggguag aaaacauuca cacuuccuau | 4140 |
| gcucugucag caggacaggg agcaaaaacg uccccaggca acgcccucgc cucugggacu | 4200 |
| uucugccugu ccuaaggccu ccccagguac caaccccgua gcuaucuggg ucuguuggc | 4260 |
| acguggauu cucaagggcc uagaacccuu gccucugaaa cugguccgcu ggugcagccc | 4320 |
| ugcugucugc agccccugcc cauacccca gcccacacca ggccaggccc acuccgggcu | 4380 |
| caccacccuc ugcagcccuug uggggcucuc ccagccccuc cagaagccca ccccacuucu | 4440 |
| cgccaaccccc cgaucucuaa augaggccug agcgucaccc uaguucugcc ccuuuuuagc | 4500 |
| uguguagacu uggacgagac auuugacuuc ccuuucuccu ugucuauaaa auguggacag | 4560 |
| uggacgucug ucacccaaga gaguugugg agacaagauc acagcuauga gcaccucgca | 4620 |
| cgguguccag gaugcacagc acaauccaug augcguuuuc ccccuuacg cacuuugaaa | 4680 |
| cccaugcuag aaaagugaau acaucugacu gugcuccacu ccaaccucca gccuggaugu | 4740 |
| cccugucugg gcccuuuuuc uguuuuuuau ucuauguuca gcaccacugg caccaaauac | 4800 |
| auuuuaauuc accgaaagca aaaaaaaaaa aaaaaa | 4836 |

<210> SEQ ID NO 30
<211> LENGTH: 2098
<212> TYPE: DNA
<213> ORGANISM: homo sapien

<400> SEQUENCE: 30

| | |
|---|---|
| ccaccucagc cccaacccca accccagccg caucccugc cccagcugac gggucaaagc | 60 |
| cucaggagag guggcucuc cccaggcgcu accaggaggg gcaggucuca gccagcuggg | 120 |
| gaaaccuuau ugccaugguu cuuagaagcc accccuuccc caggcaagac aggccccaag | 180 |
| ggagugcccc gagggcgguu cccggagccc ccgugguuc cagcacuucc acacacucug | 240 |
| aggacagaca cggccccucu ucuucagugg ggacagucau agggacaggu cagggggcc | 300 |
| ugguugaggc uggaggucag ccacagccaa gaagcuccga gaccaacgga ucgcccagcc | 360 |
| cagacccucc cccaggccua agaggagagg gaaccaggga gaaaagucua gacccgcugc | 420 |
| cccaagccgc gaugcccagg ggccccgcac agcccccgc gcagaggccg ccuggccccg | 480 |
| cggccuccuc cucucgagg cgcucacagc cgguacccca gcuacggaaa cgcagcaggu | 540 |
| gcgaaaucgc cccgagcucg gagcaggagg ucaggccggc cgccucgggg gacccucaag | 600 |

```
gggaggcgcc gggggagggg ggcagcccug ccggccgcag cggggcgcuc acggaaaagc    660
aggaggaggc ccgaagcuca uggguguuucu gcagaggccc gggggguuggg gggugguga    720 ggggccccgg aagcccagcu cccgggcccu ggagcccgcc acggcggcag cccugcggcg    780
gcggcuggac cugggcaguu gccuggacgu gcuggccuuu gcccagcagc acggagagcc    840
cggccugccg caggagaccu acgcgcugau gagcgacaac cugcugcgag ugcugggaga    900
cccgugccuc uaccgccggc ugagcgcggc cgaccgcgag cgcauccuca gccugcggac    960
cggccggggc cgggcggugc ugggcguccu cguacugccc agccucuacc agggggggccg   1020 cucagggcuc cccaggggcc cucgugggcga ggagccuccu gcggcggccc cugugucccu   1080
gccucuaccu gcgcaccugc augUguucaa ccccccgggag aacaccuggc ggccccugac   1140
ccaggugccc gaggaggccc cgcuucgggg cugcggucuc ugcaccaugc acaacuaccu   1200
guuucuggcg gggggcaucc gugggcuccgg ugccaaggcc gucugcucca acgaggucuu   1260
cugcuacaac ccucugacca acaucuggag ccagguucgg cccaugcagc aggcccgagc   1320
ccagcucaag cugguggccc uggacgggcu gcucuaugcc aucgguggcg aaugccugua   1380
cagcauggag ugcuacgacc cgcgaacaga cgccuggacc ccacgcgcgc cacucccgc   1440 aggcaccuuc ccuguggccc acgaggcugu ggccugccgu ggggacaucu acgucaccgg   1500
gggucaccuc uucuaccgcc ugcucaggua cagccccgug aaggaugcuu gggacgagug   1560
cccauacagu gccagccacc ggcguuccag cgacaucgug gcacuggggg gcuuccugua   1620
ccgcuucgac cugcugcggg gcgugggcgc cgccgugaug cgcuacaaca cagugaccgg   1680
cuccuggagc agggcugccu cccugcccu gcccgccccc gccccacugc acugcaccac   1740
ccugggcaac accauuuacu gccucaaccc caggucacu gccaccuuca cggucucugg   1800
ggggacugcc caguuccagg ccaaggagcu gcagcccuuc cccuugggga gcaccggggu   1860
ccucagucca uucauccuga cucugccccc ugaggaccgg cugcagaccu cacucugagu   1920
ggcaggcaga gaaccaaagc ugcuucgcug cucuccaggg agacccuccu gggaugggcc   1980
ugagaggccg gggcucaggg aaggggcugg gaucggaacu uccugcucuu guuucuggac   2040
aacuuucccc uucugcuuua aagguugucg auuauuuuga aaaaaaaaaa aaaaaaa      2098
```

<210> SEQ ID NO 31
<211> LENGTH: 5124
<212> TYPE: DNA
<213> ORGANISM: homo sapien

<400> SEQUENCE: 31

```
agaagcaggu uggcugugau gacagcacag agcucaggaa cgcugccuga ggacccuggg     60
gccuacgagg aggagaagag ggcaggagcu ggugggugc uugcagagac ccugggcucc    120
uauccugcca uaagccucgc ugucuccuga uaucugcagc caggcccuac ugacacccc    180 aggccugagu gcaagcagag acccccaccau ucccaggccc uggaggacug guccaccuua    240
acugggcagc ccuuggggca ggcgcuggcc ggugccucag cccaggccuc ugugcucugc    300
augcacugcc agccugccau caggccucua uugcagcccu gaaccaugau ccagggcacc    360
uuggagccag auggucccu cugggggcugg gacugggaca gugacaauga cugggauagu    420
gcugugcugg cccuccuggc gcuggcugug ugggcugcca gcgcuggcc cuuacacugg    480 uuuggcuccg ggcacgauca agaggcggca gaaccggugu ccacagcccu cggggcucaa    540
ccucaucagg caggaggagc ugagcuggcc cugcaaccga agucuaaggu cagugauggc    600
agcgaggggc agagcccagg gcaggggaaa ccagagcccc caggacgcgg ccagcagagc    660
```

```
ccugucccug cugcagcgcc gggcggggc cuggccgcca uggcccggcu uccacucaag      720
acggcugucg aggaggcccg cagagaggca uuaggacagc aacggggcag ugccacccc      780 gcggccccc gagcggaagg aaaggagccu cccaggccag gcacugcccu ccugggcagg     840
agcgaagcag ggggaugu cgccccccu cugauccacu ucacuccucg agcccuggc        900 agcgaagcgg aggcggagac agguggaguc agggcguccu cucgccaggc cgcaggccc      960 gcgggcaac aggacacug cccugggcag gcgggcgcgg ggcccucggg cucgaugggg      1020
agaggccggg gccggcggcg gcggauggac gcuggcucgg gagacagagc ccgccgcccc    1080 cggaaacug acccgcuccg ccugggcgcc gcgggagcg ugugggacgc gguggacggg      1140
gccgccgccc uggacgccca cgcgcgcggc cucccacag gaccccacu cgcccaggag       1200 cccgcacuc cggcgcugcc cgcucccgc gcccugcagc cugggucuca gacgaaggc        1260 ucuggggcca agguggcug gagcaggag gccucggggg ucccugccc cggaggaggc      1320 uggcccuggg ucagcaggga gguccccggg cccggagcu uggcccagc cccagacucc      1380 acgcgccccu ggcuagagag uccgccucaa ggucgcccac ucgucccca agggccgggu     1440 gccacagggg ccuacgaugc cggcgaggcc ggggcugaca gcucccgaga uaacaguccu     1500
gccgcugacc uggggcccac ccggccccg gagcaagcaa agccggcug agccggccac     1560 agccgcgcgc cucccggag ccgugagccu cgcccgcgcu ccgccucccc gcccgcagcu    1620
cccggcccgg gguucccacc ugaagcccug acucucccu uccuucaga cuuuuugccc     1680 cuggagguua cccaggaucc uuccgugggc gaaaaucuca gagcggcgcc agccccaagu    1740
ucagccucag cccaagucuu aacuucagcu ccagccucag uccuagcccc agccuggcu    1800 ucauccccca gcucagcacc aaccucagcc accaccucaa ccucauccc caccucagcc    1860 ccagcccag cuccaaccuc agcccaacu ucaaccccag cccagccccc aaguccagcu    1920
gcagccgcaa cuccagcccc agcccagu ccaguccca ccucacacc cccauccccca      1980 gcccuaaccc caguccccaac cccagcccua gcccagcuc caacuccagc ccuaaccccca   2040 gccgcauccc cagcccuaac cccagucccca accccagccc uaagcccagc uccaacucca   2100
gccccaaccc cagccgcauc cccugcccca gcccccaccu cagccccaac cccaacccca    2160
gccgcauccc cugccccagc ugacgggca agcccuccagg agagugggc ucucccagg     2220 cgcuaccagg aggggcaggu ucagccagc uggggaaacc uuauugccau gguucuuaga     2280 agccacccu uccccaggca agacaggccc caagggagug ucccgagggc gguucccggg    2340 agccccgug gucccagcac uuccacacac ucgaggaca gacacggccc cucuucuuca     2400 gugggacag ucauagggac agguacaggg ggccugguug aggcuggagg ucagccacag    2460
ccaagaagcu ccgagaccaa cggaucgccc agccagacc cucccccagg ccuaagagga     2520
gagggaacca gggagaaaag ucuagacccg cugcccccaag ccgcgaugcc caggggcccc    2580
gcacagcccc ccgcgcagag gccgccuggc ccgcggccu ccuccucugc gaggcgcuca    2640
cagccgguac cccagcuacg gaaacgcagc aggugcgaaa ucgccccgag ucggagcag     2700 gaggucaggc cggccgccuc ggggaccccu caaggggagg cgccggggga gggggcagc     2760 ccugccggcc gcagcgggc gcucacgaa aagcaggagg aggcccggaa gcucaugguu     2820
uuucugcaga ggcccggggg uuggggggug guggagggc cccggaagcc cagcucccgg   2880
gcccuggagc ccgccacggc ggcagcccug cggcggcgg uggaccuggg caguugccug    2940
gacgugcugg ccuuugccca gcagcacgga gagcccggcc uggcgcagga gaccuacgcg    3000
```

| | |
|---|---|
| cugaugagcg acaaccugcu gcgagugcug ggagacccgu gccucuaccg ccggcugagc | 3060 |
| gcggccgacc gcgagcgcau ccucagccug cggaccggcc ggggccgggc ggugcugggc | 3120 |
| guccucguac ugcccagccu cuaccagggg ggccgcucag ggcuccccag ggcccucgug | 3180 |
| gcgaggagcc uccugcggcg gccccugugu cccugccucu accugcgcac cugcaugugu | 3240 |
| ucaaccccg ggagaacacc uggcggcccc ugacccaggu gcccgaggag gccccgcuuc | 3300 |
| ggggcugcgg ucucugcacc augcacaacu accuguuucu ggcgggggc auccguggcu | 3360 |
| ccggugccaa ggccgucugc uccaacgagg ucuucugcua caacccucug accaacaucu | 3420 |
| ggagccaggu ucggcccaug cagcaggccc gagcccagcu caagcuggug gcccuggacg | 3480 |
| ggcugcucua ugccaucggu ggcgaaugcc uguacagcau ggagugcuac gacccgcgaa | 3540 |
| cagacgccug gaccccacgc gcgccacucc ccgcaggcac cuucccugug gcccacgagg | 3600 |
| cugugggccug ccgugggggac aucuacguca ccggggguca ccucuucuac cgccugcuca | 3660 |
| gguacagccc cgugaaggau gcuugggacg agugcccaua cagugccagc caccggcguu | 3720 |
| ccagcgacau cguggcacug gggggcuucc uguaccgcuu cgaccugcug cggggcgugg | 3780 |
| gcgccgccgu gaugcgcuac aacacaguga ccggcuccug gagcagggcu gccucccugc | 3840 |
| cccugcccgc ccccgcccca cugcacugca ccacccuggg caacaccauu uacugccuca | 3900 |
| accccccaggu cacugccacc uucacggucu cuggggggac ugcccaguuc caggccaagg | 3960 |
| agcugcagcc cuucccccuug gggagcaccg ggguccucag uccauucauc cugacucugc | 4020 |
| ccccugagga ccggcugcag accucacucu gaguggcagg cagagaacca aagcugcuuc | 4080 |
| gcugcucucc agggagaccc uccugggaug ggccugagag gccggggcuc agggaagggg | 4140 |
| cugggaucgg aacuuccugc ucuuguuucu ggacaacuuu ccccuucugc uuuaaagguu | 4200 |
| gucgauuauu uugaagccca gacucccuca gccucuuucu gccccucacu ccacacccag | 4260 |
| acuguuuccu gacucaauuc cguaccuacu uacagacccu cucagcuugc ugacaccccc | 4320 |
| cugucugugg gacucccuau ucccuagagc caggacugac ugcgucucca cagacaagga | 4380 |
| cuuggcucgc uggagcucug cugagccgag agaggagggg guagaaaaca uucacacuuc | 4440 |
| cuaugcucug ucagcaggac agggagcaaa aacguccccca ggcaacgccc ucgccucugg | 4500 |
| gacuuucugc cuguccuaag gccucccccag guaccaaccc cguagcuauc ugggucuguu | 4560 |
| uggcacugug gauucuuaag ggccuagaac ccuugccucu gaaacugguc cgcuggugca | 4620 |
| gcccugcugu cugcagcucc ugcccauacc cccagcccac accaggccag gcccacuccg | 4680 |
| ggcucaccac ccucugcagc cuugggggc ucuccccagcc ccuccagaag cccacccccac | 4740 |
| uucucgccaa cccccgaucu cuaaaugagg ccugagcguc acccuaguuc ugcccccuuuu | 4800 |
| uagcugugua gacuuggacg agacauuuga cuucccuuuc uccuugucua aaaaugugg | 4860 |
| acagugggacg ucugucaccc aagagaguug uggggagacaa gaucacagcu augagcaccu | 4920 |
| cgcacggugu ccaggaugca cagcacaaauc caugaugcgu uuucccccu uacgcacuuu | 4980 |
| gaaacccaug cuagaaaagu gaauacaucu gacugugcuc cacuccaacc uccagccugg | 5040 |
| augcccugu cugggcccuu uuucuguuuu uuauucuaug uucagcacca cuggcaccaa | 5100 |
| auacauuuua auuccaccgaa agca | 5124 |

<210> SEQ ID NO 32
<211> LENGTH: 2989
<212> TYPE: DNA
<213> ORGANISM: homo sapien

<400> SEQUENCE: 32

-continued

```
ccaccucagc cccaacccca accccagccg caucccccugc cccagcugac gggucaaagc    60
cucaggagag uguggcucuc cccaggcgcu accaggaggg caggucuca gccagcuggg      120
gaaaccuuau ugccauggu uuagaagcc accccuuccc caggcaagac aggcccaag       180
ggagugccc gagggcgguu cccgggagcc ccguggaucc cagcacuucc acacacucug     240
aggacagaca cggcccucu ucuucagugg ggacagucau agggacaggu cagggggcc      300
ugguugaggc uggaggucag ccacagccaa gaagcuccga gaccaacgga ucgcccagcc    360
cagacccucc cccaggccua agaggagagg gaaccaggga gaaaagucua gacccgcugc    420
cccaagccgc gaugcccagg ggccccgcac agccccccgc gcagaggccg ccuggccccg    480
cggccuccuc cucugcgagg cgcucacagc gguaccccca gcuacggaaa cgcagcaggu    540
gcgaaaucgc cccgagcucg gagcaggagg ucaggccggc cgccucgggg gacccucaag    600
gggaggcgcc gggggagggg ggcagcccug ccggccgcag cggggcgcuc acggaaaagc    660
aggaggaggc ccggaagcuc augugguuuc ugcagaggcc cggggguugg ggggugguug    720
aggggccccg gaagcccagc ucccgggccc uggagcccgc cacggcggca gcccugcggc    780
ggcggcugga ccugggcagu ugccuggacg ugcuggccuu ugcccagcag cacgagagc    840
ccggccuggc gcaggagacc uacgcgcuga ugagcgacaa ccugcugcga gugcugggag    900
acccgugccu cuaccgccgg cugagcgcgg ccgaccgcga gcgcauccuc agccugcgga    960
ccggccgggg ccgggcggug cugggcgucc ucguacugcc cagccucuac caggggggcc   1020
gcucagggcu ccccagggcc cucgugggcga ggagccuccu gcggcggccc cugugucccu  1080
gcccucuaccu gcgcaccugc augguucaa ccccgggag aacaccuggc ggccccugac    1140
ccaggugccc gaggaggccc cgcuucgggg cugcggucuc ugcaccaugc acaacuaccu   1200
guuucuggcg gggggcaucc guggcuccgg ugccaaggcc gucugcucca acgaggucuu   1260
cugcucacaac cccucugacca acaucuggag ccagguucgg cccaugcagc aggcccgagc  1320
ccagcucaag cugguggccc uggacgggcu gcucuaugcc aucgguggcg aaugccugua   1380
cagcauggag ugcuacgacc cgcgaacaga cgccuggacc ccacgcgcgc cacuccccgc   1440
aggcaccuuc ccugugccc acgaggcugu ggccugccgu ggggacaucu acgucaccgg    1500
gggucaccuc uucuaccgcc ugcucaggua cagccccgug aaggaugcuu gggacgagug   1560
cccauacagu gccagccacc ggcguucag cgacaucgug gcacgggg gcuuccgua        1620
ccgcuucgac cugcugcggg gcguggcgc cgccgugaug cgcuacaaca cagugaccgg    1680
cuccuggagc agggcugccu cccugccccu gcccgcccc gccccacugc acugcaccac    1740
ccugggcaac accauuuacu gccucaaccc ccaggucacu gccaccuuca cggucucugg   1800
ggggacugcc caguuccagg ccaaggagcu gcagcccuuc cccuugggga gcaccggggu   1860
ccucaguccca uucauccuga cucugccccc ugaggaccgg cugcagaccu cacucugagu  1920
ggcaggcaga gaaccaaagc ugcuucgcu cuccagggg agacccuccu gggaugggcc     1980
ugagaggccg gggcucaggg aaggggcugg gaucggaacu uccugcucuu guuucuggac   2040
aacuuucccc uucugcuuua aagguugucg auuauuuga agcccagacu cccucagccu    2100
cuuucugccc cucacuccac acccagacgu uuccgacu caauuccgua ccuacuuaca    2160
gaccccucua gcuugcugac accccccugu cugugggacu cccauuuccc uagagccagg   2220
gacugaugcg ucuccacaga caaggacuug gcucgcugga gcucgcugga ccgagagag    2280
gaggggguag aaaacauuca cacuuccuau gcucugucag caggacaggg agcaaaaacg  2340
```

| | |
|---|---:|
| ucccaggca acgcccucgc cucugggacu uucugccugu ccuaaggccu ccccagguac | 2400 |
| caaccccgua gcuaucuggg ucuguuuggc acuguggauu cucaagggcc uagaacccuu | 2460 |
| gccucugaaa cuggguccgcu ggugcagccc ugcugucugc agccucugcc cauacccca | 2520 |
| gcccacacca ggccaggccc acuccgggcu caccacccuc ugcagccuug ggggcucuc | 2580 |
| ccagccccuc cagaagccca ccccacuucu cgccaacccc cgaucucuaa augaggccug | 2640 |
| agcgucaccc uaguucugcc ccuuuuuagc uguguagacu uggacgagac auuugacuuc | 2700 |
| ccuuucuccu ugucuauaaa augguggacag uggacgucug ucacccaaga gaguugugg | 2760 |
| agacaagauc acagcuauga gcaccucgca cggguguccag gaugcacagc acaauccaug | 2820 |
| augcguuuuc uccccuuacg cacuuugaaa cccaugcuag aaaagugaau acaucugacu | 2880 |
| gugcuccacu ccaaccucca gccuggaugu cccugucugg gcccuuuuuc uguuuuuau | 2940 |
| ucuauguuca gcaccacugg caccaaauac auuuuaauuc accgaaagc | 2989 |

<210> SEQ ID NO 33
<211> LENGTH: 4836
<212> TYPE: DNA
<213> ORGANISM: homo sapien

<400> SEQUENCE: 33

| | |
|---|---:|
| acugccagcc ugccaucagg ccucuauugc agcccugaac caugauccag ggcaccuugg | 60 |
| agccagaugg uccccucugg ggcugggacu gggacaguga caaugacugg gauagugcug | 120 |
| ugcuggcccu ccuggcgcug gcugugguggg cugccacagc gcuggccuua cacugguuug | 180 |
| gcuccgggca cgaucaagag gcggcagaac cggguccac agcccucggg gcucaaccuc | 240 |
| aucaggcagg aggagcugag cuggcccugc aaccgaaguc uaaggucagu gauggcagcg | 300 |
| agggcagag cccagggcag gggaaaccag agccccagg acgcgccag cagagccug | 360 |
| ucccugcugc agcgccgggc gggggccugg ccgccauggc ccggcuucca cucaagacgg | 420 |
| cugucgagga ggcccgcaga gaggcauuag gacagcaacg gggcagugcc accccgcgg | 480 |
| ccccccgagc ggaaggaaag gagccuccca ggccaggcac ugcccuccug gcaggagcg | 540 |
| aagcaggggg gauguccgcc ccccuccuga uccacuucac uccucggagc ccuggcagcg | 600 |
| aagcggaggc ggagacaggu ggugucaggg cguccucucg ccaggccgca ggccccgcgg | 660 |
| ggcaacagga cacuggcccc uggcaggcgg gcgcggggcc cucgggcucg auggggagag | 720 |
| gccggggccg gcgcggcgg auggacgcug gcucgggaga cagagccgc cgccccggga | 780 |
| aacuggaccc gcuccgccug ggcgccgcgg ggagcgugug ggacgcggug gacggggccg | 840 |
| ccgcccugga cgcccacgcg cgcggccucc ccacaggacc cccacucgcc caggagcccg | 900 |
| cacuccggc gcugcccgcu ccccgcgccc ugcagccugg gucucagacg gaaggcucug | 960 |
| gggccaaggg uggcuggagc agggaggccu cggggguccc ugccccggga ggaggcuggc | 1020 |
| ccugggucag cagggagguc ccgggcaccc ggagcuuugg cccagcccca gacuccacgc | 1080 |
| gccccuggcu agagaguccg ccucaagguc gcccacucuc gucccaaggg ccgggugcca | 1140 |
| caggggccua cgaugccggc gaggccgggg cugacagcuc ccgagauaac aguccugccg | 1200 |
| cugaccuggg gccacccgg ccccggagc aagcaaagcc ggcugcagcc ggccacagcc | 1260 |
| gcgcgcccuc ccggagccgu gagccucgcc ccgcgcuccgc cuccccgccc gcagcucccg | 1320 |
| gcccggggu cccaccugaa gcccugacuc uccccucucc uucagacuuu uugcccugg | 1380 |
| agguuacccca ggauccuucc gugggcgaaa aucucagagc ggcgcagcc ccaaguucag | 1440 |
| ccucagccca agucuuaacu ucagucccag ccucagccu agcccagcc cuggcuucau | 1500 |

```
cccccagcuc agcaccaacc ucagccacca ccucaaccuc aucccccacc ucagccccag    1560
ccccagcucc aaccucagcu ccaacuucaa ccccagcccc agcccaagu ccagcugcag    1620 ccgcaacucc agcccagcc ccagucccag ucccaacccu cacaccccca ucccagccc    1680 uaaccccagu cccaacccca gcccuaagcc cagcuccaac uccagcccua ccccagccg    1740 caucccagc ccuaacccca gucccaaccc cagcccuaag cccagcucca acuccagccc    1800
caaccccagc cgcaucccu gcccagcccc caccucagc cccaaccccca accccagccg    1860 cauccccugc cccagcugac gggucaaagc ucaggagag uguggcucuc cccaggcgcu    1920
accaggaggg gcaggucuca gccagcuggg gaaaccuuau ugccaugguu cuuagaagcc    1980
accccuuccc caggcaagac aggccccaag ggagugucc gagggcgguu cccgggagcc    2040
ccgugggucc cagcacuucc acacacucug aggacagaca cggccccucu ucuucagugg    2100
ggacagucau agggacaggu caggggggcc ugguugaggc uggaggucag ccacagccaa    2160
gaagcuccga caccaacgga ucgcccagcc cagacccucc cccaggccua agaggagagg    2220
gaaccaggga gaaaagucua gacccgcugc cccaagccgc gaugcccagg ggccccgcac    2280
agccccccgc gcagaggccg ccuggccccg cggccuccuc ucucgcgagg cgcucacagc    2340 cgguaccccca gcuacggaaa cgcagcaggu gcgaaaucgc cccgagcucg gagcaggagg    2400
ucaggccggc cgccucgggg gacccucaag gggaggcgcc gggggagggg ggcagcccug    2460
ccggccgcag cggggcgcuc acggaaaagc aggaggaggc ccggaagcuc auguguuuc    2520 ugcagaggcc cggggguugg gggguggug aggggccccg gaagcccagc ucccgggccc    2580
uggagcccgc cacggcggca gcccugcggc ggcggcugga ccugggcagu ugccuggacg    2640
ugcuggccuu ugcccagcag cacggagagc ccggccuggc gcaggagacc uacgcgcuga    2700
ugagcgacaa ccugcugcga gugcugggag acccgugccu cuaccgccgg cugagcgcgg    2760
ccgaccgcga gcgcauccuc agccugcgga ccggccgggg ccgggcggug cugggcgucc    2820
ucguacugcc cagccucuac cagggggggcc gcucagggcu cccagggggcc cucguggcga    2880 ggagccuccu gcggcggccc cuguucccca gccucuaccu gcgcaccugc auguguucaa    2940
cccccgggag aacaccuggc ggccccugac ccaggugccc gaggaggccc cgcuucgggg    3000
cugcggucuc ugcaccaugc acaacuaccu guuucggcg gggggcaucc guggcuccgg    3060
ugccaaggcc gucugcucca acgaggucuu cugcuacaac ccucugacca acaucuggag    3120
ccagguucgg cccaugcagc aggcccgagc ccagcucaag cuggugggcc uggacgggcu    3180
gcucuaugcc aucgguggcg aaugccugua cagcauggag ugcuacgacc gcgaacagga    3240
cgccuggacc ccacgcgcgc cacuccccgc aggcaccuuc ccuguggccc acgaggcugu    3300
ggccugccgu ggggacaucu acgucaccgg gggucaccuc uucuaccgcc ugcucaggua    3360
cagccccgug aaggaugcuu gggacgagug cccauacagu gccagccacc ggcguuccag    3420
cgacaucgug gcacuggggg gcuuccugua ccgcuucgac cugcugcggg gcgugggcgc    3480
cgccgugaug cgcuacaaca cagugaccgg cuccuggagc agggcugccu cccugccccu    3540
gcccgccccc gccccacugc acugcaccac ccugggcaac accauuuacu gccucaaccc    3600
ccaggucacu gccaccuuca cggucucugg ggggacugcc caguuccagg ccaaggagcu    3660
gcagcccuuc cccuugggga gcaccggggu cccagucca uucauccuga cucugccccc    3720
ugaggaccgg cugcagaccu cacucugagu ggcaggcaga gaaccaaagc ugcuucgcug    3780
cucuccaggg agacccuccu gggaugggcc ugagaggccg gggcucaggg aaggggcugg    3840
```

| | |
|---|---|
| gaucggaacu uccugcucuu guuucuggac aacuuccccc uucugcuuua aagguugucg | 3900 |
| auuauuuuga agcccagacu cccucagccu cuuucugccc cucacuccac acccagacug | 3960 |
| uuccugacu caauuccgua ccacuuaca gacccucuca gcuugcugac acccccgu | 4020 |
| cugugggacu cccuauuccc uagagccagg gacugaugcg ucuccacaga caaggacuug | 4080 |
| gcucgcugga gcucugcuga gccgagagag gaggggguag aaaacauuca cacuuccuau | 4140 |
| gcucugucag caggacaggg agcaaaaacg uccccaggca acgcccucgc ucugggacu | 4200 |
| uucugccugu ccuaaggccu ccccagguac caaccccgua gcuaucuggg ucuguuggc | 4260 |
| acuguggauu ucaagggcc uagaacccuu gccucugaaa cuggucogcu ggugcagccc | 4320 |
| ugcugucugc agccugcc cauacccca gcccaccacca ggccaggccc acucggggcu | 4380 |
| caccacccuc ugcagccuug uggggcucuc ccagccccuc cagaagccca ccccacuucu | 4440 |
| cgccaacccc cgaucucuaa augaggccug agcgucaccc uaguucugcc ccuuuuuagc | 4500 |
| uguguagacu uggacgagac auuugacuuc ccuuucuccu ugucuauaaa augugacag | 4560 |
| uggacgucug ucacccaaga gaguuguggg agacaagauc acagcuauga gcaccucgca | 4620 |
| cggguguccag gaugcacagc acaauccaug augcguuuuc uccccuuacg cacuuugaaa | 4680 |
| cccaugcuag aaaagugaau acaucugacu gugcuccacu ccaaccucca gccuggaugu | 4740 |
| cccugucugg gcccuuuuuc uguuuuuuau ucuauguuca gcaccacugg caccaaauac | 4800 |
| auuuuaauuc accgaaagca aaaaaaaaaa aaaaaa | 4836 |

<210> SEQ ID NO 34
<211> LENGTH: 2098
<212> TYPE: DNA
<213> ORGANISM: homo sapien

<400> SEQUENCE: 34

| | |
|---|---|
| ccaccucagc cccaaccccca accccagccg caucccccugc cccagcugac gggucaaagc | 60 |
| cucaggagag guggcucuc cccaggcgcu accaggaggg gcaggucuca gccagcuggg | 120 |
| gaaaccuuau ugccaugguu cuuagaagcc acccuuccc caggcaagac aggccccaag | 180 |
| ggagugcccc gagggcgguu cccggagccc ccgugguccc cagcacuucc acacacucug | 240 |
| aggacagaca cggcccccucu ucuucagugg ggacagucau agggacaggu caggggggcc | 300 |
| ugguugaggc uggaggucag ccacagccaa gaagcuccga gaccaacgga ucgcccagcc | 360 |
| cagacccucc cccaggccua agaggagagg gaaccaggga gaaaagucua gacccgcugc | 420 |
| cccaagccgc gaugcccagg ggccccgcac agcccccgc gcagaggccg ccuggccccg | 480 |
| cggccuccuc cucugcgagg cgcucacagc cgguacccca gcuacggaaa cgcagcaggu | 540 |
| gcgaaaucgc cccgagcucg gagcaggagg ucaggccggc cgccucgggg gacccucaag | 600 |
| gggaggcgcc gggggagggg ggcagcccug ccggccgcag cggggcgcuc acggaaaagc | 660 |
| aggaggaggc ccggaagcuc augugguuuc ugcagaggcc cggggguugg ggguggugg | 720 |
| aggggccccg gaagcccagc ucccgggccc uggagcccgc acggcggca gcccugcggc | 780 |
| ggcggcugga ccugggcagu ugccuggacg ugcuggccuu ugcccagcag cacggagagc | 840 |
| ccggccuggc gcaggagacc uacgcgcuga ugagcgacaa ccugcugcga gugcgggag | 900 |
| acccgugccu cuaccgccgg cugagcgcgg ccgaccgcga gcgcauccuc agccugcgga | 960 |
| cggcccgggg ccggccgggug cugggcgucc ucguacugcc cagccucuac caggggggcc | 1020 |
| gcucagggcu cccccagggcc cucgugggcga ggagccuccu gcggcggccc cugugucccu | 1080 |
| gccucuaccu gcgcaccugc augguucaa ccccccgggag aacaccuggc ggcccccugac | 1140 |

-continued

```
ccagguqccc gaggaggccc cgcuucgggg cugcggucuc ugcaccaugc acaacuaccu    1200
guuucuggcg gggggcaucc guggcuccgg ugccaaggcc gucugcucca acgaggucuu    1260
cugcuacaac ccucugacca acaucuggag ccagguucgg cccaugcagc aggcccgagc    1320
ccagcucaag cuggugccc uggacgggcu gcucuaugcc aucggugcg aaugccugua     1380 cagcauggag ugcuacgacc cgcgaacaga cgccuggacc ccacgcgcgc cacuccccgc    1440
aggcaccuuc ccuguggccc acgaggcugu ggccugccgu ggggacaucu acgcaccgg     1500 gggucaccuc uucuaccgcc ugcucaggua cagccccgug aaggaugcuu gggacgagug    1560
cccauacagu gccagccacc ggcguucag cgacaucgug gcacgggggg cuuccugua     1620 ccgcuucgac cugcugcggg gcgugggcgc cgccgugaug cgcuacaaca cagugaccgg    1680
cuccuggagc agggcugccu cccugcccu gccccgcccc gccccacugc acugcaccac    1740
ccugggcaac accauuuacu gccucaaccc ccaggucacu gccaccuuca cggucucugg    1800
ggggacugcc caguuccagg ccaaggagcu gcagcccuuc cccuugggga gcaccggggu    1860 ccucaguca uucauccuga cucugccccc ugaggaccgg cugcagaccu cacucugagu    1920
ggcaggcaga gaaccaaagc ugcuucgcug cucuccaggg agacccuccu gggaugggcc    1980
ugagaggccg gggcucaggg aaggggcugg gaucggaacu uccugcucuu guuucuggac    2040
aacuuucccc uucugcuuua aagguugucg auuauuuuga aaaaaaaaaa aaaaaaa      2098
```

<210> SEQ ID NO 35
<211> LENGTH: 5124
<212> TYPE: DNA
<213> ORGANISM: homo sapien

<400> SEQUENCE: 35

```
agaagcaggt tggctgtgat gacagcacag agctcaggaa cgctgcctga ggaccctggg     60
gcctacgagg aggagaagag ggcaggagct ggtggggtgc ttgcagagac cctgggctcc    120
tatcctgcca taagcctcgc tgtctcctga tatctgcagc caggccctac tgacaccccc    180
aggcctgagt gcaagcagag acccaccat tcccaggccc tggaggactg gtccaccta      240 actgggcagc ccttggggca ggcgctggcc ggtgcctcag cccaggcctc tgtgctctgc    300
atgcactgcc agcctgccat caggcctcta ttgcagccct gaaccatgat ccagggcacc    360
ttggagccag atggtcccct ctggggctgg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctggcc ctgcaaccga agtctaaggt cagtgatggc    600
agcgaggggc agagcccagg gcaggggaaa ccagagcccc caggacgcgg ccagcagagc    660
cctgtccctg ctgcagcgcc gggcgggggc ctggccgcca tggcccggct tccactcaag    720
acggctgtcg aggaggcccg cagagaggca ttaggacagc aacggggcag tgccacccc      780 gcggcccccc gagcggaagg aaaggagcct cccaggccag gcactgccct cctgggcagg    840
agcgaagcag ggggatgtc cgccccctc ctgatcccact tcactcctcg gagccctggc     900
agcgaagcgg aggcggagac aggtggtgtc agggcgtcct ctcgccaggc cgcaggcccc    960
gcggggcaac aggacactgg cccctggcag gcgggcgcgg ggcctcgggg ctcgatgggg   1020
agaggccggg gccggcggcg gcggatggac gctggctcgg gagacagagc ccgccgcccc   1080
cggaaactgg acccgctccg cctgggcgcc gcggggagcg tgtgggacgc ggtggacggg   1140
```

```
gccgccgccc tggacgccca cgcgcgcggc ctccccacag gacccccact cgcccaggag    1200
cccgcactcc cggcgctgcc cgctccccgc gccctgcagc ctgggtctca gacggaaggc    1260
tctggggcca agggtggctg gagcagggag gcctcggggg tccctgcccc cggaggaggc    1320
tggccctggg tcagcaggga ggtcccggcc acccggagct ttggcccagc cccagactcc    1380
acgcgcccct ggctagagag tccgcctcaa ggtcgcccac tctcgtccca agggccgggt    1440
gccacagggg cctacgatgc cggcgaggcc ggggctgaca gctcccgaga taacagtcct    1500
gccgctgacc tggggcccac ccggcccccg gagcaagcaa agccggctgc agccggccac    1560
agccgcgcgc cctcccggag ccgtgagcct cgcccgcgct ccgcctcccc gcccgcagct    1620
cccggcccgg ggttcccacc tgaagccctg actctcccct ctccttcaga cttttttgccc    1680 ctggaggtta cccaggatcc ttccgtgggc gaaaatctca gagcggcgcc agccccaagt    1740
tcagcctcag cccaagtctt aacttcagct ccagcctcag tcctagcccc agccctggct    1800
tcatccccca gctcagcacc aacctcagcc accacctcaa cctcatcccc cacctcagcc    1860 ccagcccag ctccaacctc agctccaact tcaaccccag ccccagcccc aagtccagct    1920
gcagccgcaa ctccagcccc agcccagtc ccagtcccaa ccctcacacc cccatcccca    1980
gccctaaccc cagtcccaac cccagcccta agcccagctc caactccagc cctaacccca    2040
gccgcatccc cagccctaac cccagtccca accccagccc taagcccagc tccaactcca    2100
gccccaaccc cagccgcatc ccctgcccca gcccccacct cagccccaac cccaacccca    2160
gccgcatccc ctgccccagc tgacgggtca agcctcagg agagtgtggc tctccccagg    2220
cgctaccagg aggggcaggt tcagccagc tggggaaacc ttattgccat ggttcttaga    2280
agccacccct tccccaggca agacaggccc caagggagtg tcccgagggc ggttcccggg    2340
agccccgtgg gtcccagcac ttccacacac tctgaggaca gacacggccc ctcttcttca    2400
gtggggacag tcatagggac aggtacaggg ggcctggttg aggctggagg tcagccacag    2460
ccaagaagct ccgagaccaa cggatcgccc agcccagacc ctcccccagg cctaagagga    2520
gagggaacca gggagaaaag tctagacccg ctgccccaag ccgcgatgcc caggggcccc    2580
gcacagcccc ccgcgcagag gccgcctggc cccgcggcct cctcctctgc gaggcgctca    2640
cagccggtac cccagctacg gaaacgcagc aggtgcgaaa tcgccccgag ctcggagcag    2700
gaggtcaggc cggccgcctc ggggaccct caaggggagg cgccggggga gggggcagc    2760 cctgccggcc gcagcggggc gctcacggaa aagcaggagg aggcccgaag ctcatggtgt    2820
ttctgcagag gccggggt tggggggtgg tggagggcc ccggaagccc agctcccggg    2880
ccctggagcc cgccacggcg gcagccctgc ggcggcggct ggacctgggc agttgcctgg    2940
acgtgctggc cttttgcccag cagcacggag agcccggcct ggcgcaggag acctacgcgc    3000
tgatgagcga caacctgctg cgagtgctgg gagacccgtg cctctaccgc cggctgagcg    3060
cggccgaccg cgagcgcatc ctcagcctgc ggaccggccg gggccgggcg gtgctgggcg    3120
tcctcgtact gcccagcctc taccagggg gccgctcagg gctccccagg ggccctcgtg    3180
gcgaggagcc tcctgcggcg gcccctgtgt ccctgcctct acctgcgcac ctgcatgtgt    3240 tcaaccccg ggagaacacc tggcggcccc tgacccaggt gcccgaggag gcccgcttc    3300 ggggctgcgg tctctgcacc atgcacaact acctgtttct ggcgggggc atccgtggct    3360 ccggtgccaa ggccgtctgc tccaacgagg tcttctgcta caaccctctg accaacatct    3420
ggagccaggt tcgcccatg cagcaggccc gagcccagct caagctggtg gccctggacg    3480
ggctgctcta tgccatcggt ggcgaatgcc tgtacagcat ggagtgctac gacccgcgaa    3540
```

```
cagacgcctg gaccccacgc gcgccactcc ccgcaggcac cttccctgtg gcccacgagg    3600
ctgtggcctg ccgtggggac atctacgtca ccggggggtca cctcttctac cgcctgctca    3660
ggtacagccc cgtgaaggat gcttgggacg agtgcccata cagtgccagc caccggcgtt    3720
ccagcgacat cgtggcactg gggggcttcc tgtaccgctt cgacctgctg cggggcgtgg    3780
gcgccgccgt gatgcgctac aacacagtga ccggctcctg gagcagggct gcctccctgc    3840
ccctgcccgc ccccgcccca ctgcactgca ccacccctggg caacaccatt tactgcctca    3900
acccccaggt cactgccacc ttcacggtct ctgggggggac tgcccagttc caggccaagg    3960
agctgcagcc cttcccccttg gggagcaccg gggtcctcag tccattcatc ctgactctgc    4020 ccctgagga ccggctgcag acctcactct gagtggcagg cagagaacca agctgcttc    4080 gctgctctcc agggagaccc tcctgggatg gcctgagag gccggggctc agggaagggg    4140
ctgggatcgg aacttcctgc tcttgtttct ggacaacttt ccccttctgc tttaaaggtt    4200
gtcgattatt ttgaagccca gactccctca gcctcttct gccctcact ccacacccag    4260 actgtttcct gactcaattc cgtacctact tacagaccct ctcagcttgc tgacaccccc    4320
ctgtctgtgg gactccctat tccctagagc caggggactga tgcgtctcca cagacaagga    4380
cttggctcgc tggagctctg ctgagccgag agaggagggg gtagaaaaca ttcacacttc    4440
ctatgctctg tcagcaggac agggagcaaa aacgtcccca gcaacgccc tcgcctctgg    4500 gactttctgc ctgtcctaag gcctccccag gtaccaaccc cgtagctatc tgggtctgtt    4560
tggcactgtg gattctcaag ggcctagaac ccttgcctct gaaactggtc cgctggtgca    4620
gccctgctgt ctgcagctcc tgcccatacc cccagcccac accaggccag gcccactccg    4680
ggctcaccac cctctgcagc cttgtggggc tctcccagcc cctccagaag cccacccccac    4740 ttctcgccaa ccccgatct ctaaatgagg cctgagcgtc ccctagttc tgcccctttt    4800 tagctgtgta gacttggacg agacatttga cttccctttc tccttgtcta taaaatgtgg    4860
acagtggacg tctgtcaccc aagagagttg tgggagacaa gatcacagct atgagcacct    4920
cgcacggtgt ccaggatgca cagcacaatc catgatgcgt tttctcccct tacgcacttt    4980
gaaacccatg ctagaaaagt gaatacatct gactgtgctc cactccaacc tccagcctgg    5040
atgtccctgt ctgggccctt tttctgtttt ttattctatg ttcagcacca ctggcaccaa    5100
atacatttta attcaccgaa agca                                           5124

<210> SEQ ID NO 36
<211> LENGTH: 2989
<212> TYPE: DNA
<213> ORGANISM: homo sapien

<400> SEQUENCE: 36
ccacctcagc cccaacccca acccagccg catcccctgc cccagctgac gggtcaaagc      60
ctcaggagag tgtggctctc cccaggcgct accaggaggg gcaggtctca gccagctggg    120
gaaaccttat tgccatggtt cttagaagcc accccttccc caggcaagac aggccccaag    180
ggagtgtccc gagggcggtt cccgggagcc ccgtgggtcc cagcacttcc acacactctg    240
aggacagaca cggcccctct tcttcagtgg ggacagtcat agggacaggt acaggggcc    300 tggttgaggc tggaggtcag ccacagccaa gaagctccga gaccaacgga tcgcccagcc    360
cagaccctcc cccaggccta agaggagagg gaaccaggga gaaagtctca gaccccgctgc    420 cccaagccgc gatgcccagg ggccccgcac agccccccgc gcagaggccg cctggccccg    480
```

| | |
|---|---|
| cggcctcctc ctctgcgagg cgctcacagc cggtacccca gctacggaaa cgcagcaggt | 540 |
| gcgaaatcgc cccgagctcg gagcaggagg tcaggccggc cgcctcgggg gaccctcaag | 600 |
| gggaggcgcc gggggagggg ggcagccctg ccggccgcag cggggcgctc acggaaaagc | 660 |
| aggaggaggc ccgaagctca tggtgtttct gcagaggccc gggggttggg gggtggtgga | 720 |
| ggggccccgg aagcccagct cccgggccct ggagcccgcc acggcggcag ccctgcggcg | 780 |
| gcggctggac ctgggcagtt gcctggacgt gctggccttt gcccagcagc acggagagcc | 840 |
| cggcctggcg caggagacct acgcgctgat gagcgacaac ctgctgcgag tgctgggaga | 900 |
| cccgtgcctc taccgccggc tgagcgcggc cgaccgcgag cgcatcctca gcctgcggac | 960 |
| cggccggggc cgggcggtgc tgggcgtcct cgtactgccc agcctctacc aggggggccg | 1020 |
| ctcagggctc cccaggggcc ctcgtggcga ggagcctcct cgcgcggccc ctgtgtccct | 1080 |
| gcctctacct gcgcacctgc atgtgttcaa ccccgggag aacacctggc ggcccctgac | 1140 |
| ccaggtgccc gaggaggccc cgcttcgggg ctgcggtctc tgcaccatgc acaactacct | 1200 |
| gtttctggcg gggggcatcc gtggctccgg tgccaaggcc gtctgctcca cgaggtctt | 1260 |
| ctgctacaac cctctgacca acatctggag ccaggttcgg cccatgcagc aggcccgagc | 1320 |
| ccagctcaag ctggtggccc tggacgggct gctctatgcc atcggtggcg aatgcctgta | 1380 |
| cagcatggag tgctacgacc cgcgaacaga cgcctggacc ccacgcgcgc cactccccgc | 1440 |
| aggcaccttc cctgtggccc acgaggctgt ggcctgccgt ggggacatct acgtcaccgg | 1500 |
| gggtcacctc ttctaccgcc tgctcaggta cagccccgtg aaggatgctt gggacgagtg | 1560 |
| cccatacagt gccagccacc ggcgttccag cgacatcgtg gcactggggg cttcctgta | 1620 |
| ccgcttcgac ctgctgcggg gcgtgggcgc cgccgtgatg cgctacaaca cagtgaccgg | 1680 |
| ctcctggagc agggctgcct ccctgcccct gcccgcccccc gccccactgc actgcaccac | 1740 |
| cctgggcaac accatttact gcctcaaccc ccaggtcact gccaccttca cggtctctgg | 1800 |
| ggggactgcc cagttccagg ccaaggagct gcagcccttc cccttgggga gcaccggggt | 1860 |
| cctcagtcca ttcatcctga ctctgccccc tgaggaccgg ctgcagacct cactctgagt | 1920 |
| ggcaggcaga gaaccaaagc tgcttcgctg ctctccaggg agaccctcct gggatgggcc | 1980 |
| tgagaggccg gggctcaggg aaggggctgg gatcggaact tcctgctctt gtttctggac | 2040 |
| aactttcccc ttctgcttta aaggttgtcg attattttga agcccagact ccctcagcct | 2100 |
| ctttctgccc ctcactccac acccagactg tttcctgact caattccgta cctacttaca | 2160 |
| gaccctctca gcttgctgac accccccgt ctgtgggact ccctattccc tagagccagg | 2220 |
| gactgatgcg tctccacaga caaggacttg gctcgctgga gctctgctga gccgagagag | 2280 |
| gaggggtag aaaacattca cacttcctat gctctgtcag caggacaggg agcaaaaacg | 2340 |
| tccccaggca acgccctcgc ctctgggact ttctgcctgt cctaaggcct ccccaggtac | 2400 |
| caacccccgta gctatctggg tctgtttggc actgtggatt ctcaagggcc tagaacccctt | 2460 |
| gcctctgaaa ctggtccgct ggtgcagccc tgctgtctgc agctcctgcc cataccccca | 2520 |
| gcccacacca ggccaggccc actccggggct caccaccctc tgcagccttg tggggctctc | 2580 |
| ccagcccctc cagaagccca ccccacttct cgccaacccc cgatctctaa atgaggcctg | 2640 |
| agcgtcaccc tagttctgcc ccttttttagc tgtgtagact tggacgagac atttgacttc | 2700 |
| cctttctcct tgtctctataaa atgtggacag tggacgtctg tcacccaaga gagttgtggg | 2760 |
| agacaagatc acagctatga gcacctcgca cggtgtccag gatgcacagc acaatccatg | 2820 |
| atgcgttttc tcccccttacg cactttgaaa cccatgctag aaaagtgaat acatctgact | 2880 |

```
gtgctccact ccaacctcca gcctggatgt ccctgtctgg gccctttttc tgttttttat    2940
tctatgttca gcaccactgg caccaaatac attttaattc accgaaagc               2989

<210> SEQ ID NO 37
<211> LENGTH: 4836
<212> TYPE: DNA
<213> ORGANISM: homo sapien

<400> SEQUENCE: 37
actgccagcc tgccatcagg cctctattgc agccctgaac catgatccag ggcaccttgg      60
agccagatgg tccctctgg ggctgggact gggacagtga caatgactgg gatagtgctg     120
tgctggccct cctggcgctg gctgtggtgg ctgccacagc gctggcctta cactggtttg     180
gctccgggca cgatcaagag gcggcagaac cggtgtccac agccctcggg gctcaacctc     240
atcaggcagg aggagctgag ctggccctgc aaccgaagtc taaggtcagt gatggcagcg     300
aggggcagag cccagggcag gggaaaccag agccccagg acgcggccag cagagccctg     360
tccctgctgc agcgccgggc gggggcctgg ccgccatggc ccggcttcca ctcaagacgg     420
ctgtcgagga ggcccgcaga gaggcattag acagcaacg gggcagtgcc accccgcgg      480 cccccgagc ggaaggaaag gagcctccca ggccaggcac tgccctcctg ggcaggagcg     540 aagcagggg gatgtccgcc cccctcctga tccacttcac ctctcggagc cctggcagcg     600
aagcggaggc ggagacaggt ggtgtcaggg cgtcctctcg ccaggccgca ggccccgcgg     660
ggcaacagga cactggcccc tgcaggcgg gcgcggggcc ctcgggctcg atggggagag     720
gccggggccg gcggcggcgg atggacgctg gctcgggaga cagagcccgc cgccccgga     780 aactggaccc gctccgcctg ggcgccgcgg ggagcgtgtg ggacgcggtg gacggggccg     840 ccgcccctgga cgcccacgcg cgcggcctcc ccacaggacc cccactcgcc caggagcccg     900
cactcccggc gctgccccgct ccccgcgccc tgcagcctgg gtctcagacg gaaggctctg     960
gggccaaggg tggctggagc agggaggcct cggggggtccc tgcccccgga ggaggctggc    1020
cctgggtcag cagggaggtc ccgggcaccc ggagctttgg cccagcccca gactccacgc    1080 gccctggct agagagtccg cctcaaggtc gcccactctc gtcccaaggg ccgggtgcca    1140
caggggccta cgatgccggc gaggccgggg ctgacagctc ccgagataac agtcctgccg    1200
ctgacctggg gccaccgg ccccggagc aagcaaagcc ggctgcagcc ggccacagcc     1260
gcgcgccctc ccggagccgt gagcctcgcc cgcgctccgc ctcccgccc gcagctcccg     1320 gccccggggtt cccacctgaa gccctgactc tcccctctcc ttcagacttt ttgccctgg    1380 aggttaccca ggatccttcc gtgggcgaaa atctcagagc ggcgccagcc ccaagttcag    1440
cctcagccca agtcttaact tcagctccag cctcagtcct agccccagcc ctggcttcat     1500
cccccagctc agcaccaacc tcagccacca cctcaacctc atccccacc tcagcccag     1560 ccccagctcc aacctcagct ccaacttcaa cccccagccc agcccaagt ccagctgcag     1620 ccgcaactcc agccccagcc ccagtcccag tccaaccct cacaccccca tcccagccc     1680 taacccccagt cccaaccccca gcctaagcc cagctccaac tccagcccta acccagccg    1740 catccccagc cctaaccccca gtcccaaccc cagccctaag cccagctcca actccagccc    1800
caaccccagc cgcatcccct gcccagcccc cacctcagc ccaaccccca accccagccg     1860 catccctgc cccagctgac gggtcaaagc ctcaggagag tgtggctctc cccaggcgct     1920
accaggaggg gcaggtctca gccagctggg gaaaccttat tgccatggtt cttagaagcc    1980
```

```
acccctteee  caggeaagac  aggecccaag  ggagtgtccc  gagggcggtt  cccgggagcc   2040
ccgtgggtcc  cagcacttcc  acacactctg  aggacagaca  cggcccctct  tcttcagtgg   2100
ggacagtcat  agggacaggt  acagggggcc  tggttgaggc  tggaggtcag  ccacagccaa   2160
gaagctccga  gaccaacgga  tcgcccagcc  cagaccctcc  cccaggccta  agaggagagg   2220
gaaccaggga  gaaaagtcta  gacccgctgc  cccaagccgc  gatgcccagg  ggccccgcac   2280 agcccccgc   gcagaggccg  cctggccccg  cggcctcctc  ctctgcgagg  cgctcacagc   2340
cggtacccca  gctacggaaa  cgcagcaggt  gcgaaatcgc  cccgagctcg  gagcaggagg   2400
tcaggccggc  cgcctcgggg  gaccctcaag  ggaggcgcc   gggggagggg  ggcagccctg   2460
ccggccgcag  cggggcgctc  acggaaaagc  aggaggaggc  ccgaagctca  tggtgtttct   2520
gcagaggccc  gggggttggg  gggtggtgga  ggggccccgg  aagcccagct  cccgggccct   2580
ggagcccgcc  acgcggcag   ccctgcgcg   gcggctggac  ctgggcagtt  gcctggacgt   2640
gctggccttt  gcccagcagc  acggagagcc  cggcctggcg  caggagacct  acgcgctgat   2700
gagcgacaac  ctgctgcgag  tgctgggaga  cccgtgcctc  taccgccggc  tgagcgcggc   2760
cgaccgcgag  cgcatcctca  gcctgcggac  cggccggggc  cgggcggtgc  tgggcgtcct   2820
cgtactgccc  agcctctacc  aggggggccg  ctcaggctc   cccaggggcc  ctcgtggcga   2880
ggagcctcct  gcggcggccc  ctgtgtccct  gcctctacct  gcgcacctgc  atgtgttcaa   2940
cccccgggag  aacacctggc  ggcccctgac  ccaggtgccc  gaggaggccc  cgcttcgggg   3000
ctgcggtctc  tgcaccatgc  acaactacct  gtttctggcg  gggggcatcc  gtggctccgg   3060
tgccaaggcc  gtctgctcca  cgaggtcttc  tgctacaac   cctctgacca  acatctggag   3120
ccaggttcgg  cccatgcagc  aggcccgagc  ccagctcaag  ctggtggccc  tggacgggct   3180
gctctatgcc  atcggtggcg  aatgcctgta  cagcatggag  tgctacgacc  gcgaacaga   3240 cgcctggacc  ccacgcgcgc  cactccccgc  aggcaccttc  cctgtggccc  acgaggctgt   3300
ggcctgccgt  ggggacatct  acgtcaccgg  gggtcacctc  ttctaccgcc  tgctcaggta   3360
cagccccgtg  aaggatgctt  gggacgagtg  cccatacagt  gccagccacc  ggcgttccag   3420
cgacatcgtg  gcactggggg  gcttcctgta  ccgcttcgac  ctgctgcggg  gcgtgggcgc   3480
cgccgtgatg  cgctacaaca  cagtgaccgg  ctcctggagc  agggctgcct  ccctgcccct   3540
gcccgccccc  gccccactgc  actgcaccac  cctgggcaac  accatttact  gcctcaaccc   3600
ccaggtcact  gccaccttca  cggtctctgg  ggggactgcc  cagttccagg  ccaaggagct   3660
gcagcccttc  cccttgggga  gcaccggggt  cctcagtcca  ttcatcctga  ctctgccccc   3720
tgaggaccgg  ctgcagacct  cactctgagt  ggcaggcaga  gaaccaaagc  tgcttcgctg   3780
ctctccaggg  agaccctcct  gggatggcc   tgagaggccg  gggctcaggg  aaggggctgg   3840
gatcggaact  tcctgctctt  gtttctggac  aactttcccc  ttctgcttta  aaggttgtcg   3900
attattttga  agcccagact  ccctcagcct  ctttctgccc  ctcactccac  acccagactg   3960
tttcctgact  caattccgta  cctacttaca  gaccctctca  gcttgctgac  acccccctgt   4020
ctgtgggact  ccctattccc  tagagccagg  gactgatgcg  tctccacaga  caaggacttg   4080
gctcgctgga  gctctgctga  gccgagagag  gagggggtag  aaaacattca  cacttcctat   4140
gctctgtcag  caggacaggg  agcaaaaacg  tccccaggca  acgccctcgc  ctctgggact   4200
ttctgcctgt  cctaaggcct  ccccaggtac  caacccgta   gctatctggg  tctgtttggc   4260
actgtggatt  ctcaagggcc  tagaacccttt  gcctctgaaa  ctggtccgct  ggtgcagccc   4320
tgctgtctgc  agctcctgcc  cataccccca  gcccacacca  ggccaggccc  actccgggct   4380
```

-continued

| | |
|---|---|
| caccaccctc tgcagccttg tggggctctc ccagccectc cagaagccca ccccacttct | 4440 |
| cgccaacccc cgatctctaa atgaggcctg agcgtcaccc tagttctgcc ccttttagc | 4500 |
| tgtgtagact tggacgagac atttgacttc cctttctcct tgtctataaa atgtggacag | 4560 |
| tggacgtctg tcacccaaga gagttgtggg agacaagatc acagctatga gcacctcgca | 4620 |
| cggtgtccag gatgcacagc acaatccatg atgcgttttc tccccttacg cactttgaaa | 4680 |
| cccatgctag aaaagtgaat acatctgact gtgctccact ccaacctcca gcctggatgt | 4740 |
| ccctgtctgg gccctttttc tgttttttat tctatgttca gcaccactgg caccaaatac | 4800 |
| attttaattc accgaaagca aaaaaaaaaa aaaaaa | 4836 |

<210> SEQ ID NO 38
<211> LENGTH: 2098
<212> TYPE: DNA
<213> ORGANISM: homo sapien

<400> SEQUENCE: 38

| | |
|---|---|
| ccacctcagc cccaacccca accccagccg catccctgc cccagctgac gggtcaaagc | 60 |
| ctcaggagag tgtggctctc cccaggcgct accaggaggg gcaggtctca gccagctggg | 120 |
| gaaaccttat tgccatggtt cttagaagcc accccttccc caggcaagac aggccccaag | 180 |
| ggagtgtccc gagggcggtt cccgggagcc cgtgggtcc cagcacttcc acacactctg | 240 |
| aggacagaca cggcccctct tcttcagtgg ggacagtcat agggacaggt acaggggcc | 300 |
| tggttgaggc tggaggtcag ccacagccaa gaagctccga gaccaacgga tcgcccagcc | 360 |
| cagaccctcc cccaggccta agaggagagg gaaccaggga gaaaagtcta gacccgctgc | 420 |
| cccaagccgc gatgcccagg ggccccgcac agccccccgc gcagaggccg cctggccccg | 480 |
| cggcctcctc ctctgcgagg cgctcacagc cggtacccca gctacggaaa cgcagcaggt | 540 |
| gcgaaatcgc cccgagctcg gagcaggagg tcaggccggc cgcctcgggg gaccctcaag | 600 |
| gggaggcgcc gggggagggg ggcagccctg ccggccgcag cggggcgctc acggaaaagc | 660 |
| aggaggaggc ccgaagctca tggtgtttct gcagaggccc gggggttggg gggtggtgga | 720 |
| ggggcccccgg aagcccagct cccgggccct ggagcccgcc acggcggcag ccctgcggcg | 780 |
| gcggctggac ctgggcagtt gcctggacgt gctggccttt gcccagcagc acggagagcc | 840 |
| cggcctggcg caggagacct acgcgctgat gagcgacaac ctgctgcgag tgctgggaga | 900 |
| cccgtgcctc taccgccggc tgagcgcggc cgaccgcgag cgcatcctca gcctgcggac | 960 |
| cggccggggc cggcggtgc tgggcgtcct cgtactgccc agcctctacc aggggggccg | 1020 |
| ctcagggctc cccaggggcc ctcgtggcga ggagcctcct gcggcggccc ctgtgtccct | 1080 |
| gcctctacct gcgcacctgc atgtgttcaa ccccgggag aacacctggc ggcccctgac | 1140 |
| ccaggtgccc gaggaggccc cgcttcgggg ctgcggtctc tgcaccatgc acaactacct | 1200 |
| gtttctggcg gggggcatcc gtggctccgg tgccaaggcc gtctgctcca acgaggtctt | 1260 |
| ctgctacaac cctctgacca acatctggag ccaggttcgg cccatgcagc aggcccgagc | 1320 |
| ccagctcaag ctggtggccc tggacgggct gctctatgcc atcggtggcg aatgcctgta | 1380 |
| cagcatggag tgctacgacc cgcgaacaga cgcctggacc cacgcgcgc cactcccgc | 1440 |
| aggcaccttc cctgtggccc acgaggctgt ggcctgccgt ggggacatct acgtcaccgg | 1500 |
| gggtcacctc ttctaccgcc tgctcaggta cagcccgtg aaggatgctt gggacgagtg | 1560 |
| cccatacagt gccagccacc ggcgttccag cgacatcgtg gcactggggg gcttcctgta | 1620 |

```
ccgcttcgac ctgctgcggg gcgtgggcgc cgccgtgatg cgctacaaca cagtgaccgg      1680
ctcctggagc agggctgcct ccctgcccct gccgccccc gccccactgc actgcaccac       1740
cctgggcaac accatttact gcctcaaccc ccaggtcact gccaccttca cggtctctgg      1800
ggggactgcc cagttccagg ccaaggagct gcagccttc cccttgggga gcaccggggt       1860
cctcagtcca ttcatcctga ctctgccccc tgaggaccgg ctgcagacct cactctgagt      1920
ggcaggcaga gaaccaaagc tgcttcgctg ctctccaggg agaccctcct gggatgggcc      1980
tgagaggccg gggctcaggg aagggctgg gatcggaact tcctgctctt gtttctggac      2040
aactttcccc ttctgcttta aaggttgtcg attattttga aaaaaaaaa aaaaaaa         2098
```

<210> SEQ ID NO 39
<211> LENGTH: 5124
<212> TYPE: DNA
<213> ORGANISM: homo sapien

<400> SEQUENCE: 39

```
agaagcaggt tggctgtgat gacagcacag agctcaggaa cgctgcctga ggaccctggg       60
gcctacgagg aggagaagag ggcaggagct ggtgggtgc ttgcagagac cctgggctcc      120
tatcctgcca taagcctcgc tgtctcctga tatctgcagc caggcctac tgacaccccc      180 aggcctgagt gcaagcagag accccaccat tcccaggccc tggaggactg gtccaccta      240 actgggcagc ccttggggca ggcgctggcc ggtgcctcag cccaggcctc tgtgctctgc      300
atgcactgcc agcctgccat caggcctcta ttgcagccct gaaccatgat ccagggcacc      360
ttggagccag atggtcccct ctggggctgg gactgggaca gtgacaatga ctgggatagt      420
gctgtgctgg ccctcctggc gctggctgtg gtggctgcca cagcgctggc cttacactgg      480
tttggctccg gcacgatca agaggcgca gaaccggtgt ccacagccct cggggctcaa       540
cctcatcagg caggaggagc tgagctggcc ctgcaaccga agtctaaggt cagtgatggc      600
agcgaggggc agagcccagg gcaggggaaa ccagagcccc caggacgcgg ccagcagagc      660
cctgtccctg ctgcagcgcc gggcgggggc ctggccgcca tggcccggct tccactcaag      720
acggctgtcg aggaggcccg cagagaggca ttaggacagc aacggggcag tgccaccccc      780
gcggcccccc gagcggaagg aaaggagcct cccaggccag gcactgccct cctgggcagg      840
agcgaagcag gggggatgtc cgccccctc ctgatccact tcactcctcg agccctggc      900 agcgaagcgg aggcggagac aggtggtgtc agggcgtcct ctcgccaggc cgcaggcccc      960
gcggggcaac aggacactgg ccctggcag gcgggcgcgg ggcctcgg ctcgatgggg       1020 agaggccggg gccggcggcg gcggatggac gctggctcgg gagacagagc ccgccgcccc     1080
cggaaactgg acccgctccg cctgggcgcc gcggggagcg tgtgggacgc ggtgacgggg     1140
gccgccgccc tggacgccca cgcgcgcggc ctccccacag gacccccact cgcccaggag     1200
cccgcactcc cggcgctgcc cgctcccgc gccctgcagc ctgggtctca gacggaaggc      1260
tctggggcca agggtggctg gagcagggag gcctcggggg tccctgcccc cggaggaggc     1320
tggccctggg tcagcaggga ggtcccgggc accggagct ttggcccagc cccagactcc     1380 acgcgccct ggctagagag tccgcctcaa ggtcgcccac tctcgtccca agggccgggt     1440
gccacagggg cctacgatgc cggcgaggcc ggggctgaca gctcccgaga taacagtcct     1500
gccgctgacc tggggcccac ccggcccccg gagcaagcaa agccggctgc agccggccac     1560
agccgcgcgc cctcccggag ccgtgagcct cgccgcgct ccgcctcccc gcccgcagct     1620
cccggcccgg ggttcccacc tgaagccctg actctcccct ctccttcaga ctttttgccc     1680
```

```
ctggaggtta cccaggatcc ttccgtgggc gaaaatctca gagcggcgcc agcccccaagt   1740 tcagcctcag cccaagtctt aacttcagct ccagcctcag tcctagcccc agccctggct   1800
tcatccccca gctcagcacc aacctcagcc accacctcaa cctcatcccc cacctcagcc   1860 ccagcccccag ctccaacctc agctccaact tcaaccccag cccagcccc aagtccagct    1920 gcagccgcaa ctccagcccc agcccagtc ccagtcccaa ccctcacacc cccatcccca    1980
gccctaaccc cagtcccaac cccagcccta agcccagctc caactccagc cctaaccccca   2040 gccgcatccc cagccctaac cccagtccca accccagccc taagcccagc tccaactcca   2100
gccccaaccc cagccgcatc ccctgcccca gcccccacct cagccccaac cccaacccca   2160
gccgcatccc ctgccccagc tgacgggtca agcctcagg agagtgtggc tctcccccagg   2220 cgctaccagg aggggcaggt ctcagccagc tggggaaacc ttattgccat ggttcttaga   2280
agccacccct tccccaggca agacaggccc aagggagtg tcccgagggc ggttcccggg   2340
agccccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctcccccagg cctaagagga   2520
gagggaacca gggagaaaag tctagacccg ctgccccaag ccgcgatgcc caggggcccc   2580
gcacagcccc ccgcgcagag gccgcctggc cccgcggcct cctcctctgc gaggcgctca   2640
cagccggtac cccagctacg gaaacgcagc aggtgcgaaa tcgccccgag ctcggagcag   2700
gaggtcaggc cggccgcctc ggggggaccct caaggggagg cgccggggga ggggggcagc   2760
cctgccggcc gcagcggggc gctcacggaa aagcaggagg aggcccggaa gctcatggtg   2820
tttctgcaga ggcccggggg ttggggggtg gtggagggc cccggaagcc cagctcccgg   2880
gccctggagc ccgccacggc ggcagccctg cggcggcggc tggacctggg cagttgcctg   2940
gacgtgctgg cctttgccca gcagcacgga gagcccggcc tggcgcagga gacctacgcg   3000
ctgatgagcg acaacctgct gcgagtgctg ggagacccgt gcctctaccg ccggctgagc   3060
gcggccgacc gcgagcgcat cctcagcctg cggaccggcc ggggccgggc ggtgctgggc   3120
gtcctcgtac tgcccagcct ctaccagggg ggccgctcag gctcccccag ggccctcgtg   3180
gcgaggagcc tcctgcggcg gcccctgtgt ccctgcctct acctgcgcac ctgcatgtgt   3240 tcaaccccccg ggagaacacc tggcggcccc tgacccaggt gcccgaggag gccccgcttc   3300
ggggctgcgg tctctgcacc atgcacaact acctgtttct ggcggggggc atccgtggct   3360
ccggtgccaa ggccgtctgc tccaacgagg tcttctgcta caaccctctg accaacatct   3420
ggagccaggt tcggcccatg cagcaggccc gagcccagct caagctggtg gccctggacg   3480
ggctgctcta tgccatcggt ggcgaatgcc tgtacagcat ggagtgctac gacccgcgaa   3540
cagacgcctg gaccccacgc gcgccactcc ccgcaggcac cttccctgtg gcccacgagg   3600
ctgtggcctg ccgtggggac atctacgtca cggggggtca cctcttctac cgcctgctca   3660
ggtacagccc cgtgaaggat gcttgggacg agtgcccata cagtgccagc caccggcgtt   3720
ccagcgacat cgtggcactg gggggcttcc tgtaccgctt cgacctgctg cggggcgtgg   3780
gcgccgccgt gatcgctac aacacagtga ccggctcctg gagcagggct gcctccctgc   3840
ccctgcccgc cccgccccca ctgcactgca ccaccctggg caacaccatt tactgcctca   3900
accccccagt cactgccacc ttcacggtct ctgggggggac tgcccagttc caggccaagg   3960
agctgcagcc cttccccttg gggagcaccg gggtcctcag tccattcatc ctgactctgc   4020
```

```
cccctgagga ccggctgcag acctcactct gagtggcagg cagagaacca aagctgcttc    4080
gctgctctcc agggagaccc tcctgggatg ggcctgagag gccggggctc agggaagggg    4140
ctgggatcgg aacttcctgc tcttgtttct ggacaacttt ccccttctgc tttaaaggtt    4200
gtcgattatt ttgaagccca gactccctca gcctctttct gccccctcact ccacacccag   4260 actgtttcct gactcaattc cgtacctact tacagaccct ctcagcttgc tgacaccccc    4320
ctgtctgtgg gactccctat tccctagagc cagggactga tgcgtctcca cagacaagga    4380
cttggctcgc tggagctctg ctgagccgag agaggagggg gtagaaaaca ttcacacttc    4440
ctatgctctg tcagcaggac agggagcaaa aacgtccca ggcaacgccc tcgcctctgg     4500
gactttctgc ctgtcctaag gcctccccag gtaccaaccc cgtagctatc tgggtctgtt    4560
tggcactgtg gattctcaag ggcctagaac ccttgcctct gaaactggtc cgctggtgca    4620
gccctgctgt ctgcagctcc tgcccatacc cccagcccac accaggccag gcccactccg    4680
ggctcaccac cctctgcagc cttgtggggc tctcccagcc cctccagaag cccacccccac   4740 ttctcgccaa ccccgatct ctaaatgagg cctgagcgtc accctagttc tgcccctttt     4800
tagctgtgta gacttggacg agacatttga cttccctttc tccttgtcta taaaatgtgg    4860
acagtggacg tctgtcaccc aagagagttg tgggagacaa gatcacagct atgagcacct    4920
cgcacggtgt ccaggatgca cagcacaatc catgatgcgt tttctcccct tacgcacttt    4980
gaaacccatg ctagaaaagt gaatacatct gactgtgctc cactccaacc tccagcctgg    5040
atgtccctgt ctgggcccctt tttctgtttt ttattctatg ttcagcacca ctggcaccaa   5100
atacatttta attcaccgaa agca                                            5124

<210> SEQ ID NO 40
<211> LENGTH: 2989
<212> TYPE: DNA
<213> ORGANISM: homo sapien

<400> SEQUENCE: 40
ccacctcagc cccaaccccca accccagccg catccctgc cccagctgac gggtcaaagc      60
ctcaggagag tgtggctctc cccaggcgct accaggaggg gcaggtctca gccagctggg    120
gaaaccttat tgccatggtt cttagaagcc accccttccc caggcaagac aggccccaag    180
ggagtgtccc gagggcggtt cccgggagcc ccgtgggtcc cagcacttcc acacactctg    240
aggacagaca cggcccctct tcttcagtgg ggacagtcat agggacaggt acaggggcc     300 tggttgaggc tggaggtcag ccacagccaa gaagctccga gaccaacgga tcgcccagcc    360
cagaccctcc cccaggccta agaggagagg gaaccaggga gaaaagtcta gacccgctgc    420
cccaagccgc gatgcccagg ggccccgcac agccccccgc gcagaggccg cctggccccg    480
cggcctcctc ctctgcgagg cgctcacagc cggtacccca gctacggaaa cgcagcaggt    540
gcgaaatcgc cccgagctcg gagcaggagg tcaggccggc cgcctcgggg gaccctcaag    600
gggaggcgcc gggggagggg ggcagccctg ccggccgcag cggggcgctc acggaaaagc    660
aggaggaggc ccggaagctc atggtgtttc tgcagaggcc cgggggttgg ggggtggtgg    720 aggggcccccg gaagcccagc tcccgggccc tggagcccgc cacggcggca gccctgcggc    780
ggcggctgga cctgggcagt tgcctggacg tgctggcctt tgcccagcag cacggagagc    840
ccggcctggc gcaggagacc tacgcgctga tgagcgacaa cctgctgcga gtgctgggag    900
acccgtgcct ctaccgccgg ctgagcgcgg ccgaccgcga gcgcatcctc agcctgcgga    960
ccggccgggg ccgggcggtg ctgggcgtcc tcgtactgcc cagcctctac cagggggggcc   1020
```

```
gctcagggct ccccagggcc ctcgtggcga ggagcctcct gcggcggccc ctgtgtccct    1080
gcctctacct gcgcacctgc atgtgttcaa ccccgggag aacacctggc ggccctgac     1140 ccaggtgccc gaggaggccc cgcttcgggg ctgcggtctc tgcaccatgc acaactacct    1200
gtttctggcg gggggcatcc gtggctccgg tgccaaggcc gtctgctcca acgaggtctt    1260
ctgctacaac cctctgacca acatctggag ccaggttcgg cccatgcagc aggcccgagc    1320
ccagctcaag ctggtggccc tggacgggct gctctatgcc atcggtggcg aatgcctgta    1380
cagcatggag tgctacgacc cgcgaacaga cgcctggacc ccacgcgcgc cactccccgc    1440
aggcaccttc cctgtggccc acgaggctgt ggcctgccgt ggggacatct acgtcaccgg    1500
gggtcacctc ttctaccgcc tgctcaggta cagccccgtg aaggatgctt gggacgagtg    1560
cccatacagt gccagccacc ggcgttccag cgacatcgtg gcactggggg cttcctgta    1620 ccgcttcgac ctgctgcggg gcgtgggcgc cgccgtgatg cgctacaaca cagtgaccgg    1680
ctcctggagc agggctgcct ccctgcccct gccgcccc gccccactgc actgcaccac    1740
cctgggcaac accatttact gcctcaaccc ccaggtcact gccaccttca cggtctctgg    1800
ggggactgcc cagttccagg ccaaggagct gcagcccttc cccttgggga gcaccggggt    1860
cctcagtcca ttcatcctga ctctgccccc tgaggaccgg ctgcagacct cactctgagt    1920
ggcaggcaga gaaccaaagc tgcttcgctg ctctccaggg agaccctcct gggatgggcc    1980
tgagaggccg gggctcaggg aaggggctgg gatcggaact tcctgctctt gtttctggac    2040
aactttcccc ttctgcttta aaggttgtcg attattttga agcccagact ccctcagcct    2100
ctttctgccc ctcactccac acccagactg tttcctgact caattccgta cctacttaca    2160
gaccctctca gcttgctgac accccccgt ctgtgggact ccctattccc tagagccagg    2220
gactgatgcg tctccacaga caaggacttg gctcgctgga gctctgctga gccgagagag    2280 gaggggtag aaaacattca cacttcctat gctctgtcag caggacaggg agcaaaaacg    2340
tccccaggca acgccctcgc ctctgggact ttctgcctgt cctaaggcct ccccaggtac    2400 caacccgta gctatctggg tctgtttggc actgtggatt ctcaagggcc tagaacccatt    2460 gcctctgaaa ctggtccgct ggtgcagccc tgctgtctgc agctcctgcc catacccca    2520 gcccacacca ggccaggccc actccggggct caccaccctc tgcagccttg tggggctctc    2580
ccagcccctc cagaagccca ccccacttct cgccaaccc cgatctctaa atgaggcctg    2640
agcgtcaccc tagttctgcc cttttttagc tgtgtagact tggacgagac atttgacttc    2700
cctttctcct tgtctataaa atgtggacag tggacgtctg tcacccaaga gagttgtggg    2760
agacaagatc acagctatga gcacctcgca cggtgtccag gatgcacagc acaatccatg    2820
atgcgttttc tccccttacg cactttgaaa cccatgctag aaaagtgaat acatctgact    2880
gtgctccact ccaacctcca gcctggatgt ccctgtctgg gccttttttc tgttttttat    2940
tctatgttca gcaccactgg caccaaatac attttaattc accgaaagc             2989
```

<210> SEQ ID NO 41
<211> LENGTH: 4836
<212> TYPE: DNA
<213> ORGANISM: homo sapien
<400> SEQUENCE: 41

```
actgccagcc tgccatcagg cctctattgc agccctgaac catgatccag ggcaccttgg     60
agccagatgg tcccctctgg ggctgggact gggacagtga caatgactgg gatagtgctg    120
```

-continued

| | |
|---|---|
| tgctggccct cctggcgctg ctgtggtgg ctgccacagc gctggcctta cactggtttg | 180 |
| gctccgggca cgatcaagag gcggcagaac cggtgtccac agccctcggg gctcaacctc | 240 |
| atcaggcagg aggagctgag ctggccctgc aaccgaagtc taaggtcagt gatggcagcg | 300 |
| aggggcagag cccagggcag gggaaaccag agccccagg acgcggccag cagagccctg | 360 |
| tccctgctgc agcgccgggc gggggcctgg ccgccatggc ccggcttcca ctcaagacgg | 420 |
| ctgtcgagga ggcccgcaga gaggcattag acagcaacg gggcagtgcc accccgcgg | 480 |
| ccccccgagc ggaaggaaag gagcctccca ggccaggcac tgccctcctg ggcaggagcg | 540 |
| aagcaggggg gatgtccgcc cccctcctga tccacttcac tcctcggagc cctggcagcg | 600 |
| aagcggaggc ggagacaggt ggtgtcaggg cgtcctctcg ccaggccgca ggccccgcgg | 660 |
| ggcaacagga cactggcccc tggcaggcgg gcgcggggcc ctcgggctcg atggggagag | 720 |
| gccggggccg gcggcggcgg atggacgctg gctcgggaga cagagcccgc cgcccccgga | 780 |
| aactggaccc gctccgcctg ggcgccgcgg ggagcgtgtg ggacgcggtg gacggggccg | 840 |
| ccgccctgga cgcccacgcg cgcggcctcc ccacaggacc cccactcgcc caggagcccg | 900 |
| cactcccggc gctgcccgct ccccgcgccc tgcagcctgg gtctcagacg gaaggctctg | 960 |
| gggccaaggg tggctggagc agggaggcct cgggggtccc tgcccccgga ggaggctggc | 1020 |
| cctgggtcag cagggaggtc ccgggcaccc ggagctttgg cccagcccca gactccacgc | 1080 |
| gcccctggct agagagtccg cctcaaggtc gcccactctc gtcccaaggg ccgggtgcca | 1140 |
| caggggccta cgatgccggc gaggccgggg ctgacagctc ccgagataac agtcctgccg | 1200 |
| ctgacctggg gcccacccgg cccccggagc aagcaaagcc ggctgcagcc ggccacagcc | 1260 |
| gcgcgccctc ccggagccgt gagcctcgcc ccgcgctccgc ctccccgccc gcagctcccg | 1320 |
| gcccggggtt cccacctgaa gccctgactc tcccctctcc ttcagacttt ttgcccctgg | 1380 |
| aggttaccca ggatccttcc gtgggcgaaa atctcagagc ggcgccagcc ccaagttcag | 1440 |
| cctcagccca agtcttaact tcagctccag cctcagtcct agccccagcc ctggcttcat | 1500 |
| cccccagctc agcaccaacc tcagccacca cctcaacctc atcccccacc tcagccccag | 1560 |
| ccccagctcc aacctcagct ccaacttcaa ccccagcccc agcccaagt ccagctgcag | 1620 |
| ccgcaactcc agccccagcc ccagtcccag tcccaaccct cacaccccca tccccagccc | 1680 |
| taacccagt cccaacccca gccctaagcc cagctccaac tccagcccta accccagccg | 1740 |
| catcccccagc cctaacccca gtcccaaccc cagccctaag cccagctcca actccagccc | 1800 |
| caaccccagc cgcatcccct gccccagccc ccacctcagc cccaaccccca accccagccg | 1860 |
| catcccctgc cccagctgac gggtcaaagc ctcaggagag tgtggctctc cccaggcgct | 1920 |
| accaggaggg gcaggtctca gccagctggg gaaaccttat tgccatggtt cttagaagcc | 1980 |
| accccttccc caggcaagac aggccccaag ggagtgtccc gagggcggtt cccgggagcc | 2040 |
| ccgtgggtcc cagcacttcc acacactctg aggacagaca cggcccctct tcttcagtgg | 2100 |
| ggacagtcat agggacaggt acaggggcc tggttgaggc tggaggtcag ccacagccaa | 2160 |
| gaagctccga gaccaacgga tcgcccagcc cagaccctcc cccaggccta agaggagagg | 2220 |
| gaaccaggga gaaaagtcta gaccgctgc cccaagccgc gatgcccagg gccccgcac | 2280 |
| agccccccgc gcagaggccg cctggccccg cggcctcctc ctctgcgagg cgctcacagc | 2340 |
| cggtaccccca gctacggaaa cgcagcaggt gcgaaatcgc cccgagctcg gagcaggagg | 2400 |
| tcaggccggc cgcctcgggg gaccctcaag gggaggcgcc gggggagggg ggcagccctg | 2460 |
| ccggccgcag cggggcgctc acggaaaagc aggaggaggc ccggaagctc atggtgtttc | 2520 |

```
tgcagaggcc cggggggttgg ggggtggtgg aggggccccg gaagcccagc tcccgggccc    2580
tggagcccgc cacggcggca gccctgcggc ggcggctgga cctgggcagt tgcctggacg    2640
tgctggcctt tgcccagcag cacggagagc ccggcctggc gcaggagacc tacgcgctga    2700
tgagcgacaa cctgctgcga gtgctgggag acccgtgcct ctaccgccgg ctgagcgcgg    2760
ccgaccgcga gcgcatcctc agcctgcgga ccggccgggg ccgggcggtg ctgggcgtcc    2820
tcgtactgcc cagcctctac caggggggcc gctcagggct ccccagggcc ctcgtggcga    2880
ggagcctcct gcggcggccc ctgtgtccct gcctctacct gcgcacctgc atgtgttcaa    2940
cccccgggag aacacctggc ggcccctgac ccaggtgccc gaggaggccc cgcttcgggg    3000
ctgcggtctc tgcaccatgc acaactacct gtttctggcg gggggcatcc gtggctccgg    3060
tgccaaggcc gtctgctcca acgaggtctt ctgctacaac cctctgacca acatctggag    3120
ccaggttcgg cccatgcagc aggcccgagc ccagctcaag ctggtggccc tggacgggct    3180
gctctatgcc atcggtggcg aatgcctgta cagcatggag tgctacgacc gcgaacagat    3240
cgcctggacc ccacgcgcgc cactccccgc aggcaccttc cctgtggccc acgaggctgt    3300
ggcctgccgt ggggacatct acgtcaccgg ggtcacctc ttctaccgcc tgctcaggta    3360
cagccccgtg aaggatgctt gggacgagtg cccatacagt gccagccacc ggcgttccag    3420
cgacatcgtg gcactggggg gcttcctgta ccgcttcgac ctgctgcggg gcgtgggcgc    3480
cgccgtgatg cgctacaaca cagtgaccgg ctcctggagc agggctgcct ccctgcccct    3540
gcccgccccc gccccactgc actgcaccac cctgggcaac accatttact gcctcaaccc    3600
ccaggtcact gccaccttca cggtctctgg ggggactgcc cagttccagg ccaaggagct    3660
gcagcccttc cccttgggga gcaccggggt cctcagtcca ttcatcctga ctctgccccc    3720
tgaggaccgg ctgcagacct cactctgagt ggcaggcaga gaaccaaagc tgcttcgctg    3780
ctctccaggg agaccctcct gggatgggcc tgagaggccg gggctcaggg aaggggctgg    3840
gatcggaact tcctgctctt gtttctggac aactttcccc ttctgcttta aaggttgtcg    3900
attattttga agcccagact ccctcagcct ctttctgccc ctcactccac acccagactg    3960
tttcctgact caattccgta cctacttaca gaccctctca gcttgctgac accccctgt    4020 ctgtgggact cctattccc tagagccagg gactgatgcg tctccacaga caaggacttg    4080
gctcgctgga gctctgctga gccgagagag gagggggtag aaaacattca cacttcctat    4140
gctctgtcag caggacaggg agcaaaacg tccccaggca acgccctcgc ctctgggact    4200
ttctgcctgt cctaaggcct ccccaggtac caaccccgta gctatctggg tctgtttggc    4260
actgtggatt ctcaagggcc tagaaccctt gcctctgaaa ctggtccgct ggtgcagccc    4320
tgctgtctgc agctcctgcc cataccccca gcccacacca ggccaggccc actccgggct    4380
caccaccctc tgcagccttg tggggctctc ccagcccctc cagaagccca ccccacttct    4440 cgccaaccc cgatctctaa atgaggcctg agcgtcaccc tagttctgcc ccttttttagc    4500 tgtgtagact tggacgagac atttgacttc cctttctcct tgtctataaa atgtggacag    4560
tggacgtctg tcacccaaga gagttgtggg agacaagatc acagctatga gcacctcgca    4620
cggtgtccag gatgcacagc acaatccatg atgcgttttc tcccccttacg cactttgaaa    4680 cccatgctag aaaagtgaat acatctgact gtgctccact ccaacctcca gcctggatgt    4740
ccctgtctgg gcccttttttc tgttttttat tctatgttca gcaccactgg caccaaatac    4800
attttaattc accgaaagca aaaaaaaaaa aaaaaa                              4836
```

<210> SEQ ID NO 42
<211> LENGTH: 2098
<212> TYPE: DNA
<213> ORGANISM: homo sapien

<400> SEQUENCE: 42

```
ccacctcagc cccaaccca accccagccg catcccctgc cccagctgac gggtcaaagc      60
ctcaggagag tgtggctctc cccaggcgct accaggaggg gcaggtctca gccagctggg     120
gaaaccttat tgccatggtt cttagaagcc accccttccc caggcaagac aggccccaag     180
ggagtgtccc gagggcggtt cccgggagcc ccgtgggtcc cagcacttcc acacactctg     240
aggacagaca cggcccctct tcttcagtgg ggacagtcat agggacaggt acaggggcc      300
tggttgaggc tggaggtcag ccacagccaa gaagctccga gaccaacgga tcgcccagcc     360
cagaccctcc cccaggccta agaggagagg gaaccaggga gaaaagtcta gacccgctgc     420
cccaagccgc gatgcccagg ggccccgcac agccccccgc gcagaggccg cctggccccg     480
cggcctcctc ctctgcgagg cgctcacagc cggtacccca gctacggaaa cgcagcaggt     540
gcgaaatcgc cccgagctcg gagcaggagt tcaggccggc cgcctcgggg gaccctcaag     600
gggaggcgcc gggggagggg ggcagccctg ccggccgcag cggggcgctc acggaaaagc     660
aggaggaggc ccggaagctc atggtgtttc tgcagaggcc cgggggttgg ggggtggtgg     720
aggggccccg gaagcccagc tcccgggccc tggagcccgc cacggcggca gccctgcggc     780
ggcggctgga cctgggcagt tgcctggacg tgctggcctt tgcccagcag cacggagagc     840
ccggcctggc gcaggagacc tacgcgctga tgagcgacaa cctgctgcga gtgctgggag     900
acccgtgcct ctaccgccgg ctgagcgcgg ccgaccgcga gcgcatcctc agcctgcgga     960
ccggccgggg ccgggcggtg ctgggcgtcc tcgtactgcc cagcctctac caggggggcc    1020
gctcagggct ccccagggcc ctcgtggcga ggagcctcct gcggcggccc ctgtgtccct    1080
gcctctacct gcgcacctgc atgtgttcaa ccccgggag aacacctggc ggcccctgac     1140
ccaggtgccc gaggaggccc cgcttcgggg ctgcggtctc tgcaccatgc acaactacct    1200
gtttctggcg gggggcatcc gtggctccgg tgccaaggcc gtctgctcca acgaggtctt    1260
ctgctacaac cctctgacca acatctggag ccaggttcgg cccatgcagc aggcccgagc    1320
ccagctcaag ctggtggccc tggacgggct gctctatgcc atcggtggcg aatgcctgta    1380
cagcatggag tgctacgacc cgcgaacaga cgcctggacc ccacgcgcgc cactccccgc    1440
aggcaccttc cctgtggccc acgaggctgt ggcctgccgt ggggacatct acgtcaccgg    1500
gggtcacctc ttctaccgcc tgctcaggta cagccccgtg aaggatgctt gggacgagtg    1560
cccatacagt gccagccacc ggcgttccag cgacatcgtg gcactggggg cttcctgta    1620
ccgcttcgac ctgctgcggg gcgtgggcgc cgccgtgatg cgctacaaca cagtgaccgg    1680
ctcctggagc agggctgcct ccctgcccct gccgcccc gccccactgc actgcaccac      1740
cctgggcaac accatttact gcctcaaccc ccaggtcact gccaccttca cggtctctgg    1800
ggggactgcc cagttccagg ccaaggagct gcagcccttc ccttggggga gcaccggggt    1860
cctcagtcca ttcatcctga ctctgccccc tgaggaccgg ctgcagacct cactctgagt    1920
ggcaggcaga gaaccaaagc tgcttcgctg ctctccaggg agaccctcct gggatgggcc    1980
tgagaggccg gggctcaggg aaggggctgg gatcggaact tcctgctctt gtttctggac    2040
aactttcccc ttctgcttta aaggttgtcg attattttga aaaaaaaaaa aaaaaaa       2098
```

```
<210> SEQ ID NO 43
<211> LENGTH: 885
<212> TYPE: PRT
<213> ORGANISM: homo sapien

<400> SEQUENCE: 43
```

| | | | | | | | | | | | | | | |
|---|---|---|---|---|---|---|---|---|---|---|---|---|---|---|
| Met | Ile | Gln | Gly | Thr | Leu | Glu | Pro | Asp | Gly | Pro | Leu | Trp | Gly | Trp |
| 1 | | | | 5 | | | | | 10 | | | | | 15 |

Asp

| Trp | Asp | Ser | Asp | Asn | Asp | Trp | Asp | Ser | Ala | Val | Leu | Ala | Leu | Leu | Ala |
|---|---|---|---|---|---|---|---|---|---|---|---|---|---|---|---|
| | | | 20 | | | | | 25 | | | | | 30 | | |

| Leu | Ala | Val | Ala | Ala | Thr | Ala | Leu | Ala | Leu | His | Trp | Phe | Gly | Ser |
|---|---|---|---|---|---|---|---|---|---|---|---|---|---|---|
| | | 35 | | | | | 40 | | | | | 45 | | |

| Gly | His | Asp | Gln | Glu | Ala | Ala | Glu | Pro | Val | Ser | Thr | Ala | Leu | Gly | Ala |
|---|---|---|---|---|---|---|---|---|---|---|---|---|---|---|---|
| | 50 | | | | | 55 | | | | | 60 | | | | |

| Gln | Pro | His | Gln | Ala | Gly | Gly | Ala | Glu | Leu | Ala | Leu | Gln | Pro | Lys | Ser |
|---|---|---|---|---|---|---|---|---|---|---|---|---|---|---|---|
| 65 | | | | | 70 | | | | | 75 | | | | | 80 |

| Lys | Val | Ser | Asp | Gly | Ser | Glu | Gly | Gln | Ser | Pro | Gly | Gln | Gly | Lys | Pro |
|---|---|---|---|---|---|---|---|---|---|---|---|---|---|---|---|
| | | | | 85 | | | | | 90 | | | | | 95 | |

| Glu | Pro | Pro | Gly | Arg | Gly | Gln | Ser | Pro | Val | Pro | Ala | Ala | Ala | Pro |
|---|---|---|---|---|---|---|---|---|---|---|---|---|---|---|
| | | | 100 | | | | | 105 | | | | | 110 | |

| Gly | Gly | Gly | Leu | Ala | Ala | Met | Ala | Arg | Leu | Pro | Leu | Lys | Thr | Ala | Val |
|---|---|---|---|---|---|---|---|---|---|---|---|---|---|---|---|
| | | 115 | | | | | 120 | | | | | 125 | | | |

| Glu | Glu | Ala | Arg | Arg | Glu | Ala | Leu | Gly | Gln | Gln | Arg | Gly | Ser | Ala | Thr |
|---|---|---|---|---|---|---|---|---|---|---|---|---|---|---|---|
| 130 | | | | | 135 | | | | | 140 | | | | | |

| Pro | Ala | Ala | Pro | Arg | Ala | Glu | Gly | Lys | Glu | Pro | Pro | Arg | Pro | Gly | Thr |
|---|---|---|---|---|---|---|---|---|---|---|---|---|---|---|---|
| 145 | | | | | 150 | | | | | 155 | | | | | 160 |

| Ala | Leu | Leu | Gly | Arg | Ser | Glu | Ala | Gly | Gly | Met | Ser | Ala | Pro | Leu | Leu |
|---|---|---|---|---|---|---|---|---|---|---|---|---|---|---|---|
| | | | | 165 | | | | | 170 | | | | | 175 | |

| Ile | His | Phe | Thr | Pro | Arg | Ser | Pro | Gly | Ser | Glu | Ala | Glu | Ala | Glu | Thr |
|---|---|---|---|---|---|---|---|---|---|---|---|---|---|---|---|
| | | | 180 | | | | | 185 | | | | | 190 | | |

| Gly | Gly | Val | Arg | Ala | Ser | Ser | Arg | Gln | Ala | Ala | Gly | Pro | Ala | Gly | Gln |
|---|---|---|---|---|---|---|---|---|---|---|---|---|---|---|---|
| | | 195 | | | | | 200 | | | | | 205 | | | |

| Gln | Asp | Thr | Gly | Pro | Trp | Gln | Ala | Gly | Ala | Gly | Pro | Ser | Gly | Ser | Met |
|---|---|---|---|---|---|---|---|---|---|---|---|---|---|---|---|
| 210 | | | | | 215 | | | | | 220 | | | | | |

| Gly | Arg | Gly | Arg | Gly | Arg | Arg | Arg | Met | Asp | Ala | Gly | Ser | Gly | Asp |
|---|---|---|---|---|---|---|---|---|---|---|---|---|---|---|
| 225 | | | | 230 | | | | | 235 | | | | | 240 |

| Arg | Ala | Arg | Arg | Pro | Arg | Lys | Leu | Asp | Pro | Leu | Arg | Leu | Gly | Ala | Ala |
|---|---|---|---|---|---|---|---|---|---|---|---|---|---|---|---|
| | | | | 245 | | | | | 250 | | | | | 255 | |

| Gly | Ser | Val | Trp | Asp | Ala | Val | Asp | Gly | Ala | Ala | Ala | Leu | Asp | Ala | His |
|---|---|---|---|---|---|---|---|---|---|---|---|---|---|---|---|
| | | | 260 | | | | | 265 | | | | | 270 | | |

| Ala | Arg | Gly | Leu | Pro | Thr | Gly | Pro | Pro | Leu | Ala | Gln | Glu | Pro | Ala | Leu |
|---|---|---|---|---|---|---|---|---|---|---|---|---|---|---|---|
| | | 275 | | | | | 280 | | | | | 285 | | | |

| Pro | Ala | Leu | Pro | Ala | Pro | Arg | Ala | Leu | Gln | Pro | Gly | Ser | Gln | Thr | Glu |
|---|---|---|---|---|---|---|---|---|---|---|---|---|---|---|---|
| 290 | | | | | 295 | | | | | 300 | | | | | |

| Gly | Ser | Gly | Ala | Lys | Gly | Gly | Trp | Ser | Arg | Glu | Ala | Ser | Gly | Val | Pro |
|---|---|---|---|---|---|---|---|---|---|---|---|---|---|---|---|
| 305 | | | | | 310 | | | | | 315 | | | | | 320 |

| Ala | Pro | Gly | Gly | Gly | Trp | Pro | Trp | Val | Ser | Arg | Glu | Val | Pro | Gly | Thr |
|---|---|---|---|---|---|---|---|---|---|---|---|---|---|---|---|
| | | | | 325 | | | | | 330 | | | | | 335 | |

| Arg | Ser | Phe | Gly | Pro | Ala | Pro | Asp | Ser | Thr | Arg | Pro | Trp | Leu | Glu | Ser |
|---|---|---|---|---|---|---|---|---|---|---|---|---|---|---|---|
| | | | 340 | | | | | 345 | | | | | 350 | | |

| Pro | Pro | Gln | Gly | Arg | Pro | Leu | Ser | Ser | Gln | Gly | Pro | Gly | Ala | Thr | Gly |
|---|---|---|---|---|---|---|---|---|---|---|---|---|---|---|---|
| | | 355 | | | | | 360 | | | | | 365 | | | |

| Ala | Tyr | Asp | Ala | Gly | Glu | Ala | Gly | Ala | Asp | Ser | Ser | Arg | Asp | Asn | Ser |
|---|---|---|---|---|---|---|---|---|---|---|---|---|---|---|---|
| 370 | | | | | 375 | | | | | 380 | | | | | |

```
Pro Ala Ala Asp Leu Gly Pro Thr Arg Pro Pro Glu Gln Ala Lys Pro
385                 390                 395                 400

Ala Ala Ala Gly His Ser Arg Ala Pro Ser Arg Ser Arg Glu Pro Arg
            405                 410                 415

Pro Arg Ser Ala Ser Pro Pro Ala Ala Pro Gly Pro Gly Phe Pro Pro
            420                 425                 430

Glu Ala Leu Thr Leu Pro Ser Pro Ser Asp Phe Leu Pro Leu Glu Val
            435                 440                 445

Thr Gln Asp Pro Ser Val Gly Glu Asn Leu Arg Ala Ala Pro Ala Pro
        450                 455                 460

Ser Ser Ala Ser Ala Gln Val Leu Thr Ser Ala Pro Ala Ser Val Leu
465                 470                 475                 480

Ala Pro Ala Leu Ala Ser Ser Pro Ser Ser Ala Pro Thr Ser Ala Thr
                485                 490                 495

Thr Ser Thr Ser Ser Pro Thr Ser Ala Pro Ala Pro Ala Pro Thr Ser
            500                 505                 510

Ala Pro Thr Ser Thr Pro Ala Pro Ala Pro Ser Pro Ala Ala Ala Ala
            515                 520                 525

Thr Pro Ala Pro Ala Pro Val Pro Val Pro Thr Leu Thr Pro Pro Ser
530                 535                 540

Pro Ala Leu Thr Pro Val Pro Thr Pro Ala Leu Ser Pro Ala Pro Thr
545                 550                 555                 560

Pro Ala Leu Thr Pro Ala Ala Ser Pro Ala Leu Thr Pro Val Pro Thr
                565                 570                 575

Pro Ala Leu Ser Pro Ala Pro Thr Pro Ala Pro Thr Pro Ala Ala Ser
            580                 585                 590

Pro Ala Pro Ala Pro Thr Ser Ala Pro Thr Pro Thr Pro Ala Ala Ser
                595                 600                 605

Pro Ala Pro Ala Asp Gly Ser Lys Pro Gln Glu Ser Val Ala Leu Pro
            610                 615                 620

Arg Arg Tyr Gln Glu Gly Gln Val Ser Ala Ser Trp Gly Asn Leu Ile
625                 630                 635                 640

Ala Met Val Leu Arg Ser His Pro Phe Pro Arg Gln Asp Arg Pro Gln
                645                 650                 655

Gly Ser Val Pro Arg Ala Val Pro Gly Ser Pro Val Gly Pro Ser Thr
            660                 665                 670

Ser Thr His Ser Glu Asp Arg His Gly Pro Ser Ser Ser Val Gly Thr
            675                 680                 685

Val Ile Gly Thr Gly Thr Gly Gly Leu Val Glu Ala Gly Gly Gln Pro
            690                 695                 700

Gln Pro Arg Ser Ser Glu Thr Asn Gly Ser Pro Ser Pro Asp Pro Pro
705                 710                 715                 720

Pro Gly Leu Arg Gly Glu Gly Thr Arg Glu Lys Ser Leu Asp Pro Leu
            725                 730                 735

Pro Gln Ala Ala Met Pro Arg Gly Pro Ala Gln Pro Ala Gln Arg
            740                 745                 750

Pro Pro Gly Pro Ala Ala Ser Ser Ala Arg Arg Ser Gln Pro Val
            755                 760                 765

Pro Gln Leu Arg Lys Arg Ser Arg Cys Glu Ile Ala Pro Ser Ser Glu
            770                 775                 780

Gln Glu Val Arg Pro Ala Ala Ser Gly Asp Pro Gln Gly Glu Ala Pro
785                 790                 795                 800

Gly Glu Gly Gly Ser Pro Ala Gly Arg Ser Gly Ala Leu Thr Glu Lys
```

```
                    805                 810                 815
Gln Glu Glu Ala Arg Ser Ser Trp Cys Phe Cys Arg Gly Pro Gly Val
                820                 825                 830

Gly Gly Trp Trp Arg Gly Pro Gly Ser Pro Ala Pro Gly Pro Trp Ser
            835                 840                 845

Pro Pro Arg Arg Gln Pro Cys Gly Gly Gly Trp Thr Trp Ala Val Ala
850                 855                 860

Trp Thr Cys Trp Pro Leu Pro Ser Ser Thr Glu Ser Pro Ala Trp Arg
865                 870                 875                 880

Arg Arg Pro Thr Arg
                885

<210> SEQ ID NO 44
<211> LENGTH: 244
<212> TYPE: PRT
<213> ORGANISM: homo sapien

<400> SEQUENCE: 44

Met Val Leu Arg Ser His Pro Phe Pro Arg Gln Asp Arg Pro Gln Gly
1               5                   10                  15

Ser Val Pro Arg Ala Val Pro Gly Ser Pro Val Gly Ser Thr Ser
            20                  25                  30

Thr His Ser Glu Asp Arg His Gly Pro Ser Ser Val Gly Thr Val
        35                  40                  45

Ile Gly Thr Gly Thr Gly Gly Leu Val Glu Ala Gly Gly Gln Pro Gln
    50                  55                  60

Pro Arg Ser Ser Glu Thr Asn Gly Ser Pro Ser Pro Asp Pro Pro
65                  70                  75                  80

Gly Leu Arg Gly Glu Gly Thr Arg Glu Lys Ser Leu Asp Pro Leu Pro
                85                  90                  95

Gln Ala Ala Met Pro Arg Gly Pro Ala Gln Pro Ala Gln Arg Pro
            100                 105                 110

Pro Gly Pro Ala Ala Ser Ser Ala Arg Arg Ser Gln Pro Val Pro
        115                 120                 125

Gln Leu Arg Lys Arg Ser Arg Cys Glu Ile Ala Pro Ser Ser Glu Gln
130                 135                 140

Glu Val Arg Pro Ala Ala Ser Gly Asp Pro Gln Gly Glu Ala Pro Gly
145                 150                 155                 160

Glu Gly Gly Ser Pro Ala Gly Arg Ser Gly Ala Leu Thr Glu Lys Gln
                165                 170                 175

Glu Glu Ala Arg Ser Ser Trp Cys Phe Cys Arg Gly Pro Gly Val Gly
            180                 185                 190

Gly Trp Trp Arg Gly Pro Gly Ser Pro Ala Pro Gly Pro Trp Ser Pro
        195                 200                 205

Pro Arg Arg Gln Pro Cys Gly Gly Gly Trp Thr Trp Ala Val Ala Trp
    210                 215                 220

Thr Cys Trp Pro Leu Pro Ser Ser Thr Glu Ser Pro Ala Trp Arg Arg
225                 230                 235                 240

Arg Pro Thr Arg

<210> SEQ ID NO 45
<211> LENGTH: 145
<212> TYPE: PRT
<213> ORGANISM: homo sapien

<400> SEQUENCE: 45
```

-continued

Met Pro Arg Gly Pro Ala Gln Pro Ala Gln Arg Pro Gly Pro
1               5                   10                  15

Ala Ala Ser Ser Ser Ala Arg Arg Ser Gln Pro Val Pro Gln Leu Arg
            20                  25                  30

Lys Arg Ser Arg Cys Glu Ile Ala Pro Ser Ser Glu Gln Glu Val Arg
            35                  40                  45

Pro Ala Ala Ser Gly Asp Pro Gln Gly Glu Ala Pro Gly Glu Gly Gly
        50                  55                  60

Ser Pro Ala Gly Arg Ser Gly Ala Leu Thr Glu Lys Gln Glu Glu Ala
65                  70                  75                  80

Arg Ser Ser Trp Cys Phe Cys Arg Gly Pro Gly Val Gly Gly Trp Trp
                85                  90                  95

Arg Gly Pro Gly Ser Pro Ala Pro Gly Pro Trp Ser Pro Pro Arg Arg
                100                 105                 110

Gln Pro Cys Gly Gly Gly Trp Thr Trp Ala Val Ala Trp Thr Cys Trp
            115                 120                 125

Pro Leu Pro Ser Ser Thr Glu Ser Pro Ala Trp Arg Arg Pro Thr
130                 135                 140

Arg
145

<210> SEQ ID NO 46
<211> LENGTH: 975
<212> TYPE: PRT
<213> ORGANISM: homo sapien

<400> SEQUENCE: 46

Met Ile Gln Gly Thr Leu Glu Pro Asp Gly Pro Leu Trp Gly Trp Asp
1               5                   10                  15

Trp Asp Ser Asp Asn Asp Trp Asp Ser Ala Val Leu Ala Leu Leu Ala
            20                  25                  30

Leu Ala Val Val Ala Ala Thr Ala Leu Ala Leu His Trp Phe Gly Ser
            35                  40                  45

Gly His Asp Gln Glu Ala Ala Glu Pro Val Ser Thr Ala Leu Gly Ala
        50                  55                  60

Gln Pro His Gln Ala Gly Gly Ala Glu Leu Ala Leu Gln Pro Lys Ser
65                  70                  75                  80

Lys Val Ser Asp Gly Ser Glu Gly Gln Ser Pro Gly Gln Gly Lys Pro
                85                  90                  95

Glu Pro Pro Gly Arg Gly Gln Gln Ser Pro Val Pro Ala Ala Ala Pro
                100                 105                 110

Gly Gly Gly Leu Ala Ala Met Ala Arg Leu Pro Leu Lys Thr Ala Val
            115                 120                 125

Glu Glu Ala Arg Arg Glu Ala Leu Gly Gln Gln Arg Gly Ser Ala Thr
130                 135                 140

Pro Ala Ala Pro Arg Ala Glu Gly Lys Glu Pro Pro Arg Pro Gly Thr
145                 150                 155                 160

Ala Leu Leu Gly Arg Ser Glu Ala Gly Gly Met Ser Ala Pro Leu Leu
                165                 170                 175

Ile His Phe Thr Pro Arg Ser Pro Gly Ser Glu Ala Glu Ala Glu Thr
                180                 185                 190

Gly Gly Val Arg Ala Ser Ser Arg Gln Ala Ala Gly Pro Ala Gly Gln
            195                 200                 205

Gln Asp Thr Gly Pro Trp Gln Ala Gly Ala Gly Pro Ser Gly Ser Met

-continued

```
            210                 215                 220
Gly Arg Gly Arg Gly Arg Arg Arg Met Asp Ala Gly Ser Gly Asp
225                 230                 235                 240

Arg Ala Arg Arg Pro Arg Lys Leu Asp Pro Leu Arg Leu Gly Ala Ala
                245                 250                 255

Gly Ser Val Trp Asp Ala Val Asp Gly Ala Ala Ala Leu Asp Ala His
                260                 265                 270

Ala Arg Gly Leu Pro Thr Gly Pro Pro Leu Ala Gln Glu Pro Ala Leu
                275                 280                 285

Pro Ala Leu Pro Ala Pro Arg Ala Leu Gln Pro Gly Ser Gln Thr Glu
                290                 295                 300

Gly Ser Gly Ala Lys Gly Gly Trp Ser Arg Glu Ala Ser Gly Val Pro
305                 310                 315                 320

Ala Pro Gly Gly Gly Trp Pro Trp Val Ser Arg Glu Val Pro Gly Thr
                325                 330                 335

Arg Ser Phe Gly Pro Ala Pro Asp Ser Thr Arg Pro Trp Leu Glu Ser
                340                 345                 350

Pro Pro Gln Gly Arg Pro Leu Ser Ser Gln Gly Pro Gly Ala Thr Gly
                355                 360                 365

Ala Tyr Asp Ala Gly Glu Ala Gly Ala Asp Ser Ser Arg Asp Asn Ser
                370                 375                 380

Pro Ala Ala Asp Leu Gly Pro Thr Arg Pro Pro Glu Gln Ala Lys Pro
385                 390                 395                 400

Ala Ala Ala Gly His Ser Arg Ala Pro Ser Arg Ser Arg Glu Pro Arg
                405                 410                 415

Pro Arg Ser Ala Ser Pro Ala Ala Pro Gly Pro Gly Phe Pro Pro
                420                 425                 430

Glu Ala Leu Thr Leu Pro Ser Pro Ser Asp Phe Leu Pro Leu Glu Val
                435                 440                 445

Thr Gln Asp Pro Ser Val Gly Glu Asn Leu Arg Ala Ala Pro Ala Pro
                450                 455                 460

Ser Ser Ala Ser Ala Gln Val Leu Thr Ser Ala Pro Ala Ser Val Leu
465                 470                 475                 480

Ala Pro Ala Leu Ala Ser Ser Pro Ser Ser Ala Pro Thr Ser Ala Thr
                485                 490                 495

Thr Ser Thr Ser Ser Pro Thr Ser Ala Pro Ala Pro Ala Pro Thr Ser
                500                 505                 510

Ala Pro Thr Ser Thr Pro Ala Pro Ala Pro Ser Pro Ala Ala Ala
                515                 520                 525

Thr Pro Ala Pro Ala Pro Val Pro Val Pro Thr Leu Thr Pro Pro Ser
                530                 535                 540

Pro Ala Leu Thr Pro Val Pro Thr Pro Ala Leu Ser Pro Ala Pro Thr
545                 550                 555                 560

Pro Ala Leu Thr Pro Ala Ala Ser Pro Ala Leu Thr Pro Val Pro Thr
                565                 570                 575

Pro Ala Leu Ser Pro Ala Pro Thr Pro Ala Pro Thr Pro Ala Ala Ser
                580                 585                 590

Pro Ala Pro Ala Pro Thr Ser Ala Pro Thr Pro Ala Ala Ser
                595                 600                 605

Pro Ala Pro Ala Asp Gly Ser Lys Pro Gln Glu Ser Val Ala Leu Pro
                610                 615                 620

Arg Arg Tyr Gln Glu Gly Gln Val Ser Ala Ser Trp Gly Asn Leu Ile
625                 630                 635                 640
```

Ala Met Val Leu Arg Ser His Pro Phe Pro Arg Gln Asp Arg Pro Gln
                    645                 650                 655

Gly Ser Val Pro Arg Ala Val Pro Gly Ser Pro Val Gly Pro Ser Thr
                660                 665                 670

Ser Thr His Ser Glu Asp Arg His Gly Pro Ser Ser Ser Val Gly Thr
                675                 680                 685

Val Ile Gly Thr Gly Thr Gly Gly Leu Val Glu Ala Gly Gly Gln Pro
                690                 695                 700

Gln Pro Arg Ser Ser Glu Thr Asn Gly Ser Pro Ser Pro Asp Pro Pro
705                 710                 715                 720

Pro Gly Leu Arg Gly Glu Gly Thr Arg Glu Lys Ser Leu Asp Pro Leu
                725                 730                 735

Pro Gln Ala Ala Met Pro Arg Gly Pro Ala Gln Pro Pro Ala Gln Arg
                740                 745                 750

Pro Pro Gly Pro Ala Ala Ser Ser Ala Arg Arg Ser Gln Pro Val
                755                 760                 765

Pro Gln Leu Arg Lys Arg Ser Arg Cys Glu Ile Ala Pro Ser Ser Glu
                770                 775                 780

Gln Glu Val Arg Pro Ala Ala Ser Gly Asp Pro Gln Gly Glu Ala Pro
785                 790                 795                 800

Gly Glu Gly Gly Ser Pro Ala Gly Arg Ser Gly Ala Leu Thr Glu Lys
                805                 810                 815

Gln Glu Glu Ala Arg Lys Leu Met Val Phe Leu Gln Arg Pro Gly Gly
                820                 825                 830

Trp Gly Val Val Glu Gly Pro Arg Lys Pro Ser Ser Arg Ala Leu Glu
                835                 840                 845

Pro Ala Thr Ala Ala Ala Leu Arg Arg Arg Leu Asp Leu Gly Ser Cys
                850                 855                 860

Leu Asp Val Leu Ala Phe Ala Gln Gln His Gly Glu Pro Gly Leu Ala
865                 870                 875                 880

Gln Glu Thr Tyr Ala Leu Met Ser Asp Asn Leu Leu Arg Val Leu Gly
                885                 890                 895

Asp Pro Cys Leu Tyr Arg Arg Leu Ser Ala Ala Asp Arg Glu Arg Ile
                900                 905                 910

Leu Ser Leu Arg Thr Gly Arg Gly Arg Ala Val Leu Gly Val Leu Val
                915                 920                 925

Leu Pro Ser Leu Tyr Gln Gly Gly Arg Ser Gly Leu Pro Arg Ala Leu
                930                 935                 940

Val Ala Arg Ser Leu Leu Arg Arg Pro Leu Cys Pro Cys Leu Tyr Leu
945                 950                 955                 960

Arg Thr Cys Met Cys Ser Thr Pro Gly Arg Thr Pro Gly Gly Pro
                965                 970                 975

<210> SEQ ID NO 47
<211> LENGTH: 334
<212> TYPE: PRT
<213> ORGANISM: homo sapien

<400> SEQUENCE: 47

Met Val Leu Arg Ser His Pro Phe Pro Arg Gln Asp Arg Pro Gln Gly
1               5                   10                  15

Ser Val Pro Arg Ala Val Pro Gly Ser Pro Val Gly Pro Ser Thr Ser
                20                  25                  30

Thr His Ser Glu Asp Arg His Gly Pro Ser Ser Ser Val Gly Thr Val

```
            35                  40                  45
Ile Gly Thr Gly Thr Gly Gly Leu Val Glu Ala Gly Gly Gln Pro Gln
 50                  55                  60
Pro Arg Ser Ser Glu Thr Asn Gly Ser Pro Ser Pro Asp Pro Pro
 65                  70                  75                  80
Gly Leu Arg Gly Glu Gly Thr Arg Glu Lys Ser Leu Asp Pro Leu Pro
                 85                  90                  95
Gln Ala Ala Met Pro Arg Gly Pro Ala Gln Pro Ala Gln Arg Pro
                100                 105                 110
Pro Gly Pro Ala Ala Ser Ser Ala Arg Arg Ser Gln Pro Val Pro
            115                 120                 125
Gln Leu Arg Lys Arg Ser Arg Cys Glu Ile Ala Pro Ser Ser Glu Gln
130                 135                 140
Glu Val Arg Pro Ala Ala Ser Gly Asp Pro Gln Gly Glu Ala Pro Gly
145                 150                 155                 160
Glu Gly Gly Ser Pro Ala Gly Arg Ser Gly Ala Leu Thr Glu Lys Gln
                165                 170                 175
Glu Glu Ala Arg Lys Leu Met Val Phe Leu Gln Arg Pro Gly Gly Trp
            180                 185                 190
Gly Val Val Glu Gly Pro Arg Lys Pro Ser Ser Arg Ala Leu Glu Pro
            195                 200                 205
Ala Thr Ala Ala Ala Leu Arg Arg Arg Leu Asp Leu Gly Ser Cys Leu
210                 215                 220
Asp Val Leu Ala Phe Ala Gln Gln His Gly Glu Pro Gly Leu Ala Gln
225                 230                 235                 240
Glu Thr Tyr Ala Leu Met Ser Asp Asn Leu Leu Arg Val Leu Gly Asp
                245                 250                 255
Pro Cys Leu Tyr Arg Arg Leu Ser Ala Ala Asp Arg Glu Arg Ile Leu
            260                 265                 270
Ser Leu Arg Thr Gly Arg Gly Arg Ala Val Leu Gly Val Leu Val Leu
            275                 280                 285
Pro Ser Leu Tyr Gln Gly Gly Arg Ser Gly Leu Pro Arg Ala Leu Val
            290                 295                 300
Ala Arg Ser Leu Leu Arg Arg Pro Leu Cys Pro Cys Leu Tyr Leu Arg
305                 310                 315                 320
Thr Cys Met Cys Ser Thr Pro Gly Arg Thr Pro Gly Gly Pro
                325                 330

<210> SEQ ID NO 48
<211> LENGTH: 235
<212> TYPE: PRT
<213> ORGANISM: homo sapien

<400> SEQUENCE: 48

Met Pro Arg Gly Pro Ala Gln Pro Pro Ala Gln Arg Pro Pro Gly Pro
 1               5                  10                  15
Ala Ala Ser Ser Ser Ala Arg Arg Ser Gln Pro Val Pro Gln Leu Arg
                20                  25                  30
Lys Arg Ser Arg Cys Glu Ile Ala Pro Ser Ser Glu Gln Glu Val Arg
            35                  40                  45
Pro Ala Ala Ser Gly Asp Pro Gln Gly Glu Ala Pro Gly Glu Gly Gly
         50                     55                  60
Ser Pro Ala Gly Arg Ser Gly Ala Leu Thr Glu Lys Gln Glu Glu Ala
 65                  70                  75                  80
```

```
Arg Lys Leu Met Val Phe Leu Gln Arg Pro Gly Gly Trp Gly Val Val
                85              90              95

Glu Gly Pro Arg Lys Pro Ser Ser Arg Ala Leu Glu Pro Ala Thr Ala
            100             105             110

Ala Ala Leu Arg Arg Arg Leu Asp Leu Gly Ser Cys Leu Asp Val Leu
        115             120             125

Ala Phe Ala Gln Gln His Gly Glu Pro Gly Leu Ala Gln Glu Thr Tyr
    130             135             140

Ala Leu Met Ser Asp Asn Leu Leu Arg Val Leu Gly Asp Pro Cys Leu
145             150             155             160

Tyr Arg Arg Leu Ser Ala Ala Asp Arg Glu Arg Ile Leu Ser Leu Arg
            165             170             175

Thr Gly Arg Gly Arg Ala Val Leu Gly Val Leu Val Leu Pro Ser Leu
            180             185             190

Tyr Gln Gly Gly Arg Ser Gly Leu Pro Arg Ala Leu Val Ala Arg Ser
        195             200             205

Leu Leu Arg Arg Pro Leu Cys Pro Cys Leu Tyr Leu Arg Thr Cys Met
    210             215             220

Cys Ser Thr Pro Gly Arg Thr Pro Gly Gly Pro
225             230             235
```

What is claimed is:

1. A method of treating a subject with a therapeutic agent that treats or inhibits hearing loss, wherein the subject has hearing loss, the method comprising the steps of:
   determining whether the subject has a Kelch Domain Containing 7B (KLHDC7B) missense variant nucleic acid molecule encoding a KLHDC7B predicted loss-of-function polypeptide by:
      obtaining or having obtained a biological sample from the subject; and
      performing or having performed a sequence analysis on the biological sample to determine if the subject has a genotype comprising the KLHDC7B missense variant nucleic acid molecule encoding the KLHDC7B predicted loss-of-function polypeptide; and
   administering or continuing to administer the therapeutic agent that treats or inhibits hearing loss in a standard dosage amount to a subject that is KLHDC7B reference; and
   administering or continuing to administer the therapeutic agent that treats or inhibits hearing loss in an amount that is the same as or greater than a standard dosage amount to a subject that is heterozygous or homozygous for the KLHDC7B missense variant nucleic acid molecule;
   wherein the presence of a genotype having the KLHDC7B missense variant nucleic acid molecule encoding the KLHDC7B predicted loss-of-function polypeptide indicates the subject has an increased risk of developing hearing loss, wherein the KLHDC7B missense variant nucleic acid molecule encodes KLHDC7B K181fs or KLHDC7B G302fs.

2. The method according to claim 1, wherein the KLHDC7B missense variant nucleic acid molecule encoding the KLHDC7B predicted loss-of-function polypeptide is:
   a genomic nucleic acid molecule having a nucleotide sequence: lacking a guanine at a position corresponding to position 2,807 according to SEQ ID NO:1; or lacking a guanine at a position corresponding to position 3,170 according to SEQ ID NO:1; or
   an mRNA molecule having a nucleotide sequence: lacking a guanine at a position corresponding to position 673 according to SEQ ID NO:4, lacking a guanine at a position corresponding to position 673 according to SEQ ID NO:6, lacking a guanine at a position corresponding to position 1,036 according to SEQ ID NO:4, or lacking a guanine at a position corresponding to position 1,036 according to SEQ ID NO:6; or
   a cDNA molecule produced from an mRNA molecule, wherein the cDNA molecule has a nucleotide sequence: lacking a guanine at a position corresponding to position 673 according to SEQ ID NO:12, lacking a guanine at a position corresponding to position 673 according to SEQ ID NO:14, lacking a guanine at a position corresponding to position 1,036 according to SEQ ID NO:12, or lacking a guanine at a position corresponding to position 1,036 according to SEQ ID NO:14.

3. The method according to claim 1, wherein the sequence analysis comprises sequencing at least a portion of the nucleotide sequence of the KLHDC7B mRNA molecule in the biological sample, wherein the sequenced portion comprises: positions corresponding to positions 672-673 according to SEQ ID NO:28, or the complement thereof; positions corresponding to positions 672-673 according to SEQ ID NO:30, or the complement thereof; positions corresponding to positions 1,035-1,036 according to SEQ ID NO:32, or the complement thereof; or positions corresponding to positions 1,035-1,036 according to SEQ ID NO:34, or the complement thereof;
   wherein when the sequenced portion of the KLHDC7B mRNA molecule in the biological sample comprises: a CG dinucleotide at positions corresponding to positions 672-673 according to SEQ ID NO:28, a CG dinucleotide at positions corresponding to positions 672-673 according to SEQ ID NO:30, an AG dinucleotide at positions corresponding to positions 1,035-1,036 according to SEQ ID NO:32, or an AG dinucleotide at positions corresponding to positions 1,035-1,036 according to SEQ ID NO:34, then the KLHDC7B mRNA molecule in the biological sample is a KLHDC7B missense variant mRNA molecule encoding a KLHDC7B predicted loss-of-function polypeptide.

4. The method according to claim 1, wherein the sequence analysis comprises sequencing at least a portion of the nucleotide sequence of the KLHDC7B cDNA molecule produced from the mRNA molecule in the biological sample, wherein the sequenced portion comprises: positions corresponding to positions 672-673 according to SEQ ID NO:36, or the complement thereof; positions corresponding to positions 672-673 according to SEQ ID NO:38, or the complement thereof; positions corresponding to positions 1,035-1,036 according to SEQ ID NO:40, or the complement thereof; or positions corresponding to positions 1,035-1,036 according to SEQ ID NO:42, or the complement thereof;
wherein when the sequenced portion of the KLHDC7B cDNA molecule in the biological sample comprises: a CG dinucleotide at positions corresponding to positions 672-673 according to SEQ ID NO:36, a CG dinucleotide at positions corresponding to positions 672-673 according to SEQ ID NO:38, an AG dinucleotide at positions corresponding to positions 1,035-1,036 according to SEQ ID NO:40, or an AG dinucleotide at positions corresponding to positions 1,035-1,036 according to SEQ ID NO:42, then the KLHDC7B cDNA molecule is a KLHDC7B missense variant cDNA molecule encoding a KLHDC7B predicted loss-of-function polypeptide.

5. The method according to claim 1, wherein the sequence analysis comprises:
a) contacting the biological sample with a primer hybridizing to a portion of the nucleotide sequence of the KLHDC7B mRNA molecule that is proximate to: positions corresponding to positions 672-673 according to SEQ ID NO:28, positions corresponding to positions 672-673 according to SEQ ID NO:30, positions corresponding to positions 1,035-1,036 according to SEQ ID NO:32 or positions corresponding to positions 1,035-1,036 according to SEQ ID NO:34;
b) extending the primer at least through the position of the nucleotide sequence of the KLHDC7B mRNA molecule corresponding to: positions 672-673 according to SEQ ID NO:28, positions 672-673 according to SEQ ID NO:30, positions 1,035-1,036 according to SEQ ID NO:32, or positions 1,035-1,036 according to SEQ ID NO:34; and
c) determining whether the extension product of the primer comprises: a CG dinucleotide at positions corresponding to positions 672-673 according to SEQ ID NO:28, a CG dinucleotide at positions corresponding to positions 672-673 according to SEQ ID NO:30, an AG dinucleotide at positions corresponding to positions 1,035-1,036 according to SEQ ID NO:32, or an AG dinucleotide at positions corresponding to positions 1,035-1,036 according to SEQ ID NO:34.

6. The method according to claim 1, wherein the sequence analysis comprises:
a) contacting the biological sample with a primer hybridizing to a portion of the nucleotide sequence of the KLHDC7B cDNA molecule that is proximate to: positions corresponding to positions 2,806-2,807 according to SEQ ID NO:35, positions corresponding to positions 672-673 according to SEQ ID NO:36, positions corresponding to positions 672-673 according to SEQ ID NO:38, positions corresponding to positions 1,035-1,036 according to SEQ ID NO:40, or positions corresponding to positions 1,035-1,036 according to SEQ ID NO:42;
b) extending the primer at least through the position of the nucleotide sequence of the KLHDC7B cDNA molecule corresponding to: positions 672-673 according to SEQ ID NO:36, positions 672-673 according to SEQ ID NO:38, positions 1,035-1,036 according to SEQ ID NO:40, or positions 1,035-1,036 according to SEQ ID NO:42; and
c) determining whether the extension product of the primer comprises: a CG dinucleotide at positions corresponding to positions 672-673 according to SEQ ID NO:36 a CG dinucleotide at positions corresponding to positions 672-673 according to SEQ ID NO:38, an AG dinucleotide at positions corresponding to positions 1,035-1,036 according to SEQ ID NO:40, or an AG dinucleotide at positions corresponding to positions 1,035-1,036 according to SEQ ID NO:42.

7. The method according to claim 1, wherein the sequence analysis comprises sequencing the entire nucleic acid molecule.

8. The method according to claim 1, wherein the sequence analysis comprises:
a) amplifying at least a portion of the nucleic acid molecule that encodes the KLHDC7B polypeptide, wherein the portion comprises: a CG dinucleotide at positions corresponding to positions 672-673 according to SEQ ID NO:28, or the complement thereof; a CG dinucleotide at positions corresponding to positions 672-673 according to SEQ ID NO:30, or the complement thereof; an AG dinucleotide at positions corresponding to positions 1,035-1,036 according to SEQ ID NO:32, or the complement thereof; or an AG dinucleotide at positions corresponding to positions 1,035-1,036 according to SEQ ID NO:34, or the complement thereof;
b) labeling the amplified nucleic acid molecule with a detectable label;
c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a CG dinucleotide at positions corresponding to positions 672-673 according to SEQ ID NO:28, or the complement thereof;
a CG dinucleotide at positions corresponding to positions 672-673 according to SEQ ID NO:30, or the complement thereof; an AG dinucleotide at positions corresponding to positions 1,035-1,036 according to SEQ ID NO:32, or the complement thereof;
or an AG dinucleotide at positions corresponding to positions 1,035-1,036 according to SEQ ID NO:34, or the complement thereof; and
d) detecting the detectable label.

9. The method according to claim 1, wherein the sequence analysis comprises:
a) amplifying at least a portion of the nucleic acid molecule that encodes the KLHDC7B polypeptide, wherein the portion comprises: a CG dinucleotide at positions corresponding to positions 672-673 according to SEQ ID NO:36, or the complement thereof; a CG dinucleotide at positions corresponding to positions 672-673 according to SEQ ID NO:38, or the complement thereof; an AG dinucleotide at positions corresponding to positions 1,035-1,036 according to SEQ ID NO:40, or the complement thereof;

or an AG dinucleotide at positions corresponding to positions 1,035-1,036 according to SEQ ID NO:42, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a CG dinucleotide at positions corresponding to positions 672-673 according to SEQ ID NO:36, or the complement thereof;

a CG dinucleotide at positions corresponding to positions 672-673 according to SEQ ID NO:38, or the complement thereof; an AG dinucleotide at positions corresponding to positions 1,035-1,036 according to SEQ ID NO:40, or the complement thereof;

or an AG dinucleotide at positions corresponding to positions 1,035-1,036 according to SEQ ID NO:42, or the complement thereof; and d) detecting the detectable label.

10. The method according to claim 9, wherein the nucleic acid molecule in the sample is mRNA and the mRNA is reverse-transcribed into cDNA prior to the amplifying step.

\* \* \* \* \*